United States Patent
Wilson et al.

(10) Patent No.: US 9,315,825 B2
(45) Date of Patent: Apr. 19, 2016

(54) PHARMACOLOGICALLY INDUCED TRANSGENE ABLATION SYSTEM

(75) Inventors: James M Wilson, Glen Mills, PA (US); Anna P Tretiakova, Philadelphia, PA (US); Jenny Agnes Greig, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 729 days.

(21) Appl. No.: 13/247,306

(22) Filed: Sep. 28, 2011

(65) Prior Publication Data

US 2012/0058102 A1    Mar. 8, 2012

Related U.S. Application Data

(63) Continuation-in-part of application No. PCT/US2011/030213, filed on Mar. 28, 2011.

(60) Provisional application No. 61/318,752, filed on Mar. 29, 2010.

(51) Int. Cl.
| | |
|---|---|
| A01N 63/00 | (2006.01) |
| C12N 15/86 | (2006.01) |
| C12N 7/00 | (2006.01) |
| C12N 9/22 | (2006.01) |
| A61K 48/00 | (2006.01) |
| C07K 14/47 | (2006.01) |

(52) U.S. Cl.
CPC *C12N 15/86* (2013.01); *C12N 7/00* (2013.01); *A61K 48/0066* (2013.01); *C07K 14/4702* (2013.01); *C07K 2319/09* (2013.01); *C07K 2319/715* (2013.01); *C07K 2319/80* (2013.01); *C07K 2319/81* (2013.01); *C07K 2319/92* (2013.01); *C12N 9/22* (2013.01); *C12N 2750/14143* (2013.01); *C12N 2750/14151* (2013.01); *C12N 2800/30* (2013.01); *C12N 2800/40* (2013.01); *C12N 2800/80* (2013.01); *C12N 2830/002* (2013.01); *C12N 2830/003* (2013.01); *C12N 2830/005* (2013.01); *C12N 2830/006* (2013.01); *C12N 2830/20* (2013.01); *C12N 2840/203* (2013.01)

(58) Field of Classification Search
CPC ....................................................... C12N 15/86
USPC ....................................................... 424/93.2
See application file for complete search history.

(56) References Cited

U.S. PATENT DOCUMENTS

| | | | |
|---|---|---|---|
| 2003/0022375 A1 | 1/2003 | Itoh et al. | |
| 2003/0126624 A1* | 7/2003 | Pomerantz et al. | 800/8 |
| 2003/0232410 A1* | 12/2003 | Liljedahl et al. | 435/69.1 |
| 2005/0266567 A1 | 12/2005 | Atkinson et al. | |
| 2013/0023033 A1 | 1/2013 | Wilson et al. | |

FOREIGN PATENT DOCUMENTS

| | | |
|---|---|---|
| DE | 10023887 A1 | 11/2001 |
| WO | WO02/070740 A2 | 9/2002 |
| WO | WO2008/051854 A2 | 5/2008 |
| WO | WO2011/126808 | 10/2011 |
| WO | WO 2011/126808 A2 | 10/2011 |

OTHER PUBLICATIONS

Xiao et al., 1999, J. Virology, vol. 73(5), pp. 3994-4003.*
Wah et al., 1997, Nature, vol. 388, pp. 97-100.*
Miller et al. (2007, Nature Biotechnology, vol. 25(7), pp. 778-785).*
Yokoi et al. (2007, Molecular Therapy, vol. 15(11), pp. 1917-1923).*
Aagaard et al, The Journal of the American Society of Gene Therapy Facile lentiviral vector system for expression of doxycycline-inducible shRNAs: knockdown of the pre-miRNA Processing enzyme drosha, Molecular Therapy,15(5):938-945, (May 2007).
Auricchio et al, Isolation of highly infectious and pure adeno-associated virus type 2 vectors with a single-step gravity-flow column, Human Gene Therapy, 12(1):71-76, (Jan. 2001).
Bibikova et al, Stimulation of homologous recombination through targeted cleavage by chimeric nucleases, Molecular and Cellular Biology, 21(1):289-97, (Jan. 2001).
Brantly et al, Sustained transgene expression despite T lymphocyte responses in a clinical trial of rAAV1-AAT gene therapy, Proceedings of the National Academy of Sciences of the United States of America, 106(38)16363-16368, (Sep. 2009) Epublication (Aug. 12, 2009).
Brument et al, A versatile and scalable two-step ion-exchange chromatography process for the purification of recombinant adeno-associated virus serotypes-2 and -5, Molecular Therapy, the Journal of American Society of Gene Therapy, 6(5)678-86, (Nov. 2002).
Clement et al, Large-scale adeno-associated viral vector production using a herpesvirus-based system enables manufacturing for clinical studies, Human Gene Therapy, 20(8)796-806, (Aug. 2009).

(Continued)

*Primary Examiner* — Anoop Singh
*Assistant Examiner* — David A Montanari
(74) *Attorney, Agent, or Firm* — Howson & Howson LLP

(57) ABSTRACT

The present invention relates to gene therapy systems designed for the delivery of a therapeutic product to a subject using replication-defective virus composition(s) engineered with a built-in safety mechanism for ablating the therapeutic gene product, either permanently or temporarily, in response to a pharmacological agent—preferably an oral formulation, e.g., a pill. The invention is based, in part, on the applicants' development of an integrated approach, referred to herein as "PITA" (Pharmacologically Induced Transgene Ablation), for ablating a transgene or negatively regulating transgene expression. In this approach, replication-deficient viruses are used to deliver a transgene encoding a therapeutic product (an RNA or a protein) so that it is expressed in the subject, but can be reversibly or irreversibly turned off by administering the pharmacological agent; e.g., by administration of a small molecule that induces expression of an ablator specific for the transgene or its RNA transcript.

26 Claims, 27 Drawing Sheets

(56) References Cited

OTHER PUBLICATIONS

Figure 2A:
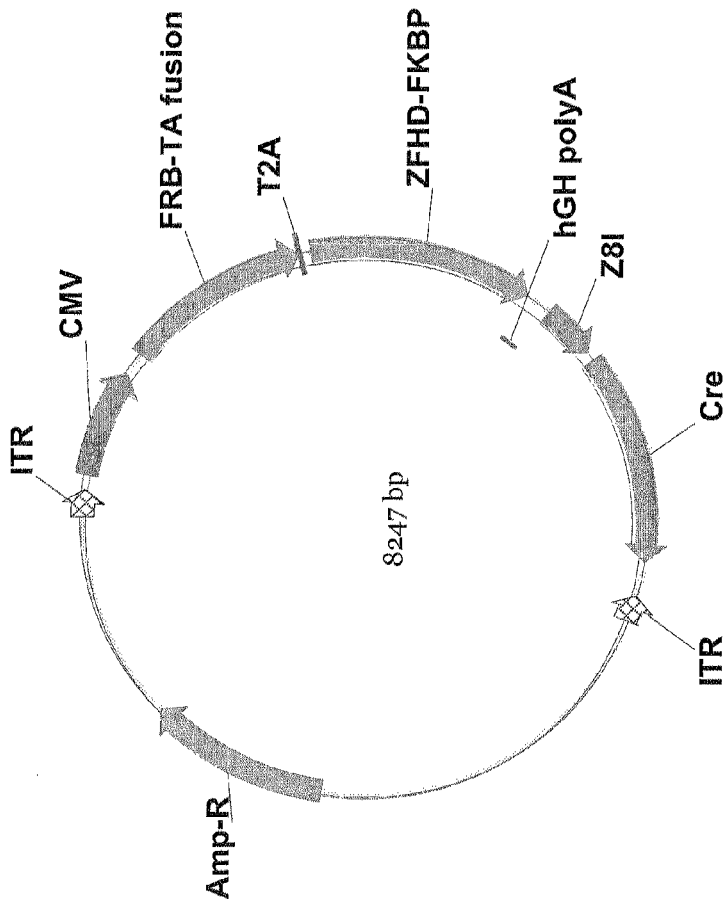

Gao et al, Novel adeno-associated viruses from rhesus monkeys as vectors for human gene therapy, Proceedings of the National Academy of Sciences of the United States of America, (Sep. 2002), 99(18):11854-9. Epublication (Aug. 21, 2002).

Grimm et al, Novel tools for production and purification of recombinant adeno-associated virus vectors, Human Gene Therapy, 9(18):2745-60, (Dec. 1998).

Kotin et al, Site-specific integration by adeno-associated virus, Proceedings of the National Academy of Sciences of the United States of America, 87(6):2211-2215, (Mar. 1990).

Li et al, Viral-Mediated Temporally Controlled Dopamine Production in a Rat Model of Parkinson Disease, Molecular Therapy, 13(1):160-166, (Jan. 1, 2006).

Maguire et al, Safety and efficacy of gene transfer for Leber's congenital amaurosis, The New England Journal of Medicine, 358(21):2240-8, (May 2008) Epublication (Apr. 27, 2008).

Maslov et al, A dual-activatoin, adenoviral-based system for the controlled induction of DNA double-strand breaks by the restriction endonuclease SacI, Biotechniques, 47(4):847-854, (Oct. 2009).

Matsushita et al, Adeno-associated virus vectors can be efficiently produced without helper virus, Gene Therapy, 5(7):938-45, (Jul. 1998).

Miller et al, An improved zinc-finger nuclease architecture for highly specific genome editing, Nature Biotechnology, 25(7):778-785, (Jul. 1, 2007).

Moss et al, Repeated adeno-associated virus serotype 2 aerosol mediated cystic fibrosis transmembrane regulator gene transfer to the lungs of patients with cystic fibrosis: a multicenter, double-blind, placebo-controlled trial, Chest, 125(2):509-21, (Feb. 2004).

Smith et al, A simplified baculovirus-AAV expression vector system couple with one-step affinity purification yields high-titer rAAV stocks from insect cells, Molecular Therapy, 17(11);1888-1896, (Nov. 2009); Epublication Jun. 16, 2009.

Shimizu et al, Restricted spacer tolerance of a zinc finger nuclease with a six amino acid linker, Bioorganic Medicinal Chemistry Letters, 19(14):3970-3972. (Jul. 15. 2009) Epublication (Mar. 3, 2009).

Shimizu et al, Adding fingers to an engineered zinc finger nuclease can reduce activity, Biochemistry, 50(22):5033-5041, (Jun. 7, 2011) Epublication (May 11, 2011).

Shyam et al, Virus Vectors Gene Therapy Using Adeno-Associated, Clinical Microbiology Reviews, 21(4):583, (Oct. 2008).

Vandenberghe et al, Efficient serotype-dependent release of functional vector into the culture medium during adeno-associated virus manufacturing, Human Gene Therapy, 21(10):1251-7, (Oct. 2010).

Virag et al, Producing recombinant adeno-associated virus in foster cells: overcoming production limitations using a baculovirus-insect cell expression strategy, Human Gene Therapy, 20(8):807-817, (Aug. 2009).

Wang et al, Systematic evaluation of AAV vectors for liver directed gene transfer in murine models, Molecular Therapy, 18(1):118-25, (Jan. 2010) Epublication (Oct. 27, 2009).

Wright et al, Transient transfection methods for clinical adeno-associated viral vector production, Human Gene Therapy, 20(7):698-706, (Jul. 2009).

Wright et al, Identification of factors that contribute to recombinant AAV2 particle aggregation and methods to prevent its occurrence during vector purification and formulation, Molecular Therapy, 12(1):171-178, (Jul. 2005).

Xiao et al, Production of high-titer recombinant adeno-associated virus vectors in the absence of helper adenovirus, Journal of Virology, 72(3):2224-2232, (Mar. 1998).

Zolotukhin et al, Recombinant adeno-associated virus purification using novel methods improves infectious titer and yield, Gene Therapy, 6(6):973-985, (Jun. 1999).

Partial International Search issued in corresponding International Patent Application No. PCT/US2011/030213, now published as WO2011/126808; Oct. 13, 2011.

Machine translation of German application DE10023887 from the Espacenet website.

Clackson et al, Controlling Mammalian Gene Expression With Small Molecules, Current Opinion in Chemical Biology, 1(2):210-218 (Aug. 1997).

Rossi et al, Recent Advances in Inducible Gene Expression Systems, Current Opinion Biotechnology, 9(5):451-456, (Oct. 1998).

Durocher et al, Scalable Serum-free Production of Recombinant Adeno-associated Virus type 2 by Transfection of 293 Suspension Cells, Journal of Virological Methods 144 (1-2):32-40, (Sep. 2007), Epublication Apr. 30, 2007.

Davidoff et al, Purification of Recombinant Adeno-associated Virus type 8 Vectors by Ion Exchange Chromatography Generates Clinical Grade Vector Stock, Journal of Virological Methods, 2121 (2):209-15, (Nov. 2004).

Hildinger et al, High-titer, Serum-free Production of Adeno-associated Virus Vectors by Polyethyleneimine-ediated Plasmid Transfection in Mammalian Suspension Cells, Biotechnology Letters, 29(11): 1713-21, (Nov. 2007), Epublication Jul. 17, 2007.

Hermens et al, Purificaiton of Recombinant Adeno-associated Virus by Iodixanol Gradient Ultracentrifuation Allows Rapid and Reproducible Preparation of Vector Stocks for Gene Transfer in the Nervous System, Human Gene Therapy, 10(11):1885-91, (Jul. 1999).

Kaludov et al, Scalable Purification of Adeno-associated Virus type 2,4, or 5 using Ion-exchange Chromatography, Human Gene Therapy, 13(10):1235-1243, (Jul. 2002).

Mueller et al, Clinical Gene Therapy Using Recombinant Adeno-associated Virus Vectors, Gene Therapy, (11):858-63, (Jun. 2008) Epublication Apr. 17, 2008.

Nienhuis et al, Dose-Excalation Study of a self complementary Adeno-Associated Viral Vector for Gene Transfer in Hemophilia B, Presentation to Recombinant DNA Advisor Committee Jun. 9 2011.

Okada et al, Scalable Purification of Adeno-Associated Virus Serotype 1 (AAV1) and AAV8 Vectors, Using Dual Ion-exchange Adsorptive Membranes, Human Gene Therapy, 20(9):1013-1021, 2009.

Qu et al, Separation of Adeno-associated Virus Type 2 Empty Particles from Genome Containing Vectors by Anion-exchange Column Chromatography, Journal of Virologic methods, 140 (1-2):183-192,2007.

Salvetti et al, Factors Influencing Recombinant Adeno-associated Virus Production, Human Gene Therapy, 9(5):695-708, 1998.

Schröder et al, Spectrophotometric Determination of Iodixanol in Subcellular Fractions of Mammalian Cells, Anal Biochem 244(1):174-176, 1997.

Shimizu et al, Adding Fingers to an Engineered Zinc Finger Nuclease can Reduce Activity, Biochemistry, 50(22):5033-5041, (Jun. 7, 2011) Epublication May 11, 2011.

Snyder et al, Production of Clinical-grade Recombinant Adeno-associated Virus Vectors, Current Opinion Biotechnology, 13(5):418-423, 2002.

Sommer et al, Quantification of Adeno-associated Virus Particles and Empty Capsids by Optical Density Measurement, Molecular Therapy, 7(1):122-128, 2003.

Warrington et al, Treatment of Human Disease by Adeno-associated Viral Gene Transfer, Human Genet, 119(6):571-603, 2006.

Zhang et al, Adenovirus Adeno-associated Virus Hybrid for Large-scale Recombinant Adeno-associated Virus Production, Human Gene Therapy, 20(9):922-929, 2009.

Zolotukhin et al, Production and Purification of Serotype 1,2, and 5 Recombinant Adeno-associated Viral Vectors, Methods, 28(2);158-167, 2002.

International Search and Written Opinion of the International Searching Authority, issued in corresponding International Patent Application No. PCT/US2011/030213, now published as WO2011/126808, mailed May 15, 2012.

(56) References Cited

OTHER PUBLICATIONS

Bhakta et al, "The Generation of Zinc Finger Proteins by Modular Assembly", Methods Mol Biol, vol. 649, pp. 3-30 (Aug. 2010).
Weitzman et al, "Recruitment of wild-type and recombinant adeno-associated virus into adenovirus replication centers", J. Virol., vol. 70(3) pp. 1845-1854 (Mar. 1996).
Gao et al, "High-titer adeno-associated viral vectors from a Rep/Cap cell line and hybrid shuttle virus", Hum. Gene Ther., vol. 9(16) pp. 2353-2362 (Nov. 1998).
Examination Report dated Apr. 29, 2014 issued in European Patent Application No. EP11713419.7.
Examiner initiated interview summary dated Jun. 4, 2013 in U.S. Appl. No. 13/638,015.
Supplemental Preliminary Amendment dated Jul. 14, 2013 in U.S. Appl. No. 13/638,015 in response to telephonic interview with examiner dated Jun. 4, 2013.
Non Final Rejection dated Apr. 18, 2014 issued in U.S. Appl. No. 13/638,015.
Final Office Action dated Oct. 31, 2014 in U.S. Appl. No. 13/638,015.
AF response to Final Office Action in U.S. Appl. No. 13/638,015, filed Feb. 2, 2015.
Advisory Action issued in U.S. Appl. No. 13/638,015, mailed Feb. 26, 2015.

\* cited by examiner

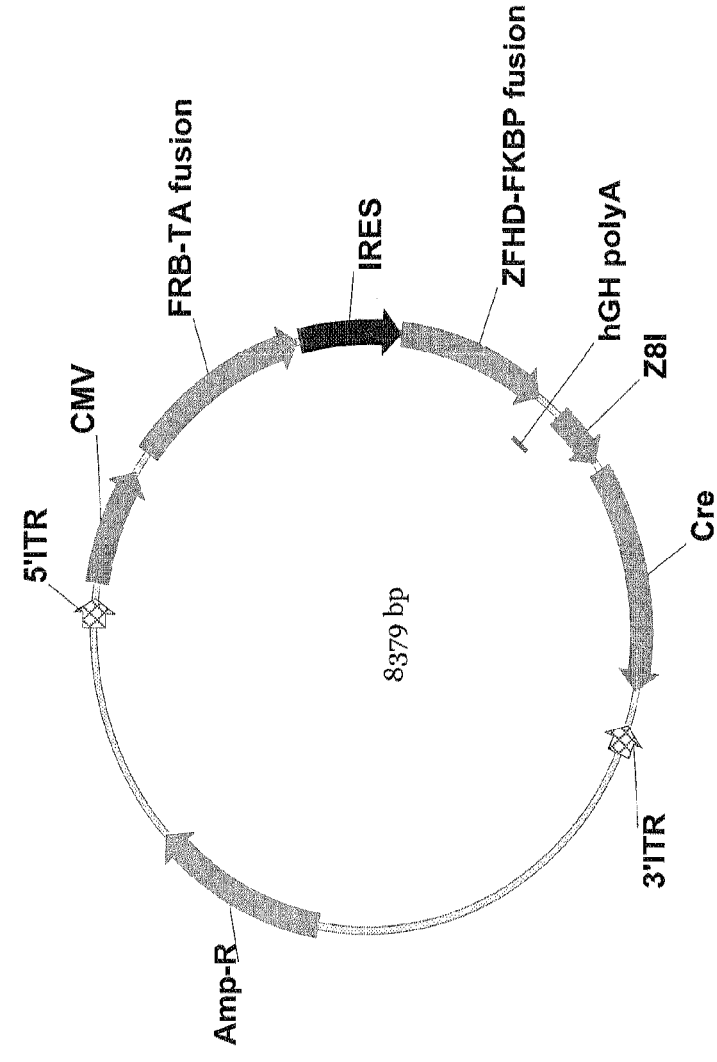
FIG. 1A
FIG. 1B

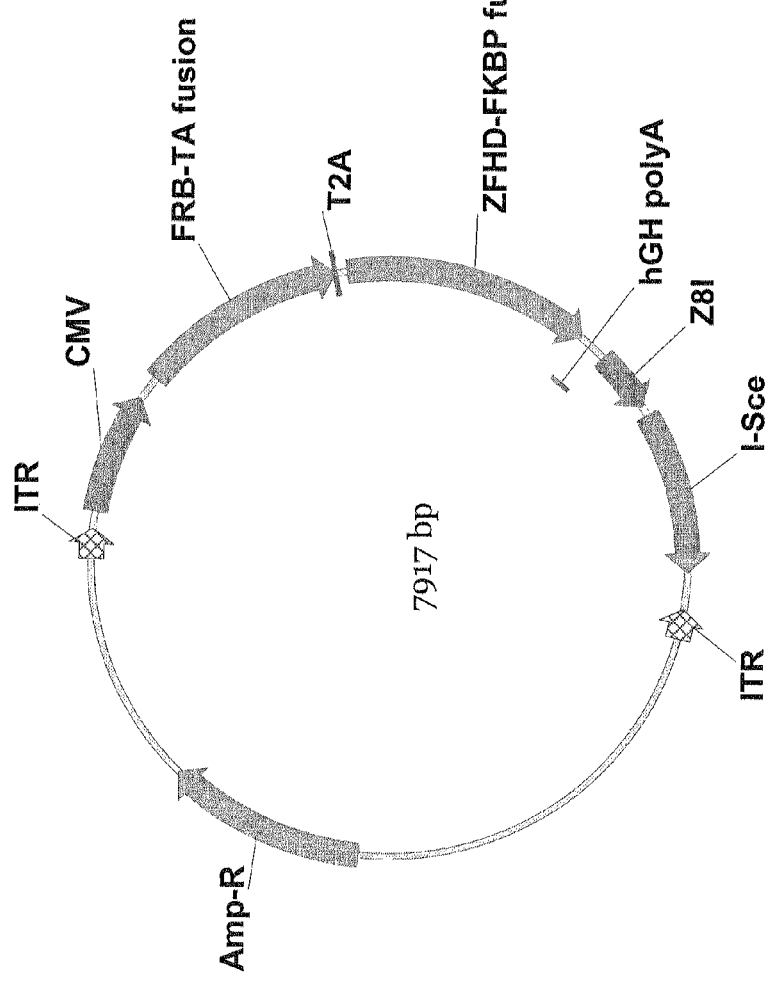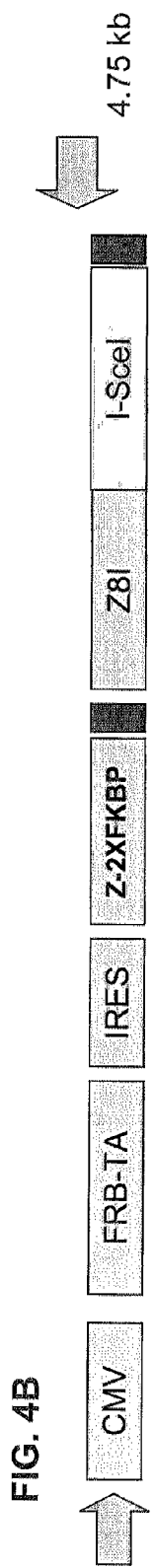
FIG. 4A
FIG. 4B

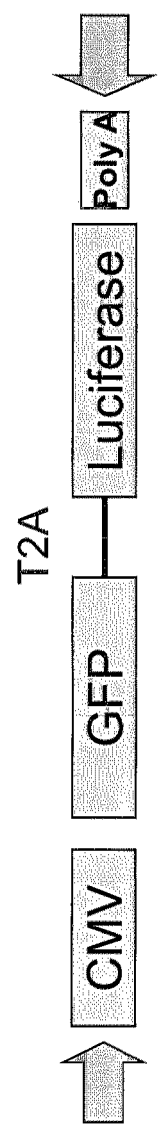
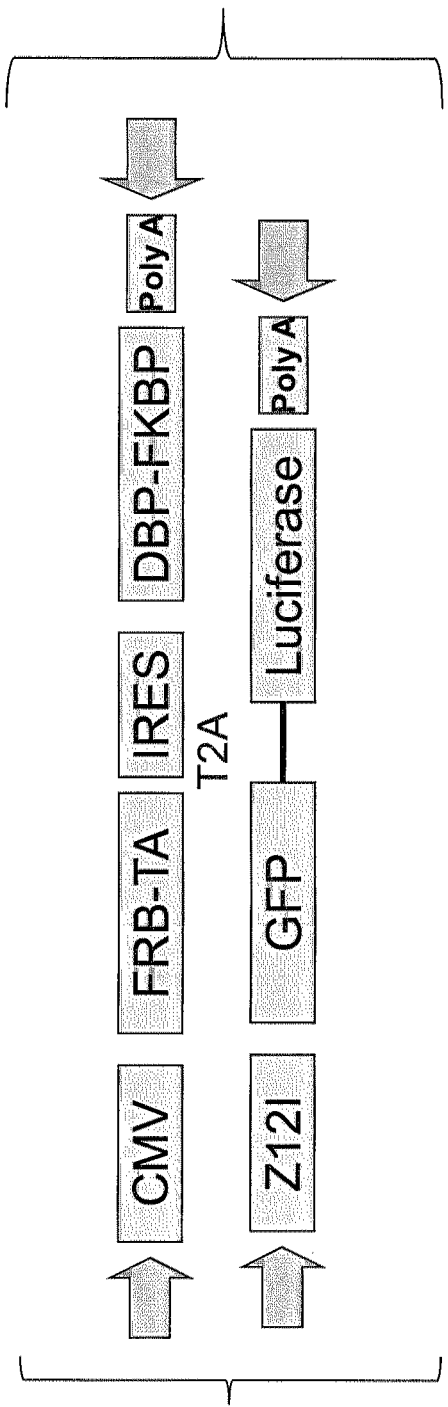
FIG. 9A
FIG 9B

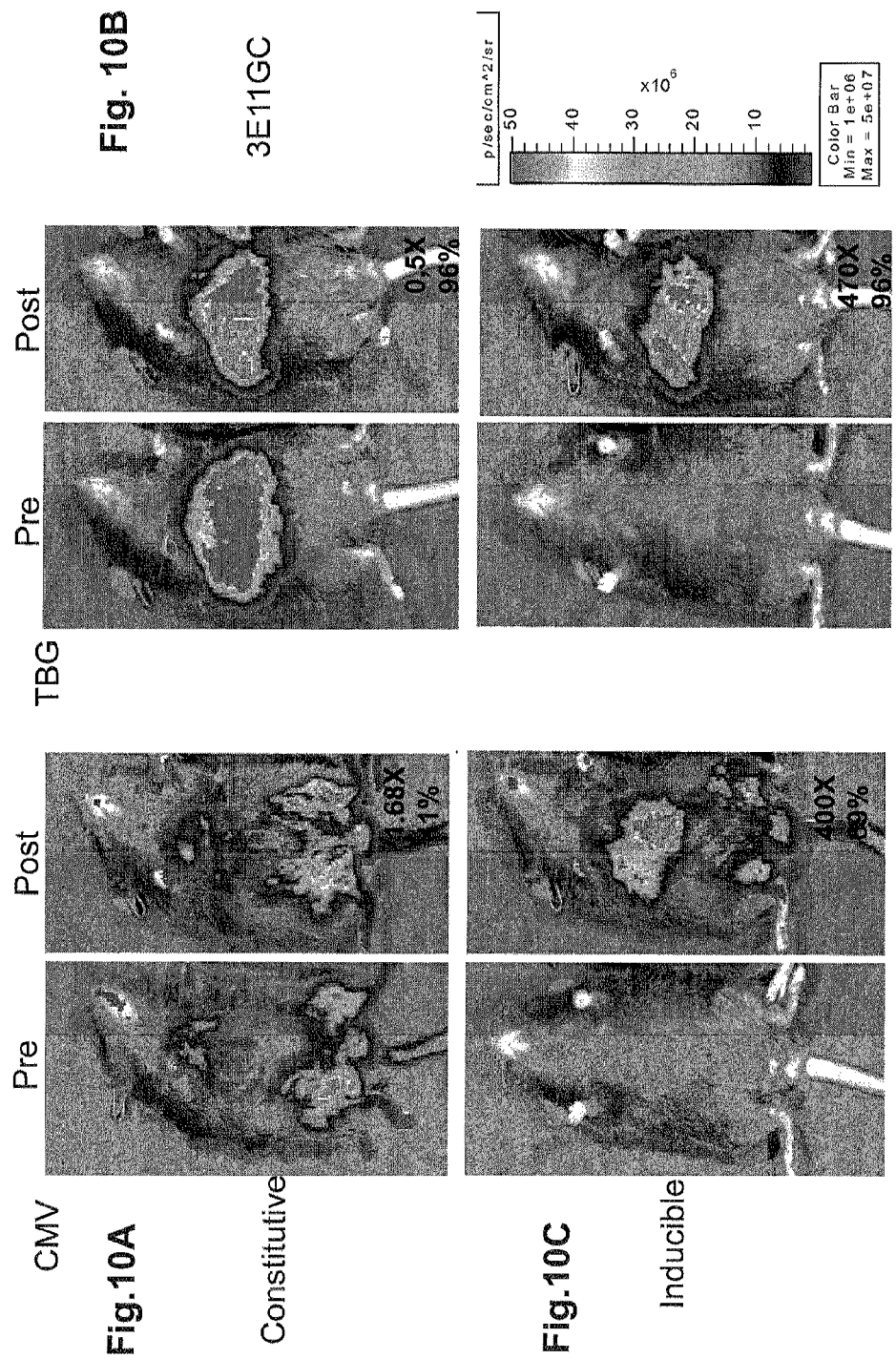

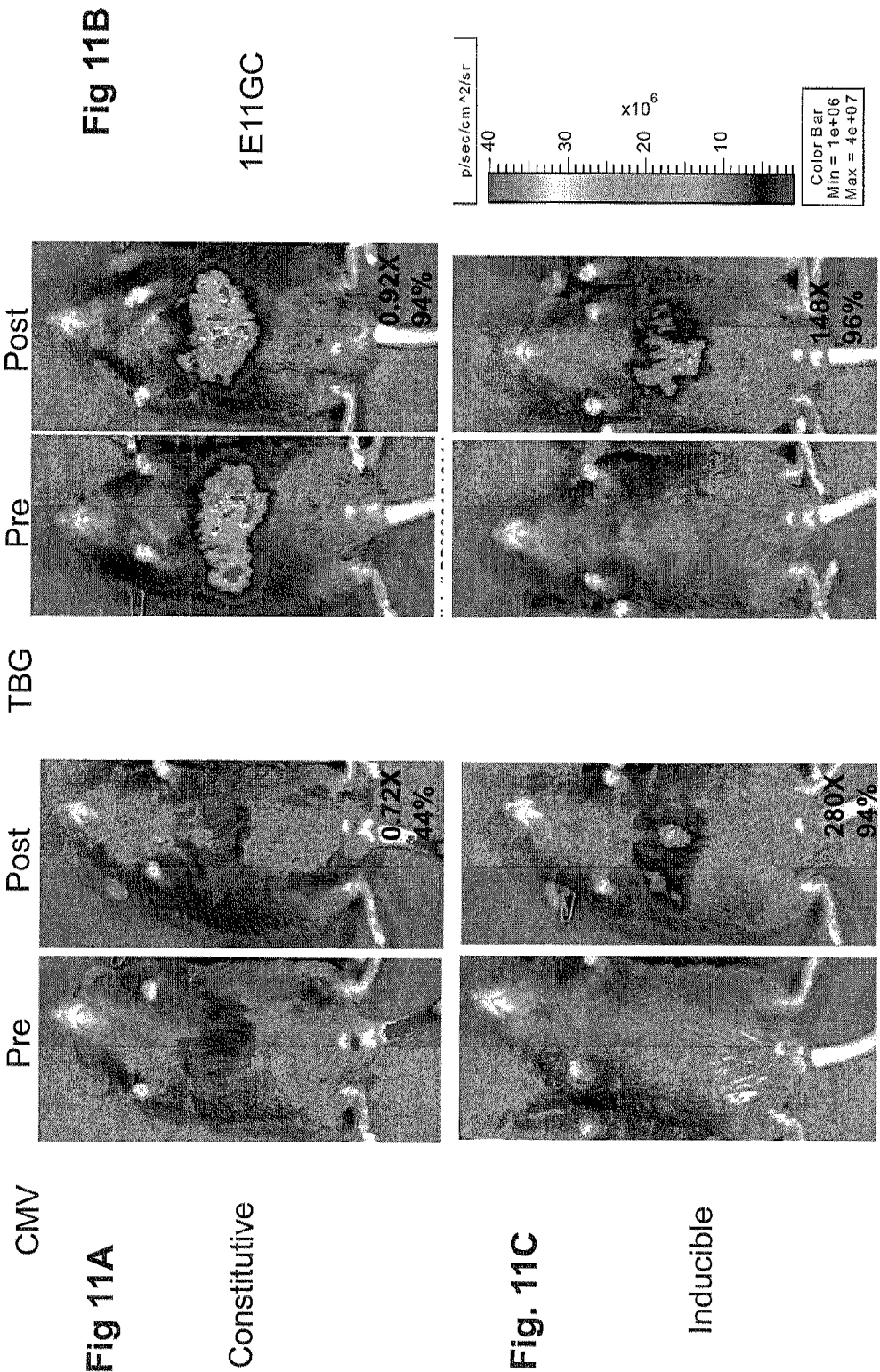

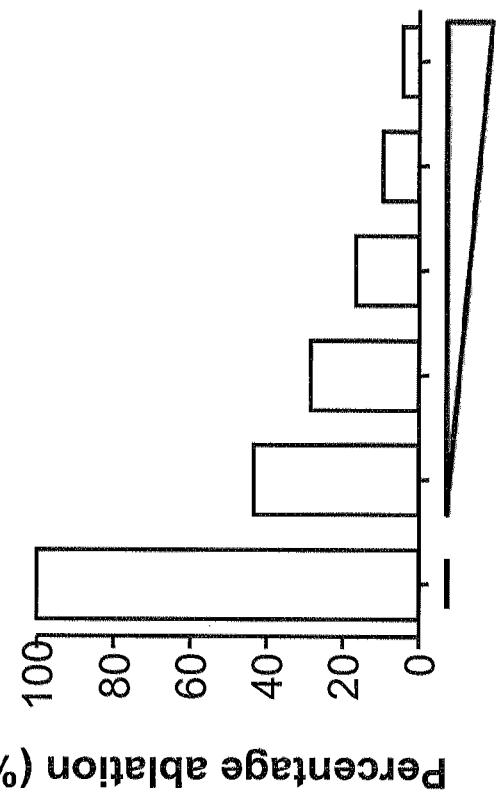
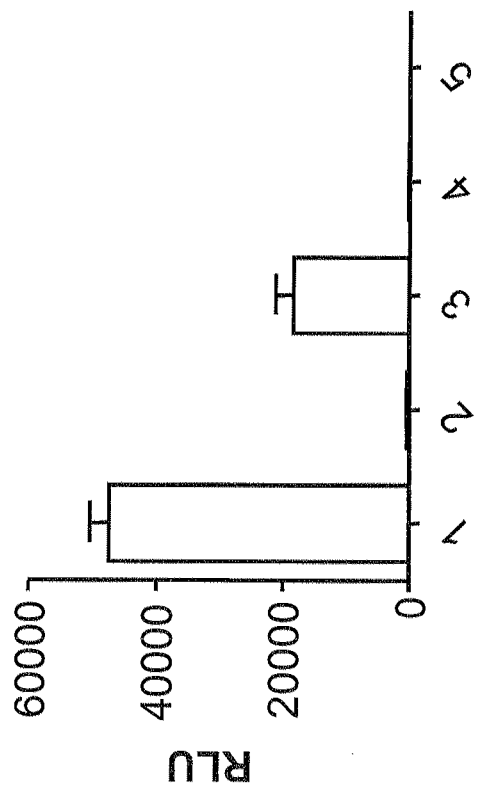
Fig. 18A
Fig. 18B

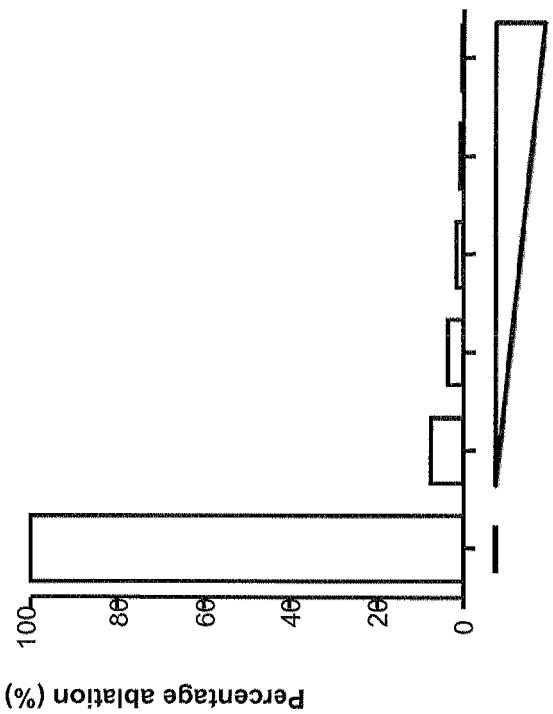
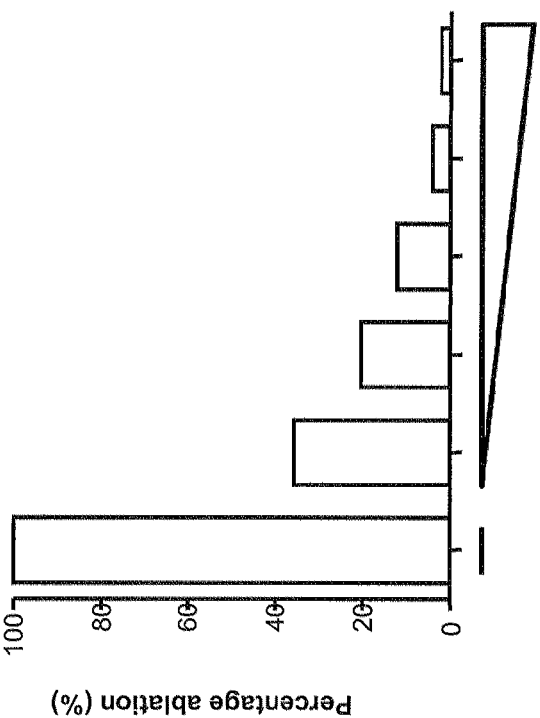
Fig. 20A
Fig. 20B

PHARMACOLOGICALLY INDUCED TRANSGENE ABLATION SYSTEM

1. CROSS-REFERENCE TO RELATED APPLICATIONS

This application is a continuation-in-part of International Patent Application No. PCT/US2011/030213, filed Mar. 28, 2011, which claims the benefit under 35 USC 119(e) of U.S. Provisional Patent Application No. 61/318,752, filed Mar. 29, 2010, both of which are incorporated herein by reference.

2. BACKGROUND OF THE INVENTION

Gene therapy involves the introduction of genetic material into host cells with the goal of treating or curing disease. Many diseases are caused by "defective" genes that result in a deficiency in an essential protein. One approach for correcting faulty gene expression is to insert a normal gene (transgene) into a nonspecific location within the genome to replace a nonfunctional, or "defective," disease-causing gene. Gene therapy can also be used as a platform for the delivery of a therapeutic protein or RNA to treat various diseases so that the therapeutic product is expressed for a prolonged period of time, eliminating the need for repeat dosing. A carrier molecule called a vector must be used to deliver a transgene to the patient's target cells, the most common vector being a virus that has been genetically altered to carry normal human genes. Viruses have evolved a way of encapsulating and delivering their genes to human cells in a pathogenic manner and thus, virus genomes can be manipulated to insert therapeutic genes.

Stable transgene expression can be achieved following in vivo delivery of vectors based on adenoviruses or adeno-associated viruses (AAVs) into non dividing cells, and also by transplantation of stem cells transduced ex vivo with integrating and non-integrating vectors, such as those based on retroviruses and lentiviruses. AAV vectors are used for gene therapy because, among other reasons, AAV is nonpathogenic, it does not elicit a deleterious immune response, and AAV transgene expression frequently persists for years or the lifetime of the animal model (see Shyam et al., Clin. Microbiol. Rev. 24(4):583-593). AAV is a small, nonenveloped human parvovirus that packages a linear strand of single stranded DNA genome that is 4.7 kb. Productive infection by AAV occurs only in the presence of a helper virus, either adenovirus or herpes virus. In the absence of a helper virus, AAV integrates into a specific point of the host genome (19q 13-qter) at a high frequency, making AAV the only mammalian DNA virus known to be capable of site-specific integration. See, Kotin et at., 1990, PNAS, 87: 2211-2215. However, recombinant AAV, which does not contain any viral genes and only a therapeutic gene, does not integrate into the genome. Instead the recombinant viral genome fuses at its ends via inverted terminal repeats to form circular, episomal forms which are predicted to be the primary cause of the long term gene expression (see Shyam et at., Clin. Microbiol. Rev. 24(4):583-593).

Virtually all pre-clinical and clinical applications of gene therapy have used vectors that express the transgene from a constitutive promoter, which means it is active at a fixed level for as long as the vector genome persists. However, many diseases that are amenable to gene therapy may need to have expression of the transgene regulated. Several systems have been described which that are based on the general principle of placing a gene of interest under the control of a drug-inducible engineered transcription factor in order to positively induce gene expression (Clackson et at., 1997, Curr Opin Chem Biol, 1 (2): 210-8; Rossi et at., Curr Opin Biotechnol, 1998. 9(5): p. 451-6). The various systems can be divided into two classes. In the first, a DNA-binding domain that is allosterically regulated by inducers such as tetracyclines, antiprogestins, or ecdysteroids is coupled to a transactivation domain. The addition (or in some cases removal) of the drug leads to DNA binding and hence transcriptional activation. In the second, allosteric control is replaced with the more general mechanism of induced proximity. DNA binding and activation domains are expressed as separate polypeptides that are reconstituted into an active transcription factor by addition of a bivalent small molecule, referred to as a chemical inducer of dimerization or "dimerizer." While these systems are useful in gene therapy systems that require inducing transgene expression, they have not addressed the need to be able to turn off or permanently ablate transgene expression if it is no longer needed or if toxicity due to long-term drug administration ensues.

3. SUMMARY OF THE INVENTION

The present invention relates to gene therapy systems designed for the delivery of a therapeutic product to a subject using replication-defective virus composition(s) engineered with a built-in safety mechanism for ablating the therapeutic gene product, either permanently or temporarily, in response to a pharmacological agent—preferably an oral formulation, e.g., a pill.

The invention is based, in part, on the applicants' development of an integrated approach, referred to herein as "PITA" (Pharmacologically Induced Transgene Ablation), for ablating a transgene or negatively regulating transgene expression. In this approach, replication-deficient viruses are used to deliver a transgene encoding a therapeutic product (an RNA or a protein) so that it is expressed in the subject, but can be reversibly or irreversibly turned off by administering the pharmacological agent.

The invention presents many advantages over systems in which expression of the transgene is positively regulated by a pharmacological agent. In such cases, the recipient must take a pharmaceutic for the duration of the time he/she needs the transgene expressed—a duration that may be very long and may be associated with its own toxicity.

In one aspect, the invention provides a composition for AAV-mediated delivery of a therapeutic product having a controlled transgene expression ablation system, said composition comprising (a) an AAV vector containing a nucleic acid molecule comprising: (i) a nucleic acid sequence encoding a therapeutic product operably linked to a promoter that controls transcription; and (ii) at least one endonuclease ablation site which comprises a sequence of at least 30 nucleic acid base pairs which are specifically and selectively recognized by at least ten (10×) zinc fingers, said at least one endonuclease ablation site being located at least 5' to the sequence encoding the therapeutic product; and (b) at least one ablator which comprises a chimeric endonuclease comprising at least ten copies of a zinc finger domain linked to a functional endonuclease catalytic domain in operative association with a promoter, wherein transcription and/or ablation activity is induced in response to a pharmacological agent, said at least ten (10×) zinc finger domain specifically and selectively recognizing said at least about 30 base pair sequence in said at least one endonuclease ablation site and comprising at least 10 independently selected recognition helices. In one embodiment, the endonuclease catalytic domain is a FokI catalytic domain.

In a further embodiment, the nucleic acid molecule consists of a double-stranded DNA molecule, wherein the at least one endonuclease ablation site is on a first strand of the DNA molecule and at least a second endonuclease ablation is located on the second strand of the DNA molecule, wherein said second endonuclease ablation site is distinct from said endonuclease ablation said on the first strand and is specifically and selectively recognized by a different zinc finger.

In a further aspect, the ablator (b) is controlled by a cassette that is activated by a transcription factor following being dimerized by a pharmacologic agent, said cassette comprising two transcription units, wherein: (c) one of said two transcription units encoding the DNA binding domain of the transcription factor fused to a binding domain for the pharmacological agent in operative association with a first promoter; and (d) a second of said two transcription units encoding the activation domain of the transcription factor fused to a binding domain for the pharmacological agent in operative association with a second promoter.

In one embodiment, the first and second promoters are both constitutive promoters and the pharmacological agent is a dimerizer that dimerizes the domains of the transcription factor.

In another embodiment, the transcription of the promoter is controlled by a rapamycin—regulatable system and the pharmacological agent is rapamycin or a rapalog.

In yet another embodiment, the unique nucleic acid sequence of least about a 30 base pair of (a)(ii) consists of contiguous nucleic acids which are less than 70% identical with any subsequence in the human genome and no more than 8 contiguous identical positions with any sub-sequence in the human genome.

Other aspects and advantages of the invention will be readily apparent from the following Detailed Description of the Invention.

As used herein, the following terms will have the indicated meaning:

"Unit" refers to a transcription unit.

"Transgene unit" refers to a DNA that comprises (1) a DNA sequence that encodes a transgene; (2) an ablation recognition site (ARS) contained within or flanking the transgene; and (3) a promoter sequence that regulates expression of the transgene.

"Ablation recognition site" or "ARS" refers to a DNA sequence that (1) can be recognized by the ablator that ablates or excises the transgene from the transgene unit; or (2) encodes an ablation recognition RNA sequence (ARRS)

"Ablation recognition RNA sequence" or "ARRS" refers to an RNA sequence that is recognized by the ablator that ablates the transcription product of the transgene or translation of its mRNA.

"Ablator" refers to any gene product, e.g., translational or transcriptional product, that specifically recognizes/binds to either (a) the ARS of the transgene unit and cleaves or excises the transgene; or (b) the ARRS of the transcribed transgene unit and cleaves or prevents translation of the mRNA transcript.

"Ablation unit" refers to a DNA that comprises (1) a DNA sequence that encodes an Ablator; and (2) a promoter sequence that controls expression of said Ablator.

"Dimerizable transcription factor (TF) domain unit" refers to (1) a DNA sequence that encodes the DNA binding domain of a TF fused to the dimerizer binding domain (DNA binding domain fusion protein) controlled by a promoter; and (2) a DNA sequence that encodes the activation domain of a TF fused to the dimerizer binding domain (activation domain fusion protein) controlled by a promoter. In one embodiment, each unit of the dimerizable domain is controlled by a constitutive promoter and the unit is utilized for control of the promoter for the ablator. Alternatively, one or more of the promoters may be an inducible promoter.

A "Dimerizable fusion protein unit" refers to (1) a first DNA sequence that encodes a unit, subunit or fragment of a protein or enzyme (e.g., an ablator) fused to a dimerizer binding domain and (2) a second DNA sequence that encodes a unit, subunit or fragment of a protein or enzyme, which when expressed and if required, activated, combine to form a fusion protein. This "Dimerizable fusion protein unit" may be utilized for a variety of purposes, including to activate a promoter for the ablator, to provide DNA specificity, to activate a chimeric ablator by bringing together the binding domain and the catalytic domain, or to produce a desired transgene. These units (1) and (2) may be in a single open reading frame separated by a suitable linker (e.g., an IRES or 2A self-cleaving protein) under the control of single promoter, or may be in separate open reading frames under the control of independent promoters. From the following detailed description, it will be apparent that a variety of combinations of constitutive or inducible promoters may be utilized in the two components of this unit, depending upon the use to which this fusion protein unit is put (e.g., for expression of an ablator). In one embodiment, the dimerizable fusion protein unit contains DNA binding domains which include, e.g., zinc finger motifs, homeo domain motifs, HMG-box domains, STAT proteins, B3, helix-loop-helix, winged helix-turn-helix, leucine zipper, helix-turn-helix, winged helix, POU domains, DNA binding domains of repressors, DNA binding domains of oncogenes and naturally occurring sequence-specific DNA binding proteins that recognize >6 base pairs.

"Dimerizer" refers to a compound or other moiety that can bind heterodimerizable binding domains of the TF domain fusion proteins or dimerizable fusion proteins and induce dimerization or oligomerization of the fusion proteins. Typically, the dimerizer is delivered to a subject as a pharmaceutical composition.

"Side effect" refers to an undesirable secondary effect which occurs in a patient in addition to the desired therapeutic effect of a transgene product that was delivered to a patient via administration of a replication-defective virus composition of the invention.

"Replication-defective virus" or "viral vector" refers to a synthetic or artificial genome containing a gene of interest packaged in replication-deficient virus particles; i.e., particles that can infect target cells but cannot generate progeny virions. The artificial genome of the viral vector does not include genes encoding the enzymes required to replicate (the genome can be engineered to be "gutless"—containing only the transgene of interest flanked by the signals required for amplification and packaging of the artificial genome). Therefore, it is deemed safe for use in gene therapy since replication and infection by progeny virions cannot occur except in the presence of the viral enzyme required for replication.

"Virus stocks" or "stocks of replication-defective virus" refers to viral vectors that package the same artificial/synthetic genome (in other words, a homogeneous or clonal population).

A "chimeric engineered ablator" or a "chimeric enzyme" is provided when a sequence encoding a catalytic domain of an endonuclease ablator fused to a binding domain and a sequence encoding a DNA binding domain of the endonuclease fused to a binding domain are co-expressed. The chimeric engineered enzyme is a dimer, the DNA binding domains may be selected from among, for example, zinc finger and other homeodomain motifs, HMG-box domains, STAT proteins, B3, helix-loop-helix, winged helix-turn-helix, leucine zipper, helix-turn-helix, winged helix, POU domains, DNA binding domains of repressors, DNA binding domains of oncogenes and naturally occurring sequence-specific DNA binding proteins that recognize >6 base pairs. [U.S. Pat. No. 5,436,150, issued Jul. 25, 1995]. When a heterodimer is formed, the binding domains are specific for a pharmacologic agent that induces dimerization in order to provide the desired enzymatic bioactivity, DNA binding specificity, and/or transcription of the ablator. Typically, an enzyme is selected which has dual domains, i.e., a catalytic domain and a DNA binding domain which are readily separable. In one embodiment, a type II restriction endonuclease is selected. In one embodiment, a chimeric endonuclease is designed based on an endonuclease having two functional domains, which are independent of ATP hydrolysis. Useful nucleases include type II S endonucleases such as FokI, or an endonuclease such as Nae I. Another suitable endonuclease may be selected from among intron endonucleases, such as e.g., I-TevI. Still other suitable nucleases include, e.g., integrases (catalyze integration), serine recombinases (catalyze recombination), tyrosine recombinases, invertases (e.g. Gin) (catalyze inversion), resolvases, (e.g., Tn3), and nucleases that catalyze translocation, resolution, insertion, deletion, degradation or exchange. However, other suitable nucleases may be selected.

4. BRIEF DESCRIPTION OF DRAWINGS

FIGS. 1A and 1B. PITA DNA construct containing a dimerizable transcription factor domain unit and an ablation unit. FIG. 1A is a map of the following DNA construct, which comprises a dimerizable transcription factor domain unit and an ablation unit: pAAV.CMV.TF.FRB-IRES-1×FKBP.Cre. FIG. 1B is a cartoon of the transcription unit inserted into the plasmid backbone. A description of the various vector domains can be found in Section 8.1 herein.

Figure 2B:
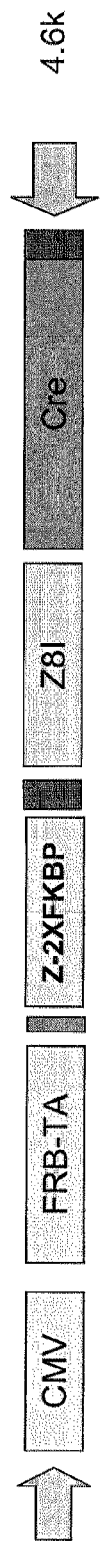

FIGS. 2A and 2B. PITA DNA construct containing a dimerizable transcription factor domain unit and an ablation unit. FIG. 2A is a map of the following DNA construct, which comprises a dimerizable transcription factor domain unit and an ablation unit: pAAV.CMV.TF.FRB-T2A-2×FKBP.Cre. FIG. 2B is a cartoon of the transcription unit inserted into the plasmid backbone. A description of the various vector domains can be found in Section 8.1 herein.

Figure 3A:
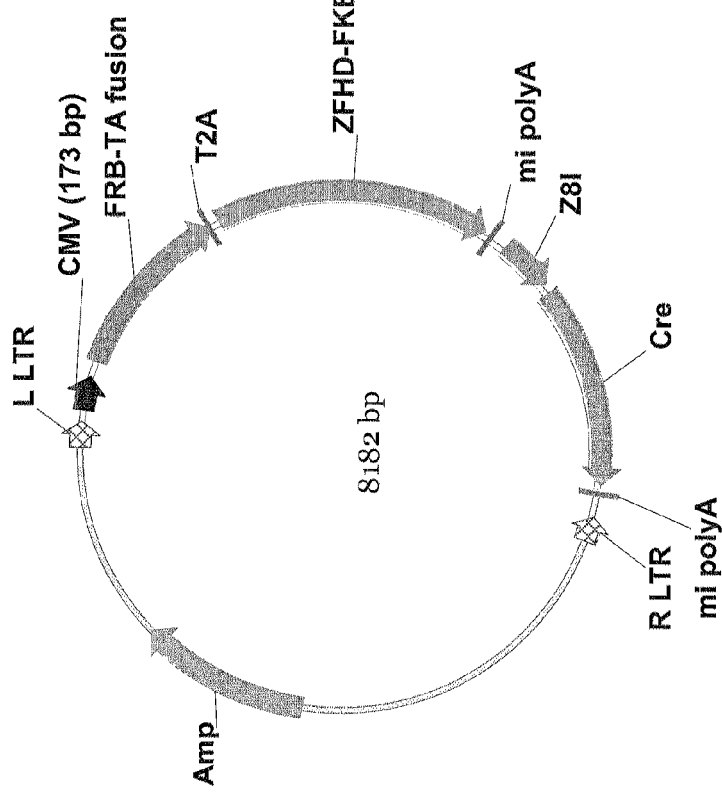
Figure 3B:
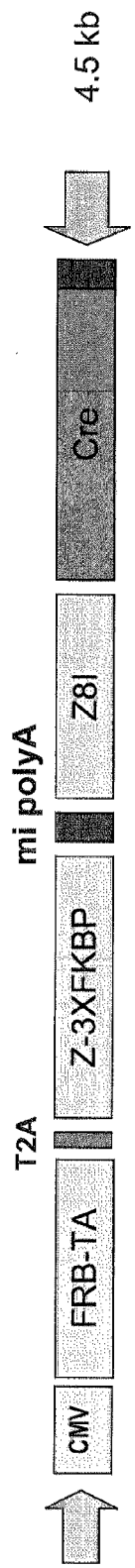

FIGS. 3A and 3B. PITA DNA construct containing a dimerizable transcription factor domain unit and an ablation unit. FIG. 3A is map of the following DNA construct, which comprises a dimerizable transcription factor domain unit and an ablation unit: pAAV.CMV173.TF.FRB-T2A-3×FKBP.Cre. FIG. 3B is a cartoon of the transcription unit inserted into the plasmid backbone. A description of the various vector domains can be found in Section 8.1 herein.

FIGS. 4A and 4B. PITA DNA construct containing a dimerizable transcription factor domain unit and an ablation unit. FIG. 4A is a map of the following DNA construct, which comprises a dimerizable transcription factor domain unit and an ablation unit: pAAV.CMV.TF.FRB-T2A-2×FKBP.ISce-I. FIG. 4B is a cartoon of the transcription unit inserted into the plasmid backbone. A description of the various vector domains can be found in Section 8.1 herein.

Figure 5A:
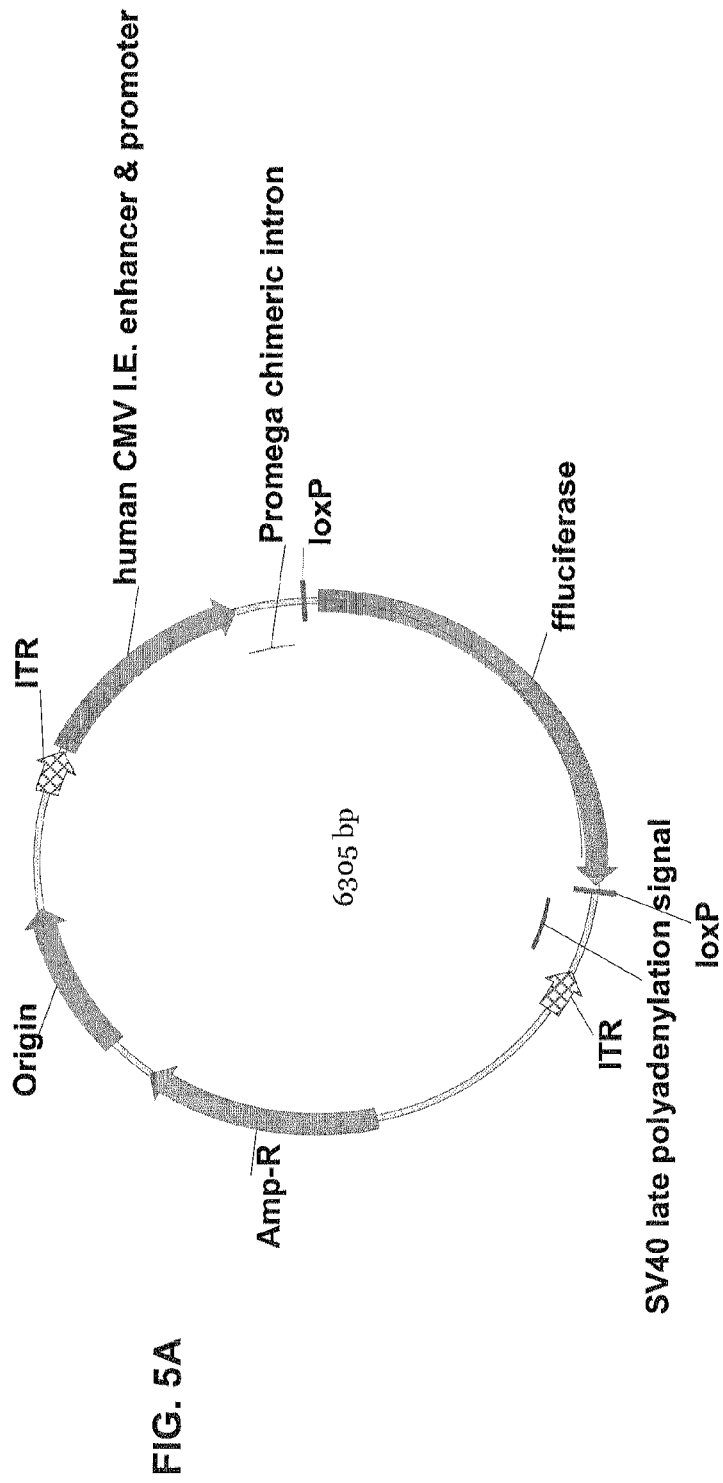
Figure 5B:
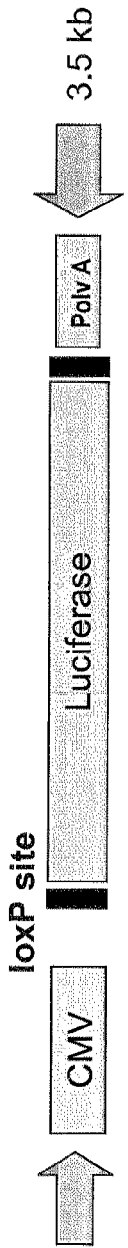

FIGS. 5A and 5B. PITA DNA construct containing a transgene unit. FIG. 5A is a map of the following DNA construct, which comprises a transgene unit: pENN.CMV.PLloxP.Luc.SV40. FIG. 5B is a cartoon of the transcription unit inserted into the plasmid backbone. A description of the various vector domains can be found in Section 8.2 herein.

Figure 6A:
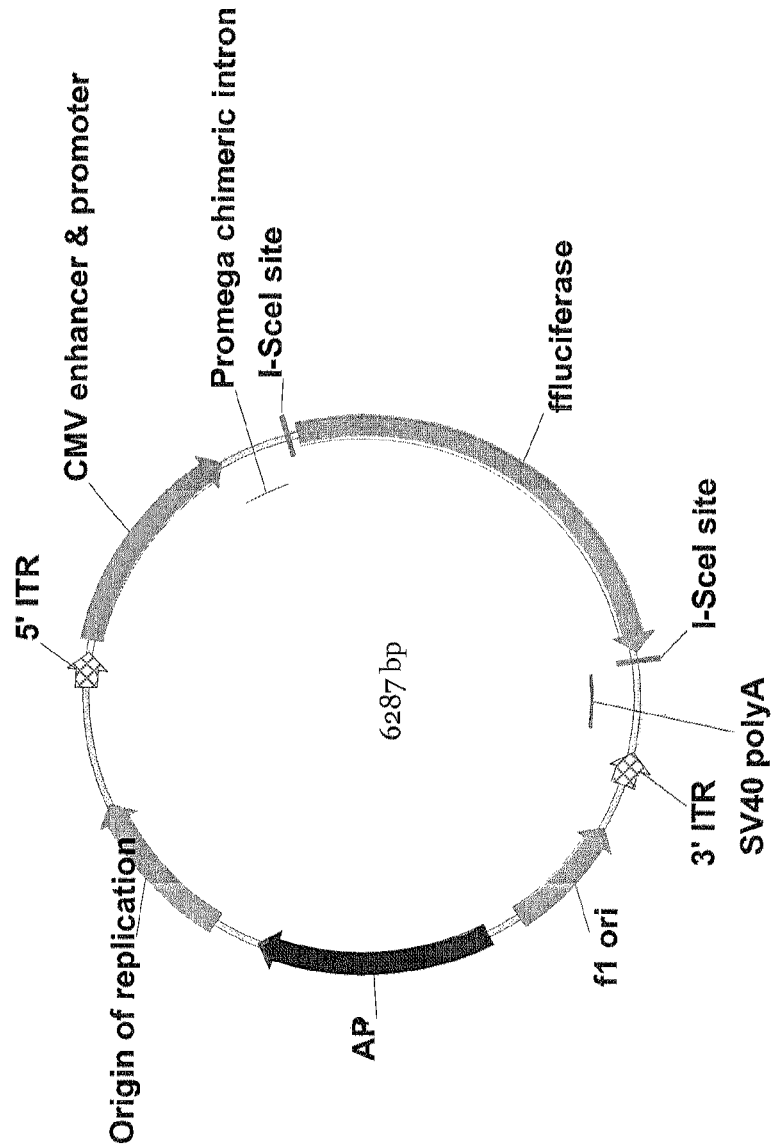
Figure 6B:
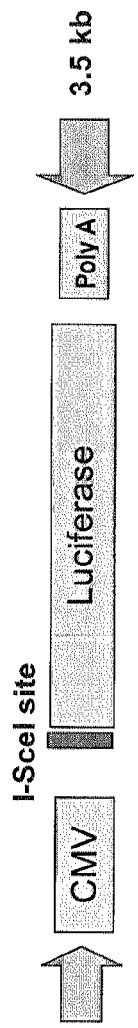

FIGS. 6A and 6B. PITA DNA construct containing a transgene unit. FIG. 6A is a map of the following DNA construct, which comprises a transgene unit: pENN.CMV.PISce-LUC.SV40. FIG. 6B is a cartoon of the transcription unit inserted into the plasmid backbone. A description of the various vector domains can be found in Section 8.2 herein.

Figure 7:
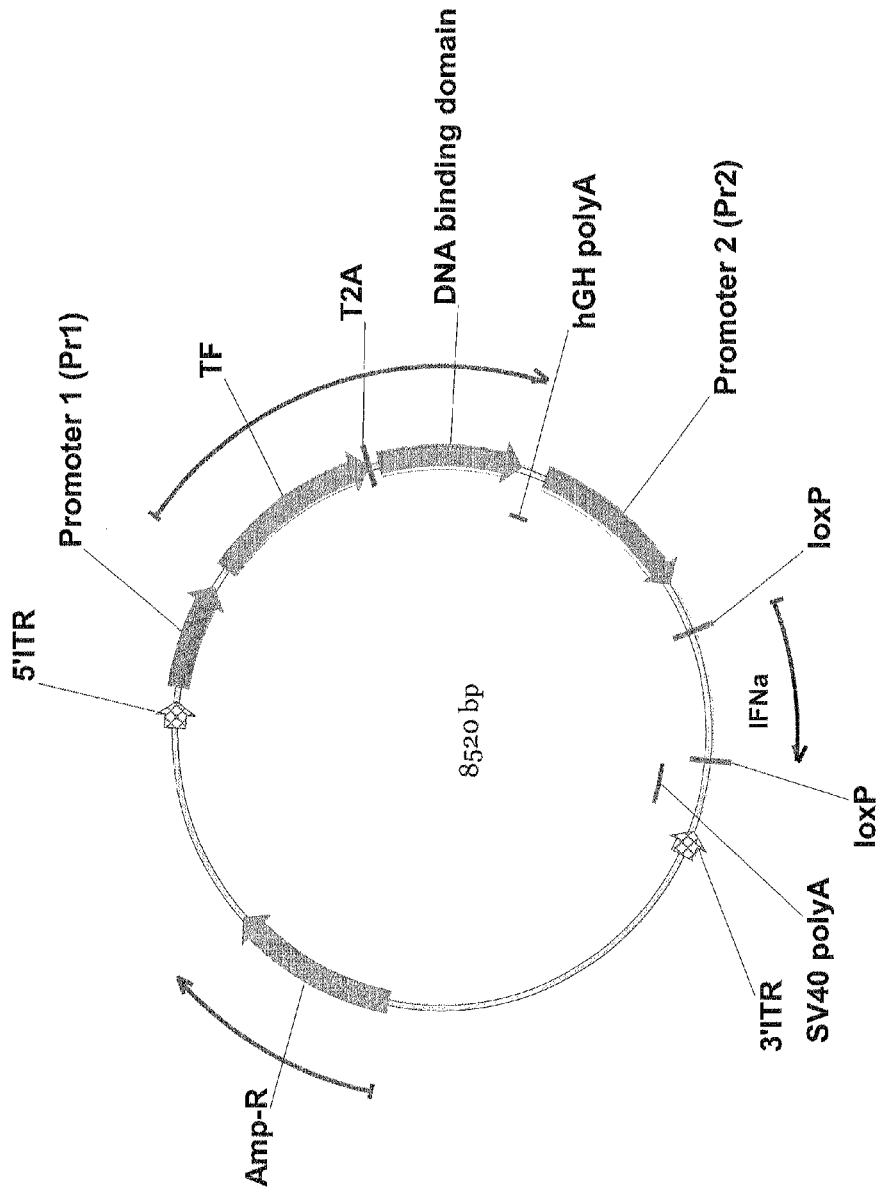

FIG. 7. PITA DNA construct containing a dimerizable transcription factor domain unit and a transgene unit. FIG. 7 is a map of a vector that contains a transgene unit and a dimerizable transcription factor domain unit. A description of the various vector domains can be found in Sections 8.1 and 8.2 herein.

Figure 8A:
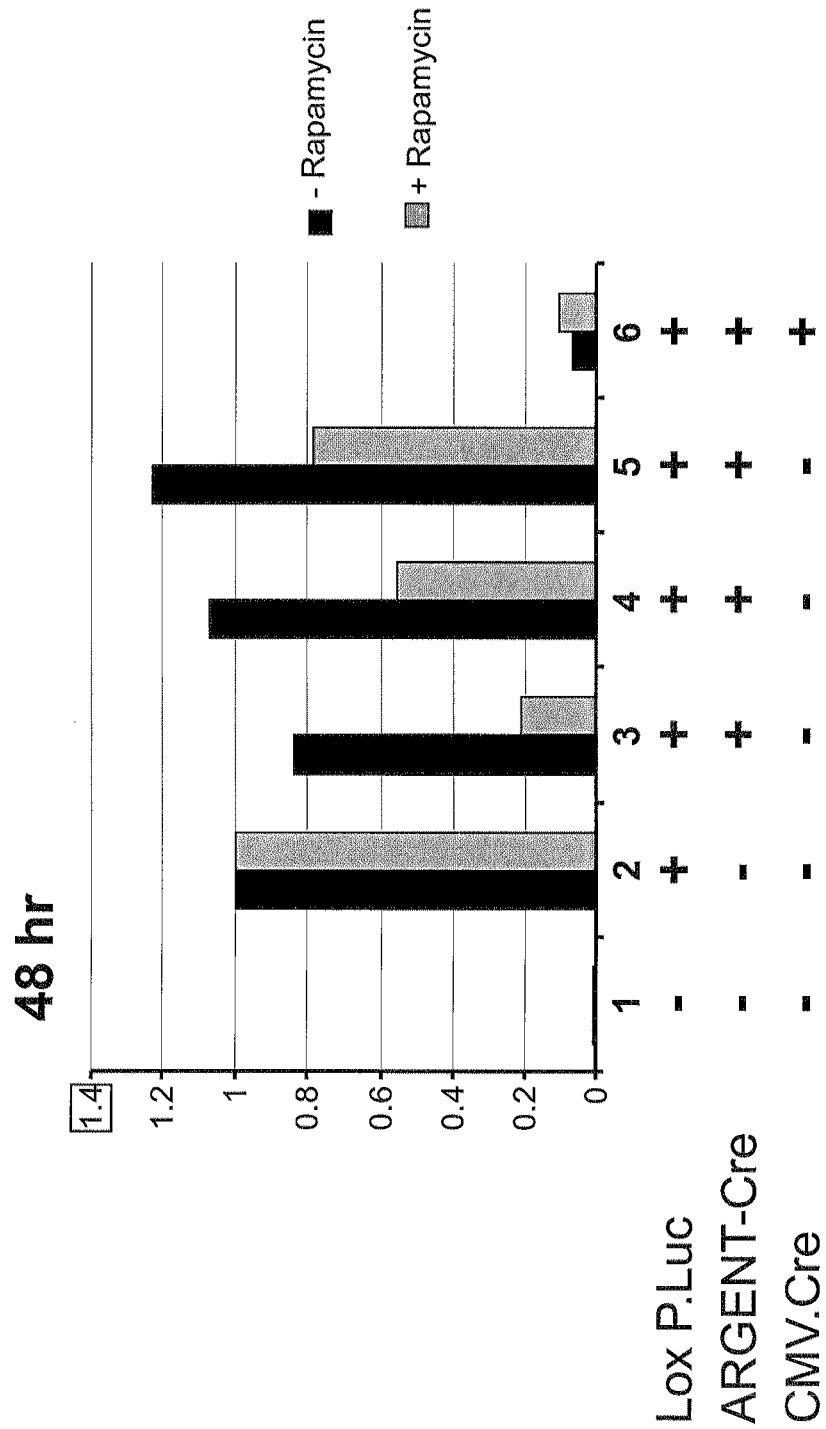
Figure 8B:
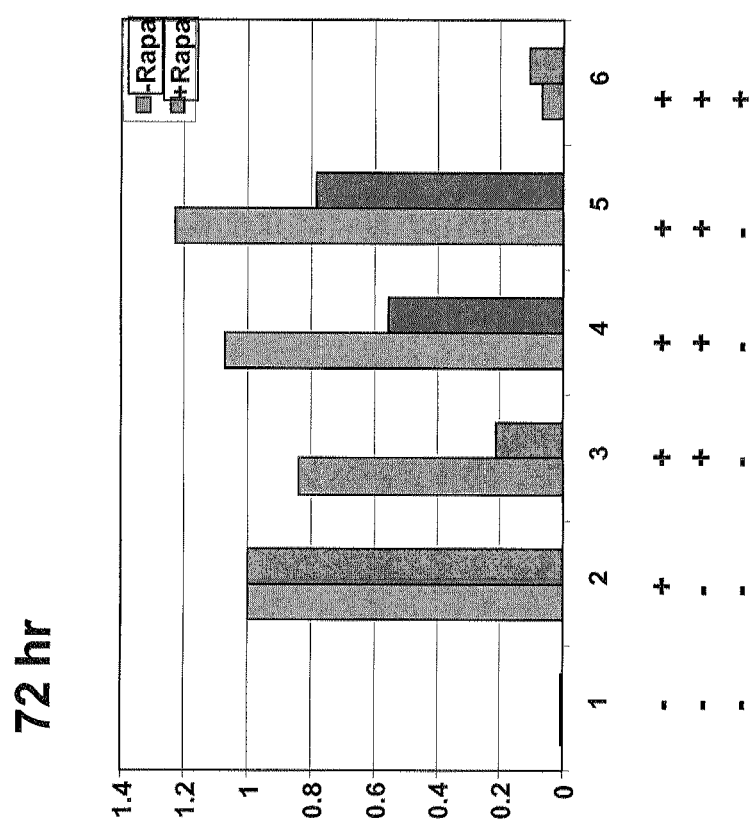

FIGS. 8A-B. In vitro induction of luciferase after rapamycin treatment. FIG. 8A is a bar graph showing relative luciferase activity in cells that were transfected with the indicated DNA constructs (DNA constructs 1 to 6) 48 hours after either being treated or not treated with rapamycin. FIG. 8B is a bar graph showing relative luciferase activity in cells that were transfected with the indicated DNA constructs (DNA constructs 1 to 6) 72 hours after either being treated or not treated with rapamycin.

Figure 9C:
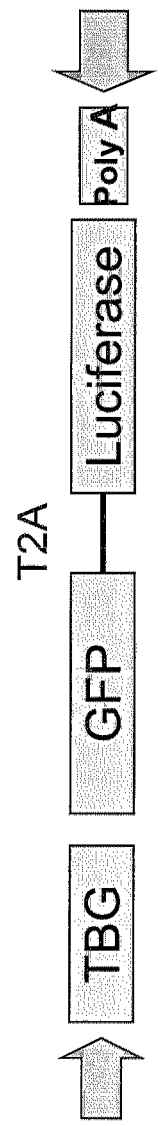
Figure 9D:
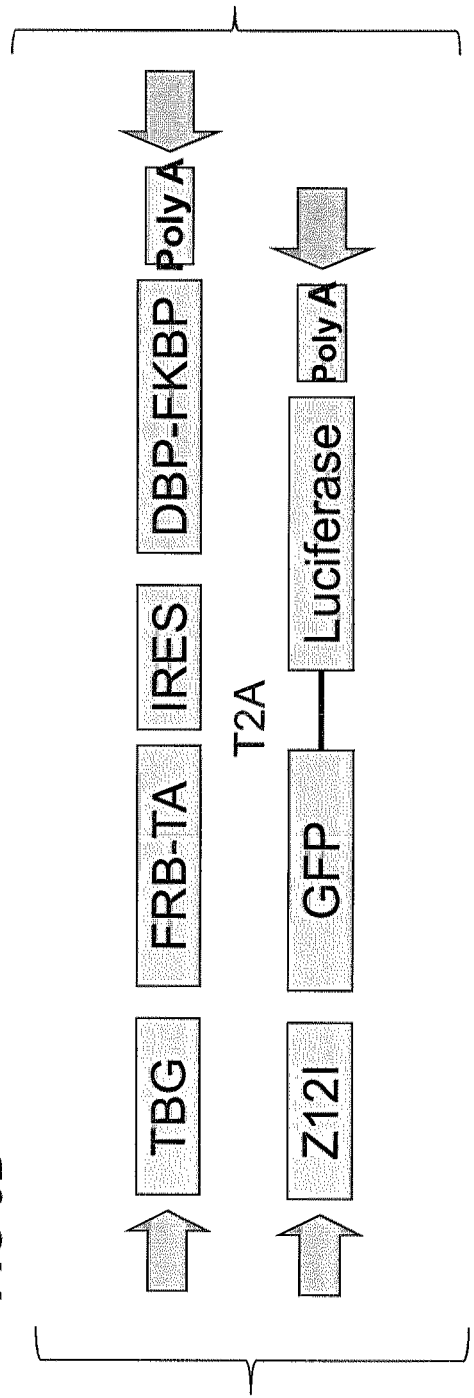

FIGS. 9A-D. In the in vivo model for a dimerizer-inducible system, four groups of mice received IV injection of AAV vectors containing the following DNA constructs. FIG. 9A is a diagram of a DNA construct encoding GFP-Luciferase under the control of ubiquitous constitutive CMV promoter, which was delivered to Group 1 mice via AAV vectors. FIG. 9B is a diagram of DNA constructs encoding (1) a dimerizable transcription factor domain unit (FRB fused with p65 activation domain and DNA binding domain ZFHD fused with 3 copies of FKBP) driven by the CMV promoter; and (2) AAV vector expressing GFP-Luciferase driven by a promoter induced by the dimerized TF, which were delivered to Group 2 mice via AAV vectors. FIG. 9C is a diagram of a DNA construct encoding GFP-Luciferase under the control of a liver constitutive promoter, TBG, which was delivered to Group 3 mice via AAV vectors. FIG. 9D is a diagram of DNA constructs encoding (1) AAV vector expressing a dimerizable transcription factor domain unit driven by the TBG promoter; and (2) AAV vector expressing GFP-Luciferase driven by a promoter induced by the dimerized TF, which were delivered to Group 4 mice via AAV vectors.

FIGS. 10 A-D. Image of 4 groups of mice that received $3 \times 10^{11}$ particles of AAV virus containing various DNA constructs 30 minutes after injection of luciferin, the substrate for luciferase. FIG. 10A shows luciferase expression in various tissues, predominantly in lungs, liver and muscle, in Group 1 mice before ("Pre") and after ("Post") rapamycin administration. FIG. 10B shows luciferase expression, predominantly in liver and muscle in Group 2 mice before ("Pre") and after ("Post") rapamycin administration. FIG. 10C shows luciferase expression predominantly in liver and muscle after ("Post") rapamycin administration, and shows that there is no luciferase expression before ("Pre") rapamycin administration in Group 3 mice. FIG. 10D shows luciferase expression is restricted to the liver ("Post") rapamycin administration and shows that there is no luciferase expression before ("Pre") rapamycin administration.

FIGS. 11 A-D. Image of 4 groups of mice that received $1 \times 10^{11}$ particles of AAV virus containing various DNA constructs 30 minutes after injection of luciferin, the substrate for luciferase. FIG. 1A shows luciferase expression in various tissues, predominantly in lungs, liver and muscle, in Group 1 mice before ("Pre") and after ("Post") rapamycin administration. FIG. 11B shows luciferase expression, predominantly in liver and muscle in Group 2 mice before ("Pre") and after ("Post") rapamycin administration. FIG. 11C shows luciferase expression predominantly in liver and muscle after ("Post") rapamycin administration, and shows that there is no luciferase expression before ("Pre") rapamycin administration in Group 3 mice. FIG. 11D shows luciferase expression is restricted to the liver ("Post") rapamycin administration and shows that there is no luciferase expression before ("Pre") rapamycin administration.

Figure 12A:
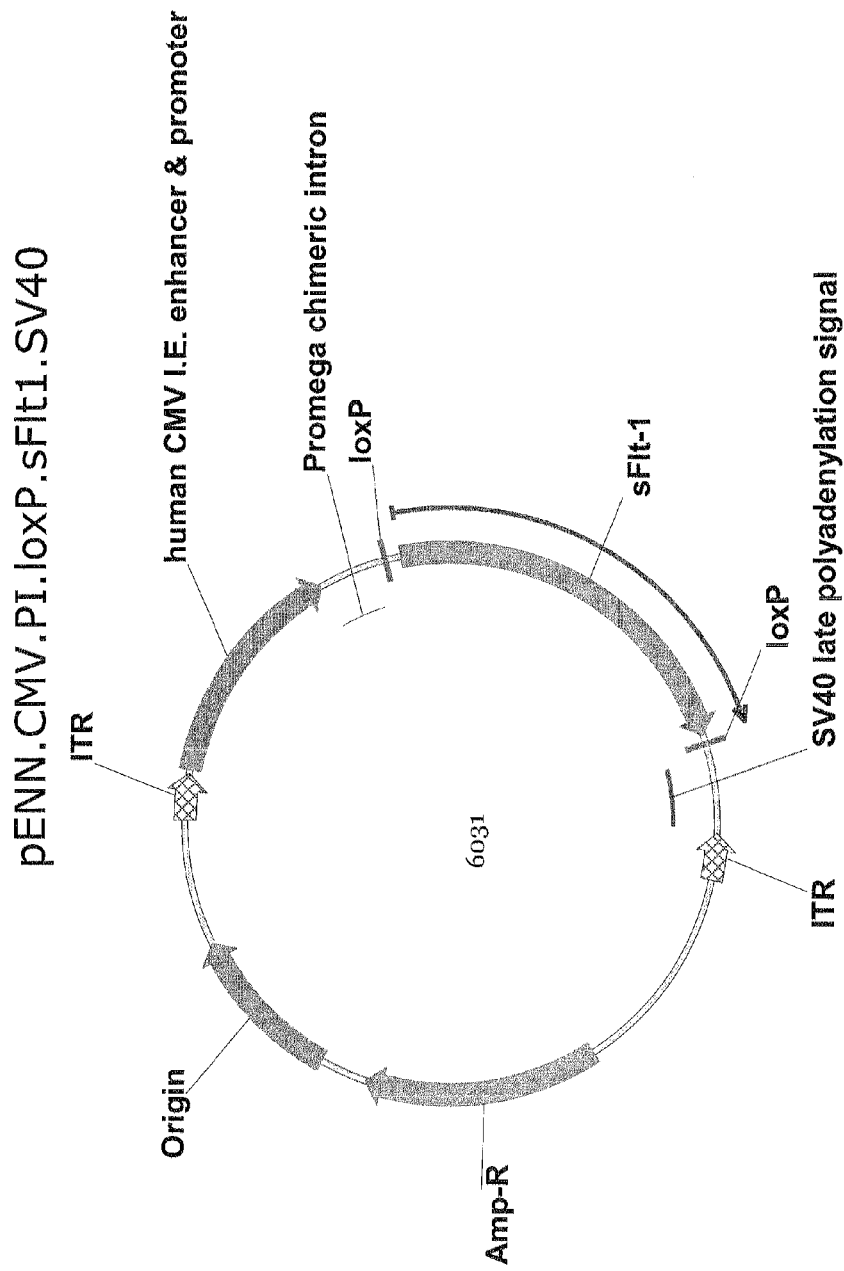
Figure 12B:
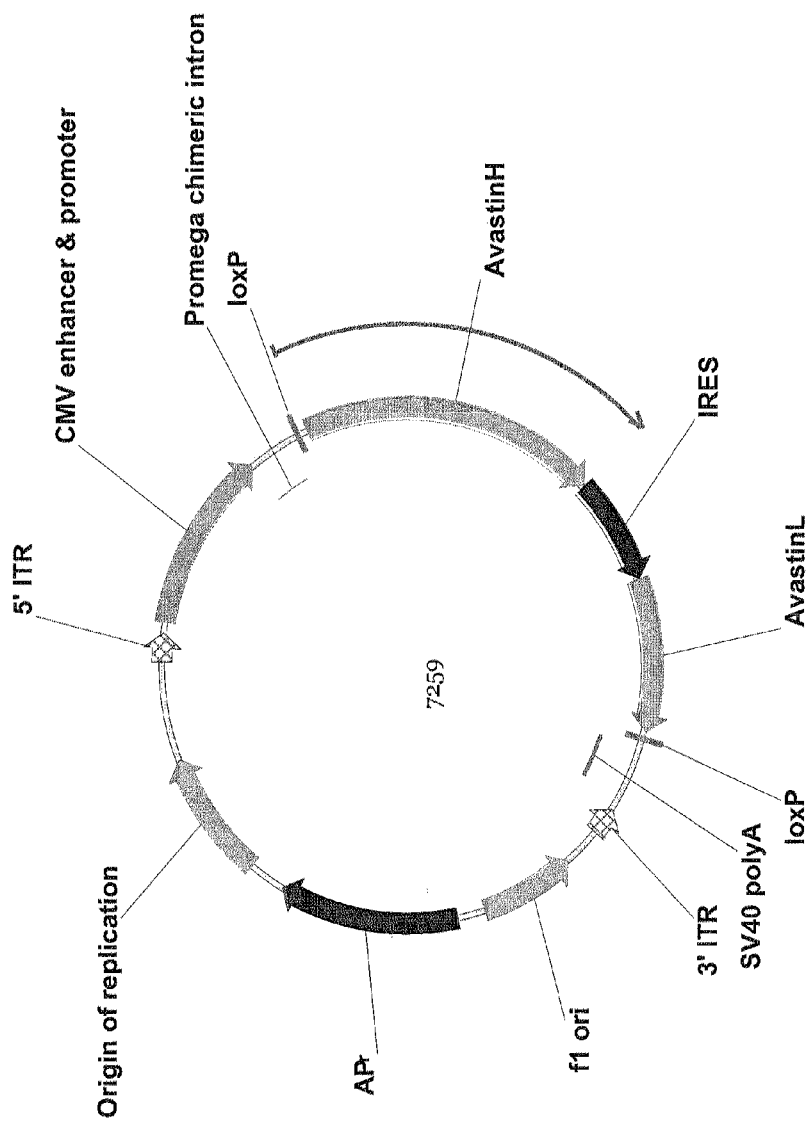
Figure 12C:
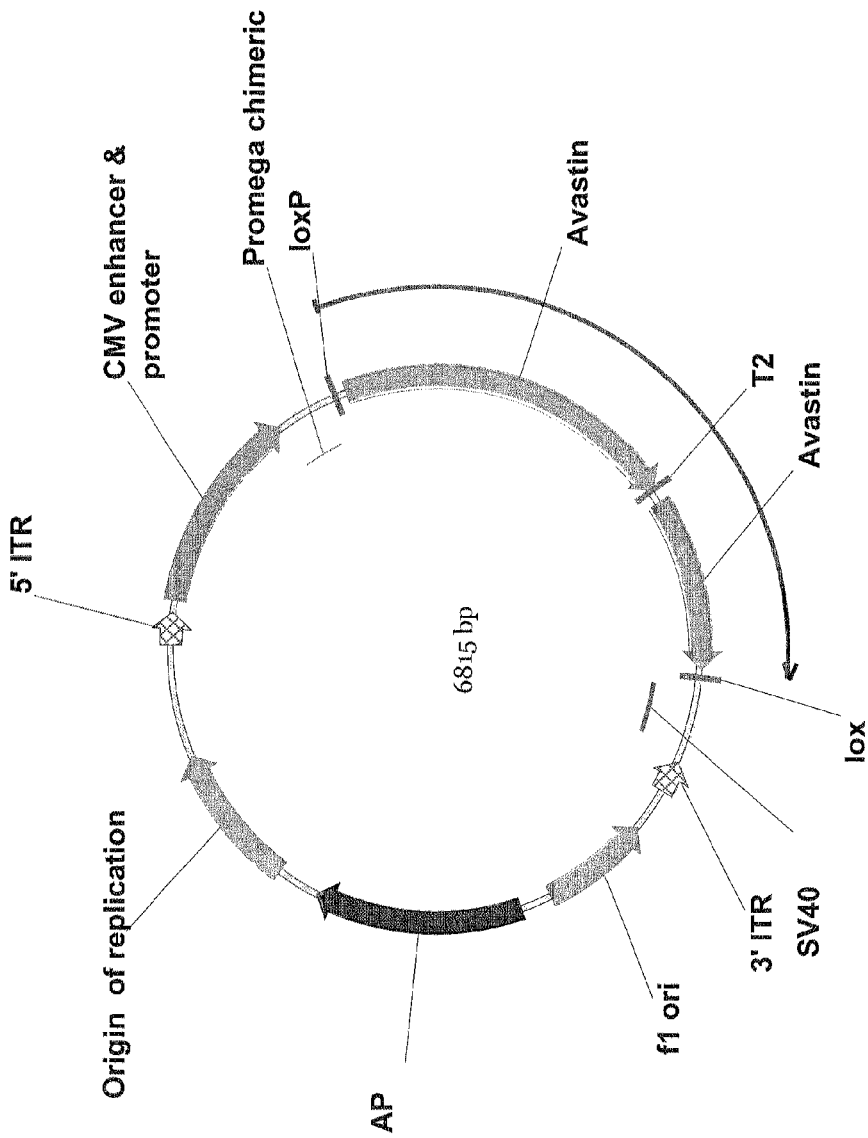

FIGS. 12 A-C. PITA DNA constructs for treating AMD. FIG. 12A shows a DNA construct comprising a transgene unit that encodes a soluble VEGF receptor, sFlt-1. FIG. 12B shows a bicistronic DNA construct comprising Avastin IgG heavy chain (AvastinH) and light chain (AvastinL) regulated by IRES. FIG. 12C shows a bicistronic DNA construct comprising Avastin IgG heavy chain (AvastinH) and light chain (AvastinL) separated by a T2A sequence.

Figure 13A:
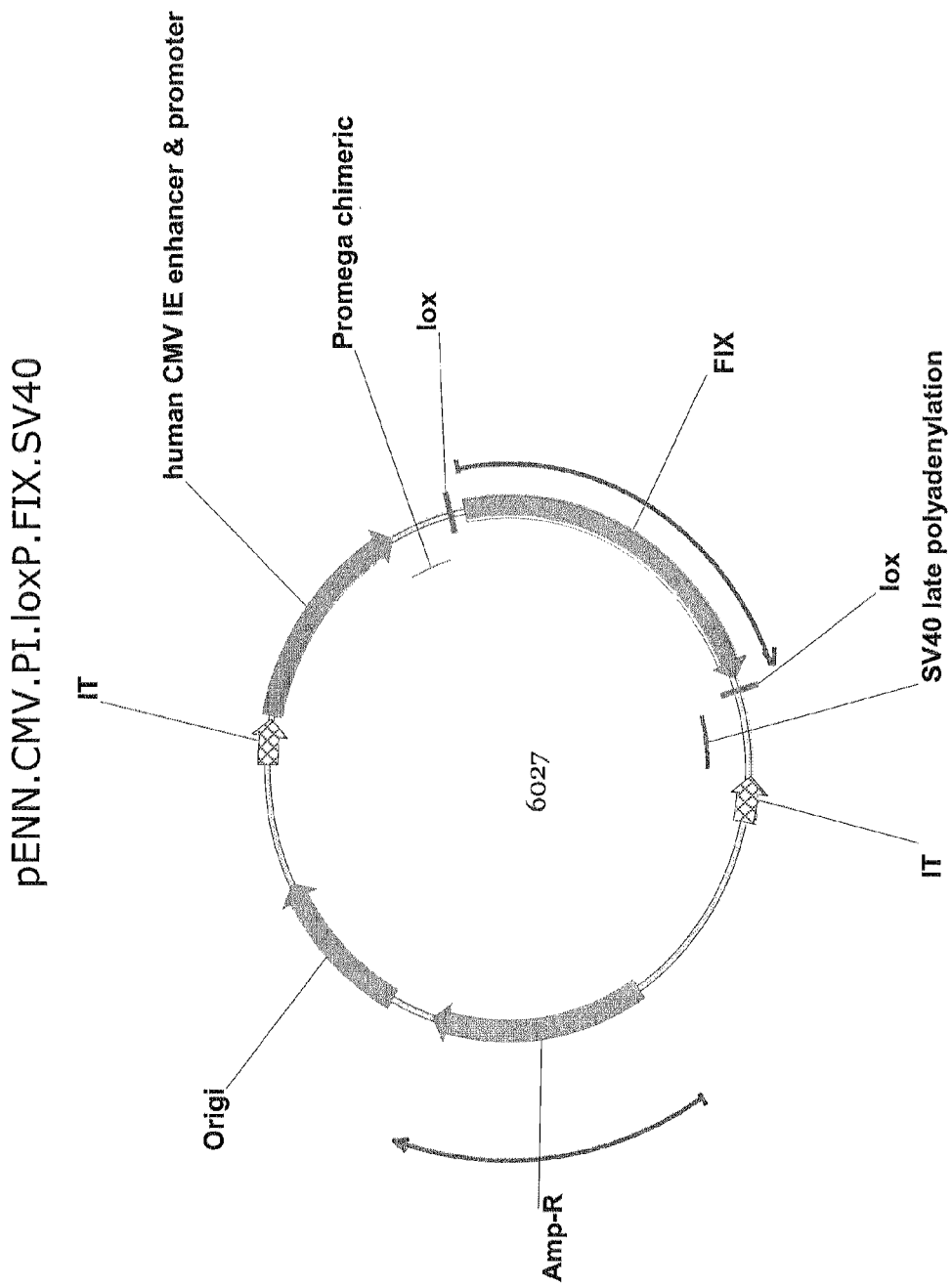
Figure 13B:
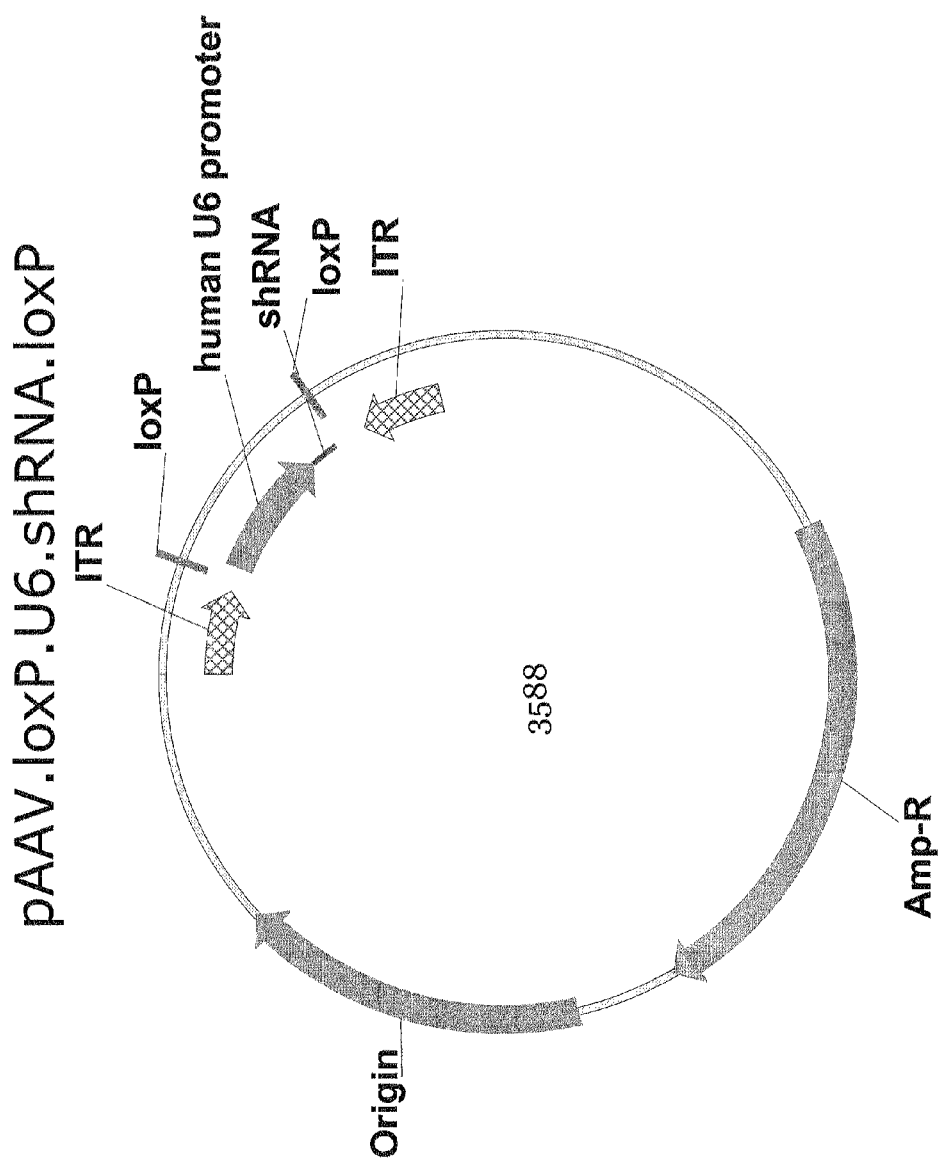

FIGS. 13 A-B. PITA DNA constructs for treating Liver Metabolic Disease. FIG. 13A shows a PITA DNA construct for treating hemophilia A and/or B, containing a transgene unit comprising Factor IX. FIG. 13B shows a DNA construct for delivery of shRNA targeting the IRES of HCV.

Figure 14A:
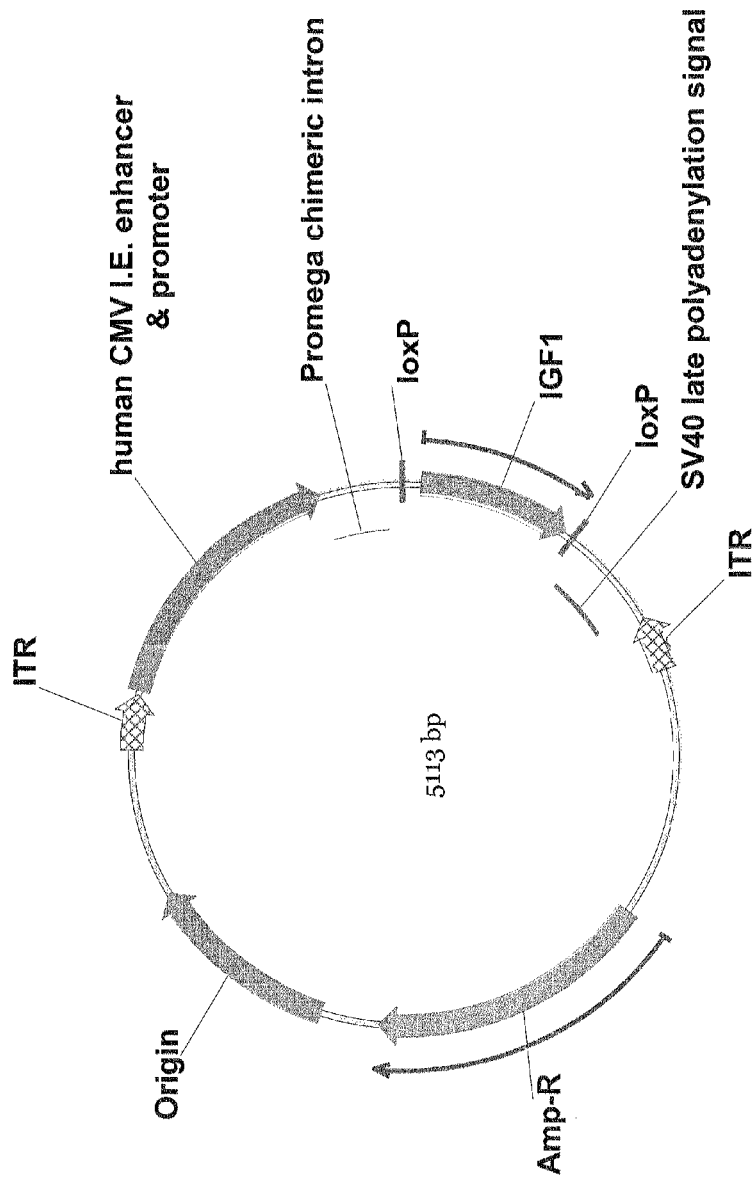
Figure 14B:
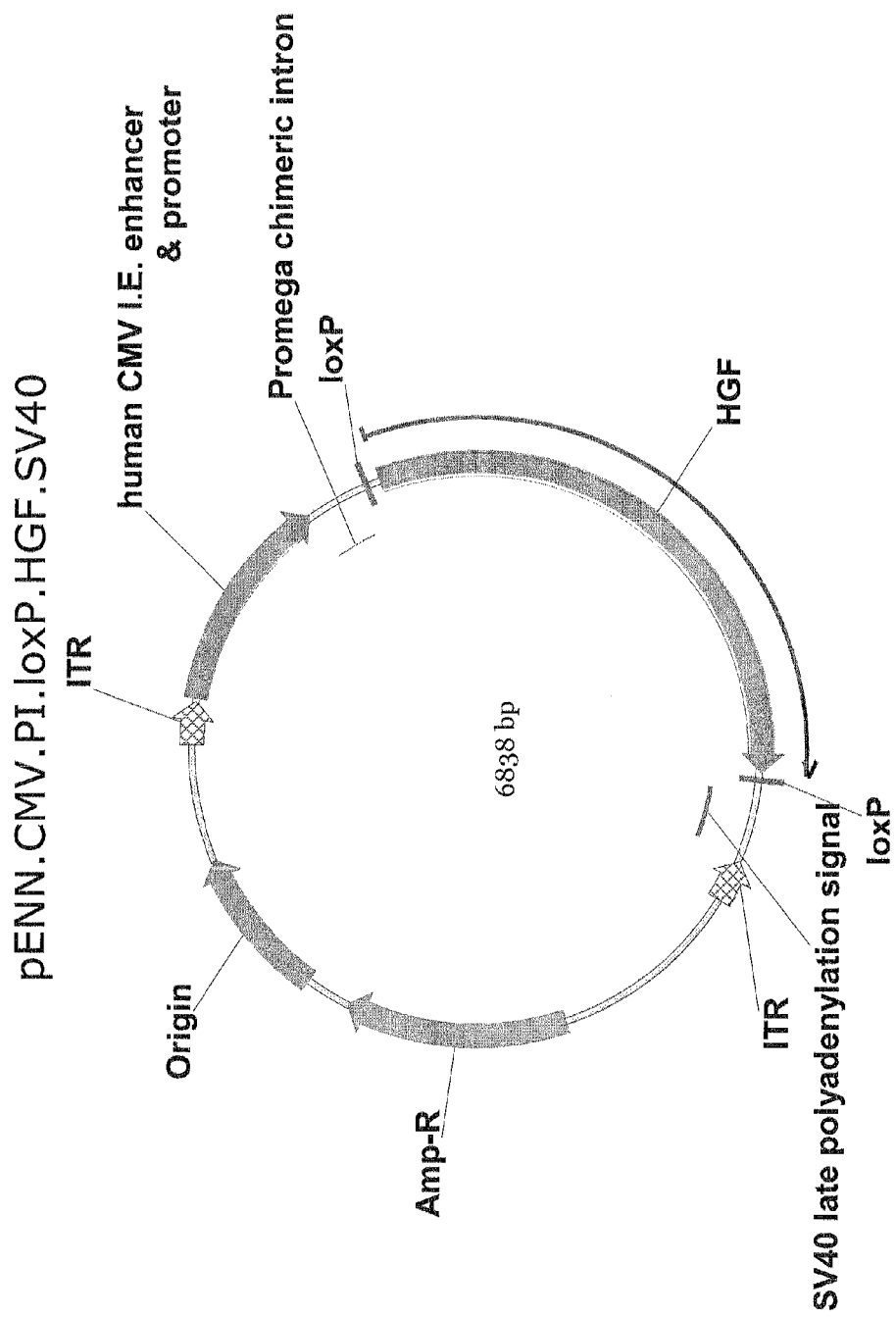

FIGS. 14 A-B. PITA DNA constructs for treating Heart Disease. FIG. 14A shows a PITA DNA construct for treating congestive heart failure, containing a transgene unit comprising insulin like growth factor (IGF1). FIG. 14B shows a PITA DNA construct for treating congestive heart failure, containing a transgene unit comprising hepatocyte growth factor (HGF).

Figure 15:
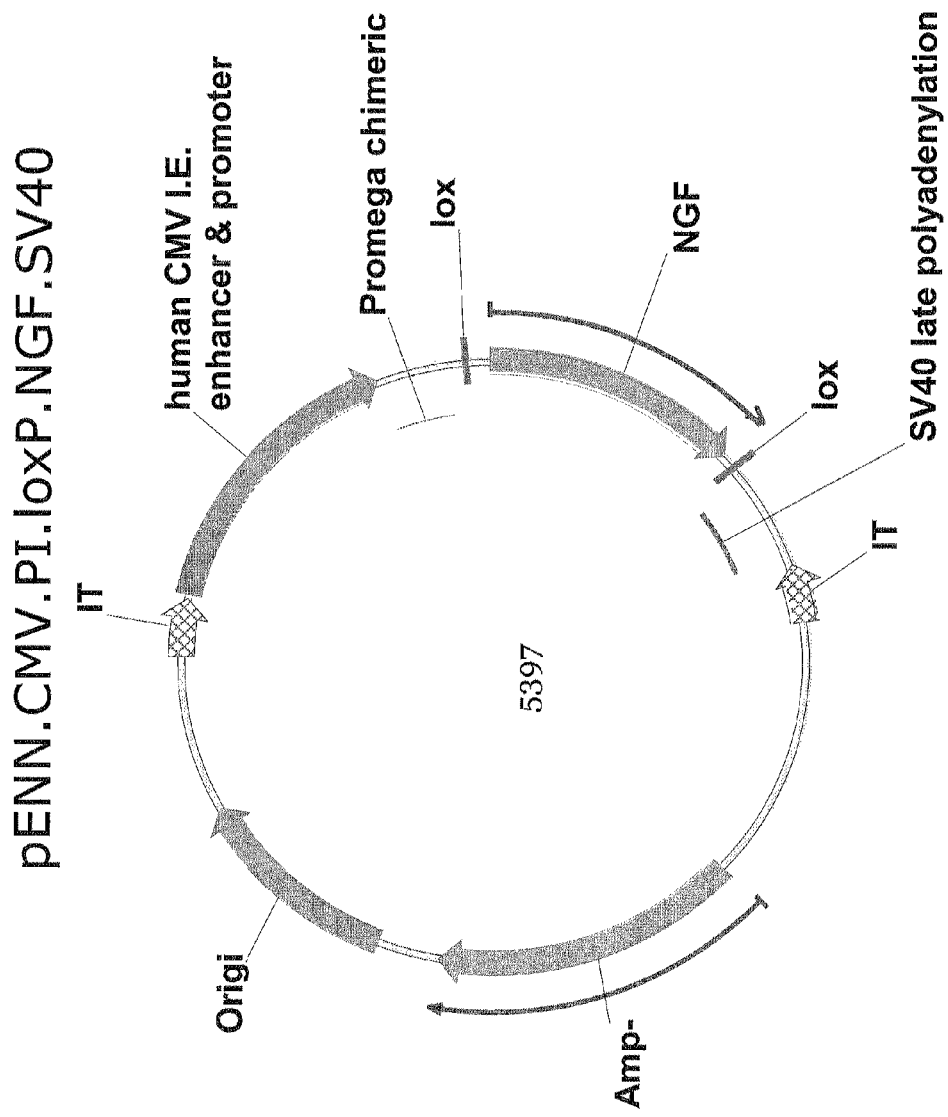

FIG. 15. PITA DNA construct for a CNS disease. FIG. 15 shows a PITA DNA construct for treating Alzheimer's disease, containing a transgene unit comprising nerve growth factor (NGF).

Figure 16:
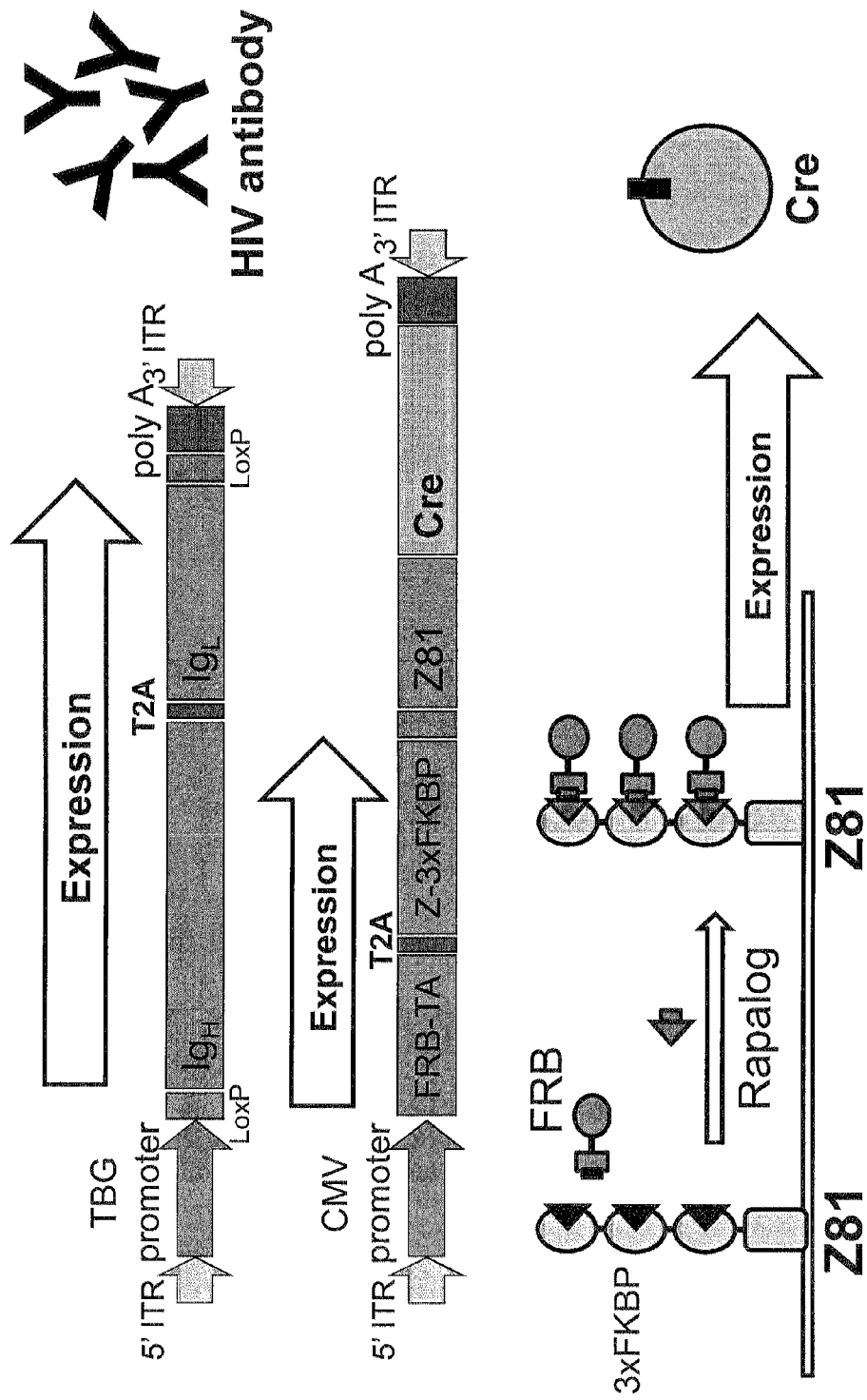

FIG. 16. PITA System for HIV treatment. FIG. 16 shows a PITA DNA construct containing a transgene unit comprising the heavy and light chains of an HIV antibody and a PITA DNA construct containing an ablation unit and a dimerizable TF domain unit. FIG. 16 also shows that a rapamycin analog (rapalog) can induce expression of the ablator, cre, to ablate the transgene (heavy and light chains of an HIV antibody) from the PITA DNA construct containing a transgene unit.

Figure 17:
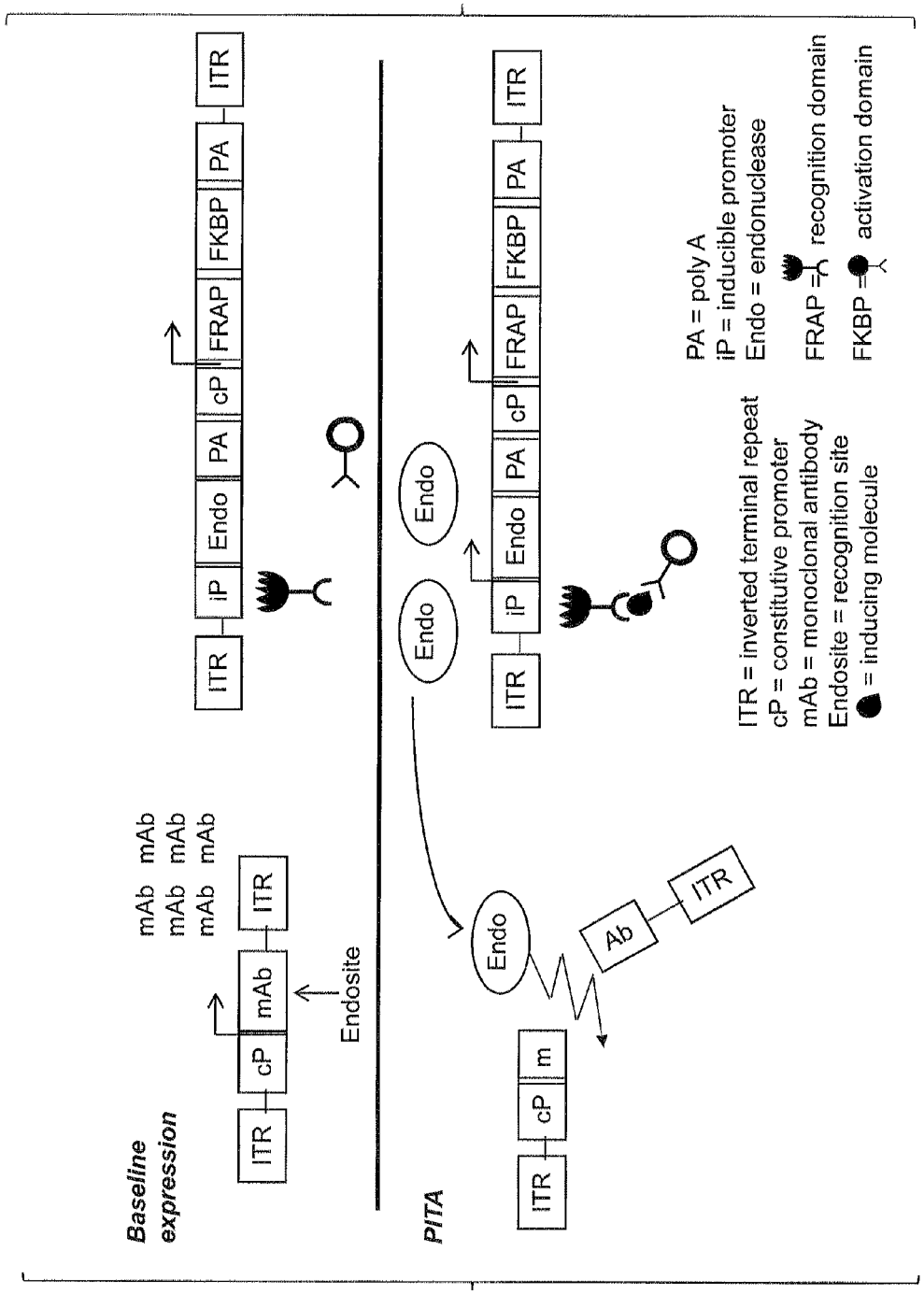

FIG. 17. Illustration of one embodiment of the PITA system. FIG. 17 shows a transgene unit encoding a therapeutic antibody that is in operative association with a constitutive promoter, an ablation unit encoding an endonuclease that is in operative association with a transcription factor inducible promoter, and a dimerizable TF domain unit, with each transcription factor domain fusion sequence in operative association with a constitutive promoter. Prior to administration of rapamycin or a rapalog, there is baseline expression of the therapeutic antibody and of the two transcription factor domain fusion proteins. Upon rapamycin administration, the dimerized transcription factor induces expression of the endonuclease, which cleaves the endonuclease recognition domain in the transgene unit, thereby ablating transgene expression.

FIGS. 18A-18B are bar charts illustrating that wild-type FokI effective ablated expression of a transgene when a DNA plasmid containing a transgene containing ablation sites for FokI was cotransfected into target cells with a plasmid encoding the FokI enzyme. FIG. 18A, bar 1 represents 50 ng pCMV.Luciferase, bar 2 represents 50 ng pCMV.Luciferase+200 ng pCMV.FokI, bar 3 represents 50 ng pCMV.Luciferase+ transfected FokI protein, bar 4 represents transfected FokI protein alone; bar 5 represents untransfected controls. FIG. 18B, bar 1 represents 50 ng pCMV.Luc alone, subsequent bars represent increasing concentrations of a ZFHD-FokI expression plasmid (6.25, 12.5, 25, 50, and 100 ng) cotransfected with pCMV.Luciferase. This study is described in Example 11A.

Figure 19B:
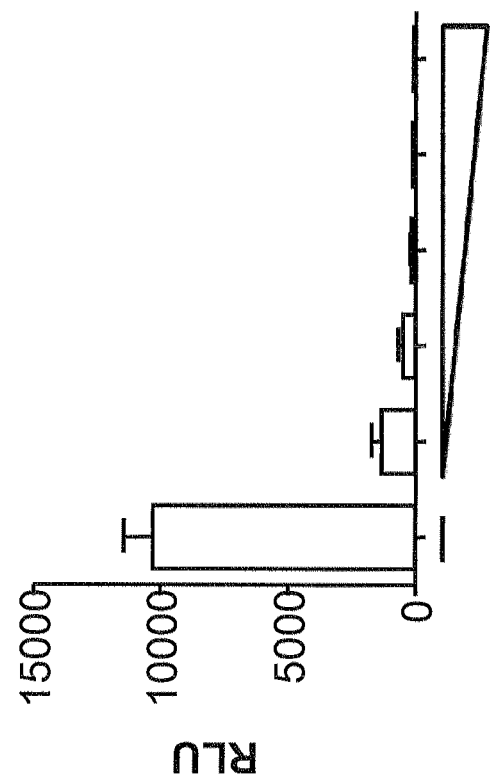
Figure 19A:
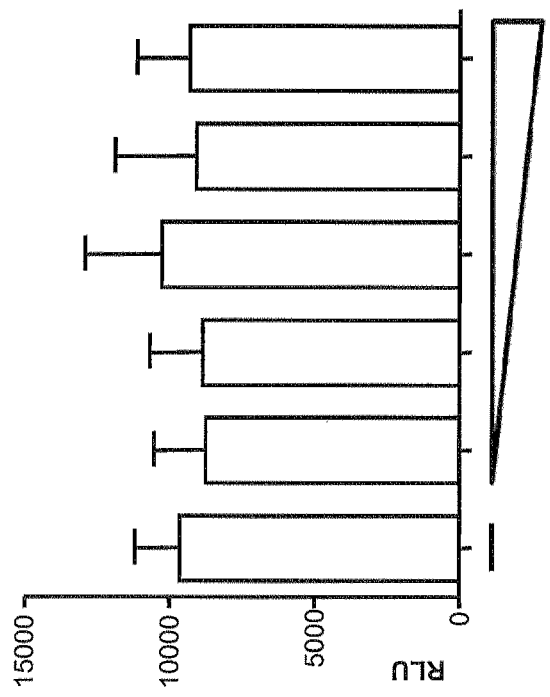

FIGS. 19A-B are bar charts illustrating that a chimeric engineered enzyme tethered to a non-cognate recognition site on the DNA by the zinc finger homeodomain effectively ablates expression of a transgene. FIG. 19A compares increasing concentrations of an expression plasmid encoding un-tethered FokI (6.25 ng, 12.5 ng, 25 ng, 50 ng and 100 ng) co-transfected with pCMV.luciferase. The first bar provides a positive control of 50 ng pCMV.Luc alone. FIG. 19B compares increasing concentrations of an expression plasmid encoding FokI tethered to DNA via fusion with the zinc finger homeodomain (6.25 ng, 12.5 ng, 25 ng, 50 ng and 100 ng) co-transfected with pCMV.luciferase. The first bar provides a control of 50 ng pCMV.Luc alone. This study is described in Example 11B.

FIGS. 20A-B are bar charts illustrating that the DNA binding specificity of chimeric FokI can be reproducible changed by fusion with various classes of heterologous DNA binding domains and ablation of target transgene can be further improved by the additional of a heterologous nuclear localization signal (NLS). FIG. 20A illustrates the results of co-transfection of pCMV.Luciferase with increasing concentrations of an expression plasmid encoding FokI tethered to DNA via an HTH fusion (6.25, 12.5, 25, 50, and 100 ng). The first bar is a control showing 50 ng pCMV.Luciferase alone. FIG. 20B illustrates the results of co-transfection of pCMV.Luciferase with increasing concentrations of an expression plasmid encoding an HTH—FokI fusion, which further has a NLS at its N-terminus (6.25, 12.5, 25, 50, and 100 ng). The first bar is a control showing 50 ng pCMV.Luciferase alone. This study is described in Example 11C.

Figure 21:
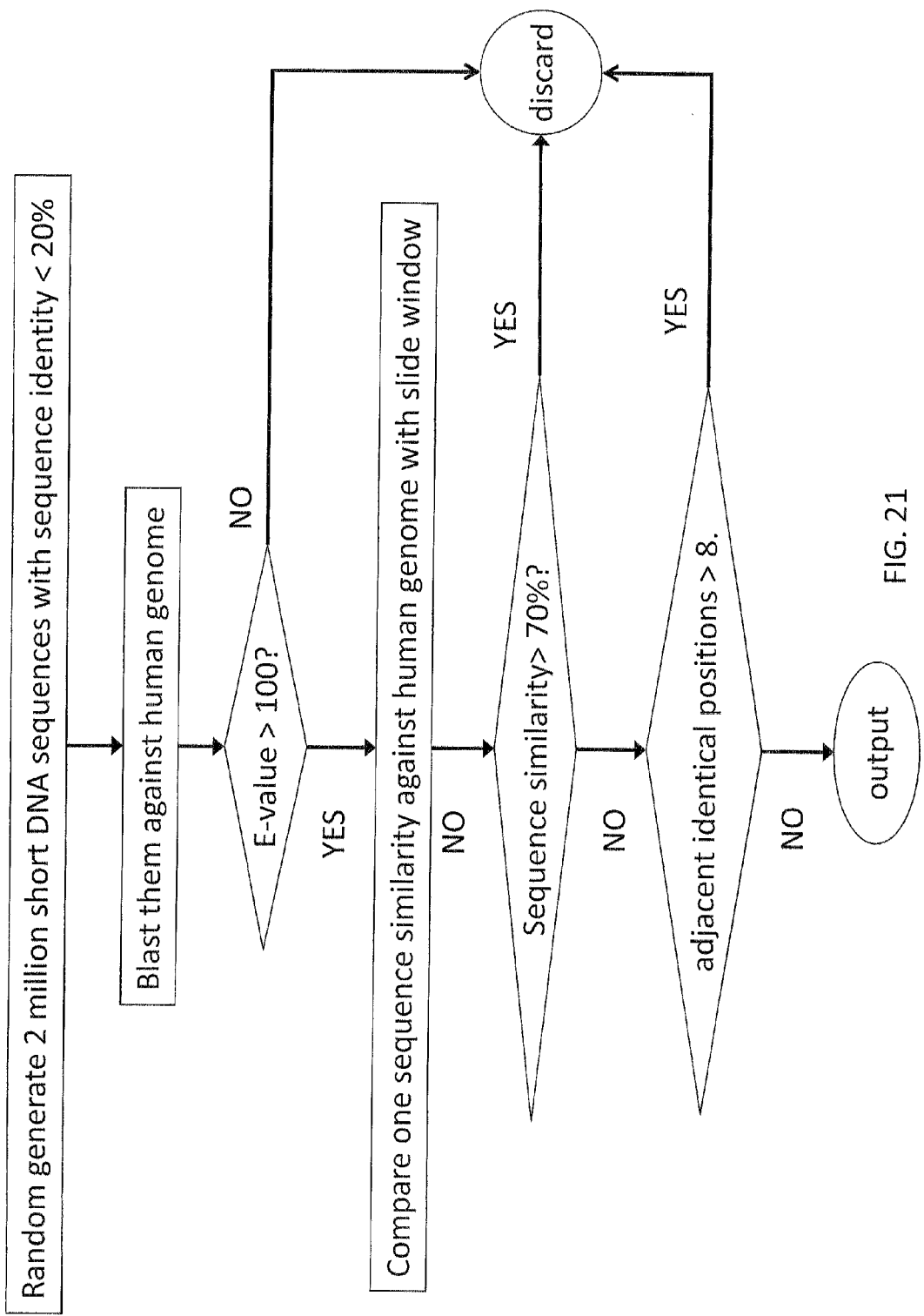

FIG. 21 is a flow chart of a method for selecting a unique nucleic acid sequence for use in an ablation recognition site as described herein.

5. DETAILED DESCRIPTION OF THE INVENTION

The present invention relates to gene therapy systems designed for the delivery of a therapeutic product to a subject using replication-defective virus composition(s) engineered with a built-in safety mechanism for ablating the therapeutic gene product, either permanently or temporarily, in response to a pharmacological agent—preferably an oral formulation, e.g., a pill.

In the PITA system, one or more replication-defective viruses are used in a replication-defective virus composition in which the viral genome(s) have been engineered to contain: (a) a first transcription unit that encodes a therapeutic product in operative association with a promoter that controls transcription, said unit containing at least one ablation recognition site; and (b) a second transcription unit that encodes an ablator (or a fragment thereof as part of a fusion protein unit) specific for the ablation recognition site in operative association with a promoter that induces transcription in response to a pharmacological agent. Any pharmacological agent that specifically dimerizes the domains of the selected binding domain can be used. In one embodiment, rapamycin and its analogs referred to as "rapalogs" can be used.

A viral genome containing a first transcription unit may contain two or more of the same ablation recognition site or two or more different ablation recognition sites (i.e., which are specific sites for a different ablator than that which recognizes the other ablation recognition site(s)). Whether the same or different, such two or more ablation recognition sites may be located in tandem to one another, or may be located in a position non-contiguous to the other. Further, the ablation recognition site(s) may be located at any position relative the coding sequence for the transgene, i.e., within the transgene coding sequence, 5' to the coding sequence (either immediately 5' or separated by one or more bases, e.g., upstream or downstream of the promoter) or 3' to the coding sequence (e.g., either immediately 3' or separated by one or more bases, e.g., upstream of the poly A sequence).

An ablator is any gene product, e.g., translational or transcriptional product, that specifically recognizes/binds to either (a) the ablation recognition site(s) (ARS) of the transgene unit and cleaves or excises the transgene; or (b) the ablation recognition RNA sequence (ARRS) of the transcribed transgene unit and cleaves or inhibits translation of the mRNA transcript. As described herein, an ablator may be selected from the group consisting of: an endonuclease, a recombinase, a meganuclease, a zinc finger endonuclease, or a novel chimeric endonuclease as described herein (comprising a catalytic domain and a multi-zinc finfer domain). These ablators are designed to binds to the ablation recognition site in the first transcription unit and excises or ablates DNA and an interfering RNA, a ribozyme, or an antisense that ablates the RNA transcript of the first transcription unit, or suppresses translation of the RNA transcript of the first transcription unit. In one specific embodiment, the ablator is Cre (which has as its ablation recognition site loxP), or the ablator is FLP (which has as its ablation recognition site FRT). In one embodiment, an endonuclease is selected which functions independently of ATP hydrolysis. Examples of such ablators may include a Type II S endonuclease (e.g., FokI), NaeI, and intron endonucleases (such as e.g., I-TevI), integrases (catalyze integration), serine recombinases (catalyze recombination), tyrosine recombinases, invertases (e.g. Gin) (catalyze inversion), resolvases, (e.g., Tn3), and nucleases that catalyze translocation, resolution, insertion, deletion, degradation or exchange.

For permanent shut down of the therapeutic transgene, the ablator can be an endonuclease that binds to the ablation recognition site(s) in the first transcription unit and ablates or excises the transgene. Where temporary shutdown of the transgene is desired, an ablator should be chosen that binds to the ablation recognition site(s) in the RNA transcript of the therapeutic transgene and ablates the transcript, or inhibits its translation. In this case, interfering RNAs, ribozymes, or antisense systems can be used. The system is particularly desirable if the therapeutic transgene is administered to treat cancer, a variety of genetic disease which will be readily apparent to one of skill in the art, or to mediate host immune response.

Expression of the ablator may be controlled by one or more elements, including, e.g., an inducible promoter and/or by use of a chimeric ablator that utilizes a homodimer or heterodimer fusion protein system, such as are described herein. Where use of a homodimer system is selected, expression of the ablator is controlled by an inducible promoter. Where use of heterodimer system is selected, expression of the ablator is controlled by additional of a pharmacologic agent and optionally, a further inducible promoter for one or both of the fusion proteins which form the heterodimer system. In one embodiment, a homo- and hetero-dimizerable ablator is selected to provide an additional layer for safety to constructs with transcription factor regulators. These systems are described in more detail later in this specification.

Any virus suitable for gene therapy may be used, including but not limited to adeno-associated virus ("AAV"); adenovirus; herpes virus; lentivirus; retrovirus; etc. In preferred embodiments, the replication-defective virus used is an adeno-associated virus ("AAV"). AAV1, AAV6, AAV7, AAV8, AAV9 or rh10 being particularly attractive for use in human subjects. Due to size constraints of the AAV genome for packaging, the transcription units can be engineered and packaged in two or more AAV stocks. Whether packaged in one viral stock which is used as a virus composition according to the invention, or in two or more viral stocks which form a virus composition of the invention, the viral genome used for treatment must collectively contain the first and second transcription units encoding the therapeutic transgene and the ablator; and may further comprise additional transcription units. For example, the first transcription unit can be packaged in one viral stock, and second, third and fourth transcription units packaged in a second viral stock. Alternatively, the second transcription unit can be packaged in one viral stock, and the first, third and fourth transcription units packaged in a second viral stock. While useful for AAV due to size contains in packaging the AAV genome, other viruses may be used to prepare a virus composition according to the invention. In another embodiment, the viral compositions of the invention, where they contain multiple viruses, may contain different replication-defective viruses (e.g., AAV and adenovirus).

In one embodiment, a virus composition according to the invention contains two or more different AAV (or another viral) stock, in such combinations as are described above. For example, a virus composition may contain a first viral stock comprising the therapeutic gene with ablator recognition sites and a first ablator and a second viral stock containing an additional ablator(s). Another viral composition may contain a first virus stock comprising a therapeutic gene and a fragment of an ablator and a second virus stock comprising another fragment of an ablator. Various other combinations of two or more viral stocks in a virus composition of the invention will be apparent from the description of the components of the present system.

In one embodiment, a composition contains one or more AAV vectors in a system for delivery of a therapeutic product having a controlled transgene expression ablation system. At least one AAV vector in the composition contains a nucleic acid molecule comprising: (i) a nucleic acid sequence encoding a therapeutic product operably linked to a promoter that controls transcription; and (ii) at least one endonuclease ablation site which comprises a sequence of at least 30 nucleic acid base pairs which are specifically and selectively recognized by at least ten (10×) zinc fingers, said at least one endonuclease ablation site being located at least 5' to the sequence encoding the therapeutic product; and (b) at least one ablator which comprises a chimeric endonuclease comprising at least ten copies of a zinc finger domain linked to a functional endonuclease catalytic domain in operative association with a promoter, wherein transcription and/or ablation activity is induced in response to a pharmacological agent, said at least ten (10×) zinc finger domain specifically and selectively recognizing said at least about 30 base pair sequence in said at least one endonuclease ablation site and comprising at least 10 independently selected recognition helices. In one embodiment, the endonuclease catalytic domain is a FokI catalytic domain. In a further embodiment, the ablator (b) is controlled by a cassette that is activated by a transcription factor following being dimerized by a pharmacologic agent, said cassette comprising two transcription units, wherein one of said two transcription units encoding the DNA binding domain of the transcription factor fused to a binding domain for the pharmacological agent in operative association with a first promoter; and a second of said two transcription units encoding the activation domain of the transcription factor fused to a binding domain for the pharmacological agent in operative association with a second promoter. Any pharmacological agent that specifically dimerizes the domains of the selected binding domain can be used. In one embodiment, rapamycin and its analogs referred to as "rapalogs" can be used. In order to conserve space within the viral genome(s), bicistronic transcription units can be engineered. For example, transcription units that can be regulated by the same promoter, e.g., the third and fourth transcription units (and where applicable, the first transcription unit encoding the therapeutic transgene) can be engineered as a bicistronic unit containing an IRES (internal ribosome entry site) or a 2A peptide, which self-cleaves in a post-translational event (e.g., furin-2A), and which allows coexpression of heterologous gene products by a message from a single promoter when the transgene (or an ablator coding sequence) is large, consists of multi-subunits, or two transgenes are co-delivered, recombinant AAV (rAAV) carrying the desired transgene(s) or subunits are co-administered to allow them to concatamerize in vivo to form a single vector genome. In such an embodiment, a first AAV may carry an expression cassette which expresses a single transgene and a second AAV may carry an expression cassette which expresses a different transgene for co-expression in the host cell. However, the selected transgene may encode any biologically active product or other product, e.g., a product desirable for study. A single promoter may direct expression of an RNA that contains, in a single open reading frame (ORF), two or three heterologous genes (e.g., the third and fourth transcription units, and where applicable, the first transcription unit encoding the therapeutic transgene) separated from one another by sequences encoding a self-cleavage peptide (e.g., 2A peptide, T2A) or a protease recognition site (e.g., furin). The ORF thus encodes a single polyprotein, which, either during (in the case of T2A) or after translation, is cleaved into the individual proteins. These IRES and polyprotein systems can be used to save AAV packaging space, they can only be used for expression of components that can be driven by the same promoter.

The invention also relates to DNA constructs used to engineer cell lines for the production of the replication-defective virus compositions; methods for producing and manufacturing the replication-defective virus compositions; expression in a variety of cell types and systems, including plants, bacteria, mammalian cells, etc., and methods of treatment using the replication-defective virus compositions for gene transfer, including veterinary treatment (e.g., in livestock and other mammals), and for in vivo or ex vivo therapy, including gene therapy in human subjects.

5.1. Transgene Ablation System

The present invention provides a Pharmacologically Induced Transgene Ablation (PITA) System designed for the delivery of a transgene (encoding a therapeutic product—protein or RNA) using replication-defective virus compositions engineered with a built-in safety mechanism for ablating the therapeutic gene product, either permanently or temporarily, in response to a pharmacological agent—preferably an oral formulation, e.g., a pill containing a small molecule that induces expression of the ablator specific for the transgene or its transcription product. However, other routes of delivery for the pharmacologic agent may be selected.

In the PITA system, one or more replication-defective viruses are used in which the viral genome(s) have been engineered to contain a transgene unit (described in Section 5.1.1 herein) and an ablation unit (described in Section 5.1.2 herein). In particular, one or more replication-defective viruses are used in which the viral genome(s) have been engineered to contain (a) a first transcription unit that encodes a therapeutic product in operative association with a promoter that controls transcription, said unit containing at least one ablation recognition site (a transgene unit); and (b) a second transcription unit that encodes an ablator specific for the ablation recognition site in operative association with a promoter that induces transcription in response to a pharmacological agent (an ablation unit).

In one embodiment, the PITA system is designed such that the viral genome(s) of the replication-defective viruses are further engineered to contain a dimerizable domain unit (described in Section 5.1.3). In one embodiment, by delivering a dimerizable TF domain unit, target cells are modified to co-express two fusion proteins: one containing a DNA-binding domain (DBD) of the transcription factor that binds the inducible promoter controlling the ablator and the other containing a transcriptional activation domain (AD) of the transcription factor that activates the inducible promoter controlling the ablator, each fused to dimerizer binding domains (described in Section 5.1.3). Addition of a pharmacological agent, or "dimerizer" (described in Section 5.1.4) that can simultaneously interact with the dimerizer binding domains present in both fusion proteins results in recruitment of the AD fusion protein to the regulated promoter, initiating transcription of the ablator. See, e.g., the Ariad ARGENT® system described in U.S. Pat. Nos. 5,834,266 and 7,109,317, each of which is incorporated by reference herein in its entirety. By using dimerizer binding domains that have no affinity for one another in the absence of ligand and an appropriate minimal promoter, transcription is made absolutely dependent on the addition of the dimerizer.

To this end, the viral genome(s) of the replication-defective viruses can be further engineered to contain a third and a fourth transcription unit (a dimerizable TF domain unit), each encoding a dimerizable domain of a transcription factor that regulates the inducible promoter of the ablator in second transcription unit, in which: (c) the third transcription unit encodes the DNA binding domain of the transcription factor fused to a binding domain for the pharmacological agent in operative association with a constitutive promoter; and (d) the fourth transcription unit encodes the activation domain of the transcription factor fused to a binding domain for the pharmacological agent in operative association with a promoter. In one embodiment, each component of the dimerizable TF domain is expressed under constitutive promoter. In another embodiment, at least one component of the dimerizable TF domain unit is expressed under an inducible promoter.

One embodiment of the PITA system is illustrated in FIG. 21, which shows a transgene unit encoding a therapeutic antibody that is in operative association with a constitutive promoter, an ablation unit encoding an endonuclease that is in operative association with a transcription factor inducible promoter, and a dimerizable TF domain unit, with each transcription factor domain fusion sequence in operative association with a constitutive promoter. Prior to administration of rapamycin or a rapalog, there is baseline expression of the therapeutic antibody and of the two transcription factor domain fusion proteins. Upon rapamycin administration, the dimerized transcription factor induces expression of the endonuclease, which cleaves the endonuclease recognition domain in the transgene unit, thereby ablating transgene expression.

In one embodiment, the replication-defective virus used in the PITA system is an adeno-associated virus ("AAV") (described in Section 5.1.5). AAV1, AAV6, AAV7, AAV8, AAV9 or rh10 are particularly attractive for use in human subjects.

Due to size constraints of the AAV genome for packaging, the transcription units can be engineered and packaged in two or more AAV stocks. For example, the first transcription unit can be packaged in one AAV stock, and the second, third and fourth transcription units packaged in a second AAV stock. Alternatively, the second transcription unit can be packaged in one AAV stock, and the first, third and fourth transcription units packaged in a second AAV stock.

5.1.1. Transgene Unit

In the PITA system, one or more replication-defective viruses are used in which the viral genome(s) have been engineered to contain a transgene unit. As used herein, the term "transgene unit" refers to a DNA that comprises: (1) a DNA sequence that encodes a transgene; (2) at least one ablation recognition site (ARS) contained in a location which disrupts transgene expression, including, within or flanking the transgene or its expression control elements (e.g., upstream or downstream of the promoter and/or upstream of the polyA signal); and (3) a promoter sequence that regulates expression of the transgene. The DNA encoding the transgene can be genomic DNA, cDNA, or a cDNA that includes one or more introns which e.g., may enhance expression of the transgene. In systems designed for removal of the transgene, the ARS used is one recognized by the ablator (described in Section 5.1.2) that ablates or excises the transgene, e.g., an endonuclease recognition sequence including but not limited to a recombinase (e.g., the Cre/loxP system, the FLP/FRT system), a meganuclease (e.g., I-ScеI system), an artificial restriction enzyme system or another artificial restriction enzyme system, such as the zinc finger nuclease, or a restriction enzyme specific for a restriction site that occurs rarely in the human genome, and the like. To repress expression of the transgene, the ARS can encode an ablation recognition RNA sequence (ARRS), i.e., an RNA sequence recognized by the ablator that ablates the transcription product of the transgene or translation of its mRNA, e.g., a ribozyme recognition sequence, an RNAi recognition sequence, or an antisense recognition sequence.

Examples of transgenes that can be engineered in the transgene units of the present invention includes, but are not limited to a transgene that encodes: an antibody or antibody fragment that neutralizes HIV infectivity, a therapeutic antibody such as VEGF antibody, TNF-a antibody (e.g., infliximab, adalimumab), an EGF-R antibody, basiliximab, cetuximab, infliximab, rituximab, alemtuzumab-CLL, daclizumab, efalizumab, omalizumab, pavilizumab, trastuzumab, gemtuzumab, adalimumab, or an antibody fragment of any of the foregoing therapeutic antibodies; soluble vascular endothelial growth factor receptor-1 (sFlt-1), soluble TNF-a receptor (e.g., etanercept), Factor VIII, Factor IX, insulin, insulin like growth factor (IGF), hepatocyte growth factor (RGF), heme oxygenase-1 (RO-1), nerve growth factor (NGF), beta-IFN, IL-6, anti-EGFR antibody, interferon (IFN), IFN beta-1a, anti-CD20 antibody, glucagon-like peptide-1 (GLP-1), anti-cellular adhesion molecule, a4-integrin antibody, glial cell line-derived neurotrophic factor (GDNF), aromatic L-amino acid decarboxylase (ADCC), brain-derived neurotrophic factor (BDNF), ciliary neurotrophic factor (CNTF), galanin, neuropeptide Y (NPY), a TNF antagonist, chemokines from the IL-8 family, BC12, IL-10, a therapeutic siRNA, a therapeutic u6 protein, endostatin, plasminogen or a fragment thereof, TIMP3, VEGF-A, RIFI alpha, PEDF, or IL-1 receptor antagonist.

The transgene can be under the control of a constitutive promoter, an inducible promoter, a tissue-specific promoter, or a promoter regulated by physiological cues. Examples of constitutive promoters suitable for controlling expression of the therapeutic products include, but are not limited to human cytomegalovirus (CMV) promoter, the early and late promoters of simian virus 40 (SV40), U6 promoter, metallothionein promoters, EF1a promoter, ubiquitin promoter, hypoxanthine phosphoribosyl transferase (HPRT) promoter, dihydrofolate reductase (DHFR) promoter (Scharfmann et al., Proc. Natl. Acad. Sci. USA 88:4626-4630 (1991), adenosine deaminase promoter, phosphoglycerol kinase (PGK) promoter, pyruvate kinase promoter phosphoglycerol mutase promoter, the β-actin promoter (Lai et al., Proc. Natl. Acad. Sci. USA 86: 10006-10010 (1989>>, the long terminal repeats (LTR) of Moloney Leukemia Virus and other retroviruses, the thymidine kinase promoter of Herpes Simplex Virus and other constitutive promoters known to those of skill in the art.

Inducible promoters suitable for controlling expression of the therapeutic product include promoters responsive to exogenous agents (e.g., pharmacological agents) or to physiological cues. These response elements include, but are not limited to a hypoxia response element (HRE) that binds HIF-Ia and β, tetracycline response element (such as described by Gossen & Bujard (1992, Proc. Natl. Acad. Sci. USA 89:5547-551); an ecdysone-inducible response element (No D et al., 1996, Proc. Natl. Acad. Sci. USA. 93:3346-3351) a metal-ion response element such as described by Mayo et al. (1982, Cell 29:99-108); Brinster et al. (1982, Nature 296:39-42) and Searle et al. (1985, Mol. Cell. Biol. 5:1480-1489); a heat shock response element such as described by Nouer et al. (in: Heat Shock Response, ed. Nouer, L., CRC, Boca Raton, Fla., pp 167-220, 1991); or a hormone response element such as described by Lee et al. (1981, Nature 294:228-232); Hynes et al. (Proc. Natl. Acad. Sci. USA 78:2038-2042, 1981); Klock et al. (Nature 329:734-736, 1987); and Israel and Kaufman (1989, Nucl. Acids Res. 17:2589-2604) and other inducible promoters known in the art. Preferably the response element is an ecdysone-inducible response element, more preferably the response element is a tetracycline response element.

Examples of tissue-specific promoters suitable for use in the present invention include, but are not limited to those listed in Table 1 and other tissue-specific promoters known in the art.

TABLE 1

Tissue-specific promoters

| Tissue | Promoter |
| --- | --- |
| Liver | TBG, A1AT |
| Heart | Troponin T (TnT) |
| Lung | CC10, SPC, FoxJ1 |
| Central Nervous System/Brain | Synapsin, Tyrosine Hydroxylase, CaMKII (Ca2+/calmodulin-dependent protein kinase) |
| Pancreas | Insulin, Elastase-I |
| Adipocyte | Ap2, Adiponectin |
| Muscle | Desmin, MHC |
| Endothelial cells | Endothelin-I (ET -I), Flt-I |
| Retina | VMD |

For example, and not by way of limitation, the replication-defective virus compositions of the invention can be used to deliver a VEGF antagonist for treating accelerated macular degeneration in a human subject; Factor VIII for treating hemophilia A in a human subject; Factor IX for treating hemophilia B in a human subject; insulin like growth factor (IGF) or hepatocyte growth factor (HGF) for treating congestive heart failure in a human subject; nerve growth factor (NGF) for treating a central nervous system disorder in a human subject; or a neutralizing antibody against HIV for treating HIV infection in a human subject.

Still other useful therapeutic products include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), platelet-derived growth factor (PDGF), insulin growth factors I and II (IGF-I and IGF-II), any one of the transforming growth factor a superfamily, including TGFa, activins, inhibins, or any of the bone morphogenic proteins (BMP) BMPs 1-15, any one of the heregluin/neuregulin/ARIAIneu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-25 (including, e.g., IL-4, IL-12 and IL-18), monocyte chemoattractant protein, leukemia inhibitory factor, granulocyte-macrophage colony stimulating factor, Fas ligand, tumor necrosis factors a and β, interferons a, β, and γ, stem cell factor, flk-2/flt3 ligand. Gene products produced by the immune system are also useful in the invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

Still other useful gene products include any one of the receptors for the hormones, growth factors, cytokines, lymphokines, regulatory proteins and immune system proteins. The invention encompasses receptors for cholesterol regulation and/or lipid modulation, including the low density lipoprotein (LDL) receptor, high density lipoprotein (HDL) receptor, the very low density lipoprotein (VLDL) receptor, and scavenger receptors. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin gene product [e.g., a mini- or micro-dystrophin]. Still other useful gene products include enzymes such as may be useful in enzyme replacement therapy, which is useful in a variety of conditions resulting from deficient activity of enzyme. For example, enzymes that contain mannose-6-phosphate may be utilized in therapies for lysosomal storage diseases (e.g., a suitable gene includes that encoding β-glucuronidase (GUSB)).

5.1.2. Ablation Unit

The viral genome(s) of one or more replication-defective viruses used in the PITA system are engineered to further contain an ablation unit or coding sequences for an ablator, as defined here.

For permanent shut down of transgene expression, the ablator can be an endonuclease, including but not limited to a recombinase, a meganuclease, a zinc finger endonuclease or any restriction enzyme with a restriction site that rarely occurs in the human genome, that binds to the ARS of the transgene unit and ablates or excises the transgene. Examples of such ablators include, but are not limited to the Cre/loxP system (Groth et al., 2000, Proc. Natl. Acad. Sci. USA 97, 5995-6000); the FLP/FRT system (Sorrell et al., 2005, Biotechnol. Adv. 23, 431-469); meganucleases such as I-SceI which recognizes a specific asymmetric 18 bp element (T AGGGAT AACAGGGT AAT (SEQ ID NO: 25)), a rare sequence in the mammalian genome, and creates double strand breaks (Jasin, M., 1996, Trends Genet., 12, 224-228); and artificial restriction enzymes (e.g., a zinc finger nucleases generated by fusing a zinc finger DNA-binding domain to a DNA-cleavage domain that can be engineered to target ARS sequences unique to the mammalian genome (Miller et al., 2008, Proc. Natl. Acad. Sci. USA, 105: 5809-5814)). In one embodiment, the ablator is a chimeric enzyme, which may be based on a homodimer or a heterodimer fusion protein.

Where temporary shutdown of the transgene is desired, an ablator should be chosen that binds to the ARRS of the RNA transcript of the transgene unit and ablates the transcript, or inhibits its translation. Examples of such ablators include, but are not limited to interfering RNAs (RNAi), ribozymes such as riboswitch (Bayer et al., 2005, Nat Biotechnol. 23(3):337-43), or antisense oligonucleotides that recognize an ARRS. RNAi, ribozymes, and antisense oligonucleotides that recognize an ARRS can be designed and constructed using any method known to those of skill in the art. This system is particularly desirable if the therapeutic transgene is administered to treat cancer or to mediate host immune response.

In one embodiment, expression of the ablator must be controlled by an inducible promoter that provides tight control over the transcription of the ablator gene e.g., a pharmacological agent, or transcription factors activated by a pharmacological agent or in alternative embodiments, physiological cues. Promoter systems that are non-leaky and that can be tightly controlled are preferred. Inducible promoters suitable for controlling expression of the ablator are e.g., response elements including but not limited to a tetracycline (tet) response element (such as described by Gossen & Bujard (1992, Proc. Natl. Acad. Sci. USA 89:5547-551); an ecdysone-inducible response element (No D et al., 1996, Proc.

Natl. Acad. Sci. USA. 93:3346-3351) a metal-ion response element such as described by Mayo et al. (1982, Cell. 29:99-108); Brinster et al. (1982, Nature 296:39-42) and Searle et al. (1985, Mol. Cell. Biol. 5: 1480-1489); a heat shock response element such as described by Nouer et al. (in: Heat Shock Response, ed. Nouer, L., CRC, Boca Raton, Fla., pp 167-220, 1991); or a hormone response element such as described by Lee et al. (1981, Nature 294:228-232); Hynes et al. (1981, Proc. Natl. Acad. Sci. USA 78:2038-2042); Klock et al. (1987, Nature 329:734-736); and Israel & Kaufman (1989, Nucl. Acids Res. 17:2589-2604) and other inducible promoters known in the art. Using such promoters, expression of the ablator can be controlled, for example, by the Tet-on/off system (Gossen et ai., 1995, Science 268:1766-9; Gossen et ai., 1992, Proc. Natl. Acad. Sci. USA., 89(12):5547-51); the TetR-KRAB system (Urrutia R., 2003, Genome Biol., 4(10): 231; Deuschle U et al., 1995, Mol Cell Biol. (4):1907-14); the mifepristone (RU486) regulatable system (Geneswitch; Wang Y et ai., 1994, Proc. Natl. Acad. Sci. USA., 91(17): 8180-4; Schillinger et al., 2005, Proc. Natl. Acad. Sci. USA. 102(39):13789-94); the humanized tamoxifen-dep regulatable system (Roscilli et al., 2002, Mol. Ther. 6(5):653-63); and the ecdysone-dep regulatable system (Rheoswitch; Karns et al., 2001, BMC Biotechnol. 1: 11; Palli et al., 2003, Eur J Biochem. 270(6):1308-15) to name but a few.

A chimeric enzyme may be controlled by a constitutive or an inducible promoter. In one embodiment, the system utilizes a chimeric endonuclease, wherein the nuclease has at least two domains, i.e., a catalytic domain and a sequence specific DNA binding domain, each of which are expressed under separately controlled promoters and which are operatively linked. When the two domains are expressed at the same time, the products of the two domains form a chimeric endonuclease. Typically, separate transcription units containing each of domains linked to a DNA binding domain are provided. Such DNA binding domains include, for example, zinc finger motifs, homeo domain motifs, HMG-box domains, STAT proteins, B3, helix-loop-helix, winged helix-turn-helix, leucine zipper, helix-turn-helix, winged helix, POU domains, DNA binding domains of repressors, DNA binding domains of oncogenes and naturally occurring sequence-specific DNA binding proteins that recognize >6 base pairs. [U.S. Pat. No. 5,436,150, issued Jul. 25, 1995].

In one embodiment, the expression of the ablator is under the control of an inducible promoter that is regulated by the dimerizable transcription factor domains described in Section 5.1.3. An example of such an inducible promoter includes, but is not limited to a GAL4 binding site minimum promoter, which is responsive to a GAL4 transcription factor. A GAL4 DNA binding domain or transactivation domain can also be fused to a steroid receptor, such as the ecdysone receptor (EcR). Still other suitable inducible promoters, such as are described herein, may be selected.

5.1.3. Dimerizable Transcription Factor Domain Unit

In one embodiment, the PITA system is designed such that the viral genome(s) of the replication-defective viruses are further engineered to contain a dimerizable units which are heterodimer fusion proteins. These units may be a dimerizable TF unit as defined herein or another dimerizable fusion protein unit (e.g., part of a chimeric enzyme). In such an instance, a dimerizer is used (see Section 5.1.4), which binds to the dimerizer binding domains and dimerizes (reversibly cross-links) the DNA binding domain fusion protein and the activation domain fusion protein, forming a bifunctional transcription factor. See, e.g., the Ariad ARGENT™ system, which is described in U.S. Publication Nos. 2002/0173474, 200910100535, U.S. Pat. Nos. 5,834,266, 7,109,317, 7,485, 441, 5,830,462, 5,869,337, 5,871,753, 6,011,018, 6,043,082, 6,046,047, 6,063,625, 6,140,120, 6,165,787, 6,972,193, 6,326,166, 7,008,780, 6,133,456, 6,150,527, 6,506,379, 6,258,823, 6,693,189, 6,127,521, 6,150,137, 6,464,974, 6,509,152, 6,015,709, 6,117,680, 6,479,653, 6,187,757, 6,649,595, 6,984,635, 7,067,526, 7,196,192, 6,476,200, 6,492,106, WO 94/18347, WO 96/20951, WO 96/06097, WO 97/31898, WO 96/41865, WO 98/02441, WO 95/33052, WO 99110508, WO 99110510, WO 99/36553, WO 99/41258, WO 01114387, ARGENT™ Regulated Transcription Retrovirus Kit, Version 2.0 (9109102), and ARGENT™ Regulated Transcription Plasmid Kit, Version 2.0 (9109/02), each of which is incorporated herein by reference in its entirety.

In one embodiment, by delivering a dimerizable unit, target cells are modified to co-express two fusion proteins that are dimerized by the pharmacologic agent used: one containing a DNA-binding domain (DBD) of the transcription factor that binds the inducible promoter controlling the ablator and the other containing a transcriptional activation domain (AD) of the transcription factor that activates the inducible promoter controlling the ablator, each fused to dimerizer binding domains. Expression of the two fusion proteins may be constitutive, or as an added safety feature, inducible. Where an inducible promoter is selected for expression of one of the fusion proteins, the promoter may regulatable, but different from any other inducible or regulatable promoters in the viral composition. Addition of a pharmacological agent, or "dimerizer" (described in Section 5.1.4) that can simultaneously interact with the dimerizer binding domains present in both fusion proteins results in recruitment of the AD fusion protein to the regulated promoter, initiating transcription of the ablator. By using dimerizer binding domains that have no affinity for one another in the absence of ligand and an appropriate minimal promoter, transcription is made absolutely dependent on the addition of the dimerizer. Suitably, a replication-defective virus composition of the invention may contain more than one dimerizable domain. The various replication-defective viruses in a composition may be of different stock, which provide different transcription units (e.g., a fusion protein to form a dimerable unit in situ) and/or additional ablators.

Fusion proteins containing one or more transcription factor domains are disclosed in WO 94/18317, PCT/US94/08008, Spencer et al, supra and Blau et al. (PNAS 1997 94:3076) which are incorporated by reference herein in their entireties. The design and use of such fusion proteins for ligand-mediated gene-knock out and for ligand-mediated blockade of gene expression or inhibition of gene product function are disclosed in PCT/US95/10591. Novel DNA binding domains and DNA sequences to which they bind which are useful in embodiments involving regulated transcription of a target gene are disclosed, e.g., in Pomeranz et al, 1995, Science 267:93 96. Those references provide substantial information, guidance and examples relating to the design, construction and use of DNA constructs encoding analogous fusion proteins, target gene constructs, and other aspects which may also be useful to the practitioner of the subject invention.

Preferably the DNA binding domain, and a fusion protein containing it, binds to its recognized DNA sequence with sufficient selectivity so that binding to the selected DNA sequence can be detected (directly or indirectly as measured in vitro) despite the presence of other, often numerous other, DNA sequences. Preferably, binding of the fusion protein comprising the DNA-binding domain to the selected DNA sequence is at least two, more preferably three and even more preferably more than four orders of magnitude greater than binding to anyone alternative DNA sequence, as measured by binding studies in vitro or by measuring relative rates or levels of transcription of genes associated with the selected DNA sequence as compared to any alternative DNA sequences. The dimerizable transcription factor (TF) domain units of the invention can encode DNA binding domains and activation domains of any transcription factor known in the art. Examples of such transcription factors include but are not limited to GAL4, ZFHD1, VPI6, and NF-KB (p65).

The dimerizer binding domain encoded by a dimerizable unit of the invention can be any dimerizer binding domain described in U.S. Publication Nos. 2002/0173474, 200910100535, U.S. Pat. Nos. 5,834,266, 7,109,317, 7,485, 441, 5,830,462, 5,869,337, 5,871,753, 6,011,018, 6,043,082, 6,046,047, 6,063,625, 6,140,120, 6,165,787, 6,972,193, 6,326,166, 7,008,780, 6,133,456, 6,150,527, 6,506,379, 6,258,823, 6,693,189, 6,127,521, 6,150,137, 6,464,974, 6,509,152, 6,015,709, 6,117,680, 6,479,653, 6,187,757, 6,649,595, 6,984,635, 7,067,526, 7,196,192, 6,476,200, 6,492,106, WO 94118347, WO 96/20951, WO 96/06097, WO 97/31898, WO 96/41865, WO 98/02441, WO 95/33052, WO 99/10508, WO 99110510, WO 99/36553, WO 99/41258, WO 01114387, ARGENT™ Regulated Transcription Retrovirus Kit, Version 2.0 (Sep. 9, 2002), and ARGENT™ Regulated Transcription Plasmid Kit, Version 2.0 (Sep. 9, 2002), each of which is incorporated herein by reference in its entirety.

A dimerizer binding domain that can be used in the PITA system is the immunophilin FKBP (FK506-binding protein). FKBP is an abundant 12 kDa cytoplasmic protein that acts as the intracellular receptor for the immunosuppressive drugs FK506 and rapamycin. Regulated transcription can be achieved by fusing multiple copies of FKBP to a DNA binding domain of a transcription factor and an activation domain of a transcription factor, followed by the addition of FK1012 (a homodimer of FK506; Ho, S. N., et al., 1996, Nature, 382(6594): 822-6); or simpler synthetic analogs such as AP1510 (Amara, J. F., et al., 1997, Proc. Natl. Acad. Sci. USA, 94(20): 10618-23). The potency of these systems can be improved by using synthetic dimerizers, such as AP1889, with designed 'bumps' that minimize interactions with endogenous FKBP (Pollock et al., 1999, Methods Enzymol, 1999.306: p. 263-81). Improved approaches based on heterodimerization, exploiting the discovery that FK506 and rapamycin naturally function by bringing together FKBP with a second target protein. This allows the natural products themselves, or analogs thereof, to be used directly as dimerizers to control gene expression.

The structure of FKBP-FK506 complexed to calcineurin phosphatase (Griffith et al., Cell, 82:507 522, 1995) has been reported. Calcineurin A (residues 12 394) was shown to be effective as a dimerizer binding domain using a three hybrid system in yeast using three FKBPs fused to Gal4 and residues 12 to 394 of murine calcineurin A fused C-terminally to the Gal4 activation domain (Ho, 1996 Nature. 382:822 826). Addition of FK506 activated transcription of a reporter gene in these cells. A "minimal" calcineurin domain termed a CAB, which is a smaller, more manipulatable domain can be used as a dimerizer binding domain.

The DNA binding domain fusion protein and activation domain fusion protein encoded by the dimerizable fusion protein units of the invention may contain one or more copies of one or more different dimerizer binding domains. The dimerizer binding domains may be N-terminal, C-terminal, or interspersed with respect to the DNA binding domain and activation domain. Embodiments involving multiple copies of a dimerizer binding domains usually have 2, 3 or 4 such copies. The various domains of the fusion proteins are optionally separated by linking peptide regions which may be derived from one of the adjacent domains or may be heterologous.

As used herein, the term "variants" in the context of variants of dimerizer binding domains refers to dimerizer binding domains that contain deletions, insertions, substitutions, or other modifications relative to native dimerizer binding domains, but that retain their specificity to bind to dimerizers. The variants of dimerizer binding domains preferably have deletions, insertions, substitutions, and/or other modifications of not more than 10, 9, 8, 7, 6, 5, 4, 3, 2, or 1 amino acid residues. In a specific embodiment, the variant of a dimerizer binding domain has the native sequence of a dimerizer binding domain as specified above, except that 1 to 5 amino acids are added or deleted from the carboxy and or the amino end of the dimerizer binding domains (where the added amino acids are the flanking amino acid(s) present in the native dimerizer binding domains).

In order to conserve space within the viral genome(s), bicistronic transcription units can be engineered. For example, the third and fourth transcription units can be engineered as a bicistronic unit containing an IRES (internal ribosome entry site), which allows coexpression of heterologous gene products by a message from a single promoter. Alternatively, a single promoter may direct expression of an RNA that contains, in a single open reading frame (ORF), two or three heterologous genes (e.g., the third and fourth transcription units) separated from one another by sequences encoding a self-cleavage peptide (e.g., T2A) or a protease recognition site (e.g., furin). The ORF thus encodes a single polyprotein, which, either during (in the case of T2A) or after translation, is cleaved into the individual proteins. It should be noted, however, that although these IRES and polyprotein systems can be used to save AAV packaging space, they can only be used for expression of components that can be driven by the same promoter.

As illustrated in the examples below, various components of the invention may include:

ITR: inverted terminal repeats (ITR) of AAV serotype 2 (168 bp). In one embodiment, the AAV2 ITRs are selected to generate a pseudotyped AAV, i.e., an AAV having a capsid from a different AAV than that the AAV from which the ITRs are derived.

CMV: full cytomegalovirus (CMV) promoter; including enhancer. CMV: minimal CMV promoter, not including enhancer. In one embodiment, the human CMV promoter and/or enhancer are selected.

FRB-TA fusion: fusion of dimerizer binding domain and an activation domain of a transcription factor. The FRB fragment corresponds to amino acids 2021-2113 of FRAP (FKBP rapamycin-associated protein, also known as mTOR [mammalian target of rapamycin]), a phosphoinositide 3-kinase homolog that controls cell growth and division. The FRAP sequence incorporates the single point-mutation Thr2098Leu (FRAP$_L$) to allow use of certain non-immunosuppressive rapamycin analogs (rapalogs). FRAP binds to rapamycin (or its analogs) and FKBP and is fused to a portion of human NF-KB p65 (190 amino acids) as transcription activator.

ZFHD-FKBP fusion: fusion of a DNA binding domain and 1 copy of a Dimerizer binding domain, 2 copies of drug binding domain (2×FKBP, or 3 (3×FKBP) copies of drug binding domain Immunophilin FKBP (FK506-binding protein) is an abundant 12 kDa cytoplasmic protein that acts as the intracellular receptor for the immunosuppressive drugs FK506 and rapamycin. ZFHD is DNA binding domains composed of a zinc finger pair and a homeodomain. In another alternative, various other copy numbers of a selected drug binding domain may be selected. Such fusion proteins may contain N-terminal nuclear localization sequence from human c-Myc at the 5' and/or 3' end.

Z8I: contains 8 copies of the binding site for ZFHD (Z8) followed by minimal promoter from the human interleukin-2 (IL-2) gene (SEQ ID NO: 32). Variants of this may be used, e.g., which contain from 1 to about 20 copies of the binding site for ZFHD followed by a promoter, e.g., the minimal promoter from IL-2 or another selected promoter.

Cre: Cre recombinase. Cre is a type I topoisomerase isolated from bacteriophage P1. Cre mediates site specific recombination in DNA between two loxP sites leading to deletion or gene conversion (1029 bp, SEQ ID NO: 33).

I-SceI: a member of intron endonuclease or homing endonuclease which is a large class of meganuclease (708 bp, SEQ ID NO: 34). They are encoded by mobile genetic elements such as introns found in bacteria and plants. I-SceI is a yeast endonuclease involved in an intron homing process. I-SceI recognizes a specific asymmetric 18 bp element, a rare sequence in mammalian genome, and creates double strand breaks. See, Jasin, M. (1996) Trends Genet., 12, 224-228.

hGH poly A: minimal poly adenylation signal from human GH (SEQ ID NO: 35).

IRES: internal ribosome entry site sequence from ECMV (encephalomyocarditis virus) (SEQ ID NO: 36).

5.1.4. Dimerizers and Pharmacologic Agents

As used herein, the term "dimerizer" is a compound that can bind to dimerizer binding domains of the TF domain fusion proteins (described in Section 5.1.3) and induce dimerization of the fusion proteins. Any pharmacological agent that dimerizer the domains of the transcription factor, as assayed in vitro can be used. Preferably, rapamycin and its analogs referred to as "rapalogs" can be used. Any of the dimerizers described in following can be used: U.S. Publication Nos. 2002/0173474, 2009/0100535, U.S. Pat. Nos. 5,834,266, 7,109,317, 7,485,441, 5,830,462, 5,869,337, 5,871,753, 6,011,018, 6,043,082, 6,046,047, 6,063,625, 6,140,120, 6,165,787, 6,972,193, 6,326,166, 7,008,780, 6,133,456, 6,150,527, 6,506,379, 6,258,823, 6,693,189, 6,127,521, 6,150,137, 6,464,974, 6,509,152, 6,015,709, 6,117,680, 6,479,653, 6,187,757, 6,649,595, 6,984,635, 7,067,526, 7,196,192, 6,476,200, 6,492,106, WO 94118347, WO 96/20951, WO 96/06097, WO 97/31898, WO 96/41865, WO 98/02441, WO 95/33052, WO 99/10508, WO 99/10510, WO 99/36553, WO 99/41258, WO 01114387, ARGENT™ Regulated Transcription Retrovirus Kit, Version 2.0 (9109/02), and ARGENT™ Regulated Transcription Plasmid Kit, Version 2.0 (Sep. 9, 2002), each of which is incorporated herein by reference in its entirety.

Examples of dimerizers that can be used in the present invention include, but are not limited to rapamycin, FK506, FKI012 (a homodimer of FK506), rapamycin analogs ("rapalogs") which are readily prepared by chemical modifications of the natural product to add a "bump" that reduces or eliminates affinity for endogenous FKBP and/or FRAP. Examples of rapalogs include, but are not limited to such as AP26113 (Ariad), AP1510 (Amara, J. F., et al., 1997, Proc Natl Acad Sci USA, 94(20): 10618-23) AP22660, AP22594, AP21370, AP22594, AP23054, AP1855, AP1856, AP1701, AP1861, AP1692 and AP1889, with designed 'bumps' that minimize interactions with endogenous FKBP.

Other dimerizers capable of binding to dimerizer binding domains or to other endogenous constituents may be readily identified using a variety of approaches, including phage display and other biological approaches for identifying peptidyl binding compounds; synthetic diversity or combinatorial approaches (see e.g. Gordon et al, 1994, J Med Chem 37(9):1233-1251 and 37(10):1385-1401); and DeWitt et al, 1993, PNAS USA 90:6909-6913) and conventional screening or synthetic programs. Dimerizers capable of binding to dimerizer binding domains of interest may be identified by various methods of affinity purification or by direct or competitive binding assays, including assays involving the binding of the protein to compounds immobilized on solid supports such as pins, beads, chips, etc.). See e.g. Gordon et al., supra.

Generally speaking, the dimerizer is capable of binding to two (or more) protein molecules, in either order or simultaneously, preferably with a Kd value below about $10^{-6}$ more preferably below about $10^{-7}$, even more preferably below about $10^{-8}$, and in some embodiments below about $10^{-9}$ M. The dimerizer preferably is a non-protein and has a molecular weight of less than about 5 kDa. The proteins so oligomerized may be the same or different.

Various dimerizers are hydrophobic or can be made so by appropriate modification with lipophilic groups. Particularly, dimerizers containing linking moieties can be modified to enhance lipophilicity by including one or more aliphatic side chains of from about 12 to 24 carbon atoms in the linker moiety.

5.1.5. Generating Replication-Defective Virus Compositions

Any virus suitable for gene transfer (e.g., gene therapy) may be used for packaging the transcription units into one or more stocks of replication-defective virus, including but not limited to adeno-associated virus ("AAV"); adenovirus; alphavirus; herpesvirus; retrovirus (e.g., lentivirus); vaccinia virus; etc. Methods well known in the art for packaging foreign genes into replication-defective viruses can be used to prepare the replication-defective viruses containing the therapeutic transgene unit, the ablation unit, and optionally (but preferably) the dimerizable transcription factor domain unit. See, for example, Gray & Samulski, 2008, "Optimizing gene delivery vectors for the treatment of heart disease," *Expert Opin. Biol. Ther.* 8:911-922; Murphy & High, 2008, "Gene therapy for haemophilia," Br. J. Haematology 140:479-487; Hu, 2008, "Baculoviral vectors for gene delivery: A review," Current Gene Therapy 8:54-65; Gomez et al., 2008, "The poxvirus vectors MV A and NYV AC as gene delivery systems for vaccination against infectious diseases and cancer," Current Gene Therapy 8:97-120.

In preferred embodiments, the replication-deficient virus compositions for therapeutic use are generated using an AAV. Methods for generating and isolating AAVs suitable for gene therapy are known in the art. See generally, e.g., Grieger & Samulski, 2005, "Adeno-associated virus as a gene therapy vector: Vector development, production and clinical applications," *Adv. Biochem. Engin/Biotechnol.* 99: 119-145; Buning et al., 2008, "Recent developments in adeno-associated virus vector technology," *J. Gene Med.* 10:717-733; and the references cited below, each of which is incorporated herein by reference in its entirety.

Adeno-associated virus (genus Dependovirus, family Parvoviridae) is a small (approximately 20-26 nm), non-enveloped single-stranded (ss) DNA virus that infects humans and other primates. Adeno-associated virus is not currently known to cause disease. Adeno-associated virus can infect both dividing and non-dividing cells. In the absence of functional helper virus (for example, adenovirus or herpesvirus) AAV is replication-defective. Adeno-associated viruses form episomal concatamers in the host cell nucleus. In non-dividing cells, these concatamers remain intact for the life of the host cell. In dividing cells, AAV DNA is lost through cell division, since the episomal DNA is not replicated along with the host cell DNA. However, AAV DNA may also integrate at low levels into the host genome.

The AAV genome is built of a ssDNA, either positive- or negative-sense, which is about 4.7 kilobases long. The genome of AAV as it occurs in nature comprises inverted terminal repeats (ITRs) at both ends of the DNA strand, and two open reading frames (ORFs): rep and cap. The former is composed of four overlapping genes encoding the Rep proteins that are required for the AAV life cycle, and the latter contains overlapping sequences that encode the capsid proteins (Cap): VP1, VP2, and VP3, which interact to form a capsid of an icosahedral symmetry.

The ITRs are 145 bases each, and form a hairpin that contributes to so-called "self-priming" that allows primase-independent synthesis of the second DNA strand. The ITRs also appear to be required for AAV DNA integration into the host cell genome (e.g., into the 19th chromosome in humans) and rescue from it, as well as for efficient encapsidation of the AAV DNA and assembly of AAV particles.

For packaging a transgene into virions, the ITRs are the only AAV components required in cis in the same construct as the transgene. The cap and rep genes can be supplied in trans. Accordingly, DNA constructs can be designed so that the AAV ITRs flank one or more of the transcription units (i.e., the transgene unit, the ablator unit, and the dimerizable transcription factor unit), thus defining the region to be amplified and packaged—the only design constraint being the upper limit of the size of the DNA to be packaged (approximately 4.5 kb). Adeno-associated virus engineering and design choices that can be used to save space are described below.

Compositions and System Utilizing 10× Zinc Finger Constructs

The invention provides a method for vector-mediated delivery of a therapeutic product having a controlled gene expression ablation system. For convenience, the method is described in the context of an AAV vector. However, one of skill in the art can select another suitable vector (e.g., a replication-defective adenovirus, replication-defective lentivirus, or other viral or genetic element) for use with the compositions and methods described herein. Examples of viral and other vectors are described earlier and incorporated herein by reference. In one embodiment, an AAV vector containing a nucleic acid molecule comprising a nucleic acid sequence encoding a therapeutic or vaccinal product (or another gene or sequence of interest) operably linked to a promoter that controls transcription and at least one endonuclease ablation site which comprises a sequence of at least 30 nucleic acid base pairs which are specifically and selectively recognized by a construct of at least ten (10×) zinc fingers. The at least one endonuclease ablation site is located at least 5' to the sequence encoding the gene of interest (e.g., a transgene such as DNA, RNA, ribozyme, siRNA, shRNA, miRNA or protein, peptide, system's biology engineered pathways, etc.). The method further involves use of at least one ablator which comprises a chimeric endonuclease comprising at least ten zinc fingers linked to a functional endonuclease catalytic domain in operative association with a promoter, wherein transcription and/or ablation activity is induced in response to a pharmacological agent. The at least ten (10×) zinc fingers specifically and selectively recognizes the at least about 30 base pair sequence in the at least one endonuclease ablation site and contains at least 10 independently selected recognition helices.

In one embodiment, the present invention utilizes chimeric endonucleases as a safety measure necessary to destroy a gene of interest in gene delivery applications in vivo [including gene therapy, vaccines etc], for example when a transgene product is no longer required or exhibits toxic/off target effects inside the organism. Thus, the chimeric endonucleases of the invention have one or more of the following features. They intentionally target sequences that are not present in mammalian (e.g., human) genomes (thus the term the "at least 30 bp unique sequence"), they have high in vivo selectivity to a target location only, and they have minimal off-target and cytotoxic effects. Due to the fact that the endonucleases described previously in the literature were used for a different purpose, i.e., for in situ engineering of mammalian genomes to allow knock-out or correction (knock-in) of specific genes of interest, the inventors were required to develop a new methodology to design a chimeric endonuclease with the features required for the present invention, including designing long stretches, (i.e., in excess of 7, 8, 9, 10, 11, 12, or more zinc fingers) and for selecting unique sequences that are not present within a target genome (e.g., a human or other mammalian subject).

In one embodiment, the zinc finger proteins are engineered to specifically target a DNA sequence which is not part of the target genome in order to mitigate off-target effects and cytotoxicity associated with customarily used designs.

For example, for delivery to humans, random sequences of at least 32 base pair are generated in order to accommodate frame shifts, although smaller sequences (e.g., at least 30 base pairs), could be selected. This size was selected because there are about $3.4 \times 10^9$ base pairs in human genome. The number of all possible 15 base pair-long sequences with permutation of 4 nucleotides is $4^{15}$, which is same as approximately $10^9$. Which means that for any given DNA sequence which is equal to or less than 15 base pairs, an identical subsequence within the human genome can be found. Conversely, for any short DNA sequence, there will be at least 15 positions that are identical to a piece of human DNA sequence. During initial assessment, no short sequences whose maximal sequence-identity with any human DNA sequence is less than 65% were identified.

Surprisingly, the first unique sequence randomly generated for use as an ablation recognition site and tested was found to meet the desired parameters: SEQ ID NO: 806-GGTCGAT-GTTCGCAACGTCGATCGTACGTGCA. The examples below illustrate the sequence being engineered into an expression plasmid vector carrying the gene of interest and being specifically recognized by a chimeric endonuclease of the invention which comprises at least ten zinc fingers. The sequences encoding the ablation recognition site and the sequences of the chimeric endonuclease can be engineered into suitable viral vectors (e.g., AAV vectors) using conventional techniques in order to obtain the AAV vectors, compositions and to perform the methods of the invention.

With reference to FIG. 21, a streamlined method for selecting a unique sequence of the invention is provided. This involves randomly generate 2 million short DNA sequences and selecting those with a sequence identity of less than (<) 20% to one another. The resulting sequences are compared via BLAST using conventional parameters against the target genome (e.g., human) and those with an E-value of greater than 100 are selected. [An E-value is an Expect value. The statistical significance threshold for reporting matches against database sequences; the default value is 10, meaning that 10 matches are expected to be found merely by chance, according to the stochastic model of Karlin and Altschul (1990). If the statistical significance ascribed to a match is greater than the Expect threshold, the match will not be reported. Lower Expect thresholds are more stringent, leading to fewer chance matches being reported. Increasing the threshold shows less stringent matches. Fractional values are acceptable.] An exemplary sequence is compared for similarity against the human genome with a slide window. [For sliding windows a window of 32 base pair slides over the nucleotides of the human genome. The window moves 1 nucleotide for each step. for every position of the window identity levels are calculated.] Any sequence with a similarity greater than 70% is discarded. If the sequence has a similarity of less than 70%, then it is analyzed against the target genome for the presence of any 8 consecutive base pairs and any having 8 or more consecutive base pairs in common with the target sequence are discarded. The remainder may be selected for use in an ablation recognition site.

Thus, a unique sequence for an ablation recognition site of the invention, has less than 70% identity with any subsequence in the human genome, has no more than 8 adjacent identical positions with any subsequence in the human genome. A zinc finger is thereafter designed which specifically targets this sequence as described herein. The unique sequence can be read by different zinc finger designs which recognize different reading frames such that it is possible for two distinct zinc fingers to be specific for a single unique at least 32 bp sequence. The sequences may be 32, 33, 34, 35, 36, 38, 41, 44, or more sequences in length, In addition to the unique sequence identified above, other unique sequences for use in the ablation recognition site were also generated:

SEQ ID NO: 801: SEQ ID NO: GGTCGGCGACGCGAATCGTCGAT TGGCGTAC

SEQ ID NO: 802: SEQ ID NO: GGTCGGCGACGCGTATCGATTG GCGTAC
and

SEQ ID NO: 803: ACTATTCGCACGCCGTACGATAGTCGGCGCGA.

Once the specific ablation site sequence is selected, the ablator can be engineered to contain the zinc finger protein which will specifically recognize this unique at least 30 bp sequence within the ablation site of the vector carrying the gene of interest.

In one embodiment, a chimeric endonuclease of the invention is engineered to contain at least the catalytic domain of an endonuclease fused to a zinc finger protein, optionally via a linker. The catalytic domain may be located on the N-terminus of the zinc finger, the C-terminus of the zinc finger, or it may be located within the zinc finger (i.e., the catalytic domain is flanked on both its N- and C-terminus by zinc finger modules). Optionally, nuclear localization signals are included at the N- or C-terminus of the chimeric endonuclease, or the N- or C-terminus of the zinc finger portion of protein. These elements are described elsewhere in the specification, which passages are incorporated herein by reference.

In one embodiment, the FokI catalytic domain is used without any other functional sequence of the FokI endonuclease, i.e., the DNA binding domain is not present. Further, because of the manner in which the chimeric endonuclease described herein has been engineered, the known FokI recognition site (5'-CATCC-3') is not required. FokI catalytic domain is a non-sequence specific endonuclease, once the ablator recognizes the ablation site, the location in the ablation recognition site where FokI cuts can be altered by the length of the optional linker sequence between the FokI catalytic domain and the zinc fingers.

For example, a linker sequence of five amino acids (e.g., SEQ ID NO: 805, GTSGK) results in the FokI chimeric ablator cutting 6 bp directly following the zinc finger binding site. [The linker length is defined using the convention set forth in Yuka Shimizu, et al, *Bioorg Med Chem Lett*. 2009 Jul. 15; 19(14): 3970-3972]. Thus, the location of the cut made by the FokI chimeric ablator can be adjusted by increasing or decreasing the length of the linker. For example, other linkers for the chimeric ablator (amino acids of 0, 1, 2, 3, 4, 5 or 6 amino acids in length) may be used in combination with spacers of 6, 7, 8, 9, or longer on the ablation site.

The zinc finger is a modular protein which binds DNA in reverse orientation (i.e., the N-terminus of the Zn finger binds starting at the 3' end of the sense strand). Typically, each module or finger uses amino acids in positions: −1, 3, and 6 of its a-helix to target a specific 3-bp recognition site on DNA (i.e., a "triplet"). These helices are specific and selected for specific DNA triplets. Thus, for a 10× zinc finger protein, each of 10 zinc fingers (or modules) may be independently selected to target the unique triplets present in the at least 30 nucleic acid sequence of the invention.

The inventors have demonstrated specific and selective ablation according to the invention using a FokI catalytic domain fused to a 10× zinc finger protein specific for the unique sequence of the ablator. Given the description in the art of zinc fingers of significantly smaller sizes (2-3) and a recent publication that zinc fingers larger than 6× are not successful proteins [Yuka Shimizu, et al, Adding Fingers to an Engineered Zinc Finger Nuclease Can Reduce Activity, Biochemistry 2011, 50, 5033-5041], this result was unexpected.

Once the size and sequence of the at least 30 base pair unique nucleic acid sequence of the ablation recognition site are known (e.g., at least 30 base pairs where the vector is to be delivered to a human), one can engineer a zinc finger which provides for at least one module (1×) for each triplet. Each zinc finger contains a recognition helix specific for a given triplet, in which sequence of recognition helix is engineered to fold into a conserved zinc finger structure in order to present the about seven amino acid sequence in the proper helical form. More particularly, applicants provide in the following Table 2 a selection of illustrative conserved sequences which may be used to construct a zinc finger. In this table, the seven dashes represent the location in which one of the seven amino acid helix recognition sequences may be inserted in order to construct a multi-(X)-zinc finger.

TABLE 2

Conserved Zinc Finger Sequences

| | SEQ ID NO: |
|---|---|
| CRCNECGKSFS-------HQRTH | 706 |
| QFACDICGRKFA-------HTKIH | 707 |
| FACEVCGVRFT-------HMRKH | 708 |
| FACSWQDCNKKFA-------HYRTH | 709 |
| FECKDCGKAFI-------HQRTH | 710 |
| FHCGYCEKSFS-------HIRTH | 711 |
| FKCPVCGKAFR-------HQRTH | 712 |
| FLCQYCAQRFG-------HMKKSH | 713 |
| FQCKTCQRKFS-------HTRTH | 714 |
| FQCNQCGASFT-------HIKLH | 715 |
| FSCSWKGCERRFA-------HRRTH | 716 |

TABLE 2-continued

Conserved Zinc Finger Sequences

| Sequence | SEQ ID NO: |
|---|---|
| GSQKPFQCRICMRNFS-------HIRTH | 717 |
| HKCLECGKCFS-------HQRTH | 718 |
| MAERPFQCRICMRKFA-------HTKIH | 719 |
| PGEKKFACPECPKRFM-------HIKTH | 720 |
| PGEKPFECKDCGKAFI-------HQRTH | 721 |
| PGEKPFKCPVCGKAFR-------HQRTH | 722 |
| PGEKPFMCTWSYCGKRFT-------HKRTH | 723 |
| PGEKPFQCKTCQRKFS-------HTRTH | 724 |
| PGEKPFQCNQCGASFT-------HIKLH | 725 |
| PGEKPHICHIQGCGKVYG-------HLRWH | 726 |
| PGEKPYECDHCGKAFS-------HRRIH | 727 |
| PGEKPYECDHCGKSFS-------HKRTH | 728 |
| PGEKPYECEKCGKAFN-------HKKSH | 729 |
| PGEKPYECHDCGKSFR-------HRRIH | 730 |
| PGEKPYECKECGKAFS-------HQRIH | 731 |
| PGEKPYECNYCGKTFS-------HQRIH | 732 |
| PGEKPYGCHLCGKAFS-------HEMIH | 733 |
| PGEKPYICRKCGRGFS-------HQRTH | 734 |
| PGEKPYKCEECGKAFN-------HKIVH | 735 |
| PGEKPYKCEECGKAFR-------HKIIH | 736 |
| PGEKPYKCEECGKAFT-------HKKIH | 737 |
| PGEKPYKCGQCGKFYS-------HQKIH | 738 |
| PGEKPYKCHQCGKAFI-------HERTH | 739 |
| PGEKPYKCKECGKAFN-------HRRIH | 740 |
| PGEKPYKCKECGQAFR-------HHKLH | 741 |
| PGEKPYKCKQCGKAFG-------HGRTH | 742 |
| PGEKPYKCMECGKAFN-------HQRIH | 743 |
| PGEKPYKCPDCGKSFS-------HQRTH | 744 |
| PGEKPYKCPECGKSFS-------HQRTH | 745 |
| PGEKPYMCSECGRGFS-------HQRTH | 746 |
| PGEKPYRCEECGKAFR-------HKRIH | 747 |
| PGEKPYRCKYCDRSFS-------HVRNIH | 748 |
| PGEKPYTCKQCGKAFS-------HETTH | 749 |
| PGEKPYTCSDCGKAFR-------HRRTH | 750 |
| PGEKPYVCDVEGCTWKFA-------HKKRH | 751 |
| PGEKPYVCRECGRGFR-------HKRTH | 752 |
| PGEKPYVCSKCGKAFT-------HQKIH | 753 |
| PGERPFMCTWSYCGKRFT-------HKRTH | 754 |
| TGEKPFACDICGKKFA-------HTKIH | 755 |
| TGEKPFACDICGRKFA-------HTKIH | 756 |
| TGEKPFQCRICMRNFS-------HIRTH | 757 |
| TGSQKPFQCRICMRNFS-------HIRTH | 758 |
| VPERPFQCQICMRNFS-------HIRTH | 759 |
| YACHLCAKAFI-------HEKTH | 760 |
| YACHLCGKAFT-------HEKTH | 761 |
| YECDHCGKAFS-------HRRIH | 762 |
| YECDHCGKSFS-------HKRTH | 763 |
| YECDVCGKTFT-------HQRTH | 764 |
| YECEKCGKAFN-------HKKSH | 765 |
| YECHDCGKSFR-------HRRIH | 766 |
| YECKECGKAFS-------HQRIH | 767 |
| YECNECGKAFA-------HQRIH | 768 |
| YECNECGKFFS-------HRRSH | 769 |
| YECNTCRKTFS-------HQRTH | 770 |
| YECQDCGRAFN-------HKRTH | 771 |
| YECVQCGKGFT-------HQRVH | 772 |
| YECVQCGKSYS-------HQRRH | 773 |
| YGCHLCGKAFS-------HEMIH | 774 |
| YHCDWDGCGWKFA-------HYRKH | 775 |
| YICRKCGRGFS-------HQRTH | 776 |
| YKCDECGKNFT-------HKRIH | 777 |
| YKCEECGKAFN-------HKIVH | 778 |
| YKCEECGKAFR-------HKIIH | 779 |
| YKCEECGKAFT-------HKKIH | 780 |
| YKCGQCGKFYS-------HQKIH | 781 |
| YKCHQCGKAFI-------HERTH | 782 |
| YKCKECGKAFN-------HHRIH | 783 |
| YKCKECGQAFR-------HHKLH | 784 |
| YKCKQCGKAFG-------HGRTH | 785 |
| YKCMECGKAFN-------HQRIH | 786 |
| YKCPDCGKSFS-------HQRTH | 787 |
| YMCSECGRGFS-------HQRTH | 788 |
| YQCNICGKCFS-------HQRTH | 789 |
| YRCEECGKAFR-------HKRIH | 790 |
| YRCKYCDRSFS-------HVRNIH | 791 |

TABLE 2-continued

Conserved Zinc Finger Sequences

| | SEQ ID NO: |
|---|---|
| YRCSWEGCEWRFA-------HFRKH | 792 |
| YSCGICGKSFS-------HCILH | 793 |
| YTCKQCGKAFS-------HETTH | 794 |
| YTCSDCGKAFR-------HRRTH | 795 |
| YTCSYCGKSFT-------HTRIH | 796 |
| YVCDVEGCTWKFA-------HKKRH | 797 |
| YVCRECGRGFR-------HRRTH | 798 |
| YVCRECRRGFS-------HQRTH | 799 |
| YVCSKCGKAFT-------HQKIH | 800 |
| TGEKPFQCRICMRNFS-------HLRTH | 807 |

An at least 10× zinc finger, or a zinc finger of another length (e.g., selected for a non-human or other application), may contain the zinc finger modules in which each of the recognition helices is inserted into the same conserved sequence. In another embodiment, an ablator may contain zinc finger modules with contain recognition helices inserted into different conserved sequences. In the examples herein, the conserved sequence of (N-terminus)-PGEKPYKCPECGKSFS-XXXXXXX-HQRTH (carboxy terminus), COOH [SEQ ID NO: 745] was used or (N-terminus)-TGEKPFQCRICM-RNFS-XXXXXXX-HLRTH (carboxy terminus)-COOH, wherein XXXXXXX [SEQ ID NO: 807] is the zinc finger recognition helix where used. However, the invention is not limited to these sequences.

According to the invention, in one embodiment, the at least 30 nucleic acid sequence may be 32 base pairs in length in order to accommodation alternate reading frames for the zinc finger.

Depending upon the sequence of the unique nucleic acid sequence of the ablation site, specific zinc finger helices are selected for insertion into the zinc finger conserved sequence. In some embodiments, the unique nucleic acid sequence of the ablation site may contain more than one of the same three base pair triplet. In this instance, one may select the same recognition helix or a different recognition helix.

In one embodiment, the zinc finger for the at least 30 base pair sequence: SEQ ID NO: 806: GGTCGATGTTCG-CAACGTCGATCGTACGTGCA was engineered, so that the zinc finger comprises a nucleic acid sequence encoding at least ten zinc fingers consisting of: (a) a first N-terminal zinc finger comprising a recognition helix which specifically binds to TGC; (b) second zinc finger comprising a recognition helix which specifically binds to ACG; (c) a third zinc finger comprising a recognition helix which specifically binds to CGT; (d) a fourth zinc finger comprising a recognition helix which specifically binds to GAT; (e) a fifth zinc finger comprising a recognition helix which specifically binds to GTC; (f) a sixth zinc finger comprising a recognition helix which specifically binds to AAC; (g) a seventh zinc finger comprising a recognition helix which binds to CGC; (h) an eighth zinc finger comprising a recognition helix that specifically binds to GTT; (i) an ninth zinc finger comprising a recognition helix that specifically binds to GAT; and (j) a tenth zinc finger comprising a recognition helix which specifically binds to GTC.

In the examples provided herein, the recognition helix of (a) which specifically binds to TGC is QRRSLGH (SEQ ID NO: 663); the recognition helix of (b) which specifically binds to ACG is KKNDLTR (aa 29-56 of SEQ ID NO: 60); the recognition helix of (c) which specifically binds to CGT is SRRTCRA (SEQ ID NO: 155); the recognition helix of (d) which specifically binds to GAT is VRHNLTR (SEQ ID NO: 270); the recognition helix of (e) which specifically binds to GTC is DRTSLAR (SEQ ID NO: 540); the recognition helix of (f) which specifically binds to AAC is DSGNLRV (SEQ ID NO: 64); the recognition helix of (g) which specifically binds to CGC is HTGHLLE (SEQ ID NO: 151); the recognition helix of (h) which specifically binds to GTT is TNQALGV (aa 197-224 of SEQ ID NO: 60); the recognition helix of (j) which specifically binds to GAT is VRHNLTR (SEQ ID NO: 270); and the recognition helix of (k) which specifically binds to GTC is DRTSLAR (SEQ ID NO: 540). However, other recognition helices exist for many of these triplets. For example, the recognition helix of (a) which specifically binds to TGC may be selected from the group consisting of: ARNTLVH, QRRSLGH, QARSLRA, QQRSLKN, and QNRSLAH, QGRSLRA, RARNLTL, RGRNLEM, RKRNLIM, RMRNLII, RNRNLVL, RRRNLHL, RRRNLTL, RSRNLDI, RSRNLLL, and RSRNLTL (SEQ ID NO: 658-673); the recognition helix of (b) which specifically binds to ACG may be selected form the group consisting of: KNNDLTR; KRIDLQR; RKHDLNM; RRQTLRQ; KGNDLTR; RNITLVR, RSHDLTV, ASADLTR, QNATRKR, QSGDLTR, RSQTLAQ; and RTDTLRD (SEQ ID NO: 104-119); the recognition helix of (c) which specifically binds to CGT may be selected from the group consisting of RSQTRKT (SEQ ID NO: 154) and SRRTCRA (SEQ ID NO: 155); the recognition helix of (d) which specifically binds to GAT may be selected from the group consisting of VRHNLTR, ISHNLAR, ISSNLQR, LGNNLKR, LNSNLAR, LSTNLTR, LTHNLRR, QSSNLAR, RSDALIQ, SKQALAV, TGQQLRV, TKQRLVV, TRQRLRI, TSANLSR, TSGNLVR, TSQMLVV, TSSNLSR, TTSNLRR, VGHNLSR, VGSNLTR (SEQ ID NO: 251-270); the recognition helix of (e) which specifically binds to GTC may be selected from the group consisting of DRTSLAR, DHSSLKR, APSSLRR, DATQLVR, DPGALVR, DPTSLNR, DRSALAR, DRSALSR, DRSSLRR, DRTPLNR, DRTPLQN, EGGALRR, ESGALRR, NTSLLRR, RSDVLSE, TGAVLRR, TGAVLTR, TKKILTV, TKSLLAR, TMAVLRR, TRAVLRR, TSTILAR, TSTLLKR, and TSTLLNR (SEQ ID NO: 530-553); the recognition helix of (0 which specifically binds to AAC may be selected from the group consisting of DRSNRKT, DSGNLRV, GASALRQ, GASALRS, GGTALRM, GGTALVM, GHTALAL, GHTALRH, GHTALRN, GPTALVN, and HRTNLIA (SEQ ID NO: 63-73); the recognition helix of (g) which specifically binds to CGC may be HTGHLLE (SEQ ID NO: 151); and the recognition helix of (h) which specifically binds to GTT may be selected from the group consisting of HKSSLTR, TNQALGV, AATALRR, HHNSLTR, HSSSLVR, IKAILTR, INHSLRR, IRTSLKR, MNSVLKR, MTSSLRR, QATLLRR, QSSALTR, THTVLAR, TKPVLKI, TNSVLGR, TRHSLGR, TSGALTR, TSGSLTR, TSGSLVR, TSTLLKR, TSTRLDI, TTALLKR, TTSALTR, TTTVLAR, and VGGSLNR (SEQ ID NO: 583-607); the recognition helix of (i) which specifically binds to GAT may be selected from the group consisting of ISHNLAR, VRHNLTR, ISSNLQR, LGNNLKR, LNSNLAR, LSTNLTR, LTHNLRR, QSSNLAR, RSDALIQ, SKQALAV, TGQQLRV, TKQRLVV, TRQRLRI, TSANLSR, TSGNLVR, TSQMLVV, TSSNLSR, TTSNLRR, VGHNLSR, and VGSNLTR (SEQ ID NO: 251-270); and the recognition helix of (j) which specifically binds to GTC may be selected from the group consisting of DRTSLAR, DHSSLRKR, APSSLRR, DATQLVR, DPGALVR, DPTSLNR, DRSALAR, DRSALSR, DRSSLRR, DRTPLNR, DRTPLQN, EGGALRR, ESGALRR, NTSLLRR, RSDVLSE, TGAVLRR, TGAVLTR, TKKILTV, TKSLLAR, TMAVLRR, TRAVLRR, TSTILAR, TSTLLKR, and TSTLLNR (SEQ ID NO: 530-553).

Still other recognition helices for these and other triplets may be utilized in various embodiments of the invention. The following Table 3 provides illustrative recognition helices for various three base pair triplets.

TABLE 3

| Triplet | Recognition Helix (SEQ ID NO:) | |
|---|---|---|
| AAA | QRANLRA (SEQ ID NO: 61) | QRSNLKV (SEQ ID NO: 62) |
| AAC | DRSNRKT (SEQ ID NO: 63) | GGTALVM (SEQ ID NO: 68) |
|  | DSGNLRV (SEQ ID NO: 64) | GHTALAL (SEQ ID NO: 69) |
|  | GASALRQ (SEQ ID NO: 65) | GHTALRH (SEQ ID NO: 70) |
|  | GASALRS (SEQ ID NO: 66) | GHTALRN (SEQ ID NO: 71) |
|  | GGTALRM (SEQ ID NO: 67) | GPTALVN (SEQ ID NO: 72) |
|  |  | HRTNLIA (SEQ ID NO: 73) |
| AAG | RKDNLKN (SEQ ID NO: 74) | RSDNLSV (SEQ ID NO: 76) |
|  | RSANLSV (SEQ ID NO: 75) | RSDNLTQ (SEQ ID NO: 77) |
| AAT | TSSNRKT (SEQ ID NO: 78) | VSSNLNV (SEQ ID NO: 80) |
|  | TTGNLTV (SEQ ID NO: 79) |  |
| ACA | QNATRIN (SEQ ID NO: 81) |  |
|  | SPADLTR (SEQ ID NO: 82) |  |
| ACC | DKKDLTR (SEQ ID NO: 83) |  |
| ACG | ASADLTR (SEQ ID NO: 84) | RKHDLNM (SEQ ID NO: 90) |
|  | KGNDLTR (SEQ ID NO: 85) | RNITLVR (SEQ ID NO: 91) |
|  | KNNDLTR (SEQ ID NO: 86) | RRQTLRQ (SEQ ID NO: 92) |
|  | KRIDLQR (SEQ ID NO: 87) | RSHDLTV (SEQ ID NO: 93) |
|  | QNATRKR (SEQ ID NO: 88) | RSQTLAQ (SEQ ID NO: 94) |
|  | QSGDLTR (SEQ ID NO: 89) | RTDTLRD (SEQ ID NO: 95) |
| ACT | ARSTRTN (SEQ ID NO: 96) | THLDLIR (SEQ ID NO: 98) |
|  | HASTRHC (SEQ ID NO: 97) |  |
| AGA | KNWKLQA (SEQ ID NO: 99) | QSSHLTT (SEQ ID NO: 101) |
|  | QLAHLRA (SEQ ID NO: 100) | RSANLAR (SEQ ID NO: 102) |
| AGC | ERSHLRE (SEQ ID NO: 103) |  |
| AGG | DSAHLTR (SEQ ID NO: 104) | RRAHLRQ (SEQ ID NO: 112) |
|  | QSAHRTK (SEQ ID NO: 105) | RRTHLRV (SEQ ID NO: 113) |
|  | RGNHLVV (SEQ ID NO: 106) | RSDHLKT (SEQ ID NO: 114) |
|  | RMAHLHA (SEQ ID NO: 107) | RSDHLSA (SEQ ID NO: 115) |
|  | RNEHLKV (SEQ ID NO: 108) | RSDHLSQ (SEQ ID NO: 116) |
|  | RPHHLDA (SEQ ID NO: 109) | RSDHLTN (SEQ ID NO: 117) |
|  | RRAHLLN (SEQ ID NO: 110) | RSDHLTQ (SEQ ID NO: 118) |
|  | RRAHLLS (SEQ ID NO: 111) | RSSHLKM (SEQ ID NO: 119) |
| AGT | HRTTLTN (SEQ ID NO: 120) | QSAHLST (SEQ ID NO: 121) |
| ATA | QKSSLIA (SEQ ID NO: 122) |  |
| ATG | RRDELNV (SEQ ID NO: 123) | RSDSLSV (SEQ ID NO: 124) |
| ATT | HKNALQN (SEQ ID NO: 125) |  |
| CAA | DRANLST (SEQ ID NO: 126) | QSGNLTE (SEQ ID NO: 128) |
|  | QKSNLII (SEQ ID NO: 127) | QSSNLTV (SEQ ID NO: 129) |
| CAC | SKKALTE (SEQ ID NO: 130) |  |
| CAG | DSANRTK (SEQ ID NO: 131) | RSDNLSE (SEQ ID NO: 134) |
|  | RADNLTE (SEQ ID NO: 132) | RTDYLVD (SEQ ID NO: 135) |
|  | RSDNLRE (SEQ ID NO: 133) |  |
| CAT | DRSNRIK (SEQ ID NO: 136) | TSGNLTE (SEQ ID NO: 137) |
| CCA | DRSDLSR (SEQ ID NO: 138) | QNSTRIG (SEQ ID NO: 140) |
|  | NRTDLIR (SEQ ID NO: 139) | TSHSLTE (SEQ ID NO: 141) |
| CCC | SKKHLAE (SEQ ID NO: 142) |  |

TABLE 3-continued

| Triplet | Recognition Helix (SEQ ID NO:) | |
|---|---|---|
| CCG | DSSSLTR (SEQ ID NO: 143) | RNDTLTE (SEQ ID NO: 145) |
| | DYDVRKR (SEQ ID NO: 144) | RSDTLSE (SEQ ID NO: 146) |
| CCT | TKNSLTE (SEQ ID NO: 147) | |
| CGA | QSGHLTE (SEQ ID NO: 148) | QSTHLTQ (SEQ ID NO: 150) |
| | QSSHLNV (SEQ ID NO: 149) | |
| CGC | HTGHLLE (SEQ ID NO: 151) | |
| CGG | RSDNLTE (SEQ ID NO: 152) | RSDKLTE (SEQ ID NO: 153) |
| CGT | RSQTRKT (SEQ ID NO: 154) | SRRTCRA (SEQ ID NO: 155) |
| CTA | DSSSRTK (SEQ ID NO: 156) | QNSTLTE (SEQ ID NO: 157) |
| CTC | ASDDLTQ (SEQ ID NO: 158) | |
| CTG | HNYARDC (SEQ ID NO: 159) | RSDALSA (SEQ ID NO: 162) |
| | RNDALTE (SEQ ID NO: 160) | RSDALSN (SEQ ID NO: 163) |
| | RSDALRE (SEQ ID NO: 161) | RSDTLSE (SEQ ID NO: 164) |
| CTT | TTGALTE (SEQ ID NO: 165) | |
| GAA | HKPNLHR (SEQ ID NO: 166) | QRNNLGR (SEQ ID NO: 181) |
| | HRPNLTR (SEQ ID NO: 167) | QRSNLAR (SEQ ID NO: 182) |
| | LGENLRR (SEQ ID NO: 168) | QRSNLVR (SEQ ID NO: 183) |
| | QASNLAR (SEQ ID NO: 169) | QRTNLQR (SEQ ID NO: 184) |
| | QASNLLR (SEQ ID NO: 170) | QSGNLAR (SEQ ID NO: 185) |
| | QASNLTR (SEQ ID NO: 171) | QSNNLNR (SEQ ID NO: 186) |
| | QDGNLGR (SEQ ID NO: 172) | QSSNLTK (SEQ ID NO: 187) |
| | QDGNLTR (SEQ ID NO: 173) | QSSNLTR (SEQ ID NO: 188) |
| | QGSNLAR (SEQ ID NO: 174) | QSSNLVR (SEQ ID NO: 189) |
| | QHPNLTR (SEQ ID NO: 175) | QTNNLGR (SEQ ID NO: 190) |
| | QKGNLLR (SEQ ID NO: 176) | QTNNLNR (SEQ ID NO: 191) |
| | QKSNLIR (SEQ ID NO: 177) | QTNNLTR (SEQ ID NO: 192) |
| | QLSNLTR (SEQ ID NO: 178) | QTVNLDR (SEQ ID NO: 193) |
| | QQSNLSR (SEQ ID NO: 179) | RKPNLLR (SEQ ID NO: 194) |
| | QQTNLTR (SEQ ID NO: 180) | TTTNLRR (SEQ ID NO: 195) |
| GAC | CPSNLRR (SEQ ID NO: 196) | DRANLSR (SEQ ID NO: 207) |
| | | DRGNLTR (SEQ ID NO: 208) |
| | DDANLRR (SEQ ID NO: 197) | DRSNLTR (SEQ ID NO: 209) |
| | DEANLRR (SEQ ID NO: 198) | EEANLRR (SEQ ID NO: 210) |
| | DLSNLKR (SEQ ID NO: 199) | EESNLRR (SEQ ID NO: 211) |
| | DMGNLGR (SEQ ID NO: 200) | EEVNLRR (SEQ ID NO: 212) |
| | DPANLRR (SEQ ID NO: 201) | EGGNLMR (SEQ ID NO: 213) |
| | DPGNLVR (SEQ ID NO: 202) | EKANLTR (SEQ ID NO: 214) |
| | DPSNLIR (SEQ ID NO: 203) | EQANLRR (SEQ ID NO: 215) |
| | DPSNLQR (SEQ ID NO: 204) | HSSNFNK (SEQ ID NO: 216) |
| | DPSNLRR (SEQ ID NO: 205) | RSDNLSE (SEQ ID NO: 217) |
| | DQGNLIR (SEQ ID NO: 206) | |
| GAG | KHSNLAR (SEQ ID NO: 218) | RQMNLDR (SEQ ID NO: 234) |
| | KHSNLTR (SEQ ID NO: 219) | RRDNLLR (SEQ ID NO: 235) |
| | KKTNLTR (SEQ ID NO: 220) | RRDNLNR (SEQ ID NO: 236) |
| | KSSNLRR (SEQ ID NO: 221) | RSANLTR (SEQ ID NO: 237) |
| | QSFNLRR (SEQ ID NO: 222) | RSDHLSR (SEQ ID NO: 238) |
| | REDNLGR (SEQ ID NO: 223) | RSDNLAR (SEQ ID NO: 239) |
| | RGDNLKR (SEQ ID NO: 224) | RSDNLSR (SEQ ID NO: 240) |
| | RGDNLNR (SEQ ID NO: 225) | RSDNLST (SEQ ID NO: 241) |
| | RHDQLTR (SEQ ID NO: 226) | RSDNLTR (SEQ ID NO: 242) |
| | RIDNLGR (SEQ ID NO: 227) | RSDNLVR (SEQ ID NO: 243) |
| | RKSNLIR (SEQ ID NO: 228) | RSSNLQR (SEQ ID NO: 244) |
| | RMSNLDR (SEQ ID NO: 229) | RTHNLKR (SEQ ID NO: 245) |
| | RNTNLTR (SEQ ID NO: 230) | RTHNLTR (SEQ ID NO: 246) |
| | RPHNLLR (SEQ ID NO: 231) | RVDNLPR (SEQ ID NO: 247) |
| | RQDNLGR (SEQ ID NO: 232) | SGSNFTR (SEQ ID NO: 248) |
| | RQDNLQR (SEQ ID NO: 233) | TNNNLAR (SEQ ID NO: 249) |
| | | VHWNLMR (SEQ ID NO: 250) |
| GAT | ISHNLAR (SEQ ID NO: 251) | TKQRLVV (SEQ ID NO: 261) |
| | ISSNLQR (SEQ ID NO: 252) | TRQRLRI (SEQ ID NO: 262) |
| | LGNNLKR (SEQ ID NO: 253) | TSANLSR (SEQ ID NO: 263) |
| | LNSNLAR (SEQ ID NO: 254) | TSGNLVR (SEQ ID NO: 264) |
| | LSTNLTR (SEQ ID NO: 255) | TSQMLVV (SEQ ID NO: 265) |
| | LTHNLRR (SEQ ID NO: 256) | TSSNLSR (SEQ ID NO: 266) |
| | QSSNLAR (SEQ ID NO: 257) | TTSNLRR (SEQ ID NO: 267) |

TABLE 3-continued

| Triplet | Recognition Helix (SEQ ID NO:) | |
|---|---|---|
| | RSDALIQ (SEQ ID NO: 258) | VGHNLSR (SEQ ID NO: 268) |
| | SKQALAV (SEQ ID NO: 259) | VGSNLTR (SEQ ID NO: 269) |
| | TGQQLRV (SEQ ID NO: 260) | VRHNLTR (SEQ ID NO: 270) |
| GCA | DKAQLGR (SEQ ID NO: 271) | QPNTLTR (SEQ ID NO: 286) |
| | DRSALSR (SEQ ID NO: 272) | QRGTLNR (SEQ ID NO: 287) |
| | DRSQLAR (SEQ ID NO: 273) | QSGDLRR (SEQ ID NO: 288) |
| | ERGTLAR (SEQ ID NO: 274) | QSGDLTR (SEQ ID NO: 289) |
| | HNGTLKR (SEQ ID NO: 275) | QSGSLTR (SEQ ID NO: 290) |
| | KNTRLSV (SEQ ID NO: 276) | QSNVLSR (SEQ ID NO: 291) |
| | LKHSLLR (SEQ ID NO: 277) | QSTTLKR (SEQ ID NO: 292) |
| | LNHTLKR (SEQ ID NO: 278) | QTATLKR (SEQ ID NO: 293) |
| | LRHSLSR (SEQ ID NO: 279) | QTNTLKR (SEQ ID NO: 294) |
| | QDNTLRR (SEQ ID NO: 280) | RGQELRR (SEQ ID NO: 295) |
| | QDVSLVR (SEQ ID NO: 281) | RRQELHR (SEQ ID NO: 296) |
| | QGGTLRR (SEQ ID NO: 282) | RRQELKR (SEQ ID NO: 297) |
| | QGNTLTR (SEQ ID NO: 283) | RRQELTR (SEQ ID NO: 298) |
| | QKGTLGR (SEQ ID NO: 284) | RRVDLLR (SEQ ID NO: 299) |
| | QNGTLTR (SEQ ID NO: 285) | SPEQLAR (SEQ ID NO: 300) |
| GCC | DCRDLAR (SEQ ID NO: 301) | DSPTLRR (SEQ ID NO: 313) |
| | DGSTLNR (SEQ ID NO: 302) | DSSVLRR (SEQ ID NO: 314) |
| | DGSTLRR (SEQ ID NO: 303) | EHRGLKR (SEQ ID NO: 315) |
| | DHSNLSR (SEQ ID NO: 304) | ERGTLAR (SEQ ID NO: 316) |
| | DKSCLNR (SEQ ID NO: 305) | ERRGLAR (SEQ ID NO: 317) |
| | DKSVLAR (SEQ ID NO: 306) | ERRGLDR (SEQ ID NO: 318) |
| | DPSNLRR (SEQ ID NO: 307) | KRRDLDR (SEQ ID NO: 319) |
| | DPSTLRR (SEQ ID NO: 308) | LKKDLLR (SEQ ID NO: 320) |
| | DRRTLDR (SEQ ID NO: 309) | SHTVLTR (SEQ ID NO: 321) |
| | DRSDLTR (SEQ ID NO: 310) | SKKSLTR (SEQ ID NO: 322) |
| | DRSSLTR (SEQ ID NO: 311) | SNKDLTR (SEQ ID NO: 323) |
| | DRSSRTK (SEQ ID NO: 312) | VRKDLTR (SEQ ID NO: 324) |
| GCG | KADTLVR (SEQ ID NO: 325) | RRHTLTR (SEQ ID NO: 343) |
| | | RRLTLLR (SEQ ID NO: 344) |
| | KHDTLHR (SEQ ID NO: 326) | RSDDLQR (SEQ ID NO: 345) |
| | KNNDLTR (SEQ ID NO: 327) | RSDDLTR (SEQ ID NO: 346) |
| | RADTLRR (SEQ ID NO: 328) | RSDDLVR (SEQ ID NO: 347) |
| | RAHTLRR (SEQ ID NO: 329) | RSDELNR (SEQ ID NO: 348) |
| | REDSLPR (SEQ ID NO: 330) | RSDELQR (SEQ ID NO: 349) |
| | RHAALLS (SEQ ID NO: 331) | RSDELSR (SEQ ID NO: 350) |
| | RKDGLTR (SEQ ID NO: 332) | RSDELTR (SEQ ID NO: 351) |
| | RKGTLDR (SEQ ID NO: 333) | RSDERKR (SEQ ID NO: 352) |
| | RKLGLLR (SEQ ID NO: 334) | RSDSLSK (SEQ ID NO: 353) |
| | RLDMLAR (SEQ ID NO: 335) | RSDTLKK (SEQ ID NO: 354) |
| | RLRDLPR (SEQ ID NO: 336) | RSDVLTR (SEQ ID NO: 355) |
| | RNLTLAR (SEQ ID NO: 337) | RSNTLLR (SEQ ID NO: 356) |
| | RNLTLVR (SEQ ID NO: 338) | RTDLLRR (SEQ ID NO: 357) |
| | RPDGLAR (SEQ ID NO: 339) | RTDSLPR (SEQ ID NO: 358) |
| | RRDDLTR (SEQ ID NO: 340) | RTDTLAR (SEQ ID NO: 359) |
| | RRDGLTR (SEQ ID NO: 341) | RVDDLGR (SEQ ID NO: 360) |
| | RRHGLDR (SEQ ID NO: 342) | |
| GCT | ARSTRTT (SEQ ID NO: 361) | QSSDLRR (SEQ ID NO: 377) |
| | EGSGLKR (SEQ ID NO: 362) | QSSDLSR (SEQ ID NO: 378) |
| | GATALKR (SEQ ID NO: 363) | QSSDLTR (SEQ ID NO: 379) |
| | KHQTLQR (SEQ ID NO: 364) | THSMLAR (SEQ ID NO: 380) |
| | LKHDLRR (SEQ ID NO: 365) | TKPILVR (SEQ ID NO: 381) |
| | LRASLRR (SEQ ID NO: 366) | TKQILGR (SEQ ID NO: 382) |
| | LRQTLAR (SEQ ID NO: 367) | TKQVLDR (SEQ ID NO: 383) |
| | LRTSLVR (SEQ ID NO: 368) | TSGELVR (SEQ ID NO: 384) |
| | MKNTLTR (SEQ ID NO: 369) | TSSGLTR (SEQ ID NO: 385) |
| | NGQGLRR (SEQ ID NO: 370) | TTQALRR (SEQ ID NO: 386) |
| | NKQALDR (SEQ ID NO: 371) | VGASLKR (SEQ ID NO: 387) |
| | NRSDRTR (SEQ ID NO: 372) | VGNSLTR (SEQ ID NO: 388) |
| | QRQALDR (SEQ ID NO: 373) | VKNTLTR (SEQ ID NO: 389) |
| | QRSDLHR (SEQ ID NO: 374) | VRQGLTR (SEQ ID NO: 390) |
| | QRSDLTR (SEQ ID NO: 375) | VSNSLAR (SEQ ID NO: 391) |
| | QSSDLQR (SEQ ID NO: 376) | VSNTLTR (SEQ ID NO: 392) |
| GGA | DKTKLNV (SEQ ID NO: 393) | QSQHLVR (SEQ ID NO: 409) |
| | DKTKLRV (SEQ ID NO: 394) | QSTHLTR (SEQ ID NO: 410) |
| | DNAHLAR (SEQ ID NO: 395) | QTTHLRR (SEQ ID NO: 411) |
| | QANHLSR (SEQ ID NO: 396) | QTTHLSR (SEQ ID NO: 412) |
| | QGGHLKR (SEQ ID NO: 397) | QTTHLSR (SEQ ID NO: 413) |
| | QHSHLVR (SEQ ID NO: 398) | QVSHLTR (SEQ ID NO: 414) |
| | QKPHLSR (SEQ ID NO: 399) | RMERLDR (SEQ ID NO: 415) |
| | QMSHLKR (SEQ ID NO: 400) | RPAKLVL (SEQ ID NO: 416) |

TABLE 3-continued

| Triplet | Recognition Helix (SEQ ID NO:) | |
|---|---|---|
| | QNSHLRR (SEQ ID NO: 401) | RPSKLVL (SEQ ID NO: 417) |
| | QNSHLRR (SEQ ID NO: 402) | RRDHRTT (SEQ ID NO: 418) |
| | QRAHLER (SEQ ID NO: 403) | RSTHLRV (SEQ ID NO: 419) |
| | QRAHLIR (SEQ ID NO: 404) | RTDRLIR (SEQ ID NO: 420) |
| | QSAHLKR (SEQ ID NO: 405) | THAHLTR (SEQ ID NO: 421) |
| | QSGHLAR (SEQ ID NO: 406) | TSAHLAR (SEQ ID NO: 422) |
| | QSGHLQR (SEQ ID NO: 407) | YNTHLTR (SEQ ID NO: 423) |
| | QSGHLSR (SEQ ID NO: 408) | |
| GGC | AKSKLDR (SEQ ID NO: 424) | KNHSLNN (SEQ ID NO: 437) |
| | APSKLDR (SEQ ID NO: 425) | KNVSLTH (SEQ ID NO: 438) |
| | DGGHLTR (SEQ ID NO: 426) | LKEHLTR (SEQ ID NO: 439) |
| | DKSHLPR (SEQ ID NO: 427) | QSSHLAR (SEQ ID NO: 440) |
| | DPGHLVR (SEQ ID NO: 428) | SKHKLER (SEQ ID NO: 441) |
| | DRSHLAR (SEQ ID NO: 429) | SPSKLAR (SEQ ID NO: 442) |
| | DRSHLSR (SEQ ID NO: 430) | SPSKLVR (SEQ ID NO: 443) |
| | DRSHLTR (SEQ ID NO: 431) | TNSKLTR (SEQ ID NO: 444) |
| | EKSHLKR (SEQ ID NO: 432) | TPSKLDR (SEQ ID NO: 445) |
| | EKSHLTR (SEQ ID NO: 433) | TRAKLHI (SEQ ID NO: 446) |
| | ENSKLNR (SEQ ID NO: 434) | VPSKLAR (SEQ ID NO: 447) |
| | ESGHLKR (SEQ ID NO: 435) | VPSKLKR (SEQ ID NO: 448) |
| | ESGHLRR (SEQ ID NO: 436) | VPSKLLR (SEQ ID NO: 449) |
| GGG | KGDHLRR (SEQ ID NO: 450) | RNTHLAR (SEQ ID NO: 464) |
| | | RQGHLKR (SEQ ID NO: 465) |
| | KKDHLHR (SEQ ID NO: 451) | RRAHLQN (SEQ ID NO: 466) |
| | KRERLDR (SEQ ID NO: 452) | RREHLVR (SEQ ID NO: 467) |
| | KRERLER (SEQ ID NO: 453) | RRSHLTR (SEQ ID NO: 468) |
| | KSNHLHV (SEQ ID NO: 454) | RSAHLAR (SEQ ID NO: 469) |
| | KTSHLRA (SEQ ID NO: 455) | RSAHLSR (SEQ ID NO: 470) |
| | RGDKLAL (SEQ ID NO: 456) | RSDHLAR (SEQ ID NO: 471) |
| | RGDKLGP (SEQ ID NO: 457) | RSDHLSK (SEQ ID NO: 472) |
| | RGNHLRR (SEQ ID NO: 458) | RSDHLSR (SEQ ID NO: 473) |
| | RIDKLGG (SEQ ID NO: 459) | RSDHLTR (SEQ ID NO: 474) |
| | RKHHLGR (SEQ ID NO: 460) | RSDKLNR (SEQ ID NO: 475) |
| | RKHRLDG (SEQ ID NO: 461) | RSDKLVR (SEQ ID NO: 476) |
| | RNDKLVP (SEQ ID NO: 462) | RTEHLAR (SEQ ID NO: 477) |
| | RNHGLVR (SEQ ID NO: 463) | |
| GGT | DSSKLSR (SEQ ID NO: 478) | RRQKLTI (SEQ ID NO: 493) |
| | | RRSRLVR (SEQ ID NO: 494) |
| | | RSDHLST (SEQ ID NO: 495) |
| | EAHHLSR (SEQ ID NO: 479) | RSDHLTT (SEQ ID NO: 496) |
| | HGHRLKT (SEQ ID NO: 480) | TKQKLQT (SEQ ID NO: 497) |
| | IPNHLAR (SEQ ID NO: 481) | TKQRLEV (SEQ ID NO: 498) |
| | IRHHLKR (SEQ ID NO: 482) | TRQKLET (SEQ ID NO: 499) |
| | LTQGLRR (SEQ ID NO: 483) | TRTRLVI (SEQ ID NO: 500) |
| | MGHHLKR (SEQ ID NO: 484) | TSGHLSR (SEQ ID NO: 501) |
| | MKHHLAR (SEQ ID NO: 485) | TSGHLVR (SEQ ID NO: 502) |
| | MKHHLDA (SEQ ID NO: 486) | TTTKLAI (SEQ ID NO: 502) |
| | MSDHLSR (SEQ ID NO: 487) | VDHHLRR (SEQ ID NO: 504) |
| | MSHHLSR (SEQ ID NO: 488) | VKHGLGR (SEQ ID NO: 505) |
| | QPHHLPR (SEQ ID NO: 489) | VKHGLTR (SEQ ID NO: 506) |
| | QSSHLAR (SEQ ID NO: 490) | WPSNLTR (SEQ ID NO: 507) |
| | QSSHLTR (SEQ ID NO: 491) | YNWHLQR (SEQ ID NO: 508) |
| | RQSRLQR (SEQ ID NO: 492) | |
| GTA | QGGALQR (SEQ ID NO: 509) | QRSSLVR (SEQ ID NO: 520) |
| | QGTSLAR (SEQ ID NO: 510) | QSGALAR (SEQ ID NO: 521) |
| | QKQALDR (SEQ ID NO: 511) | QSGALTR (SEQ ID NO: 522) |
| | QKQALTR (SEQ ID NO: 512) | QSGSLTR (SEQ ID NO: 523) |
| | QKVSLKR (SEQ ID NO: 513) | QSGTLTR (SEQ ID NO: 524) |
| | QMNALQR (SEQ ID NO: 514) | QSSSLIR (SEQ ID NO: 525) |
| | QQQALKR (SEQ ID NO: 515) | QSSSLVR (SEQ ID NO: 526) |
| | QQQALTR (SEQ ID NO: 516) | QSSTLTR (SEQ ID NO: 527) |
| | QQQALVR (SEQ ID NO: 517) | QSTSLQR (SEQ ID NO: 528) |
| | QQSSLLR (SEQ ID NO: 518) | TSSARTT (SEQ ID NO: 529) |
| | QRASLTR (SEQ ID NO: 519) | |
| GTC | APSSLRR (SEQ ID NO: 530) | ESGALRR (SEQ ID NO: 542) |
| | DATQLVR (SEQ ID NO: 531) | NTSLLRR (SEQ ID NO: 543) |
| | DHSSLKR (SEQ ID NO: 532) | RSDVLSE (SEQ ID NO: 544) |
| | DPGALVR (SEQ ID NO: 533) | TGAVLRR (SEQ ID NO: 545) |
| | DPTSLNR (SEQ ID NO: 534) | TGAVLTR (SEQ ID NO: 546) |
| | DRSALAR (SEQ ID NO: 535) | TKKILTV (SEQ ID NO: 547) |
| | DRSALSR (SEQ ID NO: 536) | TKSLLAR (SEQ ID NO: 548) |
| | DRSSLRR (SEQ ID NO: 537) | TMAVLRR (SEQ ID NO: 549) |
| | DRTPLNR (SEQ ID NO: 538) | TRAVLRR (SEQ ID NO: 550) |

TABLE 3-continued

| Triplet | Recognition Helix (SEQ ID NO:) | |
|---|---|---|
| | DRTPLQN (SEQ ID NO: 539) | TSTILAR (SEQ ID NO: 551) |
| | DRTSLAR (SEQ ID NO: 540) | TSTLLKR (SEQ ID NO: 552) |
| | EGGALRR (SEQ ID NO: 541) | TSTLLNR (SEQ ID NO: 553) |
| GTG | RASVLDI (SEQ ID NO: 554) | RRFILSR (SEQ ID NO: 569) |
| | RGDALAR (SEQ ID NO: 555) | RRHILDR (SEQ ID NO: 570) |
| | RHTSLTR (SEQ ID NO: 556) | RSAALSR (SEQ ID NO: 571) |
| | RKDALHV (SEQ ID NO: 557) | RSDALAR (SEQ ID NO: 572) |
| | RKHILIH (SEQ ID NO: 558) | RSDALRT (SEQ ID NO: 573) |
| | RKTALNR (SEQ ID NO: 559) | RSDALSR (SEQ ID NO: 574) |
| | RNFILAR (SEQ ID NO: 560) | RSDALTR (SEQ ID NO: 575) |
| | RNFILQR (SEQ ID NO: 561) | RSDELVR (SEQ ID NO: 576) |
| | RNFVLAR (SEQ ID NO: 562) | RSHILTN (SEQ ID NO: 577) |
| | RNTALQH (SEQ ID NO: 563) | RTSSLKR (SEQ ID NO: 578) |
| | RNVALGN (SEQ ID NO: 564) | RTVALNR (SEQ ID NO: 579) |
| | RNVNLVT (SEQ ID NO: 565) | SRFTLGR (SEQ ID NO: 580) |
| | RPDALPR (SEQ ID NO: 566) | SRFTLGR (SEQ ID NO: 581) |
| | RRAALGP (SEQ ID NO: 567) | VSSSLRR (SEQ ID NO: 582) |
| | RREVLEN (SEQ ID NO: 568) | |
| GTT | AATALRR (SEQ ID NO: 583) | TKPVLKI (SEQ ID NO: 595) |
| | HHNSLTR (SEQ ID NO: 584) | TRHSLGR (SEQ ID NO: 598) |
| | HKSSLTR (SEQ ID NO: 585) | TSGALTR (SEQ ID NO: 599) |
| | HSSSLVR (SEQ ID NO: 586) | TSGSLTR (SEQ ID NO: 600) |
| | IKAILTR (SEQ ID NO: 587) | TSGSLVR (SEQ ID NO: 601) |
| | INHSLRR (SEQ ID NO: 588) | TSTLLKR (SEQ ID NO: 602) |
| | IRTSLKR (SEQ ID NO: 589) | TSTRLDI (SEQ ID NO: 603) |
| | MNSVLKR (SEQ ID NO: 590) | TTALLKR (SEQ ID NO: 604) |
| | MTSSLRR (SEQ ID NO: 591) | TTSALTR (SEQ ID NO: 605) |
| | QATLLRR (SEQ ID NO: 592) | TTTVLAR (SEQ ID NO: 606) |
| | QSSALTR (SEQ ID NO: 593) | VGGSLNR (SEQ ID NO: 607) |
| | THTVLAR (SEQ ID NO: 594) | |
| TAA | QGGNLAL (SEQ ID NO: 608) | QQGNLRN (SEQ ID NO: 611) |
| | QGGNLTL (SEQ ID NO: 609) | QRGNLNM (SEQ ID NO: 612) |
| | QQGNLQL (SEQ ID NO: 610) | QSGNLHT (SEQ ID NO: 613) |
| TAC | NSDHLTN (SEQ ID NO: 614) | |
| TAG | QGYNLAG (SEQ ID NO: 615) | RPESLAP (SEQ ID NO: 625) |
| | RAHNLLL (SEQ ID NO: 616) | RPESLRP (SEQ ID NO: 626) |
| | REDNLHT (SEQ ID NO: 617) | RRDGLAG (SEQ ID NO: 627) |
| | RGHNLLV (SEQ ID NO: 618) | RRDHLSL (SEQ ID NO: 628) |
| | RGTNLRT (SEQ ID NO: 619) | RRDHLSP (SEQ ID NO: 629) |
| | RHDGLAG (SEQ ID NO: 620) | RRDNLPK (SEQ ID NO: 630) |
| | RIDHLVP (SEQ ID NO: 621) | RRRNLQI (SEQ ID NO: 631) |
| | RKTGLLI (SEQ ID NO: 622) | RSHNLKL (SEQ ID NO: 632) |
| | RLDGLAG (SEQ ID NO: 623) | RSHNLRL (SEQ ID NO: 633) |
| | RPEGLST (SEQ ID NO: 624) | TSSNRKK (SEQ ID NO: 634) |
| TCA | QSADRTK (SEQ ID NO: 635) | |
| TCC | DKRSLPH (SEQ ID NO: 636) | |
| TCG | ASSTRTK (SEQ ID NO: 637) | RMDSLGG (SEQ ID NO: 644) |
| | HSSDLTR (SEQ ID NO: 638) | RRDGLSG (SEQ ID NO: 645) |
| | KNNDLLK (SEQ ID NO: 639) | RSDELRT (SEQ ID NO: 646) |
| | NRSDLSR (SEQ ID NO: 640) | RSDGLRG (SEQ ID NO: 647) |
| | QSSDLSK (SEQ ID NO: 641) | RSDTLPA (SEQ ID NO: 648) |
| | RADGLQL (SEQ ID NO: 642) | RSDTLPL (SEQ ID NO: 649) |
| | RGDSLKK (SEQ ID NO: 643) | RSSDLSR (SEQ ID NO: 650) |
| | | RTDSLQP (SEQ ID NO: 651) |
| TCT | NNRDRTK (SEQ ID NO: 652) | SKPNLKM (SEQ ID NO: 654) |
| | QRNTLKG (SEQ ID NO: 653) | |
| TGA | QAGHLAS (SEQ ID NO: 655) | QSGHLTK (SEQ ID NO: 657) |
| | QREHLTT (SEQ ID NO: 656) | |
| TGC | ANRTLVH (SEQ ID NO: 658) | RRRNLHL (SEQ ID NO: 669) |
| | QARSLRA (SEQ ID NO: 659) | RRRNLTL (SEQ ID NO: 670) |
| | QGRSLRA (SEQ ID NO: 660) | RSRNLDI (SEQ ID NO: 671) |
| | QNRSLAH (SEQ ID NO: 661) | RSRNLLL (SEQ ID NO: 672) |
| | QQRSLKN (SEQ ID NO: 662) | RSRNLTL (SEQ ID NO: 673) |
| | QRRSLGH (SEQ ID NO: 663) | |
| | RARNLTL (SEQ ID NO: 664) | |
| | RGRNLEM (SEQ ID NO: 665) | |
| | RKRNLEM (SEQ ID NO: 666) | |

TABLE 3-continued

| Triplet | Recognition Helix (SEQ ID NO:) | |
|---|---|---|
| | RMRNLII (SEQ ID NO: 667) | |
| | RNRNLVL (SEQ ID NO: 668) | |
| TGG | RMDHLAG (SEQ ID NO: 674) | RSDHLSL (SEQ ID NO: 679) |
| | RNAHRIN (SEQ ID NO: 675) | RSDHLST (SEQ ID NO: 680) |
| | RRDHLSL (SEQ ID NO: 676) | RSDHLTT (SEQ ID NO: 681) |
| | RREHLTI (SEQ ID NO: 677) | RTESLHI (SEQ ID NO: 682) |
| | RSDHLRE (SEQ ID NO: 678) | |
| TGT | KRQHLEY (SEQ ID NO: 683) | QQHGLRH (SEQ ID NO: 691) |
| | QAHGLTA (SEQ ID NO: 684) | QRHGLSS (SEQ ID NO: 692) |
| | QAHGLTG (SEQ ID NO: 685) | RHQHLKL (SEQ ID NO: 693) |
| | QPGHLTA (SEQ ID NO: 686) | RKQHLQL (SEQ ID NO: 694) |
| | QPHGLAH (SEQ ID NO: 687) | RKQHLTL (SEQ ID NO: 695) |
| | QPHGLGA (SEQ ID NO: 688) | RKQHLVL (SEQ ID NO: 696) |
| | QPHGLRA (SEQ ID NO: 689) | RRQALEY (SEQ ID NO: 697) |
| | QPHGLRH (SEQ ID NO: 690) | RRQHLQY (SEQ ID NO: 698) |
| TTA | QQTGLNV (SEQ ID NO: 699) | |
| TTC | QRNALRG (SEQ ID NO: 700) | RANHLTI (SEQ ID NO: 701) |
| TTG | RADALMV (SEQ ID NO: 702) | RSDSLSA (SEQ ID NO: 703) |
| TTT | HSNARKT (SEQ ID NO: 704) | QRNALSG (SEQ ID NO: 705) |

In one embodiment, the endonuclease catalytic domain is linked to a zinc finger in which the at least 10 independently selected recognition helices are all different. In certain embodiments, it will be desirable to include different recognition helices to a repeated triplet of base pairs in the ablation site. In other embodiments, recognition helices to any repeated triplets are the same. For example, 0, 1, 2, or 3 of the recognition helices selected are the same.

In certain embodiments, an AAV vector contains two or more endonuclease ablation sites, which may the same or different from one another. These endonuclease ablation sites may be engineered into the vector in a variety of configurations. More particularly, an AAV vector carrying a gene of interest (GOI) is engineered to contain at least one ablation site 5' to the coding strand of the gene of interest. Where the vector contains two or more ablation sites, the second ablation site may be located: 3' to the gene of interest in sense orientation; 3' to the gene of interest in inverted orientation; two ablation sites can be located 5' to the gene of interest, with one of sense orientation and the other in inverted orientation, or both in sense orientation; or the vector may contain one or two ablation sites 5' to the gene of interest (one in sense and one in inverted orientation or both in sense orientation) and two ablation sites 3' to the gene of interest (one in sense and one in inverted orientation or both in sense orientation).

Where two ablation sites are located such that there is no intervening gene of interest, i.e., two 5' or two 3' ablation sites, the ablation sites may be separated by a spacer. Any suitable spacer may be selected and the spacer sequence may be a non-coding sequence. In another embodiment, the spacer sequence may be a reporter gene, transgene, or gene of interest.

In one embodiment, when a composition of the invention contains more than one ablation site, the ablation sites are the same. In another embodiment, when a composition or vector system of the invention contains more than one ablation site, each site differs from the other and each is specifically and selectively targeted by a different chimeric endonuclease.

In the working examples below, an ablator encoded by the sequence: 10×ZF-FokI_Cat nucleotide sequence: SEQ ID NO: 59, is illustrated:

ATGGGCGAGAAGCCCTACAAGTGCCCTGAGTGCGGCAAGAGCTTCAGCCA
GAGAAGAAGCCTGGGCCACCACCAGCGTACGCACCCCGGCGAGAAACCTT
ATAAGTGTCCCGAATGTGGCAAGTCCTTCAGCAAGAAGAACGACCTGACC
CGGCACCAGCGGACACACCCCGGGGAAAAGCCATACAAATGTCCAGAGTG
TGGGAAGTCTTTCTCCAGCCGGCGGACCTGCAGAGCCCATCAGAGAACAC
ATACCGGGGAGAAGCCTTTCCAGTGCCGGATCTGCATGAGAAACTTCAGC
GTGCGGCACAACCTGACCAGACACCTGAGGACCCATACCGGCGAAAAACC
CTTTCAGTGCAGAATCTGTATGCGGAACTTCTCCGACCGGACCAGCCTGG
CCCGGCATCTGAGAACTCATCCTGGGGAAAAGCCCTATAAGTGTCCAGAA
TGCGGGAAATCCTTTAGCGACAGCGGCAACCTGCGGGTGCACCAGAGGAC
TCATCCAGGCGAGAAACCCTACAAATGCCCCGAATGCGGAAAGTCATTCT
CCCACACCGGCCATCTGCTCGAGCATCAGCGGACCCACACTGGGGAGAAA
CCATTTCAGTGTCGCATCTGTATGAGGAATTTCAGCACCAACCAGGCCCT
GGGCGTGCACCTGAGAACACACCCAGGCGAGAAGCCTTACAAGTGTCCAG
AGTGCGGAAAGTCATTTTCCGTGCGCCACAATCTGACACGGCATCAGCGC
ACCCATCCCGGCGAGAAGCCTTACAAATGCCCCGAGTGTGGCAAATCTTT
CAGTGACCGGACCTCTCTGGCCAGACATCAGAGGACACACGGCACTAGT
GGCAAGCAGCTGGTGAAAAGCGAGCTGGAAGAGAAGAAGTCCGAGCTGC
GGCACAAGCTGAAATACGTGCCCCACGAGTACATCGAGCTGATCGAGAT
CGCCCCGGAACCCCACCCAGGACAGAATCCTGGAAATGAAGGTCATGGA
ATTTTTCATGAAGGTGTACGGCTACCGGGGCGAGCACCTGGGCGGCAGCA
GAAAACCCGACGGCGCCATCTACACCGTGGGCAGCCCCATCGACTACGG
CGTGATCGTGGACACCAAGGCCTACAGCGGCGGCTACAACCTGCCCATC
GGACAGGCCGACGAGATGCAGAGATACGTGGAAGAGAACCAGACCCGG

```
                                                    -continued
AACAAGCACATCAACCCCAACGAGTGGTGGAAGGTGTACCCCAGCAGCG

TGACCGAGTTCAAGTTCCTGTTCGTGTCCGGCCACTTCAAGGGCAACTAC

AAGGCCCAGCTGACCCGGCTGAACCACATCACCAACTGCAACGGCGCTG

TGCTGAGCGTGGAAGAACTGCTGATCGGCGGCGAGATGATCAAGGCCGG

CACCCTGACCCTGGAAGAAGTGCGGCGGAAGTTCAACAACGGCGAGATC

AACTTCTGATAG.
```

The transcribed illustrative ablator has the sequence: 10×ZF-FokI_Cat amino acid sequence: SEQ ID NO: 60:

```
MGEKPYKCPECGKSFSQRRSLGHHQRTHPGEKPYKCPECGKSFSKKNDLT

RHQRTHPGEKPYKCPECGKSFSSRRTCRAHQRTHTGEKPFQCRICMRNF

SVRHNLTRHLRTHTGEKPFQCRICMRNFSDRTSLARHLRTHPGEKPYKCP

ECGKSFSDSGNLRVHQRTHPGEKPYKCPECGKSFSHTGHLLEHQRTHTG

EKPFQCRICMRNFSTNQALGVHLRTHPGEKPYKCPECGKSFSVRHNLTRH

QRTHPGEKPYKCPECGKSFSDRTSLARHQRTHGTSGKQLVKSELEEKKSE

LRHKLKYVPHEYIELIEIARNPTQDRILEMKVMEFFMKVYGYRGEHLGGS

RKPDGAIYTVGSPIDYGVIVDTKAYSGGYNLPIGQADEMQRYVEENQTRN

KHINPNEWWKVYPSSVTEFKFLFVSGHFKGNYKAQLTRLNHITNCNGAV

LSVEELLIGGEMIKAGTLTLEEVRRKFNNGEINF.
```

In an additional embodiment, the ablator is engineered such that it is controlled by a cassette that is activated by a transcription factor following being dimerized by a pharmacologic agent, such as described in detail in this specification and incorporated herein by reference. Typically, this cassette is comprises two transcription units. One of the two transcription units encodes the DNA binding domain of the transcription factor fused to a binding domain for the pharmacological agent in operative association with a first promoter; and a second of the two transcription units encoding the activation domain of the transcription factor fused to a binding domain for the pharmacological agent in operative association with a second promoter. As described in more detail elsewhere in the specification and incorporated herein, the first promoter and the second promoter are independently selected from a constitutive promoter and an inducible promoter. In one embodiment, the first and second promoters are both constitutive promoters and the pharmacological agent is a dimerizer that dimerizes the domains of the transcription factor. In another embodiment, one of the first promoter and the second promoters is an inducible promoter. Optionally, the two transcription units are a bicistronic unit containing an IRES or furin-2A. Various genetic elements and methods suitable for vector construction are described elsewhere in the specification and incorporated herein by reference.

In a further embodiment, the promoter is controlled by a rapamycin—regulatable system and the pharmacological agent is rapamycin or a rapalog.

This embodiment, using the unique (at least 30 bp) nucleic acid sequence in the ablation recognition site and the chimeric endonuclease containing at least 10× zinc fingers, can be generated as described herein and other techniques known to those of skill in the art.

Methods for Generating the Replication-Defective Virus Compositions

Many methods have been established for the efficient production of recombinant AAVs (rAAVs) that package a transgene—these can be used or adapted to generate the replication-defective virus compositions of the invention. In a one system, a producer cell line is transiently transfected with a construct that encodes the transgene flanked by ITRs and a construct(s) that encodes rep and cap. In a second system, a packaging cell line that stably supplies rep and cap is transiently transfected with a construct encoding the transgene flanked by ITRs. In a third system, a stable cell line that supplies the transgene flanked by ITRs and rep/cap is used. One method for minimizing the possibility of generating replication competent AAV (rcAAV) using these systems is by eliminating regions of homology between regions flanking the rep/cap cassette and the ITRs that flank the transgene. However, in each of these systems, AAV virions are produced in response to infection with helper adenovirus or herpesvirus, requiring the separation of the rAAVs from contaminating virus.

More recently, systems have been developed that do not require infection with helper virus to recover the AAV—the required helper functions (i.e., adenovirus E1, E2a, VA, and E4 or herpesvirus UL5, UL8, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level. In yet another system, the transgene flanked by ITRs and rep/cap genes are introduced into insect cells by infection with baculovirus-based vectors. For reviews on these production systems, see generally, e.g., Grieger & Samulski, 2005; and Btining et al., 2008; Zhang et ai., 2009, "Adenovirus-adeno-associated virus hybrid for large-scale recombinant adeno-associated virus production," *Human Gene Therapy* 20:922-929, the contents of each of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065. See also the paragraphs below, which describe methods for scaling up AAV production using these systems and variants thereof.

Due to size constraints of AAV for packaging (tolerating a transgene of approximately 4.5 kb), the transcription unites) (i.e., the transgene unit, the ablator unit, and the dimerizable transcription factor unit) described may need to be engineered and packaged into two or more replication-deficient AAV stocks. This may be preferable, because there is evidence that exceeding the packaging capacity may lead to the generation of a greater number of "empty" AAV particles.

Alternatively, the available space for packaging may be conserved by combining more than one transcription unit into a single construct, thus reducing the amount of required regulatory sequence space. For example, a single promoter may direct expression of a single RNA that encodes two or three or more genes of interest, and translation of the downstream genes are driven by IRES sequences. In another example, a single promoter may direct expression of an RNA that contains, in a single open reading frame (ORF), two or three or more genes of interest separated from one another by sequences encoding a self-cleavage peptide (e.g., T2A) or a protease recognition site (e.g., furin). The ORF thus encodes a single polyprotein, which, either during (in the case of T2A) or after translation, is cleaved into the individual proteins (such as, e.g., transgene and dimerizable transcription factor). It should be noted, however, that although these IRES and polyprotein systems can be used to save AAV packaging space, they can only be used for expression of components that can be driven by the same promoter.

In another alternative, the transgene capacity of AAV can be increased by providing AAV ITRs of two genomes that can anneal to form head to tail concatamers. Generally, upon entry of the AAV into the host cell, the single-stranded DNA containing the transgene is converted by host cell DNA polymerase complexes into double-stranded DNA, after which the ITRs aid in concatamer formation in the nucleus. As an alternative, the AAV may be engineered to be a self-complementary (sc) AAV, which enables the virus to bypass the step of second-strand synthesis upon entry into a target cell, providing an scAAV virus with faster and, potentially, higher (e.g., up to 100-fold) transgene expression. For example, the AAV may be engineered to have a genome comprising two connected single-stranded DNAs that encode, respectively, a transgene unit and its complement, which can snap together following delivery into a target cell, yielding a double-stranded DNA encoding the transgene unit of interest. Self-complementary AAV s are described in, e.g., U.S. Pat. Nos. 6,596,535; 7,125,717; and 7,456,683, each of which is incorporated herein by reference in its entirety.

The transcription units(s) in the replication-deficient rAAVs may be packaged with any AAV capsid protein (Cap) described herein, known in the art, or to be discovered. Caps from serotypes AAV1, AAV6, AAV7, AAV8, AAV9 or rh10 are particularly preferred for generating rAAVs for use in human subjects. In a preferred embodiment, an rAAV Cap is based on serotype AAV8. In another embodiment, an rAAV Cap is based on Caps from two or three or more AAV serotypes. For example, in one embodiment, an rAAV Cap is based on AAV6 and AAV9.

Cap proteins have been reported to have effects on host tropism, cell, tissue, or organ specificity, receptor usage, infection efficiency, and immunogenicity of AAV viruses. See, e.g., Grieger & Samulski, 2005; Buning et al., 2008; and the references cited below in this sub-section; all of which are incorporated herein by reference in their entirety. Accordingly, an AAV Cap for use in an rAAV may be selected based on consideration of, for example, the subject to be treated (e.g., human or non-human, the subject's immunological state, the subject's suitability for long or short-term treatment, etc.) or a particular therapeutic application (e.g., treatment of a particular disease or disorder, or delivery to particular cells, tissues, or organs).

In some embodiments, an rAAV Cap is selected for its ability to efficiently transduce a particular cell, tissue, or organ, for example, to which a particular therapy is targeted. In some embodiments, an rAAV Cap is selected for its ability to cross a tight endothelial cell barrier, for example, the blood-brain barrier, the blood-eye barrier, the blood-testes barrier, the blood-ovary barrier, the endothelial cell barrier surrounding the heart, or the blood-placenta barrier.

Tissue specificity of adeno-associated viruses (AAV) serotypes is determined by the serotype of the capsid, and viral vector based on different AAV capsids may generated taking into consideration their ability to infect different tissues. AAV2 presents a natural tropism towards skeletal muscles, neurons of the central nervous system, vascular smooth muscle cells. AAV1 has been described as being more efficient than AAV2 in transducing muscle, arthritic joints, pancreatic islets, heart, vascular endothelium, central nervous system (CNS) and liver cells, whereas AAV3 appears to be well suited for the transduction of cochlear inner hair cells, AAV4 for brain, AAV5 for CNS, lung, eye, arthritic joints and liver cells, AAV6 for muscle, heart and airway epithelium, AAV7 for muscle, AAV8 for muscle, pancreas, heart and liver, and AAV9 for heart. See, e.g., Buning et at., 2008. Any serotype of AAV known in the art, e.g., serotypes AAV1, AAV2, AAV3A, AAV3B, AAV4, AAV5, AAV6, AAV7 [see, WO 2003/042397], AAV8 [see, e.g., U.S. Pat. Nos. 7,790, 449; 7,282,199], AAV9 [see, WO 2005/033321], AAV10, AAV11, AAV12, rh10, modified AAV [see, e.g., WO 2006/110689], or yet to be discovered, or a recombinant AAV based thereon, may be used as a source for the rAAV capsid.

Various naturally occurring and recombinant AAVs, their encoding nucleic acids, AAV Cap and Rep proteins and their sequences, as well as methods for isolating or generating, propagating, and purifying such AAV s, and in particular, their capsids, suitable for use in producing rAAV s are described in Gao et al., 2004, "Clades of adeno-associated viruses are widely disseminated in human tissues," J. Virol. 78:6381-6388; U.S. Pat. Nos. 7,319,002; 7,056,502; 7,282, 199; 7,198,951; 7,235,393; 6,156,303; and 7,220,577; U.S. Patent Application Publication Nos. US 2003-0138772; US 2004-0052764; US 2007-0036760; US 2008-0075737; and US 2008-0075740; and International Patent Application Publication Nos. WO 20031014367; WO 20011083692; WO 2003/042397 (AAV7 and various simian AAV); WO 2003/052052; WO 2005/033321; WO 20061110689; WO 2008/027084; and WO 2007/127264; each of which is incorporated herein by reference in its entirety.

In some embodiments, an AAV Cap for use in the rAAV can be generated by mutagenesis (i.e., by insertions, deletions, or substitutions) of one of the aforementioned AAV Caps or its encoding nucleic acid. In some embodiments, the AAV Cap is at least 70% identical, 75% identical, 80% identical, 85% identical, 90% identical, 95% identical, 98% identical, or 99% or more identical to one or more of the aforementioned AAV Caps.

In some embodiments, the AAV Cap is chimeric, comprising domains from two or three or four or more of the aforementioned AAV Caps. In some embodiments, the AAV Cap is a mosaic of Vp1, Vp2, and Vp3 monomers from two or three different AAVs or recombinant AAVs. In some embodiments, an rAAV composition comprises more than one of the aforementioned Caps.

In some embodiments, an AAV Cap for use in an rAAV composition is engineered to contain a heterologous sequence or other modification. For example, a peptide or protein sequence that confers selective targeting or immune evasion may be engineered into a Cap protein. Alternatively or in addition, the Cap may be chemically modified so that the surface of the rAAV is polyethylene glycolated (PEGylated), which may facilitate immune evasion. The Cap protein may also be mutagenized, e.g., to remove its natural receptor binding, or to mask an immunogenic epitope.

Methods for Scalable Manufacture of AAV

Methods for the scalable (e.g., for production at commercial scale) manufacture of AAV, which may be adapted in order to generate rAAV compositions that are suitably homogeneous and free of contaminants for use in clinical applications, are also known in the art, and are summarized briefly below.

Adeno-associated viruses can be manufactured at scale using a mammalian cell line-based approach, such as the approach using stable producer cell lines described in Thorne et al., 2009, "Manufacturing recombinant adeno-associated viral vectors from producer cell clones," *Human Gene Therapy* 20:707-714, which is incorporated herein by reference in its entirety. In the approach described by Thorpe and colleagues, producer cell lines stably containing all the components needed to generate an rAAV—the transgene construct (transgene flanked by ITRs) and AAV rep and cap genes—are engineered, which are induced to make virus by infection with a helper virus, such as a live adenovirus type 5 (Ad5) (methods of scalable production of which are also well known in the art). Producer cell lines are stably transfected with construct(s) containing (i) a packaging cassette (rep and cap genes of the desired serotype and regulatory elements required for their expression), (ii) the transgene flanked by ITRs, (iii) a selection marker for mammalian cells, and (iv) components necessary for plasmid propagation in bacteria. Stable producer cell lines are obtained by transfecting the packaging construct(s), selecting drug-resistant cells, and replica-plating to ensure production of the recombinant AAV in the presence of helper virus, which are then screened for performance and quality. Once appropriate clones are chosen, growth of the cell lines is scaled up, the cells are infected with the adenovirus helper, and resulting rAAVs are harvested from the cells.

In an alternative to the methods described in Thorpe et al., a packaging cell line is stably transfected with the AAV rep and cap genes, and the transgene construct is introduced separately when production of the rAAV is desired. Although Thorpe and colleagues use HeLa cells for the producer cell line, any cell line (e.g., Vero, A549, HEK 293) that is susceptible to infection with helper virus, able to maintain stably integrated copies of the rep gene and, preferably, able to grow well in suspension for expansion and production in a bioreactor may be used in accordance with the methods described in Thorpe et al.

In the foregoing methods, rAAVs are produced using adenovirus as a helper virus. In a modification of these methods, rAAV s can be generated using producer cells stably transfected with one or more constructs containing adenovirus helper functions, avoiding the requirement to infect the cells with adenovirus. In a variation, one or more of the adenovirus helper functions are contained within the same construct as the rep and cap genes. In these methods, expression of the adenovirus helper functions may be placed under transcriptional or post-transcriptional control to avoid adenovirus-associated cytotoxicity.

In an alternative to producing stable cell lines, AAV s may also be produced at scale using transient transfection methods, such as described by Wright, 2009, "Transient transfection methods for clinical adeno-associated viral vector production," *Human Gene Therapy* 20:698-706, which is incorporated herein by reference in its entirety. Wright's approach involves transfection of cells with constructs that contain (i) the transgene of interest flanked by ITRs; (ii) the AAV rep and cap genes; and (iii) helper virus (e.g., adenovirus) genes required to support genome replication and packaging (or alternatively, a helper virus, as described in Thorpe et al.), Alternatively, the adenovirus helper functions may be contained within the same construct as the rep and cap genes. Thus, rAAV s are produced without having to ensure stable transfection of the transgene and rep/cap constructs. This provides a flexible and quick method for generating AAV s, and is thus ideal for pre-clinical and early-phase clinical development. Recombinant AAVs can be generated by transiently transfecting mammalian cell lines with the constructs using transient transfection methods known in the art. For example, transfection methods most suited for large-scale production include DNA co-precipitation with calcium phosphate, the use of poly-cations such as polyethylenimine (PE), and cationic lipids.

The effectiveness of adenovirus as a helper has also been exploited to develop alternative methods for large-scale recombinant AAV production, for example using hybrid viruses based on adenovirus and AAV (an "Ad-AAV hybrid"). This production method has the advantage that it does not require transfection—all that is required for rAAV production is infection of the rep/cap packaging cells by adenoviruses. In this process, a stable rep/cap cell line is infected with a helper adenovirus possessing functional E1 genes and, subsequently, a recombinant Ad-AAV hybrid virus in which the AAV transgene plus ITRs sequence is inserted into the adenovirus E1 region. Methods for generating Ad-AAV hybrids and their use in recombinant AAV production are described in Zhang et al., 2009, which is incorporated by reference herein in its entirety.

In another variation, rAAVs can be generated using hybrid viruses based on AAV and herpes simplex virus type 1 (HSV) (an "HSV/AAV hybrid"), such as described in Clement et al., 2009, "Large-scale adeno-associated viral vector production using a herpesvirus-based system enables manufacturing for clinical studies," *Human Gene Therapy* 20:796-806, which is incorporated herein by reference in its entirety. This method expands on the possibility of using HSV as a helper virus for AAV production (well known in the art, and also reviewed in Clement et al.). Briefly, HSV/AAV hybrids comprise an AAV transgene construct within an HSV backbone. These hybrids can be used to infect producer cells that supply the rep/cap and herpesvirus helper functions, or can be used in co-infections with recombinant HSV s that supply the helper functions, resulting in generation of rAAV s encapsidating the transgene of interest.

In another method, rAAV compositions may produced at scale using recombinant baculovirus-mediated expression of AAV components in insect cells, for example, as described in Virag et al., 2009, "Producing recombinant adeno-associated virus in foster cells: Overcoming production limitations using a baculovirus-insect cell expression strategy," *Human Gene Therapy* 20:807-817, which is incorporated herein by reference in its entirety. In this system, the well-known baculovirus expression vector (BEV) system is adapted to produce recombinant AAVs. For example, the system described by Virag et al. comprises the infection of Sf9 insect cells with two (or three) different BEVs that provide (i) AAV rep and cap (either in one or two BEVs) and (ii) the transgene construct. Alternatively, the Sf9 cells can be stably engineered to express rep and cap, allowing production of recombinant AAV s following infection with only a single BEV containing the transgene construct. In order to ensure stoichiometric production of the Rep and Cap proteins, the latter of which is required for efficient packaging, the BEV s can be engineered to include features that enable pre- and post-transcriptional regulation of gene expression. The Sf9 cells then package the transgene construct into AAV capsids, and the resulting rAAV can be harvested from the culture supernatant or by lysing the cells.

Each of the foregoing methods permit the scalable production of rAAV compositions. The manufacturing process for an rAAV composition suitable for commercial use (including use in the clinic) must also comprise steps for removal of contaminating cells; removing and inactivating helper virus (and any other contaminating virus, such as endogenous retrovirus-like particles); removing and inactivating any rcAAV; minimizing production of, quantitating, and removing empty (transgene-less) AAV particles (e.g., by centrifugation); purifying the rAAV (e.g., by filtration or chromatography based on size and/or affinity); and testing the rAAV composition for purity and safety. These methods are also provided in the references cited in the foregoing paragraphs and are incorporated herein for this purpose.

One disadvantage of the foregoing methods of scalable rAAV production is that much of the rAAV is obtained by lysing the producer cells, which requires significant effort to not only obtain the virus but also to isolate it from cellular contaminants. To minimize these requirements, scalable methods of rAAV production that do not entail cell lysis may be used, such as provided in International Patent Application Publication No. WO 2007/127264, the contents of which is incorporated by reference herein in its entirety. In the example of Section 6 infra, a new scalable method obtaining rAAV from cell culture supernatants is provided, which may also be adapted for the preparation of rAAV composition for use in accordance with the methods described herein.

In still another embodiment, the invention provides human or non-human cells which contain one or more of the DNA constructs and/or virus compositions of the invention. Such cells may be genetically engineered and may include, e.g., plant, bacterial, non-human mammalian or mammalian cells. Selection of the cell types is not a limitation of the invention.

5.2. Compositions

The present invention provides replication-defective virus compositions suitable for use in therapy (in vivo or ex vivo) in which the genome of the virus (or the collective genomes of two or more replication-defective virus stocks used in combination) comprise the therapeutic transgene unit and the ablator unit defined in Section 3.1, and described supra; and may further comprise dimerizable fusion protein or TF domain units(s) (referred to for purposes of convenience as dimerizable unit(s)). Any virus suitable for gene therapy may be used in the compositions of the invention, including but not limited to adeno-associated virus ("AAV"), adenovirus, herpes simplex virus, lentivirus, or a retrovirus. In a preferred embodiment, the compositions are replication-defective AAVs, which are described in more detail in Section 5.2.1 herein.

The compositions of the invention comprise a replication-defective virus(es) suitable for therapy (in vivo or ex vivo) in which the genome of the virus(es) comprises a transgene unit, an ablation unit, and/or a dimerizable unit. In one embodiment, a composition of the invention comprises a virus suitable for gene therapy in which the genome of the virus comprises a transgene unit. In another embodiment, a composition of the invention comprises a virus suitable for gene therapy in which the genome of the virus comprises an ablation unit. In another embodiment, a composition of the invention comprises a virus suitable for gene therapy in which the genome of the virus comprises a dimerizable unit. In another embodiment, a composition of the invention comprises a virus suitable for gene therapy in which the genome of the virus comprises a transgene unit and an ablation unit. In another embodiment, a composition of the invention comprises a virus suitable for gene therapy in which the genome of the virus comprises a transgene unit and a dimerizable unit. In another embodiment, a composition of the invention comprises a virus suitable for gene therapy in which the genome of the virus comprises an ablation unit and a dimerizable unit. In another embodiment, a composition of the invention comprises viruses suitable for gene therapy in which the genome of the virus comprises a transgene unit, an ablation unit and a dimerizable unit.

The invention also provides compositions comprising recombinant DNA constructs that comprise one or more transcriptional units described herein. Compositions comprising recombinant DNA constructs are described in more detail in Section 5.2.2.

5.2.1. Replication-Defective Virus Compositions for Gene Therapy

The invention provides compositions comprising a replication-defective virus stock(s) and formulations of the replication-defective virus(es) in a physiologically acceptable carrier. These formulations can be used for gene transfer and/or gene therapy. The viral genome of the compositions comprises: (a) a first transcription unit that encodes a therapeutic product in operative association with a promoter that controls transcription, said unit containing at least one ablation recognition site (transgene unit); and (b) a second transcription unit that encodes an ablator specific for the ablation recognition site, or a fragment thereof, in operative association with a promoter. In one embodiment, the viral genome of the replication-defective virus. The ablator is as defined elsewhere in this specification.

AAV Stocks

In a preferred embodiment, the replication-defective virus of a composition of the invention is an AAV, preferably AAV1, AAV6, AAV6.2, AAV7, AAV8, AAV9 or rh10. In one embodiment, the AAV of the composition is AAV8. Due to the packaging constraints of AAV (approximately 4.5 kb) in most cases, for ease of manufacture, the transgene unit, the ablation unit, and the dimerizable unit will be divided between two or more viral vectors and packaged in a separate AAV stock. In one embodiment, the replication-defective virus composition comprises the first transcription unit (a transgene unit) packaged in one AAV stock, and the second (an ablator unit), third and fourth transcription units (dimerizable TF domain unit) packaged in a second AAV stock. In another embodiment, the replication-defective virus composition comprises the second transcription unit (an ablator unit) packaged in one AAV stock, and the first (a transgene unit), third and fourth transcription units (dimerizable TF domain unit) packaged in a second AAV stock. In another embodiment, all four units can be packaged in one AAV stock, but this imposes limits on the size of the DNAs that can be packaged. For example, when using Cre as the ablator and FRB/FKB as the dimerizable TF domains (as shown in the examples, infra), in order to package all four units into one AAV stock, the size of the DNA encoding the therapeutic transgene should be less than about 900 base pairs in length; this would accommodate DNAs encoding cytokines, RNAi therapeutics, and the like.

Due to size constraints of the AAV genome for packaging, the transcription units can be engineered and packaged in two or more AAV stocks. Whether packaged in one viral stock which is used as a virus composition according to the invention, or in two or more viral stocks which form a virus composition of the invention, the viral genome used for treatment must collectively contain the first and second transcription units encoding the therapeutic transgene and the ablator; and may further comprise additional transcription units (e.g., the third and fourth transcription units encoding the dimerizable TF domains). For example, the first transcription unit can be packaged in one viral stock, and second, third and fourth transcription units packaged in a second viral stock. Alternatively, the second transcription unit can be packaged in one viral stock, and the first, third and fourth transcription units packaged in a second viral stock. While useful for AAV due to size contains in packaging the AAV genome, other viruses may be used to prepare a virus composition according to the invention. In another embodiment, the viral compositions of the invention, where they contain multiple viruses, may contain different replication-defective viruses (e.g., AAV and adenovirus).

In one embodiment, a virus composition according to the invention contains two or more different AAV (or another viral) stock, in such combinations as are described above. For example, a virus composition may contain a first viral stock comprising the therapeutic gene with ablator recognition sites and a first ablator and a second viral stock containing an additional ablator(s). Another viral composition may contain a first virus stock comprising a therapeutic gene and a fragment of an ablator and a second virus stock comprising another fragment of an ablator. Various other combinations of two or more viral stocks in a virus composition of the invention will be apparent from the description of the components of the present system.

Viral Formulations

Compositions of the invention may be formulated for delivery to animals for veterinary purposes (e.g., livestock (cattle, pigs, etc), and other non-human mammalian subjects, as well as to human subjects. The replication-defective viruses can be formulated with a physiologically acceptable carrier for use in gene transfer and gene therapy applications. Because the viruses are replication-defective, the dosage of the formulation cannot be measured or calculated as a PFU (plaque forming unit). Instead, quantification of the genome copies ("GC") may be used as the measure of the dose contained in the formulation.

Any method known in the art can be used to determine the genome copy (GC) number of the replication-defective virus compositions of the invention. One method for performing AAV GC number titration is as follows: Purified AAV vector samples are first treated with DNase to eliminate un-encapsidated AAV genome DNA or contaminating plasmid DNA from the production process. The DNase resistant particles are then subjected to heat treatment to release the genome from the capsid. The released genomes are then quantitated by real-time PCR using primer/probe sets targeting specific region of the viral genome (usually poly A signal).

Also, the replication-defective virus compositions can be formulated in dosage units to contain an amount of replication-defective virus that is in the range of about $1.0 \times 10^9$ GC to about $1.0 \times 10^{15}$ GC (to treat an average subject of 70 kg in body weight), and preferably $1.0 \times 10^{12}$ GC to $1.0 \times 10^{14}$ GC for a human patient. Preferably, the dose of replication-defective virus in the formulation is $1.0 \times 10^9$ GC, $5.0 \times 10^9$ GC, $1.0 \times 10^{10}$ GC, $5.0 \times 10^{10}$ GC, $1.0 \times 10^{11}$ GC, $5.0 \times 10^{11}$ GC, $1.0 \times 10^{12}$ GC, $5.0 \times 10^{12}$ GC, or $1.0 \times 10^{13}$ GC, $5.0 \times 10^{13}$ GC, $1.0 \times 10^{14}$ GC, $5.0 \times 10^{14}$ GC, or $1.0 \times 10^{15}$ GC.

The replication-defective viruses can be formulated in a conventional manner using one or more physiologically acceptable carriers or excipients. The replication-defective viruses may be formulated for parenteral administration by injection, e.g., by bolus injection or continuous infusion. Formulations for injection may be presented in unit dosage form, e.g., in ampoules or in multi-dose containers, with an added preservative. The replication-defective virus compositions may take such forms as suspensions, solutions or emulsions in oily or aqueous vehicles, and may contain formulatory agents such as suspending, stabilizing and/or dispersing agents. Liquid preparations of the replication-defective virus formulations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts. Alternatively, the compositions may be in powder form for constitution with a suitable vehicle, e.g., sterile pyrogen-free water, before use.

Also encompassed is the use of adjuvants in combination with or in admixture with the replication-defective viruses of the invention. Adjuvants contemplated include but are not limited to mineral salt adjuvants or mineral salt gel adjuvants, particulate adjuvants, microparticulate adjuvants, mucosal adjuvants, and immunostimulatory adjuvants. Adjuvants can be administered to a subject as a mixture with replication-defective viruses of the invention, or used in combination with the replication-defective viruses of the invention.

5.2.2. Recombinant DNA Construct Compositions for Production of Replication-Defective Viral Vectors Useful for Therapeutic Purposes The invention provides recombinant DNA construct compositions comprising a transgene unit, an ablation unit, and/or one or two dimerizable domain units flanked by viral signals that define the region to be amplified and packaged into replication-defective viral particles. These DNA constructs can be used to generate the replication-defective virus compositions and stocks.

In one embodiment, the recombinant DNA construct comprises a transgene unit flanked by packaging signals of a viral genome. In another embodiment, a composition of the invention comprises a recombinant DNA construct comprising an ablation unit flanked by packaging signals of a viral genome. In another embodiment, the recombinant DNA construct comprises a dimerizable unit flanked by packaging signals of a viral genome. In another embodiment, the recombinant DNA construct comprises a transgene unit and an ablation unit flanked by packaging signals of a viral genome. In another embodiment, the recombinant DNA construct comprises a transgene unit and a dimerizable unit flanked by packaging signals of a viral genome. In another embodiment, the recombinant DNA construct comprises an ablation unit and a dimerizable unit flanked by packaging signals of a viral genome. In another embodiment, the recombinant DNA construct comprises a transgene unit, an ablation unit and a dimerizable unit flanked by packaging signals of a viral genome.

The first transcription unit encodes a therapeutic product in operative association with a promoter that controls transcription, said unit containing at least one ablation recognition site (transgene unit); and (b) the second transcription unit that encodes an ablator specific for the ablation recognition site, or a fragment thereof fused to a binding domain, in operative association with a promoter that induces transcription in response to a pharmacological agent (ablation unit). In another embodiment, the recombinant DNA construct comprises a dimerizable TF domain unit flanked by packaging signals of a viral genome.

In a preferred embodiment, the recombinant DNA construct composition further comprises a dimerizable unit nested within the viral packaging signals. In one embodiment, each unit encodes a dimerizable domain of a transcription factor that regulates the inducible promoter of the second transcription unit, in which (c) a third transcription unit encodes the DNA binding domain of the transcription factor fused to a binding domain for the pharmacological agent in operative association with a constitutive promoter; and (d) a fourth transcription unit encodes the activation domain of the transcription factor fused to a binding domain for the pharmacological agent in operative association with a constitutive promoter. In another embodiment, at least one of (c) or (d) is expressed under an inducible promoter. In a specific embodiment, the pharmacological agent that induces transcription of the promoter that is in operative association with the second unit of the recombinant DNA construct composition is a dimerizer that dimerizes the domains of the transcription factor as measured in vitro. In yet another specific embodiment, the pharmacological agent that induces transcription of the promoter that is in operative association with the second unit of the recombinant DNA construct composition is rapamycin. In still a further embodiment, the recombinant DNA construct comprises a dimerizable fusion protein unit. For example, the dimerizable fusion protein unit may be encode (a) a binding domain of an enzyme fused to a binding domain and (b) a catalytic domain of the enzyme fused to a binding domain, where the binding domains are either DNA binding domains or the binding domains for a dimerizer.

In order to conserve space within the viral genome(s), bicistronic transcription units can be engineered. For example, the third and fourth transcription units can be engineered as a bicistronic unit containing an IRES (internal ribosome entry site), which allows coexpression of heterologous gene products by a message from a single promoter. Alternatively, a single promoter may direct expression of an RNA that contains, in a single open reading frame (ORF), two or three heterologous genes (e.g., the third and fourth transcription units) separated from one another by sequences encoding a self-cleavage peptide (e.g., T2A) or a protease recognition site (e.g., furin). The ORF thus encodes a single polyprotein, which, either during (in the case of T2A) or after translation, is cleaved into the individual proteins. It should be noted, however, that although these IRES and polyprotein systems can be used to save AAV packaging space, they can only be used for expression of components that can be driven by the same promoter.

In a specific embodiment, a recombinant DNA construct composition that comprises a dimerizable unit comprises an IRES. In another specific embodiment, a recombinant DNA construct composition that comprises a third and fourth transcription unit (a dimerizable TF domain unit) comprises and IRES In another specific embodiment, a recombinant DNA construct composition that comprises a transgene unit comprises an IRES. In another specific embodiment, a recombinant DNA construct composition that comprises an ablation unit comprises an IRES. In another specific embodiment, a recombinant DNA construct composition that comprises a dimerizable unit comprises an IRES.

In a specific embodiment, a recombinant DNA construct composition that comprises a third and a fourth transcription unit (a dimerizable TF domain unit) comprises T2A sequence. In another specific embodiment, a recombinant DNA construct composition that comprises a transgene unit comprises T2A sequence. In another specific embodiment, a recombinant DNA construct composition that comprises an ablation unit comprises T2A sequence. In another specific embodiment, a recombinant DNA construct composition that comprises a dimerizable TF domain unit comprises T2A sequence. In an embodiment, the ablator that is encoded by the second transcription unit of the recombinant DNA construct composition is an endonuclease, a recombinase, a meganuclease, or an artificial zinc finger endonuclease that binds to the ablation recognition site in the first transcription unit and excises or ablates DNA. In a specific embodiment, the ablator is ere and the ablation recognition site is LoxP, or the ablator is FLP and the ablation recognition site is FRT. In another embodiment, the ablator that is encoded by the second transcription unit of the recombinant DNA construct composition is an interfering RNA, a ribozyme, or an antisense that ablates the RNA transcript of the first transcription unit, or suppresses translation of the RNA transcript of the first transcription unit. In a specific embodiment, transcription of the ablator is controlled by a tet-on/off system, a tetR-KRAB system, a mifepristone (RU486) regulatable system, a tamoxifen-dep regulatable system, or an ecdysone-dep regulatable system.

The recombinant DNA construct composition contains packaging signals flanking the transcription units desired to be amplified and packaged in replication-defective virus vectors. In a specific embodiment, the packaging signals are AAV ITRs. Where a pseudotyped AAV is to be produced, the ITRs are selected from a source which differs from the AAV source of the capsid. For example, AAV2 ITRs may be selected for use with an AAV1, AAV8, or AAV9 capsid, and so on. In another specific embodiment, the AAV ITRs may be from the same source as the capsid, e.g., AAV1, AAV6, AAV7, AAV8, AAV9, rh10 ITRs, etc. In another specific embodiment, a recombinant DNA construct composition comprises a first transcription unit (transgene unit) flanked by AAV ITRs, and the second (ablation unit), and optional third and fourth transcription units (a dimerizable TF domain unit), and/or a dimerizable fusion protein unit(s), flanked by AAV ITRs. In yet another specific embodiment, a recombinant DNA construct composition comprises a second transcription unit (ablation unit) flanked by AAV ITRs, and the first (transgene unit), third and fourth transcription units (a dimerizable TF domain unit) are flanked by AAV ITRs. In a preferred embodiment, the transcription units of a PIT A system are contained in two or more recombinant DNA compositions.

In a specific embodiment, recombinant DNA construct contains a transgene unit that encodes anyone or more of the following therapeutic products: an antibody or antibody fragment that neutralizes HIV infectivity, soluble vascular endothelial growth factor receptor-1 (sFlt-I), Factor VIII, Factor IX, insulin like growth factor (IGF), hepatocyte growth factor (HGF), heme oxygenase-1 (HO-1), or nerve growth factor (NGF). In a specific embodiment, recombinant DNA construct contains a transgene unit that comprises anyone of the following promoters that controls transcription of the therapeutic gene: a constitutive promoter, a tissue-specific promoter, a cell-specific promoter, an inducible promoter, or a promoter responsive to physiologic cues.

The DNA constructs can be used in any of the methods described in Section 5.1.5 to generate replication-defective virus stocks.

5.2.3. Pharmaceutical Compositions and Formulations of Dimerizers

The present invention provides pharmaceutical compositions comprising the dimerizers of the invention, described in Section 5.1.4. In a preferred embodiment, the pharmaceutical compositions comprise a pharmaceutically acceptable carrier or excipient. Optionally, these pharmaceutical compositions are adapted for veterinary purposes, e.g., for delivery to a non-human mammal (e.g., livestock), such as are described herein.

The pharmaceutical compositions of the invention can be administered to a subject at therapeutically effective doses to ablate or excise the transgene of a transgene unit of the invention or to ablate the transcript of the transgene, or inhibit its translation. A therapeutically effective dose refers to an amount of the pharmaceutical composition sufficient to result in amelioration of symptoms caused by expression of the transgene, e.g., toxicity, or to result in at least 60%, 65%, 70%, 75%, 80%, 85%, 90%, 95%, or 100% inhibition of expression of the transgene.

In an embodiment, an amount of pharmaceutical composition comprising a dimerizer of the invention is administered that is in the range of about 0.1-5 micrograms (μg)/kilogram (kg). To this end, a pharmaceutical composition comprising a dimerizer of the invention is formulated in doses in the range of about 7 mg to about 350 mg to treat to treat an average subject of 70 kg in body weight. The amount of pharmaceutical composition comprising a dimerizer of the invention administered is: 0.1, 0.2, 0.3, 0.4, 0.5, 0.6, 0.7, 0.8, 0.9, 1.0, 1.5, 2.0, 2.5, 3.0, 3.5, 4.0, 4.5 or 5.0 mg/kg. The dose of a dimerizer in a formulation is 7, 8, 9, 10, 20, 25, 30, 35, 40, 45, 50, 55, 60, 65, 70, 75, 80, 85 90, 95, 100, 125, 150, 175, 200, 225, 250, 275, 300, 325, 350, 375, 400, 400, 425, 450, 475, 500, 525, 550, 575, 600, 625, 650, 675, 700, 725, or 750 mg (to treat to treat an average subject of 70 kg in body weight). These doses are preferably administered orally. These doses can be given once or repeatedly, such as daily, every other day, weekly, biweekly, or monthly. Preferably, the pharmaceutical compositions are given once weekly for a period of about 4-6 weeks. In some embodiments, a pharmaceutical composition comprising a dimerizer is administered to a subject in one dose, or in two doses, or in three doses, or in four doses, or in five doses, or in six doses or more. The interval between dosages may be determined based the practitioner's determination that there is a need for inhibition of expression of the transgene, for example, in order to ameliorate symptoms caused by expression of the transgene, e.g., toxicity. For example, in some embodiments when the need for transgene ablation is acute, daily dosages of a pharmaceutical composition comprising a dimerizer may be administered. In other embodiments, e.g., when the need for transgene ablation is less acute, or is not acute, weekly dosages of a pharmaceutical composition comprising a dimerizer may be administered.

Pharmaceutical compositions for use in accordance with the present invention may be formulated in conventional manner using one or more physiologically acceptable carriers or excipients. Thus, the dimerizers and their physiologically acceptable salts and solvates may be formulated for administration by inhalation or insufflation (either through the mouth or the nose) oral, buccal, parenteral, rectal, or transdermal administration. Noninvasive methods of administration are also contemplated.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the dimerizers.

For buccal administration the compositions may take the form of tablets or lozenges formulated in conventional manner.

For administration by inhalation, the dimerizers for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the dimerizers and a suitable powder base such as lactose or starch.

The dimerizers may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The dimerizers may also be formulated in rectal compositions such as suppositories or retention enemas, e.g., containing conventional suppository bases such as cocoa butter or other glycerides.

In addition to the formulations described previously, the dimerizers may also be formulated as a depot preparation. Such long acting formulations may be administered by implantation (for example subcutaneously or intramuscularly) or by intramuscular injection. Thus, for example, the dimerizers may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

Also encompassed is the use of adjuvants in combination with or in admixture with the dimerizers of the invention. Adjuvants contemplated include but are not limited to mineral salt adjuvants or mineral salt gel adjuvants, particulate adjuvants, microparticulate adjuvants, mucosal adjuvants, and immunostimulatory adjuvants. Adjuvants can be administered to a subject as a mixture with dimerizers of the invention, or used in combination with the dimerizers of the invention.

5.3. Treatment of Diseases and Disorders

The invention provides methods for treating any disease or disorder that is amenable to gene therapy. In one embodiment, "treatment" or "treating" refers to an amelioration of a disease or disorder, or at least one discernible symptom thereof. In another embodiment, "treatment" or "treating" refers to an amelioration of at least one measurable physical parameter associated with a disease or disorder, not necessarily discernible by the subject. In yet another embodiment, "treatment" or "treating" refers to inhibiting the progression of a disease or disorder, either physically, e.g., stabilization of a discernible symptom, physiologically, e.g., stabilization of a physical parameter, or both. Other conditions, including cancer, immune disorders, and veterinary conditions, may also be treated.

5.3.1. Target Diseases

Types of diseases and disorders that can be treated by methods of the present invention include, but are not limited to age-related macular degeneration; diabetic retinopathy; infectious diseases e.g., HIV pandemic flu, category 1 and 2 agents of biowarfare, or any new emerging viral infection; autoimmune diseases; cancer; multiple myeloma; diabetes; systemic lupus erythematosus (SLE); hepatitis C; multiple sclerosis; Alzheimer's disease; parkinson's disease; amyotrophic lateral sclerosis (ALS), huntington's disease; epilepsy; chronic obstructive pulmonary disease (COPD); joint inflammation, arthritis; myocardial infarction (MI); congestive heart failure (CHF); hemophilia A; or hemophilia B.

Infectious diseases that can be treated or prevented by the methods of the present invention are caused by infectious agents including, but not limited to, viruses, bacteria, fungi, protozoa, helminths, and parasites. The invention is not limited to treating or preventing infectious diseases caused by intracellular pathogens. Many medically relevant microorganisms have been described extensively in the literature, e.g., see C. G. A Thomas, Medical Microbiology, Bailliere Tindall, Great Britain 1983, the entire contents of which are hereby incorporated herein by reference.

Bacterial infections or diseases that can be treated or prevented by the methods of the present invention are caused by bacteria including, but not limited to, bacteria that have an intracellular stage in its life cycle, such as mycobacteria (e.g., *Mycobacteria tuberculosis, M bovis, M avium, M leprae*, or *M africanum*), rickettsia, mycoplasma, chlamydia, and legionella. Other examples of bacterial infections contemplated include but are not limited to infections caused by Gram positive bacillus (e.g., *Listeria, Bacillus* such as *Bacillus anthracis, Erysipelothrix* species), Gram negative bacillus (e.g., *Bartonella, Brucella, Campylobacter, Enterobacter, Escherichia, Francisella, Hemophilus, Klebsiella, Morganella, Proteus, Providencia, Pseudomonas, Salmonella, Serratia, Shigella, Vibrio*, and *Yersinia* species), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, *Pneumococcus* species, *Staphylococcus* species, *Neisseria* species. Specific examples of infectious bacteria include but are not limited to: *Helicobacter pyloris, Borelia burgdorferi, Legionella pneumophilia, Mycobacteria tuberculosis, M avium, M intracellulare, M kansaii, M gordonae, Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus viridans, Streptococcus faecalis, Streptococcus bovis, Streptococcus pneumoniae, Haemophilus influenzae, Bacillus antracis, corynebacterium diphtheriae, Erysipelothrix rhusiopathiae, Clostridium perfringers, Clostridium tetani, Enterobacter aerogenes, Klebsiella pneumoniae, Pasturella multocida, Fusobacterium nucleatum, Streptobacillus moniliformis, Treponema pallidum, Treponema pertenue, Leptospira, Rickettsia*, and *Actinomyces israeli*.

Infectious virus of both human and non-human vertebrates, include retroviruses, RNA viruses and DNA viruses. Examples of virus that have been found in humans include but are not limited to: Retroviridae (e.g. human immunodeficiency viruses, such as HIV-1 (also referred to as HTL V-III, LA V or HTLV-HULA V, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae, (e.g. Hantaan viruses, bunga viruses, phleboviruses and Nairo viruses); Arena viridae (hemorrhagic fever viruses); Reoviridae (e.g. reoviruses, orbiviurses and rotaviruses); Bimaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and lridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Parasitic diseases that can be treated or prevented by the methods of the present invention including, but not limited to, amebiasis, malaria, leishmania, coccidia, giardiasis, cryptosporidiosis, toxoplasmosis, and trypanosomiasis. Also encompassed are infections by various worms, such as but not limited to ascariasis, ancylostomiasis, trichuriasis, strongyloidiasis, toxoccariasis, trichinosis, onchocerciasis, filaria, and dirofilariasis. Also encompassed are infections by various flukes, such as but not limited to schistosomiasis, paragonimiasis, and clonorchiasis. Parasites that cause these diseases can be classified based on whether they are intracellular or extracellular. An "intracellular parasite" as used herein is a parasite whose entire life cycle is intracellular. Examples of human intracellular parasites include *Leishmania* spp., *Plasmodium* spp., *Trypanosoma cruzi, Toxoplasma gondii, Babesia* spp., and *Trichinella spiralis*. An "extracellular parasite" as used herein is a parasite whose entire life cycle is extracellular. Extracellular parasites capable of infecting humans include *Entamoeba histolytica, Giardia lamblia, Enterocytozoon bieneusi, Naegleria* and *Acanthamoeba* as well as most helminths. Yet another class of parasites is defined as being mainly extracellular but with an obligate intracellular existence at a critical stage in their life cycles. Such parasites are referred to herein as "obligate intracellular parasites". These parasites may exist most of their lives or only a small portion of their lives in an extracellular environment, but they all have at least one obligate intracellular stage in their life cycles. This latter category of parasites includes *Trypanosoma rhodesiense* and *Trypanosoma gambiense, Isospora* spp., *Cryptosporidium* spp, *Eimeria* spp., *Neospora* spp., *Sarcocystis* spp., and *Schistosoma* spp.

Types of cancers that can be treated or prevented by the methods of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

5.3.2. Dosage and Mode of Administration of Viral Vectors

The replication-defective virus compositions of the invention can be administered to a human subject by any method or regimen known in the art. For example, the replication-defective virus compositions of the invention can be administered to a human subject by any method described in the following patents and patent applications that relate to methods of using AAV vectors in various therapeutic applications: U.S. Pat. Nos. 7,282,199; 7,198,951; U.S. Patent Application Publication Nos. US 2008-0075737; US 2008-0075740; International Patent Application Publication Nos. WO 2003/024502; WO 2004/108922; WO 20051033321, each of which is incorporated by reference in its entirety.

In an embodiment, the replication-defective virus compositions of the invention are delivered systemically via the liver by injection of a mesenteric tributary of portal vein. In another embodiment, the replication-defective virus compositions of the invention are delivered systemically via muscle by intramuscular injection in to e.g., the quadriceps or bicep muscles. In another embodiment, the replication-defective virus compositions of the invention are delivered to the basal forebrain region of the brain containing the nucleus basalis of Meynert (NBM) by bilateral, stereotactic injection. In another embodiment, the replication-defective virus compositions of the invention are delivered to the eNS by bilateral intraputaminal and/or intranigral injection. In another embodiment, the replication-defective virus compositions of the invention are delivered to the joints by intraarticular injection. In another embodiment, the replication-defective virus compositions of the invention are delivered to the heart by intracoronary infusion. In another embodiment, the replication-defective virus compositions of the invention are delivered to the retina by injection into the subretinal space.

In another embodiment, an amount of replication-defective virus composition is administered at an effective dose that is in the range of about $1.0 \times 10^8$ genome copies (GC)/kilogram (kg) to about $1.0 \times 10^{14}$ GC/kg, and preferably $1.0 \times 10^{11}$ GC/kg to $1.0 \times 10^{13}$ GC/kg to a human patient. Preferably, the amount of replication-defective virus composition administered is $1.0 \times 10^8$ GC/kg, $5.0 \times 10^8$ GC/kg, $1.0 \times 10^9$ GC/kg, $5.0 \times 10^9$ GC/kg, $1.0 \times 10^{10}$ GC/kg, $5.0 \times 10^{10}$ GC/kg, $1.0 \times 10^{11}$ GC/kg, $5.0 \times 10^{11}$ GC/kg, or $1.0 \times 10^{12}$ GC/kg, $5.0 \times 10^{12}$ GC/kg, $1.0 \times 10^{13}$ GC/kg, $5.0 \times 10^{13}$ GC/kg, $1.0 \times 10^{14}$ GC/kg These doses can be given once or repeatedly, such as daily, every other day, weekly, biweekly, or monthly, or until adequate transgene expression is detected in the patient. In an embodiment, replication-defective virus compositions are given once weekly for a period of about 4-6 weeks, and the mode or site of administration is preferably varied with each administration. Repeated injection is most likely required for complete ablation of transgene expression. The same site may be repeated after a gap of one or more injections. Also, split injections may be given. Thus, for example, half the dose may be given in one site and the other half at another site on the same day.

When packaged in two or more viral stocks, the replication-defective virus compositions can be administered simultaneously or sequentially. When two or more viral stocks are delivered sequentially, the later delivered viral stocks can be delivered one, two, three, or four days after the administration of the first viral stock. Preferably, when two viral stocks are delivered sequentially, the second delivered viral stock is delivered one or two days after delivery of the first viral stock.

Any method known in the art can be used to determine the genome copy (GC) number of the replication-defective virus compositions of the invention. One method for performing AAV GC number titration is as follows: Purified AAV vector samples are first treated with DNase to eliminate un-encapsidated AAV genome DNA or contaminating plasmid DNA from the production process. The DNase resistant particles are then subjected to heat treatment to release the genome from the capsid. The released genomes are then quantitated by real-time PCR using primer/probe sets targeting specific region of the viral genome (usually poly A signal).

In one embodiment, the replication-defective virus compositions of the invention are delivered systemically via the liver by injection of a mesenteric tributary of portal vein at a dose of about $3.0 \times 10^{12}$ GC/kg. In another embodiment, the replication-defective virus compositions of the invention are delivered systemically via muscle by up to twenty intramuscular injections in to either the quadriceps or bicep muscles at a dose of about $5.0 \times 10^{12}$ GC/kg. In another embodiment, the replication-defective virus compositions of the invention are delivered to the basal forebrain region of the brain containing the nucleus basalis of Meynert (NBM) by bilateral, stereotactic injection at a dose of about $5.0 \times 10^{11}$ GC/kg. In another embodiment, the replication-defective virus compositions of the invention are delivered to the CNS by bilateral intraputaminal and/or intranigral injection at a dose in the range of about $1.0 \times 10^{11}$ GC/kg to about $5.0 \times 10^{11}$ GC/kg. In another embodiment, the replication-defective virus compositions of the invention are delivered to the joints by intra-articular injection at a dose of about $1.0 \times 1011$ GC/mL of joint volume for the treatment of inflammatory arthritis. In another embodiment, the replication-defective virus compositions of the invention are delivered to the heart by intracoronary infusion injection at a dose in the range of about $1.4 \times 10^{11}$ GC/kg to about $3.0 \times 10^{12}$ GC/kg. In another embodiment, the replication-defective virus compositions of the invention are delivered to the retina by injection into the subretinal space at a dose of about $1.5 \times 10^{10}$ GC/kg.

Table 3 shows examples of transgenes that can be delivered via a particular tissue/organ by the PITA system of the invention to treat a particular disease.

TABLE 3

Treatment of Diseases

| Disease | Examples of transgenes | Target Tissue |
|---|---|---|
| Age relation macular degeneration | s-Flt-1, an anti-VEGF antibody such as bevacizumab (Avastin), ranibizumab (Lucentis), or a domain antibody (dAB) | Retina |
| HIV | a neutralizing antibody against HIV | Muscle and/or liver |
| Cancer | Antiangiogenic agents (s-Flt-I, an anti-VEGF antibody such as bevacizumab (Avastin), ranibizumab (Lucentis), or a domain antibody (dAB); cytokines that enhance tumor immune responses, anti-EGFR, IFN | Muscle and/or liver |
| Autoimmune diseases, e.g., arthritis, systemic lupus with T cell activation; erythematosus, psoriasis, cytokines that bias immune multiple sclerosis (MS) | Antibodies that interfere responses e.g., β-IFN; adhesion molecule a4-integrin antibody | Muscle and/or liver |
| Multiple myeloma | anti-CD20 antibody | Muscle and/or liver |
| Diabetes | GLP-1, IL-6 | Muscle and/or liver |
| Hepatitis C | β-IFN, shRNA targeting IRES | Muscle and/or liver |
| Alzheimer's disease | NGF | Central nervous system (CNS) |
| Amyotrophic lateral sclerosis (ALS) | IGF-1 | CNS |
| Huntington's disease | NGF, BDNF AND CNTF, shRNA targeting mutant Huntington | CNS |
| Epilepsy | galanin, neuropeptide Y (NPY), glial cell line derived neurotrophic factor (GDNF) | CNS |
| COPD | chemokines from IL 8 family, TNF antagonist | Lung |
| Inflammatory arthritis | TNF antagonist, IL-1, anti-CD 20, IL-6, IL-1r antagonist | Joint |
| Myocardial infarction | Heme oxygenase-1 | Heart |
| Congestive heart failure | insulin like growth factor (IGF), hepatocyte growth factor (HGF) | Heart |
| Parkinson's Disease | GDNF, aromatic L-amino acid decarboxylase (ADCC), NGF | CNS |

In one embodiment a method for treating age-related macular degeneration in a human subject comprises administering an effective amount of a replication-defective virus composition, in which the therapeutic product is a VEGF antagonist.

In another embodiment, a method for treating hemophilia A in a human subject, comprises administering an effective amount of a replication-defective virus composition, in which the therapeutic product is Factor VIII or its variants, such as the light chain and heavy chain of the heterodimer and the B-deleted domain; U.S. Pat. Nos. 6,200,560 and 6,221,349). The Factor VIII gene codes for 2351 amino acids and the protein has six domains, designated from the amino to the terminal carboxy terminus as A1-A2-B-A3-C1-C2 [Wood et al, *Nature,* 312:330 (1984); Vehar et al., *Nature* 312:337 (1984); and Toole et al, *Nature,* 342:337 (1984)]. Human Factor VIII is processed within the cell to yield a heterodimer primarily comprising a heavy chain containing the A1, A2 and B domains and a light chain containing the A3, C1 and C2 domains. Both the single chain polypeptide and the heterodimer circulate in the plasma as inactive precursors, until activated by thrombin cleavage between the A2 and B domains, which releases the B domain and results in a heavy chain consisting of the A1 and A2 domains. The B domain is deleted in the activated procoagulant form of the protein. Additionally, in the native protein, two polypeptide chains ("a" and "b"), flanking the B domain, are bound to a divalent calcium cation. In some embodiments, the minigene comprises first 57 base pairs of the Factor VIII heavy chain which encodes the 10 amino acid signal sequence, as well as the human growth hormone (hGH) polyadenylation sequence. In alternative embodiments, the minigene further comprises the A1 and A2 domains, as well as 5 amino acids from the N-terminus of the B domain, and/or 85 amino acids of the C-terminus of the B domain, as well as the A3, C1 and C2 domains In yet other embodiments, the nucleic acids encoding Factor VIII heavy chain and light chain are provided in a single minigene separated by 42 nucleic acids coding for 14 amino acids of the B domain [U.S. Pat. No. 6,200,560]. Examples of naturally occurring and recombinant forms of Factor VII can be found in the patent and scientific literature including, U.S. Pat. Nos. 5,563,045, 5,451,521, 5,422,260, 5,004,803, 4,757,006, 5,661,008, 5,789,203, 5,681,746, 5,595,886, 5,045,455, 5,668,108, 5,633,150, 5,693,499, 5,587,310, 5,171,844, 5,149,637, 5,112,950, 4,886,876; International Patent Publication Nos. WO 94/11503, WO 87/07144, WO 92/16557, WO 91/09122, WO 97/03195, WO 96/21035, and WO 91/07490; European Patent Application Nos. EP 0 672 138, EP 0 270 618, EP 0 182 448, EP 0 162 067, EP 0 786 474, EP 0 533 862, EP 0 506 757, EP 0 874 057, EP 0 795 021, EP 0 670 332, EP 0 500 734, EP 0 232 112, and EP 0 160 457; Sanberg et al., XXth Int. Congress of the World Fed. Of Hemophilia (1992), and Lind et al., *Eur. J. Biochem.*, 232:19 (1995).

In another embodiment, a method for treating hemophilia B in a human subject, comprises administering an effective amount of a replication-defective virus composition of, in which the therapeutic product is Factor IX.

In another embodiment, a method for treating congestive heart failure in a human subject, comprises administering an effective amount of a replication-defective virus composition, in which the therapeutic product is insulin like growth factor or hepatocyte growth factor.

In another embodiment, a method for treating a central nervous system disorder in a human subject, comprises administering an effective amount of a replication-defective virus composition, in which the therapeutic product is nerve growth factor.

5.4. Monitoring Transgene Expression and Undesired Side Effects 5.4.1. Monitoring Transgene Expression After administration of the replication-defective virus compositions of the invention, transgene expression can be monitored by any method known to one skilled in the art. The expression of the administered transgenes can be readily detected, e.g., by quantifying the protein and/or RNA encoded by said transgene. Many methods standard in the art can be thus employed, including, but not limited to, immunoassays to detect and/or visualize protein expression (e.g., western blot, immunoprecipitation followed by sodium dodecyl sulfate polyacrylamide gel electrophoresis (SDS-PAGE), immunocytochemistry, immunohistochemical staining on sections etc.) and/or hybridization assays to detect gene expression by detecting and/or visualizing respectively mRNA encoding a gene (e.g., northern assays, dot blots, in situ hybridization, etc.). The viral genome and RNA derived from the transgene can also be detected by Quantitative-PCR (Q-PCR). Such assays are routine and well known in the art Immunoprecipitation protocols generally comprise lysing a population of cells in a lysis buffer such as RIPA buffer (1% NP-40 or Triton x-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40° C., adding protein A and/or protein G Sepharose beads to the cell lysate, incubating for about an hour or more at 40° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads).

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), incubating the membrane with primary antibody (the antibody of interest) diluted in blocking buffer, washing the membrane in washing buffer, incubating the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32p or 125I) diluted in blocking buffer, washing the membrane in wash buffer, and detecting the presence of the antigen. One of skill in the art would be knowledgeable as to the parameters that can be modified to increase the signal detected and to reduce the background noise.

ELISAs generally comprise preparing antigen, coating the well of a 96 well microtiter plate with the antigen, adding the antibody of interest conjugated to a detectable agent such as an enzymatic substrate (e.g., horseradish peroxidase or alkaline phosphatase) to the well and incubating for a period of time, and detecting the presence of the antigen. In ELISAs the antibody of interest does not have to be conjugated to a detectable agent; instead, a second antibody (which recognizes the antibody of interest) conjugated to a detectable compound may be added to the well. Further, instead of coating the well with the antigen, the antibody may be coated to the well. In this case, a second antibody conjugated to a detectable agent may be added following the addition of the antigen of interest to the coated well. One of skill in the art would be knowledgeable as to the parameters that can be modified to increase the signal detected as well as other variations of ELISAs known in the art.

A phenotypic or physiological readout can also be used to assess expression of a transgene. For example, the ability of a transgene product to ameliorate the severity of a disease or a symptom associated therewith can be assessed. Moreover, a positron emission tomography (PET) scan and a neutralizing antibody assay can be performed.

Moreover, the activity a transgene product can be assessed utilizing techniques well-known to one of skill in the art. For example, the activity of a transgene product can be determined by detecting induction of a cellular second messenger (e.g., intracellular Ca2+, diacylglycerol, 1P3, etc.), detecting the phosphorylation of a protein, detecting the activation of a transcription factor, or detecting a cellular response, for example, cellular differentiation, or cell proliferation or apoptosis via a cell based assay. The alteration in levels of a cellular second messenger or phosphorylation of a protein can be determined by, e.g., immunoassays well-known to one of skill in the art and described herein. The activation or inhibition of a transcription factor can be detected by, e.g., electromobility shift assays, and a cellular response such as cellular proliferation can be detected by, e.g., trypan blue cell counts, $^3$H-thymidine incorporation, and flow cytometry.

5.4.2. Monitoring Undesirable Side Effects/Toxicity

After administration of a replication-defective virus composition of the invention to a patient, undesired side effects and/or toxicity can be monitored by any method known to one skilled in the art for determination of whether to administer to the patient a pharmaceutical composition comprising a dimerizer (described in Section 5.2.3) in order to ablate or excise a transgene or to ablate the transcript of the transgene, or inhibit its translation.

The invention provides for methods of determining when to administer a pharmacological agent for ablating the therapeutic product to a subject who received a replication-defective virus composition encoding a therapeutic product and an ablator, comprising: (a) detecting expression of the therapeutic product in a tissue sample obtained from the patient, and (b) detecting a side effect associated with the presence of the therapeutic product in said subject, wherein detection of a side effect associated with the presence of the therapeutic product in said subject indicates a need to administer the pharmacological agent that induces expression of the ablator.

The invention also provides methods for determining when to administer a pharmacological agent for ablating the therapeutic product to a subject who received a replication-defective virus composition encoding a therapeutic product and an ablator, comprising: detecting the level of a biochemical marker of toxicity associated with the presence of the therapeutic product in a tissue sample obtained from said subject, wherein the level of said marker reflecting toxicity indicates a need to administer the pharmacological agent that induces expression of the ablator. Biochemical markers of toxicity are known in the art, and include clinical pathology serum measures such as, but not limited to, markers for abnormal kidney function (e.g., elevated blood urea nitrogen (BUN) and creatinine for renal toxicity); increased erythrocyte sedimentation rate as a marker for generalized inflammation; low white blood count, platelets, or red blood cells as a marker for bone marrow toxicity; etc. Liver function tests (lft) can be performed to detect abnormalities associated with liver toxicity. Examples of such lfts include tests for albumin, alanine transaminase, aspartate transaminase, alkaline phosphatase, bilirubin, and gamma glutamyl transpeptidase.

The invention further comprises methods for determining the presence of DNA encoding the therapeutic gene product, its RNA transcript, or its encoded protein in a tissue sample from the subject subsequent to treatment with the pharmacological agent that induces expression of the ablator, wherein the presence of the DNA encoding the therapeutic gene product, its RNA transcript, or its encoded protein indicates a need for a repeat treatment with the pharmacological agent that induces expression of the ablator.

One undesired side effect that can be monitored in a patient that has received a replication-defective virus composition of the invention is an antibody response to a secreted transgene product. Such an antibody response to a secreted transgene product occurs when an antibody binds the secreted transgene product or to self antigens that share epitopes with the transgene product. When the transgene product is an antibody, the response is referred to as an "anti-idiotype" response. When soluble antigens combine with antibodies in the vascular compartment, they may form circulating immune complexes that are trapped nonspecifically in the vascular beds of various organs, causing so-called immune complex diseases, such as serum sickness, vasculitis, nephritis systemic lupus erythematosus with vasculitis or glomerulonephritis.

In another, more generalized undesirable immune reaction to the secreted transgene product, an antibody response to the transgene product results in a cross reacting immune response to one or more self antigens, causing almost any kind of autoimmunity. Autoimmunity is the failure of an the immune system to recognize its own constituent parts as self, which allows an immune response against its own cells and tissues, giving rise to an autoimmune disease. Autoimmunity to the transgene product of the invention can give rise to any autoimmune disease including, but not limited to, Ankylosing Spondylitis, Crohns Disease, Idiopathic inflammatory bowel disease, Dermatomyositis, Diabetes mellitus type-1, Goodpasture's syndrome, Graves' disease, Guillain-Barre syndrome (GBS), Anti-ganglioside, Hashimoto's disease, Idiopathic thrombocytopenic purpura, Lupus erythematosus, Mixed Connective Tissue Disease, Myasthenia gravis, Narcolepsy, Pemphigus vulgaris, Pernicious anaemia, Psoriasis, Psoriatic Arthritis, Polymyositis, Primary biliary cirrhosis, Rheumatoid arthritis, Sjogren's syndrome, Temporal arteritis (also known as "giant cell arteritis"), Ulcerative Colitis (one of two types of idiopathic inflammatory bowel disease "IBD"), Vasculitis, and Wegener's granulomatosis.

Immune complex disease and autoimmunity can be detected and/or monitored in patients that have been treated with replication-defective virus compositions of the invention by any method known in the art. For example, a method that can be performed to measure immune complex disease and/or autoimmunity is an immune complex test, the purpose of which is to demonstrate circulating immune complexes in the blood, to estimate the severity of immune complex disease and/or autoimmune disease, and to monitor response after administration of the dimerizer. An immune complex test can be performed by any method known to one of skill in the art. In particular, an immune complex test can be performed using anyone or more of the methods described in U.S. Pat. Nos. 4,141,965, 4,210,622, 4,210,622, 4,331,649, 4,544,640, 4,753,893, and 5,888,834, each of which is incorporated herein by reference in its entirety.

Detection of symptoms caused by or associated with anyone of the following autoimmune diseases using methods known in the art is yet another way of detecting autoimmunity or immune complex disease caused by a secreted transgene product that was encoded by a replication-defective virus composition administered to a human subject: Ankylosing Spondylitis, Crohns Disease, Idiopathic inflammatory bowel disease, Dermatomyositis, Diabetes mellitus type-I, Goodpasture's syndrome, Graves' disease, Guillain-Barre syndrome (GBS), Anti-ganglioside, Hashimoto's disease, Idiopathic thrombocytopenic purpura, Lupus erythematosus, Mixed Connective Tissue Disease, Myasthenia gravis, Narcolepsy, Pemphigus vulgaris, Pernicious anaemia, Psoriasis, Psoriatic Arthritis, Polymyositis, Primary biliary cirrhosis, Rheumatoid arthritis, Sjogren's syndrome, Temporal arteritis (also known as "giant cell arteritis"), Ulcerative Colitis (one of two types of idiopathic inflammatory bowel disease "IBD"), Vasculitis, and Wegener's granulomatosis.

A common disease that arises out of autoimmunity and immune complex disease is vasculitis, which is an inflammation of the blood vessels. Vasculitis causes changes in the walls of blood vessels, including thickening, weakening, narrowing and scarring. Common tests and procedures that can be used to diagnose vasculitis include, but are not limited to blood tests, such as erythrocyte sedimentation rate, C-reactive protein test, complete blood cell count and anti-neutrophil cytoplasmic antibodies test; urine tests, which may show increased amounts of protein; imaging tests such as X-ray, ultrasound, computerized tomography (CT) and magnetic resonance imaging (MRI) to determine whether larger arteries, such as the aorta and its branches, are affected; X-rays of blood vessels (angiograms); and performing a biopsy of part of a blood vessel. General signs and symptoms of vasculitis that can be observed in patients treated by the methods of the invention include, but are not limited to, fever, fatigue, weight loss, muscle and joint pain, loss of appetite, and nerve problems, such as numbness or weakness.

When administration of a replication-defective virus composition of the invention results in local transgene expression, localized toxicities can be detected and/or monitored for a determination of whether to administer to the patient a pharmaceutical composition comprising a dimerizer (described in Section 5.2.3) in order to ablate or excise a transgene or to ablate the transcript of the transgene, or inhibit its translation. For example, when administering to the retina a replication-defective virus composition that comprises a transgene unit encoding a VEGF inhibitor for treatment of age-related macular degeneration, it is believed that VEGF may be neuroprotective in the retina, and inhibiting it could worsen eyesight due to drop out of ganglion cells. Thus, after administration of such a replication-defective virus composition, eyesight can be regularly monitored and ganglion cell drop out can be detected by any method known the art, e.g., noninvasive imaging of retina. Moreover, VEGF inhibition may also depleted necessary micro vasculature in the retina, which can be monitored using fluorescien angiography or any other method known in the art.

In general, side effects that can be detected/monitored in a patient after administration of a replication-defective virus of the invention for a determination of whether to administer a pharmaceutical composition comprising a dimerizer (described in Section 5.2.3) to the patient, include, but are not limited to bleeding of the intestine or any organ, deafness, loss of eye-sight, kidney failure, dementia, depression, diabetes, diarrhea, vomiting, erectile dysfunction, fever, glaucoma, hair loss, headache, hypertension, heart palpitations, insomnia, lactic acidosis, liver damage, melasma, thrombosis, priapism rhabdomyolysis, seizures, drowsiness, increase in appetite, decrease in appetite, dizziness, stroke, heart failure, or heart attack. Any method commonly used in the art for detecting the foregoing symptoms or any other side effects can be employed.

Ablator Therapy; Once it has been determined that a transgene product that was delivered to a patient by a method of the invention has caused undesirable side effects in a patient, a pharmaceutical composition comprising a dimerizer can be administered to a patient using any of the regimens, modes of administrations, or doses described in Section 5.2.3 herein.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

6. EXAMPLE 1

Manufacturing of Recombinant AAV Vectors at Scale

A high yielding, recombinant AAV production process based upon poly-ethylenimine (PEI)-mediated transfection of mammalian cells and iodixanol gradient centrifugation of concentrated culture supernatant. AAV vectors produced with the new process demonstrate equivalent or better transduction both in vitro and in vivo when compared to small scale, cesium chloride (CsCl) gradient-purified vectors. In addition, the iodixanol gradient purification process described effectively separates functional vector particles from empty capsids, a desirable property for reducing toxicity and unwanted immune responses during pre-clinical studies.

Recently it was observed that, in contrast to AAV2, most other AAV serotypes are primarily released into the media of calcium phosphate-transfected production cultures and not retained in the cell lysate (Vandenberghe, L. H., Lock, M., Xiao, R., Lin, J., Korn, M., and Wilson, J. M. 2010. Heparin-dependent release of AAV into the supernatant simplifies manufacturing, now published as "Efficient serotype-dependent Release of Functional Vector into the Culture Medium During Adeno-Associated Virus Manufacturing", Hu Gene Ther, 21:1251-1257 (October 2010)).

A scaled rAAV production method suitable for large animal studies, which is based upon PEI transfection and supernatant harvest can be utilized The method is high yielding, versatile for the production of vectors with different serotypes and transgenes, and simple enough that it may be performed in most laboratories with a minimum of specialized techniques and equipment. This method is now published in Lock et al, Hum Gen Ther, 2010 October; 21 (10): 1259-71, which is incorporated herein by reference.

REFERENCES

Atkinson, M. A., Fung, V. P., Wilkins, P. C., Takeya, R., K, Reynolds, T. C., and Aranha, I. L. 2005. Methods for generating high titer helper free preparations of release recombinant AAV vectors. US Published Patent Application No. 2005/0266567.

Auricchio, A., Hildinger, M., O'Connor, E., Gao, G. P., and Wilson, J. M. 2001, Isolation of highly infectious and pure adeno-associated virus type 2 vectors with a single step gravity-flow column. Hum Gene Ther 12(1): 71-76.

Brantly, M. L., Chulay, J. D., Wang, L., Mueller, C., Humphries, M., Spencer, L. T., Rouhani, F., Conlon, T. J., Calcedo, R., Betts, M. R. 2009. Sustained transgene expression despite T lymphocyte responses in a clinical trial of rAAV 1-AAT gene therapy. Proc Natl Acad Sci USA 106(38): 16363-16368.

Brument, N., Morenweiser, R., Blouin, V., Toublanc, E., Raimbaud, 1., Cherel, Y., Folliot, S., Gaden, F., Boulanger, P., Kroner-Lux, G. 2002. A versatile and scalable two-step ion-exchange chromatography process for the purification of recombinant adeno-associated virus serotypes-2 and -5. Mol Ther 6(5): 678-686.

Clement, N., Knop, D. R., and Byrne, B. J. 2009. Large-scale adeno-associated viral vector production using a herpesvirus-based system enables manufacturing for clinical studies. Hum Gene Ther 20(8): 796-806.

Davidoff, A. M., Ng, C. Y., Sleep, S., Gray, J., Azam, S., Zhao, Y., McIntosh, J. H., Karimipoor, M., and Nathwani, A. C. 2004. Purification of recombinant adeno-associated virus type 8 vectors by ion exchange chromatography generates clinical grade vector stock. J Virol Methods 121(2): 209-215.

Durocher, Y., Pham, P. L., St-Laurent, G., Jacob, D., Cass, B., Chahal, P., Lau, C. J., Nalbantoglu, J., and Kamen, A. 2007. Scalable serum-free production of recombinant adeno-associated virus type 2 by transfection of 293 suspension cells. J Virol Methods 144(1-2): 32-40.

Gao, G. P., Alvira, M. R., Wang, L., Calcedo, R., Johnston, J., and Wilson, J. M. 2002. Novel adeno-associated viruses from rhesus monkeys as vectors for human gene therapy. Proc Natl Acad Sci USA 99(18): 11854-11859.

Grimm, D., Kern, A., Rittner, K., and Kleinschmidt, Z. A. 1998. Novel tools for production and purification of recombinant adeno-associated virus vectors. Hum Gene Ther 9(18): 2745-2760.

Hermens, W. T., Dijkhuizen, P. A., Sonnemans, M. A., Grimm, D., Kleinschmidt, J. A., and Verhaagen, J. 1999. Purification of recombinant adeno-associated virus by iodixanol gradient ultracentrifugation allows rapid and reproducible preparation of vector stocks for gene transfer in the nervous system. Hum Gene Ther 10(11): 1885-1891.

Hildinger, M., Baldi, L., Stettler, M., and Wurm, F. M. 2007. High-titer, serum free production of adeno-associated virus vectors by polyethyleneimine-mediated plasmid transfection in mammalian suspension cells. Biotechnol Lett 29(11): 1713-1721.

Kaludov, N., Handelman, B., and Chiorini, J. A. 2002. Scalable purification of adeno-associated virus type 2, 4, or 5 using ion-exchange chromatography. Hum Gene Ther 13(10): 1235-1243.

Maguire, A. M., Simonelli, F., Pierce, E. A., Pugh, E. N., Jr., Mingozzi, F., Bennicelli, J., Banfi, S., Marshall, K. A., Testa, F., Surace, E. M. 2008. Safety and efficacy of gene transfer for Leber's congenital amaurosis. N Engl J Med 358(21): 2240-2248.

Matsushita, T., Elliger, S., Elliger, C., Podsakoff, G., Villarreal, L., Kurtzman, G. J., Iwaki, Y., and Colosi, P. 1998. Adeno-associated virus vectors can be efficiently produced without helper virus. Gene Ther 5(7): 938-945.

Moss, R B., Rodman, D., Spencer, L. T., Aitken, M. L., Zeitlin, P. L., Waltz, D., MiHa, C., Brody, A. S., Clancy, J. P., Ramsey, B. 2004. Repeated adeno-associated virus serotype 2 aerosol-mediated cystic fibrosis transmembrane regulator gene transfer to the lungs of patients with cystic fibrosis: a multicenter, double-blind, placebo-controlled trial. Chest 125(2): 509-521.

Mueller, C. and Flotte, T. R 2008. Clinical gene therapy using recombinant adeno-associated virus vectors. Gene Ther 15(11): 858-863.

Neinhuis, A. 2009. Dose-Escalation Study Of A Self Complementary Adeno-Associated Viral Vector For Gene Transfer in Hemophilia B.

Okada, T., Nonaka-Sarukawa, M., Uchibori, R., Kinoshita, K., Hayashita-Kinoh, H., Nitahara-Kasahara, Y., Takeda, S., and Ozawa, K. 2009. Scalable purification of adeno-associated virus serotype 1 (AAV1) and AAV8 vectors, using dual ion-exchange adsorptive membranes. Hum Gene Ther 20(9): 1013-1021.

Qu, G., Bahr-Davidson, J., Prado, J., Tai, A., Cataniag, F., McDonnell, J., Zhou, J., Hauck, B., Luna, J., Sommer, J. M. 2007. Separation of adeno-associated virus type 2 empty particles from genome containing vectors by anion-exchange column chromatography. J Virol Methods 140(1-2): 183-192.

Salvetti, A., Oreve, S., Chadeuf, G., Favre, D., Cherel, Y., Champion-Arnaud, P., David-Ameline, J., and Moullier, P. 1998. Factors influencing recombinant adeno-associated virus production. Hum Gene Ther 9(5): 695-706.

Schroder, M., Schafer, R, and Friedl, P. 1997. Spectrophotometric determination of iodixanol in subcellular fractions of mammalian cells. Anal Biochem 244(1): 174-176.

Smith, R. H., Levy, J. R., and Kotin, R. M. 2009. A simplified baculovirus-AAV expression vector system coupled with one-step affinity purification yields high-titer rAAV stocks from insect cells. Mol Ther 17(11): 1888-1896.

Snyder, R O. and Flotte, T. R 2002. Production of clinical-grade recombinant adeno-associated virus vectors. Curr Opin Biotechnol 13(5): 418-423.

Sommer, J. M., Smith, P. H., Parthasarathy, S., Isaacs, J., Vijay, S., Kieran, J., Powell, S. K., McClelland, A., and Wright, J. F. 2003. Quantification of adeno-associated virus particles and empty capsids by optical density measurement. Mol Ther 7(1): 122-128.

Vandenberghe, L. H., Lock, M., Xiao, R., Lin, J., Korn, M., and Wilson, J. M. 2010. Heparin-dependent release of AAV into the supernatant simplifies manufacturing. Submitted, and now published as "Efficient serotype-dependent Release of Functional Vector into the Culture Medium During Adeno-Associated Virus Manufacturing", Hu Gene Ther, 21:1251-1257 (October 2010).

Virag, T., Cecchini, S., and Kotin, R. M. 2009. Producing recombinant adeno-associated virus in foster cells: overcoming production limitations using a baculovirusinsect cell expression strategy. Hum Gene Ther 20(8): 807-817.

Wang, L., Wang, H., Bell, P., McCarter, R. J., He, 1, Calcedo, R., Vandenberghe, L. H., Morizono, H., Batshaw, M. L., and Wilson, J. M. 2010. Systematic evaluation of AAV vectors for liver directed gene transfer in murine models. Mol Ther 18(1): 118-125.

Warrington, K. H., Jr. and Herzog, R. W. 2006. Treatment of human disease by adeno-associated viral gene transfer. Hum Genet 119(6): 571-603.

Wright, J. F. 2009. Transient transfection methods for clinical adeno-associated viral vector production. Hum Gene Ther 20(7): 698-706.

Wright, J. F., Le, T., Prado, J., Bahr-Davidson, J., Smith, P. H., Zhen, Z., Sommer, J. M., Pierce, G. F., and Qu, G. 2005. Identification of factors that contribute to recombinant AAV2 particle aggregation and methods to prevent its occurrence during vector purification and formulation. Mol Ther 12(1): 171-178.

Xiao, X., Li, J., and Samulski, R. J. 1998. Production of high-titer recombinant adeno-associated virus vectors in the absence of helper adenovirus. J Virol 72(3): 2224-2232.

Zhang, H., Xie, J., Xie, Q., Wilson, J. M., and Gao, G. 2009. Adenovirus-adeno-associated virus hybrid for large-scale recombinant adeno-associated virus production. Hum Gene Ther 20(9): 922-929.

Zolotukhin, S., Byrne, B. J., Mason, E., Zolotukhin, I., Potter, M., Chesnut, K., Summerford, C., Samulski, R. J., and Muzyczka, N. 1999. Recombinant adeno-associated virus purification using novel methods improves infectious titer and yield. Gene Ther 6(6): 973-985.

Zolotukhin, S., Potter, M., Zolotukhin, I., Sakai, Y., Loiler, S., Fraites, T. J., Jr., Chiodo, V. A., Phillipsberg, T., Muzyczka, N., Hauswirth, W. W. 2002. Production and purification of serotype 1, 2, and 5 recombinant adeno-associated viral vectors. Methods 28(2): 158-167.

7. EXAMPLE 2

Cesium Purification of AAV Vectors

This example describes a new procedure for cesium chloride (CsCl) purification of AAV vectors from transfected cell pellets.

Day 1—Pellet Processing and CsCl Spin

1) Lysate Preparation

Thaw cells from −80° C. freezer for 15 minutes at 37° C.

Resuspend the cell pellet in ~20 mL of Resuspension Buffer 1(50 mM Tris, pH 8.0, 2 mM MgCl) for 40 plates of cells and for a final volume of 20 mL, and place on ice.

Freeze/thaw 3 times (dry ice and ethanol bath/37° C. water bath).

Add 100 µL of Benzonase (250 U/mL) per prep and invert gently, incubate the samples at 37° C. for 20 minutes, inverting the tube every 5 min.

Add 6 mL of 5M NaCl to bring the final salt concentration to 1 M. Mix.

Spin at 8,000 rpm for 15 min at 4° C. in Sorval centrifuge. Note: Ensure the Sorval is clean. After centrifugation, sterilize tube with 70% before proceeding further. Transfer supernatant to a new tube.

Spin again at 8,000 rpm for 15 min at 4° C. in Sorval. Note: Ensure the Sorval is clean. After centrifugation, sterilize tube with 70% before proceeding further.

Add 1.8 mL of 10% OGP for a final concentration of 0.5%, and mix gently by inversion.

2) Cesium Chloride Step Gradient Purification

For each preparation, prepare two 2-tier gradients consisting of 7.5 mL of 1.5 g/mL CsCl and 15 mL 1.3 g/mL CsCl in Beckman SW-28 tubes (do not use ultraclear tubes). Load the less dense CsCl first and then bottom load the heavier CsCl.

Add 15 mL of sample to the top of each gradient. Add sample slowly to the side of the tube so as not to disturb the gradient. Label the tubes with lot #.

Spin at 25,000 rpm at 15° C. for 20 hours minimum.

Day 2—Collect AAV band from 1st CsCl Spin and set up 2nd CsCl spin

1) Collect Band from CsCl Spin

Carefully remove the centrifuge tubes (A & B) out of the bucket, taking care not to disturb the gradient. Secure the first tube (A) on a tube holder.

Take a pre-sterilized 2 ft length of tygon-silicone tubing (1.6 mm inner diameter; Fisher NC9422080) fitted with two $1/16$th inch male luers (Fisher NC9507090) and insert 18 G 1" needles into the luers.

Pierce the tube at a right angle as close to the bottom as possible with one of the 18 G 1" needles (bevel facing up), and clamp the tubing into the easy load rollers of the masterflex pump. Gently increase the speed to ~1 mL/min. Collect the first 4.5 mL into a 15 mL falcon tube and then start to collect fractions (250 μL) into a 96 well plate (from tube A). Collect 48 fractions.

Run the rest of the gradient into a beaker containing a 20% bleach solution and discard the needle/tubing assembly.

Take another pre-sterilized 2 ft length of tygon-silicone tubing (1.6 mm inner diameter; Fisher NC9422080) fitted with two $1/16$th inch male luers (Fisher NC9507090) and insert 18 G 1" needles into the luers for collecting fractions from second tube (from tube B).

Repeat the entire harvest for the tube B. Discard the needle/tubing assembly after use.

2) Read Refraction Index (RJ)

Using a multichannel pipetter, transfer 10 μL of each fraction (of the 48 collected, first from 96-well plate A) to a fresh plate (label with 1 to 48) and leave the remainder of the fractions in the biosafety cabinet.

Take 5 μL of each fraction and read the RI using a refractometer. The fractions containing AAV should have a refractive index of 1.3740-1.3660. Read the RI down to 1.3650 and then pool the fractions in the biosafety cabinet with RI in the 1.3740 to 1.3660 range. (Measure the total volume after pooling both the 96-well plates belonging to tube 1 and 2. In case there is still some space for adding more, add from wells with RI of 1.375.)

Repeat this process for the second 96-well plate (from tube B).

3) Load the Second Gradient

The total pooled volume from each gradient (from tubes A and B) should be 5-6 mL. Pool the two gradient harvests in a 50 mL falcon tube and bring the volume to 13 mL with a 1.41 g/mL solution of CsCl. Mix well with a pipette.

Using a 10 mL syringe and 18 G needle, add the pooled first gradient harvest to a 13 mL sealable centrifuge tube. The solution should be added to the line on the neck of the tube with no bubbles.

Seal the tube using the portable sealer, metal tube caps and heat sink.

Squeeze the tube to test for leaks and then place in a Ti70.1 rotor with the appropriate balance. Insert the rotor caps and lid and then spin at 60,000 rpm, 15° C. for 20 hours.

Day 3—Collect AAV band from 2nd CsCl Spin and Desalt

1) Collect Band from CsCl Spin

Carefully remove the centrifuge tube out of the bucket, taking care not to disturb the gradient. Secure the tube on a tube holder. At this point a single band should be visible after bottom illumination about halfway up the tube.

Take a pre-sterilized 2 ft length of tygon-silicone tubing (1.6 mm inner diameter; Fisher NC9422080) fitted with two $1/16$th inch male luers (Fisher NC9507090) and insert 18 G 1" needles into the luers. Use 1 length of tubing per prep.

Pierce the tube at a right angle as close to the bottom as possible with one of the 18 G 1" needles (bevel facing up) and clamp the tubing into the easy load rollers of the masterflex pump. Pierce the tube again at the top with a second 18 G needle. Gently increase the speed to ~1 mL/min and then start to collect fractions (250 μL) into a 96 well plate. Collect the whole gradient (~45 fractions).

2) Read Refractive Index (RI):

Using a multichannel pipetter, transfer 10 μL of each fraction to a fresh plate and leave the remainder of the fractions in the biosafety cabinet.

Take 5 μL of each fraction and read the RI using a refractometer. The fractions containing AAV should have a refractive index of 1.3750-1.3660. Read the RI down to 1.3650, and then pool fractions with RI in range of 1.3750 to 1.3660.

3) Desalting: Amicon Ultra-I 5 Centrifugal Concentrators

In this procedure the vector is diluted with PBS and spun at low speed through the 100 kDa MWCO filter device. Because of the large molecular weight of AAV Particles (5000 kDa), the vector is retained by the membrane and the salt passes through. Vector can build up on the membranes, so rinsing is required at the final stage.

Aliquot 50 mL PBS+35 mM NaCl into a 50 mL tube.

Dilute the pooled fractions from step 2 above with the PBS+35 mM NaCl to 15 mL total volume. Mix gently and add to Amicon filter device.

Spin in a bench top Sorvall centrifuge at 2,000 to 4,000 rpm for 2 minutes. Because it is important to keep the level of the liquid above the top of the filter surface (~1.8 mL) at all times so that the vector does not dry onto the membrane, it is recommended that the lower speed spin is attempted first to determine the flow rate of the sample. The goal is to reduce the volume of the retentate to ~1.8 mL. An additional short spines) may be necessary to achieve this. If the volume does go below that desired, bring it back to 1.8 mL with PBS+35 mM NaCl.

Add a further 13.2 mL PBS+35 mM NaCl, mix by pipette with the retentate remaining in the device, and repeat the spinning process described above. Continue this process until all the 50 mL PBS+35 mM NaCl aliquoted previously is spun through the device.

Rinse the membrane with the final retentate (~1.8 mL) by repeatedly pipetting against the entire surface. Recover the retentate into a suitably-sized sterile centrifuge tube using 1 mL and 200 μL Eppendorf tips (the 200 μL tip is for the final retentate at the bottom of the device that is inaccessible to a 1 mL tip). Rinse the membrane twice using a minimum of 100 µL of PBS+35 mM NaCl and pool it with your final retentate.

Determine the exact volume and add glycerol to 5%.

Aliquot into 5×25 aliquots, 1×100 µL for archive, and the rest into 105 µL aliquots.

Freeze immediately at −80° C.

Reagents Used in rAAV Purification

Resuspension buffer 1[50 mM Tris (pH 8.0), 2 mM MgCl]: 50 mL 1 M Tris (pH 8.0), 2 mL/M MgCh to 948 mL MQ water, filter sterilize.

1.5 g/mL CsCl solutions: dissolve 675 g of CsCl in 650 mL PBS and adjust final volume to 1000 mL. Weigh 1 mL of the solution to check the density. Filter sterilize the solution.

1.3 g/mL CsCl solutions: dissolve 405 g of CsCl in 906 mL PBS and adjust final volume to 1000 mL. Weigh 1 mL of the solution to check the density. Filter sterilize the solution.

10% (W/V) Octyl-PD-glucopyranoside (OGP) (Sigma, 08001-10G): Bring 10 grams to 100 mL with milliQ water. Filter sterilize the solution.

Final formulation buffer: PBS+35 mM NaCl. To 1 liter sterile PBS, add 7.05 mL sterile 5 M NaCl.

Sterile glycerol: Aliquot glycerol into 100 mL glass bottles. Autoclave for 20 minutes on liquid cycle.

8. EXAMPLE 3

DNA Constructs for Preparation of PITA AAV Vectors

The invention is illustrated by Examples 3-5, which demonstrate the tight regulation of ablator expression using rapamycin, to dimerize transcription factor domains that induce expression of Cre recombinase; and the successful inducible ablation of a transgene containing Cre recognition sites (loxP) in cells. The tight regulation of expression of the ablator is demonstrated in animal models.

The following are examples of DNA constructs DNA constructs and their use to generate replication-defective AAV vectors for use in accordance with the PITA system of the invention is illustrated in the examples below.

8.1. Constructs Encoding a Dimerizable Transcription Factor Domain Unit and an Ablation Unit FIGS. 1A-B through FIG. 5B are diagrams of the following DNA constructs that can be used to generate AAV vectors that encode a dimerizable transcription factor domain unit and an ablation unit: (1) pAAV.CMV.TF.FRB-IIRES-1×FKBP.Cre (FIGS. 1A-B); (2) pAAV.CMV.TF.FRB-T2A-2×FKBP.Cre (FIGS. 2A-B); (3) pAAV.CMVI73.TF.FRB-T2A-3× FKBP.Cre (FIGS. 3A-B); and (4) pAAV.CMV.TF.FRB-T2A-2×FKBP.ISce-I (FIGS. 4A-B).

A description of the various domains contained in the DNA constructs follows:

ITR: inverted terminal repeats of AAV serotype 2 (168 bp). [SEQ ID NO: 26]

CMV: full cytomegalovirus (CMV) promoter; including enhancer. [SEQ ID NO 27]

CMV (173 bp): minimal CMV promoter, not including enhancer. [SEQ ID NO: 28]

FRB-TA fusion: fusion of dimerizer binding domain and an activation domain of a transcription factor (900 bp, SEQ ID NO: 29). The protein is provided herein as SEQ ID NO: 30. The FRB fragment corresponds to amino acids 2021-2113 of FRAP (FKBP rapamycin-associated protein, also known as mTOR [mammalian target of rapamycin]), a phosphoinositide 3-kinase homolog that controls cell growth and division. The FRAP sequence incorporates the single point-mutation Thr2098Leu (FRAP$_L$) to allow use of certain non-immunosuppressive rapamycin analogs (rapalogs). FRAP binds to rapamycin (or its analogs) and FKBP and is fused to a portion of human NF-KB p65 (190 amino acids) as transcription activator.

ZFHD-FKBP fusion: fusion of a DNA binding domain and 1 copy of a Dimerizer binding domain (1×FKBP; 732 bp), 2 copies of drug binding domain (2×FKBP; 1059 bp), or 3 (3×FKBP; 1389 bp) copies of drug binding domain. Immunophilin FKBP (FK506-binding protein) is an abundant 12 kDa cytoplasmic protein that acts as the intracellular receptor for the immunosuppressive drugs FK506 and rapamycin. ZFHD is DNA binding domains composed of a zinc finger pair and a homeodomain. Both fusion proteins contain N-terminal nuclear localization sequence from human c-Myc at the 5' end. See, SEQ ID NO: 45.

T2A: self cleavage peptide 2A (54 bp) (SEQ ID NO: 31).

Z8I: 8 copies of the binding site for ZFHD (Z8) followed by minimal promoter from the human interleukin-2 (IL-2) gene (SEQ ID NO: 32). Variants of this promoter may be used, e.g., which contain from 1 to about 20 copies of the binding site for ZFHD followed by a promoter, e.g., the minimal promoter from IL-2.

Cre: Cre recombinase. Cre is a type I topoisomerase isolated from bacteriophage P1. Cre mediates site specific recombination in DNA between two loxP sites leading to deletion or gene conversion (1029 bp, SEQ ID NO: 33).

I-SceI: a member of intron endonuclease or homing endonuclease which is a large class of meganuclease (708 bp, SEQ ID NO: 34). They are encoded by mobile genetic elements such as introns found in bacteria and plants. I-SceI is a yeast endonuclease involved in an intron homing process. I-SceI recognizes a specific asymmetric 18 bp element, a rare sequence in mammalian genome, and creates double strand breaks. See, Jasin, M. (1996) Trends Genet., 12, 224-228.

hGH poly A: minimal poly adenylation signal from human GH (SEQ ID NO: 35).

IRES: internal ribosome entry site sequence from ECMV (encephalomyocarditis virus) (SEQ ID NO: 36).

8.2. Constructs Encoding Transgene Units

FIGS. 5A-B and FIGS. 6A-B are diagrams of the following DNA constructs for generating an AAV vector encoding a transgene flanked by loxP recognition sites for Cre recombinase:

(1) pENN.CMV.Pl.loxP.Luc.SV40 (FIGS. 5A-B); and (2) pENN.CMV.Pl.sce.Luc.SV40 (FIGS. 6A-B). A description of the various domains of the constructs follows:

ITR: inverted terminal repeats of AAV serotype 2 (SEQ ID NO: 26).

CMV: cytomegalovirus (CMV) promoter and enhancer regulating immediate early genes expression (832 bp, SEQ ID NO: 27).

loxP: recognition sequences of Cre. It is a 34 bp element comprising of two 13 bp inverted repeat flanking an 8 bp region which confers orientation (34 bp, SEQ ID NO: 37).

Ffluciferase: fire fly luciferase (1656 bp, SEQ ID NO: 38).

SV 40: late polyadenylation signal (239 bp, SEQ ID NO: 39).

I-SceI site: SceI recognition site (18 bp, SEQ ID NO: 25).

8.3. Constructs Encoding a Transgene Unit and a Dimerizable Transcription Factor Domain Unit FIG. 7 is a diagram of DNA construct for generating an AAV vector that contains a transgene unit and a dimerizable transcription factor domain unit. This plasmid provides, on AAV plasmid backbone containing an ampicillin resistance gene, an AAV 5' ITR, a transcription factor (TF) domain unit, a CMV promoter, an FRB (amino acids 2021-2113 of FRAP (FKBP rapamycin-associated protein, also known as mTOR [mammalian target of rapamycin]), a phosphoinositide 3-kinase homolog that controls cell growth and division), a T2A self-cleavage domain, an FKBP domain, and a human growth hormone polyA site, a CMV promoter, a loxP site, an interferon alpha coding sequence, and an SV40 polyA site. The ablation unit (cre expression cassette) can be located on a separate construct.

This strategy could minimize any potential background level expression of cre derived from upstream CMV promoter.

9. EXAMPLE 4

In Vitro Model for PITA

This example demonstrates that the DNA elements (units) engineered into the AAV vectors successfully achieve tightly controlled inducible ablation of the transgene in cells. In particular, this example shows that luciferase transgene expression can be ablated upon dimerizer (rapamycin) treatment of cells transfected with constructs containing a transgene unit (expressing luciferase and containing lox p sites), an ablation unit (expressing Cre), and a dimerizable transcription factor domain unit.

Human embryonic kidney fibroblast 293 cells were seeded onto 12 well plates. Transfection of the cells with various DNA constructs described in section 9.1 herein was carried out the next day when the cell density reached 90% confluency using Lipofectamine™ 2000 transfection reagent purchased from Invitrogen. A vector encoding enhanced green fluorescent protein (EGFP) was added at 10% of total DNA in each well to serve as internal control for transfection. The DNA suspended in DMEM was mixed with Lipofectamine™ 2000 transfection reagent to form DNA-lipid complex and added to 293 cells for transfection following instructions provided by Invitrogen Corporation. At 6 hours post transfection, half of the wells were treated with rapamycin at a final concentration of 50 nM. Culture medium (DMEM supplemented with 10% FBS) was replaced daily with fresh rapamycin. At 48 and 72 hour post transfection, cells were washed once with PBS and then scraped out of the well, resuspended in lysis buffer supplied in Luciferase assay kit purchased from Promega. The cell suspension was vortexed and the debri spun down. The luciferase activity was determined by mixing 10 µL of the lysate with 100 µL of the substrate and light emission per second read from a luminometer.

9.1. Constructs

The following constructs, most of which are described in Section 8, Example 1, were used to generate infectious, replication-defective AAV vectors:

1. pENN.AAV.CMV.RBG as a control, containing a CMV promoter and no transgene
2. pENN.CMV.Pl.loxP.Luc.SV40 (FIGS. 5A-B)/pENN.AAV.CMV.RBG (CMV promoter and no transgene)
3. pENN.CMV.Pl.loxP.Luc.SV40(FIGS. 5A-B/pAAV.TF.CMV.FRB-T2A-2×FKBP.Cre (FIGS. 2A-B)
4. pENN.CMV.Pl.loxP.Luc.Sv40(FIGS. 5A-B/pAAV.TF.CMV.FRB-IRES-FKBP.Cre (FIGS. 1A-B)
5. pENN.CMV.Pl.loxP.Luc.Sv40(FIGS. 5A-B)/pAAV.CMVI73.FRB-T2A-3×FKBP.Cre (FIGS. 3A-B)
6. pENN.CMV.Pl.loxP.Luc.Sv40(FIGS. 5A-B)/pENN.AAV.CMV.PI.Cre.RBG, which expresses the Cre gene from a constitutive promoter

9.2. Results

The results at 48 hours are shown in FIG. 8A and the results at 72 hours are shown in FIG. 8B. In the control (treatment 6), where Cre is constitutively expressed, luciferase expression was ablated independently of rapamycin compared to the control expression of luciferase without 10×P sites (treatment 2, cells transfected with luciferase construct). In contrast, in cells receiving the 10×P flanking luciferase construct plus one of the constructs carrying cre under the control of PITA system (treatment 3, 4 and 5), the level of the reporter gene expression is comparable to the control in the absence of dimerizer, rapamycin, indicating very little or no cre expression is induced. However, upon induction by treatment with rapamycin, the level of reporter gene expression in cells receiving PIT A controlled cre constructs were significantly reduced compared to the control (treatment 2), indicating cre expression was activated. The results confirm that the expression of the ablator is specifically regulated by the dimerizer, rapamycin.

10. EXAMPLE 5

In Vivo Model for a Dimerizer-Inducible System

This example shows tight tissue-specific control of transgene expression using a liver-specific promoter that is regulated by the dimerizer-inducible system described herein. These data serves as a model for tight regulation of the ablator in the PITA system.

Four groups of three mice received IV injection of AAV vectors encoding bicistronic reporter genes (GFP-Luciferase) at doses of $3\times10^{10}$, $1\times10^{11}$ and $3\times10^{11}$ particles of virus, respectively: Group 1 (G1, G2, and G3) received AAV vectors expressing GFP Luciferase under the control of ubiquitous constitutive CMV promoter (see FIG. 9A for a diagram of the DNA construct). Group 2 (G4, G5, and G6) received co-injection of the following 2 AAV vectors: (1) AAV vector expressing a dimerizable transcription factor domain unit (FRB fused with p65 activation domain and DNA binding domain ZFHD fused with 3 copies of FKBP) driven by the CMV promoter (the DNA construct shown in FIG. 2B; and (2) AAV vector expressing GFP-Luciferase driven by a promoter induced by the dimerized TF (see FIG. 12C for a diagram of the DNA constructs). Group 3 (G7, G8, and G9) received AAV vector expressing GFP-Luciferase under the control of a liver constitutive promoter, TBG (see FIG. 9C for a diagram of the DNA construct). Group 4 (G10, G11, G12) received co-injection of the following 2 AAV vectors: (1) AAV vector expressing a dimerizable transcription factor domain unit (FRB fused with p65 activation domain and DNA binding domain ZFHD fused with 3 copies of FKBP) driven by the TBG promoter; and (2) AAV vector expressing GFP-Luciferase driven by a promoter induced by the dimerized TF (see FIG. 9D for a diagram of the DNA constructs).

About 2 weeks post virus administration, the mice were given IP injection of the dimerizer, rapamycin, at the dose of 2 mg/kg. Starting the next day the luciferase expression was monitored by Xenogen imaging analysis. Approximately 24 hours post rapamycin injection, the mice were IP injected with luciferin, the substrate for luciferase, then anesthetized for imaging.

The mice that received $3\times10^{11}$ particles of virus had images taken 30 min post luciferin injection (FIGS. 10A-D). For Group 1 mice that received vectors carrying GFP-Luciferase, expression driven by CMV promoter, the luciferase expression was observed in various tissues and predominantly in lungs, liver and muscle (See FIG. 10A). In contrast, luciferase expression was restricted to liver in Group 3 mice, which received luciferase vector in which the expression was controlled by TBG promoter (see FIG. 10B). In Group 2 mice, the level of luciferase expression was elevated by more than 2 logs compared to level of pre-induction, and the expression is predominantly in liver and muscle (see FIG. 10C). In Group 4 mice, more than 100 fold of luciferase expression was induced and restricted in the liver, compared to pre-inducement (see FIG. 10D).

The mice that received $1 \times 10^{11}$ particles of viruses, show results similar to that of high dose groups but with lower level of expression upon induction, and predominantly in liver (see FIGS. 11A-D).

CONCLUSIONS

1. The dimerizer-inducible system is robust with peak level of luciferase expression more than 2 logs over baseline and back to close to baseline within a week (not shown).

2. Liver is the most efficient tissue to be infected when viruses were given IV.

3. Liver is also the most efficient tissue to be cotransduced with 2 viruses which is critical for the dimerizer-inducible system to work.

4. The luciferase expression regulated by that dimerizer-inducible system with transcription factor expression controlled by CMV promoter is significantly higher in mouse liver than expression coming from CMV promoter without regulation. This indicated that inducible promoter is a stronger promoter in liver once it is activated compared to the CMV promoter.

5. Luciferase expression was detected specifically in liver upon induction by rapamycin in mice receiving vectors carrying the inducible TBG promoter system. Luciferase expression mediated by the liver-specific regulatable vectors was completely dependent upon induction by rapamycin and the peak level of luciferase expression is comparable to that under the control of TBG promoter. This study confirmed that liver specific gene regulation can be achieved by AAV mediated gene delivery of liver specific dimerizer-inducible system.

11. EXAMPLE 6

PITA for Age-Related Macular Degeneration (AMD) Therapy

Intravitreal administration of a monoclonal antibody has proven to be an effective therapy for AMD to slow down disease progression and improve visual acuity in a subpopulation of patients. A key limitation of this approach, however, is the requirement for repeated intravitreal injections. Gene therapy has the potential to provide long term correction and a single injection should be sufficient to achieve a therapeutic effect. FIGS. 12 A-C show PITA DNA constructs for treating AMD, containing transgene units comprising a VEGF antagonist, such as an anti-VEGF antibody (Avastin heavy chain (AvastinH) and Avastin light chain (AvastinL); FIGS. 12B and 12C) or a soluble VEGF receptor (sFlt-1; FIG. 12A). Vectors comprising these DNA constructs can be delivered via subretinal injection at the dose of 0.1-10 mg/kg. Ablation of transgene expression can be achieved by oral dimerizer administration if adverse effects of long term anti-VEGF therapy are observed.

12. Example 7

PITA for Liver Metabolic Disease Therapy

PITA is potentially useful for treating liver metabolic disease such as hepatitis C and hemophilia. FIG. 13A shows a PITA construct for treating hemophilia A and/or B, containing a transgene unit comprising Factor IX. Factor VIII can also be delivered for treatment of hemophilia A and B respectively (Factor VIII and IX for hemophilia A and B, respectively). The therapy could be ablated in patients if inhibitor formation occurs. FIG. 13B shows a PITA construct for delivery of shRNA targeting the IRES of HCV. A vector comprising this construct could be injected via a mesenteric tributary of portal vein at the dose of $3 \times 10^{12}$ GC/kg. The expression of shRNA can be ablated if nonspecific toxicity of RNA interference arises or the therapy is no longer needed.

13. EXAMPLE 8

PITA for Heart Disease Therapy

PITA could be utilized for heart disease applications including, but not limited to, congestive heart failure (CHF) and myocardial infarction (MI). The treatment of CHF could involve the delivery of insulin like growth factor (IGF) or hepatocyte growth factor (HGF) using the constructs shown in FIGS. 14A and 14B. For the treatment of myocardial infarction, delivery of genes in the early stages of MI could protect the heart from the deleterious effects of ischemia but allow ablation of the therapy when no longer required. Therapeutic genes for this approach include heme oxygenase-1 (HO-1) which can function to limit the extent of ischemic injury. Delivery methods for vector-mediated gene delivery to the heart include transcutaneous, intravascular, intramuscular and cardiopulmonary bypass techniques. For the human, the optimal vector-mediated gene delivery protocol would likely utilize retrograde or ante grade trans coronary delivery into the coronary artery or anterior cardiac vein.

14. EXAMPLE 9

PITA for Central Nervous System (CNS) Disease Therapy

Attractive candidates for the application of PITA in the central nervous system include neurotrophic factors for the treatment of Alzheimer's disease, Parkinson's disease, amyotrophic lateral sclerosis (ALS), Huntington's disease and ocular diseases. FIG. 15 shows a PITA construct for treating Alzheimer's disease, containing a transgene unit comprising nerve growth factor (NGF). AAV vector-mediated gene delivery of NGF, is currently being studied in a Phase I clinical trial conducted by Ceregene for the treatment of Alzheimer's disease. NGF is a neurotrophic factor, which has been shown to be effective in reducing cholinergic cell loss in animal models of neurodegenerative disease and may be effective in preventing loss of memory and cognitive abilities in patients with AD. The delivery method for the approach consists of bilateral, stereotactic injection to target the basal forebrain region of the brain containing the nucleus basalis of Meynert (NBM). Due to the potential for side-effects resulting in the need to end treatment, further engineering the construct to include PITA is warranted.

The application of PITA in the central nervous system for the treatment of epilepsies could also be of value both due to the potential to ablate gene expression once the issue surrounding the seizures becomes resolved as well as due to the limited alternative approaches available for the treatment of epilepsies that are unresponsive to drug therapy and surgically difficult to treat. In these cases, in particular, delivery methods involving sterotactic injection of vectors expressing therapeutic genes, would be far less invasive than alternative surgical treatments. Candidates for gene expression could include galanin, neuropeptide Y (NPY) and glial cell line-derived neurotrophic factor, GDNF, which have been shown to have therapeutic effects in animal models of epilepsy. Other applications include to deliver nerve growth factor (NGF) for Alzheimer's and aromatic L-amino acid decarboxylase (ADCC) for Parkinson's Disease.

15. EXAMPLE 10

PITA for HIV Therapy

Naturally induced neutralizing antibody against HIV has been identified in the sera of long term infected patients. As an alternative to active vaccine approaches, which have resulted in inefficient induction but sufficient levels of neutralizing antibody delivered by AAV, PITA is a promising approach to deliver anti-HIV neutralizing antibody for passive immunity therapy. See FIG. 16. The construct design is similar to avastin gene delivery for AMD therapy (see FIGS. 12B and 12C). A vector comprising a construct encoding an antibody regulated by the liver specific promoter (TBG) could be injected into the liver at a dose of $3 \times 10^{12}$ GC/kg. Alternatively, a vector comprising a construct carrying a ubiquitous CB7 promoter driving antibody expression could be delivered by intramuscular injection at a dose of $5 \times 10^{12}$ GC/mL for up to 20 injections into the quadriceps or biceps muscle. The therapy can be ablated if it is no longer needed or if toxicity develops due to induction of anti-drug antibody.

16. EXAMPLE 11

The DNA constructs described in the following example may be used to prepare replication-defective AAV viruses and virus compositions according to the invention.

Open reading frames encoding for various endonucleases were codon optimized and de novo synthesized by GeneArt. Ablator expression and target plasmids were produced using standard molecular biological cloning techniques. Transfections were performed in HEK293 cells using Lipofectamine™ 2000 transfection reagent (Life Technologies). All transfections were performed using optimal transfection conditions as defined in transfection reagent protocol. Briefly, 200-250 ng plasmid DNA (excluding transfection control plasmid) was complexed with Lipofectamine™ 2000 transfection reagent and added to cells in 96 well plates. DNA quantities were consistent across all conditions by supplementation with an unrelated plasmid containing the same promoter as test plasmids. Transfection complexes were incubated with cells for 4-6 hours as transfection reagent protocol before the addition of FBS supplemented media. Transfected cells were incubated at 37° C. for 24-72 hours. Following incubation, cells were assayed for reporter gene expression using Promega Dual Luciferase detection kit according to the manufacturer's instructions on a BioTek Clarity platereader and renilla luciferase was used to control for transfection efficiency. All samples were performed in quadruplicate and standard errors of the mean were calculated.

A. Coexpression of Wild-type FokI Ablates Expression of Transgene More effectively than delivery of FokI protein The amino acid sequence of the FokI enzyme is provided in SEQ ID NO: 12, wherein amino acids 1 to 387 are the DNA binding domain and amino acids 387 to 584 are the catalytic domain. The codon optimized FokI sequence is provided in SEQ ID NO:1.

FIG. 18 illustrates that wild-type FokI effective ablated expression of the luciferase reporter gene following contrasfection into HEK295 cells (FIG. 18A bar 2), while only partial ablation was observed when FokI protein was delivered to the cells (FIG. 18A, bar 3).

In a dose-dependent experiment, the FokI expression vector contained the FokI catalytic domain fused to a zinc finger DNA binding domain (ZFHD). This construct, which is 963 bp, is provided in SEQ ID NO: 21 and is composed of base pairs 1 to 366 bp ZFHD, 367 to 372 bp linker, and 373 to 963 bp FokI catalytic domain. The resulting expression product comprises amino acids 1 to 122 (ZFHD), amino acids 123-124 are a linker and amino acids 125 to 321 are from the FokI catalytic domain. FIG. 18B illustrates that increasing the concentration of FokI resulted in dose dependent ablation of Luc reporter. No ablation sites were required to be engineered into the transcription unit containing the transgene in this illustration, as luciferase contains multiple native FokI sites.

This provides support for the use of the PITA system using a transfected FokI enzyme directed to specific ablation sites in a transcription unit containing a transgene for delivery to the cell.

B. Chimeric Engineered FokI Tethered to Non-cognate Recognition Site on the DNA by the Zinc Finger—Homeodomain Effectively Ablates Expression of Luc Reporter Gene The plasmid contructs in this example contains either the FokI catalytic domain (198 amino acids (SEQ ID NO: 14), corresponding to amino acids 387 to 584 of the full-length protein) (untethered FokI) or a ZFHD-FokI catalytic domain of 963 bp as described in Part A above (tethered FokI). Even at the highest concentration, the catalytic domain of FokI which is un-tethered to DNA does have no effect on expression of Luc reporter gene (FIG. 19A). Chimeric engineered FokI tethered to DNA via fusion with ZFHD effectively ablated expression of luciferase reporter in a dose dependent manner when increasing concentrations of ZF-HD-FokI expression plasmid were cotransfected into HEK293 cells (FIG. 19B).

This supports the use of the PITA system and the additional safety element provided by a chimeric enzyme directed to specific ablation sites in a transcription unit containing a transgene for delivery to the cell.

C. DNA Binding Specificity of Chimeric FokI can be Reproducibly Changed by Fusion with Various Classes of Heterologous DNA Binding Domains and Ablation of Target Transgene can be Further Improved by Addition of Heterologous NLS This example illustrates that the zinc finger homeodomain (ZFHD) is not the only domain suitable for altering the specificity of ablation mediated by a chimeric engineered enzyme. FokI effectively ablated expression of luciferase reporter in a dose dependent manner when HTH DNA binding domain was fused to FokI catalytic domain (FIG. 20A). In a separate experiment (FIG. 27B), the activity of HTH-FokI was further improved by adding heterologous NLS at the N-terminus of the HTH-FokI coding sequence.

The HTH-FokI Catalytic domain (SEQ ID NO:5), is composed of 1-171 bp HTH from Gin (a serine recombinase), a linker (bp 172-177), and a FokI catalytic domain (178-768 bp) derived from codon-optimized FokI. The resulting chimeric enzyme (SEQ ID NO: 6) contains aa 1-57 of HTH from Gin, a linker (aa 58-59), and a FokI catalytic domain (amino acids 60-256).

FIGS. 20A-20B are bar charts illustrating that the DNA binding specificity of chimeric FokI can be reproducible changed by fusion with another classes of heterologous DNA binding domains and ablation of target transgene can be further improved by the additional of a heterologous nuclear localiazation signal (NLS). FIG. 20A illustrates the results of co-transfection of pCMV.Luciferase with increasing concentrations of an expression plasmid encoding FokI tethered to DNA via an HTH fusion (6.25, 12.5, 25, 50, and 100 ng). The first bar is a control showing 50 ng pCMV.Luciferase alone. FIG. 20B pCMV.Luciferase with increasing concentrations of an expression plasmid encoding an HTH—FokI fusion, which further has a NLS at its N-terminus.

17. EXAMPLE 12

Although not illustrated here, other chimeric enzymes have been made using the techniques described herein:

- An AAV plasmid containing SV40 T-Ag NLS-Helix-turn-helix (HTH) from Gin (192 bp, SEQ ID NO:7), which includes the nuclear localization signal (1-24 bp) of SV40 T-Ag and HTH from Gin, a serine recombinase (25-192 bp). In the resulting enzyme (SEQ ID NO:8), amino acids 1-8 are from the SV40 T-Ag NLS and amino acids 9-64 are the HTH from Gin;
- An AAV plasmid containing SV40 T-Ag NLS-HTH-FokI Catalytic domain (789 bp, SEQ ID NO:9), which includes the SV40 T-Ag NLS (bp 1-24), the HTH from Gin (bp 25-192), a linker (bp 193-198), and the catalytic domain of the FokI (bp 199-789). In the resulting chimeric enzyme (SEQ ID NO:10), amino acids 1-8 are from the SV40 T-Ag NLS, amino acids 9-64 are HTH from Gin, amino acids 65-66 are linker residues, and amino acids 67-263 are the FokI catalytic domain
- An AAV plasmid containing a SV40 T-Ag NLS-ZFHD-FokI catalytic domain (984 bp) was prepared (SEQ ID NO: 23), which includes the SV40 T-Ag NLS (bp 1-24), the zinc finger homodomain (bp 25-387), a linker (bp 388-393), and the FokI catalytic domain (bp acids 394-984). In the resulting chimeric enzyme (SEQ ID NO: 21, 328 aa), amino acids 1-8 are the SV40 T-Ag NLS, amino acids 9-129 are the ZFHD, amino acids 130-131 are linker residues, and amino acids 132-138 are FokI catalytic domain.

These and other constructs can be used to prepare viruses according the method of the invention for use in a virus composition and the PITA system.

18. EXAMPLE 13

Use of Replication-Defective AAV Virus Composition in Treatment of HIV

This composition could be potentially used as a safety mechanism in the treatment of HIV. Recently, broadly neutralizing antibodies from long-term non-progressors, individuals which maintain an HIV$^+$ status for several decades without progression to AIDS, have been identified by several research groups.

All coding regions of the neutralizing antibody to HIV (HIV NAb) are placed between the inverted terminal repeats (ITRs) of the AAV. If the overall size of the constructs are below 4.7 kb (including the two ITRs), they are packaged into the AAV capsid. The AAV serotype capsid chosen will depend of the level of gene expression, the method of delivery and the extent of biodistribution from the injection site required. In addition, the constitutive promoters used for expression of the HIV NAb (and potentially the parts of the inducible system in the one small molecule situation) would depend on the tissue type targeted. In the following example of a potential clinical study the vector serotype chosen would be AAV8 administered by intravenous injection which would enable utilization of the liver specific promoter TBG.

In HIV$^+$ patients, administration of AAV vectors expressing one or more of these HIV neutralizing antibodies would lead to long-term, high level expression of one or more broadly HIV NAb and would reduce viral load and potentially prevent acquisition of HIV. In this situation, individuals would receive intravenous injection of two AAV vectors at a dose of $5\times10^{12}$ genome copies/kilogram of each vector. Contained within the two AAV vectors would be the HIV neutralizing antibody under control of a constitutive promoter, allowing expression to occur rapidly following administration of the vector.

A. Heterodimer and Two Small Molecules

Following the first signs of potential toxicity to the HIV NAb, the first small molecule drug would be administered to induce expression of the components of the inducible system, in this case the DNA binding domain linked to FKBP and FRAP$_L$ linked to the catalytic domain of a endonuclease enzyme. This would allow the system to be primed for action should further toxicity to the HIV NAb develop. If toxicity levels continue to rise then initiation of endonuclease activity would be induced by administration of a second small molecule drug which would lead to the formation of an active enzyme and ablation of HIV NAb gene expression.

B. Heterodimer and One Small Molecule

Also under the control of constitutive expression would be the elements of the rapamycin inducible system, FKBP and FRAP$_L$. Following administration of the AAV vectors, patients would be closely monitored at regular intervals for several years. If toxicity to the HIV NAb develops then delivery of rapamycin or a rapalog would be implemented. IV administration of 1 mg/kg rapamycin/rapalog in the first instance with the potential to increase to repeated dosing would be administered to ablate expression of the HIV antibody.

Toxicity and HIV antibody levels would be closely monitored until expression of the HIV NAb had reached undetectable levels. Therefore, the ablation of gene expression of the HIV NAb would provide a safety switch to ablate gene expression should insurmountable toxicity occur.

In one aspect, the invention provides a replication-defective virus composition suitable for use in human subjects in which the viral genome has been engineered to contain: (a) a first transcription unit that encodes a therapeutic product in operative association with a promoter that controls transcription, said unit containing at least one ablation recognition site; and (b) a second transcription unit that encodes an ablator specific for the at least one ablation recognition site in operative association with a promoter, wherein transcription and/or ablation activity is controlled by a pharmacological agent, e.g., a dimerizer. For example, one suitable pharmacologic agent may be rapamycin or a rapamycin analog. The virus composition may contain two or more different virus stocks.

In one aspect, the invention provides a replication-defective virus composition suitable for use in human subjects in which the viral genome comprises (a) a first transcription unit that encodes a therapeutic product in operative association with a promoter that controls transcription, said first transcription unit containing an ablation recognition site; and a second transcription unit that encodes an ablator specific for the ablation recognition site in operative association with a promoter, wherein transcription and/or ablation activity is controlled by a pharmacological agent. The first transcription unit can contains more than one ablation recognition site. Where the genome comprises more than one ablation recognition site, said more than one ablation recognition site comprising a first ablation recognition site and a second ablation recognition site which differs from said first ablation recognition site, said virus further comprising a first ablator specific for the first ablation recognition site and a second ablator specific for the second recognition site.

In one embodiment, the transcription, bioactivity and/or the DNA binding specificity of the ablator is controlled by a regulatable system. The regulatable system can be selected from a tet-on/off system, a tetR-KRAB system, a mifepristone (RU486) regulatable system, a tamoxifen-dependent regulatable system, a rapamycin—regulatable system, or an ecdysone-based regulatable system.

In one embodiment, the ablator is selected from the group consisting of: an endonuclease, a recombinase, a meganuclease, or a zinc finger endonuclease that binds to the ablation recognition site in the first transcription unit and excises or ablates DNA and an interfering RNA, a ribozyme, or an antisense that ablates the RNA transcript of the first transcription unit, or suppresses translation of the RNA transcript of the first transcription unit. In one specific embodiment, the ablator is Cre and the ablation recognition site is loxP, or the ablator is FLP and the ablation recognition site is FRT.

In an embodiment, the ablator is a chimeric engineered endonuclease, wherein the virus composition comprises (i) a first sequence comprising the DNA binding domain of the endonuclease fused to a binding domain for a first pharmacological agent; and wherein the virus composition further comprises (ii) a second sequence encoding the nuclease cleavage domain of the endonuclease fused to a binding domain for the first pharmacological agent, wherein the first sequences (i) and the second sequence (ii) are each in operative association with at least one promoter which controls expression thereof. The chimeric engineered endonuclease can be contained within a single bicistronic open reading frame in the second transcription unit, said transcription unit further comprising a linker between (i) and (ii). Optionally, the sequence (ii) has an inducible promoter. In another embodiment, the fusion partners/fragments of the chimeric engineered endonuclease are contained within separate open reading frames. In one embodiment, each of the first sequence and the second sequence are under the control of a constitutive promoter and the ablator is bioactivated by the first pharmacological agent.

The coding sequence for the ablator may further comprise a nuclear localization signal located 5' or 3' to the ablator coding sequence.

In one embodiment, the DNA binding domain is selected from the group consisting of a zinc finger, helix-turn-helix, a HMG-Box, Stat proteins, B3, helix-loop-helix, winged helix-turn-helix, leucine zipper, a winged helix, POU domains, and a homeodomain.

In still another embodiment, the endonuclease is selected from the group consisting of a type II restriction endonuclease, an intron endonuclease, and serine or tyrosine recombinases. In one specific embodiment, the ablator is a chimeric FokI enzyme.

In yet another embodiment, in a replication-defective virus composition of the invention, the viral genome further comprises a third and a fourth transcription unit, each encoding a dimerizable domain of a transcription factor that regulates an inducible promoter for the ablator, in which: (c) the third transcription unit encodes the DNA binding domain of the transcription factor fused to a binding domain for the pharmacological agent in operative association with a first promoter; and (d) the fourth transcription unit encodes the activation domain of the transcription factor fused to a binding domain for the pharmacological agent in operative association with a second promoter. The first promoter of (c) and the second promoter of (d) are independently selected from a constitutive promoter and an inducible promoter. In another embodiment, the first and second promoters are both constitutive promoters and the pharmacological agent is a dimerizer that dimerizes the domains of the transcription factor. In still a further embodiment, one of the first promoter and the second promoters is an inducible promoter. The third and fourth transcription units can be a bicistronic unit containing an IRES or furin-2A.

In one embodiment, the pharmacological agent is rapamycin or a rapalog.

In one embodiment, the virus is an AAV. Such an AAV may be selected from among, e.g., AAV1, AAV6, AAV7, AAV8, AAV9 and rh10. Still other viruses may be used to generate the DNA constructs and replication-defective viruses of the invention including, e.g., adenovirus, herpes simplex viruses, and the like.

In one embodiment, the therapeutic product is an antibody or antibody fragment that neutralizes HIV infectivity, soluble vascular endothelial growth factor receptor-1 (sFlt-1), Factor VIII, Factor IX, insulin like growth factor (IGF), hepatocyte growth factor (HGF), heme oxygenase-1 (HO-1), or nerve growth factor (NGF).

In one embodiment of the replication-defective virus composition, the first transcription unit and the second transcription unit are on different viral stocks in the composition. Optionally, the first transcription unit and the second transcription unit are in a first viral stock and the a second viral stock comprises a second ablator(s).

In one embodiment, a recombinant DNA construct comprises a first and second transcription unit flanked by packaging signals of a viral genome, in which: (a) a first transcription unit that encodes a therapeutic product in operative association with a promoter that controls transcription, said first transcription unit containing at least one ablation recognition site; and (b) a second transcription unit that encodes an ablator specific for the at least one ablation recognition site in operative association with a promoter that induces transcription in response to a pharmacological agent. The packaging signals flanking the transcription units may be an AAV 5' inverted terminal repeats (ITR) and a AAV 3' ITR. Optionally, the AAV ITRs are AAV2, or AAV1, AAV6, AAV7, AAV8, AAV9 or rh10 ITRs. In one embodiment, the first transcription unit is flanked by AAV ITRs, and the second, third and fourth transcription units are flanked by AAV ITRs. Optionally, the transcription units are contained in two or more DNA constructs.

In one embodiment, the therapeutic product is an antibody or antibody fragment that neutralizes HIV infectivity, soluble vascular endothelial growth factor receptor-1 (sFlt-1), Factor VIII, Factor IX, insulin like growth factor (IGF), hepatocyte growth factor (HGF), heme oxygenase-1 (HO-1), or nerve growth factor (NGF).

In one embodiment, the promoter that controls transcription of the therapeutic product is a constitutive promoter, a tissue-specific promoter, a cell-specific promoter, an inducible promoter, or a promoter responsive to physiologic cues.

A method is described for treating age-related macular degeneration in a human subject, comprising administering an effective amount of the replication-defective virus composition as described herein, in which the therapeutic product is a VEGF antagonist.

A method is provided for treating hemophilia A in a human subject, comprising administering an effective amount of the replication-defective virus composition as described herein, in which the therapeutic product is Factor VIII.

A method is provided for treating hemophilia B in a human subject, comprising administering an effective amount of the replication-defective virus composition as described herein, in which the therapeutic product is Factor IX.

A method is provided for treating congestive heart failure in a human subject, comprising administering an effective amount of the replication-defective virus composition as described herein, in which the therapeutic product is insulin like growth factor or hepatocyte growth factor.

A method is provided for treating a central nervous system disorder in a human subject, comprising administering an effective amount of the replication-defective virus composition as described herein, in which the therapeutic product is nerve growth factor.

A method is provided for treating HIV infection in a human subject, comprising administering an effective amount of the replication-defective virus composition as described herein in which the therapeutic product is a neutralizing antibody against HIV.

A replication-defective virus is provided herein for use in controlling delivery of the transgene product. The product may be selected from the group consisting of a VEGF antagonist, Factor IX, Factor VIII, insulin like growth factor, hepatocyte growth factor, nerve growth factor, and a neutralizing antibody against HIV.

A genetically engineered cell is provided which comprises a replication-defective virus or a DNA construct as provided herein. The genetically engineered cell may be selected from a plant, bacterial or non-human mammalian cell.

A method is provided for determining when to administer a pharmacological agent for ablating a therapeutic product to a subject who received the replication-defective virus as provided herein containing a therapeutic product and an ablator, comprising: (a) detecting expression of the therapeutic product in a tissue sample obtained from the patient, and (b) detecting a side effect associated with the presence of the therapeutic product in said subject, wherein detection of a side effect associated with the presence of the therapeutic product in said subject indicates a need to administer the pharmacological agent that induces expression of the ablator.

A method is provided for determining when to administer a pharmacological agent for ablating a therapeutic product to a subject who received the replication-defective virus composition as described herein encoding a therapeutic product and an ablator, comprising: detecting the level of a biochemical marker of toxicity associated with the presence of the therapeutic product in a tissue sample obtained from said subject, wherein the level of said marker reflecting toxicity indicates a need to administer the pharmacological agent that induces expression of the ablator.

These methods may further comprise determining the presence of DNA encoding the therapeutic gene product, its RNA transcript, or its encoded protein in a tissue sample from the subject subsequent to treatment with the pharmacological agent that induces expression of the ablator, wherein the presence of the DNA encoding the therapeutic gene product, its RNA transcript, or its encoded protein indicates a need for a repeat treatment with the pharmacological agent that induces expression of the ablator.

The invention further provides a replication-defective virus as described herein for use in controlling delivery of the transgene product.

In another embodiment, the invention provides a genetically engineered cell, comprising a replication-defective virus or a DNA construct as described herein. Such a cell may be a plant, yeast, fungal, insect, bacterial, non-human mammalian cells, or a human cell.

In yet a further embodiment, the invention provides a method of determining when to administer a pharmacological agent for ablating a therapeutic product to a subject who received the replication-defective virus as described herein encoding a therapeutic product and an ablator, comprising: (a) detecting expression of the therapeutic product in a tissue sample obtained from the patient, and (b) detecting a side effect associated with the presence of the therapeutic product in said subject, wherein detection of a side effect associated with the presence of the therapeutic product in said subject indicates a need to administer the pharmacological agent that induces expression of the ablator. In still a further embodiment, the invention provides a method of determining when to administer a pharmacological agent for ablating a therapeutic product to a subject who received the replication-defective virus composition as described herein encoding a therapeutic product and an ablator, comprising: detecting the level of a biochemical marker of toxicity associated with the presence of the therapeutic product in a tissue sample obtained from said subject, wherein the level of said marker reflecting toxicity indicates a need to administer the pharmacological agent that induces expression of the ablator.

EXAMPLE 14

Generation of 10×ZF Constructs

Open reading frames encoding for various endonucleases were codon optimized and de novo synthesized by GeneArt (Invitrogen). Ablator expression and target reporter plasmids were produced using standard molecular biological cloning techniques. Transfections were performed in HEK293 cells using Lipofectamine™ 2000 transfection reagent (Life Technologies). All transfections were performed using optimal transfection conditions as defined in transfection reagent protocol. Briefly, 150-200 ng plasmid DNA (excluding transfection control plasmid) was complexed with Lipofectamine™ 2000 transfection reagent and added to cells in 96 well plates. DNA quantities were consistent across all conditions by supplementation with an unrelated plasmid containing the same promoter as test plasmids. Transfection complexes were incubated with cells for 4 hours as transfection reagent protocol before the addition of FBS supplemented media. Transfected cells were incubated at 37° C. for 24-48 hours. Following incubation, cells were assayed for reporter gene expression using Promega Dual Luciferase detection kit according to the manufacturer's instructions on a BioTek Clarity plate reader and renilla luciferase was used to control for transfection efficiency. All samples were performed in quadruplicate and standard errors of the mean were calculated.

A. Generation of 10×ZF Expression Plasmid

Once random sequence 1 was generated and determined to be targetable by standard zinc finger design methodologies, the design of the nucleases was performed using the resources available from The Zinc Finger (ZF) Consortium and the zinc finger database (these are publically available. See, e.g., bindr.gdcb.iastate.edu:8080/ZiFDB/). Based on the breakdown of the 28-32 bp sequence into 10×3 bp ZF binding sites, ZF domains which bind to each of the 3 bp sequences were identified.

The following 28-32 bp sequences were generated:

[SEQ ID NO: 806] GGTCGATGTTCGCAACGTC-GATCGTACGTGCA. For this sequence, there are two reading frames which are targetable by different zinc fingers: GGT-CGA-TGT-TCG-CAA-CGT-CGA-TCG-TAC-GTG-CA—targetable G-GTC-GAT-GTT-CGC-AAC-GTC-GAT-CGT-ACG-TGC-A—targetable (the experiments described herein were generated for this sequence)

[SEQ ID NO: 817]: GGTCGGCGACGCGTAATCGTC-GATTGGCGTAC. For this sequence, there are two reading frames which are targetable by different zinc fingers. G-GTC-GGC-GAC-GCG-TAA-TCG-TCG-ATT-GGC-GTA-C—targetable GG-TCG-GCG-ACG-CGT-AAT-CGT-CGA-TTG-GCG-TAC—targetable

[SEQ ID NO: 801] GGTCGGCGACGCGAATCGTC-GATTGGCGTAC. For this sequence, there are two reading frames which are targetable by different zinc fingers. G-GTC-GGC-GAC-GCG-TAA-TCG-TCG-ATT-GGC-GTA-C—targetable GG-TCG-GCG-ACG-CGT-AAT-CGT-CGA-TTG-GCG-TAC—targetable

[SEQ ID NO: 802] GGTCGGCGACGCGTATCGATTG-GCGTAC. For this sequence, there is one potential targetable by a zinc finger: GGT-CGG-CGA-CGC-GTA-TCG-ATT-GGC-GTA-C—targetable

[SEQ ID NO: 803] ACTATTCGCACGCCGTACGAT-AGTCGGCGCGA. For this sequence, there are two reading frames targetable by zinc fingers: ACT-ATT-CGC-ACG-CCG-TAC-GAT-AGT-CGG-CGC-GA—targetable and A-CTA-TTC-GCA-CGC-CGT-ACG-ATA-GTC-GGC-GCG-A—targetable.

For any 3 bp sequence for which only one known ZF sequence was available within the consortium, this sequence was chosen for the final protein. This was the case for 3 out of the 10×ZF domains.

Provided within the consortium database was a table of previously tested combination of 2 or 3 ZFs linked together in a particular orientation for binding to DNA. Within our random sequence 1, there are two regions which contain previously tested combinations. One is a 3×3 bp stretch and the other is a 2×3 bp stretch. Where a previous combination of ZFs was reported to work, this was incorporated into the 10×ZF sequence.

For 3 out of 10×ZF sequences, only the recognition helix of the DNA binding region was included in the consortium. For 7 out of the 10×ZF sequences, the full ZF sequence was available in the consortium. Therefore, the full sequence of the ZFs where only the recognition helix was available through the consortium had to be generated. In addition, to prevent high level sequence homology between the 10×ZF protein, the conserved protein sequence of the ZF protein domain was varied between one of the two conserved sequences in the consortium:

```
P start conserved sequence
                                        [SEQ ID NO: 745]
PGEKPYKCPECGKSFS--------HQRTH T start conserved sequence
                                        [SEQ ID NO: 807]
TGEKPFQCRICMRNFS--------HLRTH
```

The ZFs were linked N terminus to C terminus directly as there innate protein sequence would allow for the correct structure of the final protein.

The 10×ZF sequence was then linked to the catalytic domain of the FokI enzyme (the DNA binding domain was removed from the wild-type sequence) through a standard linker sequence on the C terminal of the 10×ZF protein.

In the working examples below, an ablator encoded by the sequence: 10×ZF-FokI_Cat nucleotide sequence: SEQ ID NO: 59, is illustrated:

ATGGGCGAGAAGCCCTACAAGTGCCCTGAGTGCGGCAAGAGCTTCAGCCA

GAGAAGAAGCCTGGGCCACCACCAGCGTACGCACCCCGGCGAGAAACCTT

ATAAGTGTCCCGAATGTGGCAAGTCCTTCAGCAAGAAGAACGACCTGACC

CGGCACCAGCGGACACACCCCGGGGAAAAGCCATACAAATGTCCAGAGTG

TGGGAAGTCTTTCTCCAGCCGGCGGACCTGCAGAGCCCATCAGAGAACAC

ATACCGGGGAGAAGCCTTTCCAGTGCCGGATCTGCATGAGAAACTTCAGC

GTGCGGCACAACCTGACCAGACACCTGAGGACCCATACCGGCGAAAAACC

CTTTCAGTGCAGAATCTGTATGCGGAACTTCTCCGACCGGACCAGCCTG

GCCCGGCATCTGAGAACTCATCCTGGGGAAAAGCCCTATAAGTGTCCAGA

ATGCGGGAAATCCTTTAGCGACAGCGGCAACCTGCGGGTGCACCAGAGGA

CTCATCCAGGCGAGAAACCCTACAAATGCCCCGAATGCGGAAAGTCATTC

TCCCACACCGGCCATCTGCTCGAGCATCAGCGGACCCACACTGGGGAGA

AACCATTTCAGTGTCGCATCTGTATGAGGAATTTCAGCACCAACCAGGCC

CTGGGCGTGCACCTGAGAACACACCCAGGCGAGAAGCCTTACAAGTGTCC

AGAGTGCGGAAAGTCATTTTCCGTGCGCCACAATCTGACACGGCATCAGC

GCACCCATCCCGGCGAGAAGCCTTACAAATGCCCCGAGTGTGGCAAATCT

TTCAGTGACCGGACCTCTCTGGCCAGACATCAGAGGACACACGGCACTAG

TGGCAAGCAGCTGGTGAAAAGCGAGCTGGAAGAGAAGAAGTCCGAGCTGC

GGCACAAGCTGAAATACGTGCCCCACGAGTACATCGAGCTGATCGAGATC

GCCCGGAACCCCACCCAGGACAGAATCCTGGAAATGAAGGTCATGGAATT

TTTCATGAAGGTGTACGGCTACCGGGGCGAGCACCTGGGCGGCAGCAGAA

AACCCGACGGCGCCATCTACACCGTGGGCAGCCCCATCGACTACGGCGTG

ATCGTGGACACCAAGGCCTACAGCGGCGGCTACAACCTGCCCATCGGACA

GGCCGACGAGATGCAGAGATACGTGGAAGAGAACCAGACCCGGAACAAGC

ACATCAACCCCAACGAGTGGTGGAAGGTGTACCCCAGCAGCGTGACCGAG

TTCAAGTTCCTGTTCGTGTCCGGCCACTTCAAGGGCAACTACAAGGCCCA

GCTGACCCGGCTGAACCACATCACCAACTGCAACGGCGCTGTGCTGAGCG

TGGAAGAACTGCTGATCGGCGGCGAGATGATCAAGGCCGGCACCCTGACC

CTGGAAGAAGTGCGGCGGAAGTTCAACAACGGCGAGATCAACTTCTG

ATAG.

In this construct, bp1-84: zinc finger N1 (recognition helix QRRSLGH, P form, binds to TGC); by 85-168: zinc finger N2 (recognition helix KKNDLTR, P form, binds to ACG); by 169-252: zinc finger N3 (recognition helix SRRTCRA, P form, binds to CGT); by 253-336: zinc finger N4 (recognition helix VRHNLTR, T form, binds to GAT); by 337-420: zinc finger N5 (recognition helix DRTSLAR, T form, binds to GTC), by 421-504 bp: zinc finger N6 (recognition helix DSGNLRV, P faint., binds to AAC); by 505-588: zinc finger N7 (recognition helix HTGHLLEM, P form, binds to CGC); by 589-672: zinc finger N8 (recognition helix TNQALGV, T form, binds to GTT); by 673-756: zinc finger N9 (recognition helix VRHNLTR, P form, binds to GAT); by 757-840: zinc finger N10 (recognition helix DRTSLAR, P faun, binds to GTC); by 841-855: 5 amino acid linker; by 856-1443: FokI catalytic domain.

The transcribed illustrative ablator has the sequence: 10×ZF-FokI_Cat amino acid sequence: SEQ ID NO: 60: MGEKPYKCPECGKSFSQRRSLGHHQRTH-PGEKPYKCPECGKSFSKKNDLTRHQR THPGEK-PYKCPECGKSFSSRRTCRAHQRTHTGEK-PFQCRICMRNFSVRHNLTRH LRTHTGEKPFQCRICMRNFSDRTSLAR-HLRTHPGEKPYKCPECGKSFSDSGNLRV HQRTH-PGEKPYKCPECGKSFSHTGHLLEHQRTH-TGEKPFQCRICMRNFSTNQAL GVHLRTHPGEKPYKCPECGKSFSVRHNL-TRHQRTHPGEKPYKCPECGKSFSDRT SLARHQRTH-GTSGKQLVKSELEEKKSELRH-KLKYVPHEYIELIEIARNPTQDRILE MKVMEFFMKVYGYRGEHLGGSRKPD-GAIYTVGSPIDYGVIVDTKAYSGGYNLP IGQADEM-QRYVEENQTRNKHINPNEWWKVYPSS-VTEFKFLFVSGHFKGNYKAQ LTRLNHITNCNGAVLSVEELLIGGEMIK-AGTLTLEEVRRKFNNGEINF. 1-28 aa—zinc finger N1 (recognition helix QRRSLGH, P form, binds to TGC); 29-56 aa—zinc finger N2 (recognition helix KKNDLTR, P form, binds to ACG); 57-84 aa—zinc finger N3 (recognition helix SRRTCRA, P form, binds to CGT); 85-112 aa—zinc finger N4 (recognition helix VRHNLTR, T form, binds to GAT); 113-140 aa—zinc finger N5 (recognition helix DRTSLAR, T form, binds to GTC); 141-168 aa—zinc finger N6 (recognition helix DSGNLRV, P form, binds to AAC); 169-196 aa—zinc finger N7 (recognition helix HTGHLLEM, P form, binds to CGC); 197-224 aa—zinc finger N8 (recognition helix TNQALGV, T form, binds to GTT); 225-252 aa—zinc finger N9 (recognition helix VRHNLTR, P form, binds to GAT); 253-280 aa—zinc finger N10 (recognition helix DRTSLAR, P form, binds to GTC); 281-284 aa—5 amino acid linker; and 285-481 aa—FokI catalytic domain.

In another embodiment, the 10×ZF sequence is linked to the catalytic domain of the FokI enzyme (the DNA binding domain was removed from the wild-type sequence) through a linker sequence on the N terminus of the 10×ZF protein.

N-linked FokI_Cat-10×ZF nucleotide sequence: SEQ ID NO: 808:

ATGAAGCAGCTGGTGAAAAGCGAGCTGGAAGAGAAGAAGTCCGAGCTGCG

GCACAAGCTGAAATACGTGCCCCACGAGTACATCGAGCTGATCGAGATCG

CCCGGAACCCCACCCAGGACAGAATCCTGGAAATGAAGGTCATGGAATT

TTTCATGAAGGTGTACGGCTACCGGGCGAGCACCTGGGCGGCAGCAGAA

AACCCGACGGCGCCATCTACACCGTGGGCAGCCCCATCGACTACGGCGTG

ATCGTGGACACCAAGGCCTACAGCGGCGGCTACAACCTGCCCATCGGACA

GGCCGACGAGATGCAGAGATACGTGGAAGAGAACCAGACCCGGAACAAGC

ACATCAACCCCAACGAGTGGTGGAAGGTGTACCCCAGCAGCGTGACCGAG

TTCAAGTTCCTGTTCGTGTCCGGCCACTTCAAGGGCAACTACAAGGCCCA

GCTGACCCGGCTGAACCACATCACCAACTGCAACGGCGCTGTGCTGAGCG

TGGAAGAACTGCTGATCGGCGGCGAGATGATCAAGGCCGGCACCCTGACC

CTGGAAGAAGTGCGGCGGAAGTTCAACAACGGCGAGATCAACTTCGGCAC

TAGTGGCGGCGAGAAGCCCTACAAGTGCCCTGAGTGCGGCAAGAGCTTCA

GCCAGAGAAGAAGCCTGGGCCACCACCAGCGTACGCACCCCGGCGAGAAA

CCTTATAAGTGTCCCGAATGTGGCAAGTCCTTCAGCAAGAAGAACGACCT

GACCCGGCACCAGCGGACACACCCCGGGGAAAAGCCATACAAATGTCCAG

AGTGTGGGAAGTCTTTCTCCAGCCGGCGGACCTGCAGAGCCCATCAGAGA

ACACATACCGGGGAGAAGCCTTTCCAGTGCCGGATCTGCATGAGAAACTT

CAGCGTGCGGCACAACCTGACCAGACACCTGAGGACCCATACCGGCGAAA

AACCCTTTCAGTGCAGAATCTGTATGCGGAACTTCTCCGACCGGACCAGC

CTGGCCCGGCATCTGAGAACTCATCCTGGGGAAAAGCCCTATAAGTGTCC

AGAATGCGGGAAATCCTTTAGCGACAGCGGCAACCTGCGGGTGCACCAGA

GGACTCATCCAGGCGAGAAACCCTACAAATGCCCCGAATGCGGAAAGTCA

TTCTCCCACACCGGCCATCTGCTCGAGCATCAGCGGACCCACACTGGGGA

GAAACCATTTCAGTGTCGCATCTGTATGAGGAATTTCAGCACCAACCAGG

CCCTGGGCGTGCACCTGAGAACACACCCAGGCGAGAAGCCTTACAAGTGT

CCAGAGTGCGGAAAGTCATTTTCCGTGCGCCACAATCTGACACGGCATCA

GCGCACCCATCCCGGCGAGAAGCCTTACAAATGCCCCGAGTGTGGCAAAT

CTTTCAGTGACCGGACCTCTCTGGCCAGACATCAGAGGACACAC.

This nucleic acid sequence encodes, at: FokI catalytic domain (1-594 bp), 4 amino acid linker (595-606 bp), zinc finger N1 (recognition helix QRRSLGH, P form, binds to TGC) (607-687 bp), zinc finger N2 (recognition helix KKNDLTR, P form, binds to ACG) (688-771 bp), zinc finger N3 (recognition helix SRRTCRA, P form, binds to CGT) (772-855 bp), zinc finger N4 (recognition helix VRHNLTR, T form, binds to GAT) (856-939 bp), zinc finger N5 (recognition helix DRTSLAR, T form, binds to GTC) (940-1023 bp), zinc finger N6 (recognition helix DSGNLRV, P form, binds to AAC) (1024-1107 bp), zinc finger N7 (recognition helix HTGHLLEM, P form, binds to CGC) (1108-1191 bp), zinc finger N8 (recognition helix TNQALGV, T form, binds to GTT) (1192-1275 bp), zinc finger N9 (recognition helix VRHNLTR, P form, binds to GAT) (1276-1359 bp), zinc finger N10 (recognition helix DRTSLAR, P form, binds to GTC) (1360-1443 bp).

The transcribed N-linked 10×ZF-FokI_Cat amino acid sequence: SEQ ID NO: 809: is as follows.

MKQLVKSELEEKKSELRHKLKYVPHEYIELIEIARNPTQDRILEMKVMEF

FMKVYGYRGEHLGGSRKPDGAIYTVGSPIDYGVIVDTKAYSGGYNLPIGQ

ADEMQRYVEENQTRNKHINPNEWWKVYPSSVTEFKFLFVSGHFKGNYKAQ

LTRLNHITNCNGAVLSVEELLIGGEMIKAGTLTLEEVRRKFNNGEINFGT

SGGEKPYKCPECGKSFSQRRSLGHHQRTHPGEKPYKCPECGKSFSKKNDL

TRHQRTHPGEKPYKCPECGKSFSSRRTCRAHQRTHTGEKPFQCRICMRNF

SVRHNLTRHLRTHTGEKPFQCRICMRNFSDRTSLARHLRTHPGEKPYKCP

ECGKSFSDSGNLRVHQRTHPGEKPYKCPECGKSFSHTGHLLEHQRTHTGE

-continued
KPFQCRICMRNFSTNQALGVHLRTHPGEKPYKCPECGKSFSVRHNLTRHQ

RTHPGEKPYKCPECGKSFSDRTSLARHQRTH.

This chimeric endonuclease is: FokI catalytic domain (1-198 aa), 5 amino acid linker (199-202 aa), zinc finger N1 (recognition helix QRRSLGH, P form, binds to TGC) (203-229 aa), zinc finger N2 (recognition helix KKNDLTR, P form, binds to ACG) (230-257 aa), zinc finger N3 (recognition helix SRRTCRA, P form, binds to CGT) (258-285 aa), zinc finger N4 (recognition helix VRHNLTR, T form, binds to GAT) (286-313 aa), zinc finger N5 (recognition helix DRTSLAR, T form, binds to GTC) (314-341 aa), zinc finger N6 (recognition helix DSGNLRV, P form, binds to AAC) (342-369 aa), zinc finger N7 (recognition helix HTGHLLEM, P form, binds to CGC) (370-397 aa), zinc finger N8 (recognition helix TNQALGV, T form, binds to GTT) (398-425 aa), zinc finger N9 (recognition helix VRHNLTR, P form, binds to GAT) (426-453 aa), and zinc finger N10 (recognition helix DRTSLAR, P form, binds to GTC) (454-481 aa).

B. Generation of Reporter Plasmids for 10×ZF-FokI_Cat Protein

In order to study the efficiency of the 10×ZF expression plasmid, a series of luciferase reporter plasmids were also designed with the unique 32 bp sequence: [SEQ ID NO: 806] GGTCGATGTTCGCAACGTCGATCGTACGTGCA generated as described in A above. These vectors include:

pITA-030, which contains, from 5' to 3': a cytomegalovirus (CMV) immediate early (IE) enhancer and promoter (bp 1-832), a Promega™ intron (833-1029 bp), the 32 bp sequence in sense orientation (1069-1100 bp), a spacer (1101-1106 bp), the 32 bp sequence in inverted orientation (1107-1138 bp), a Kozak sequence (1147-1152 bp), the coding sequence for a luciferase reporter gene (1153-2802 bp), and an SV40 polyA sequence (2822-3061 bp), of SEQ ID NO: 811.

pITA-031, which contains, from 5' to 3': a CMV promoter LE enhancer/promoter (1-832 bp), a Promega™ intron (833-1029 bp), the 32 bp sequence in direct/sense orientation (1069-1100 bp), a spacer (1101-1106 bp), the 32 bp sequence in inverted orientation (1107-1138 bp), a Kozak sequence (1147-1152 bp), the coding sequence for a luciferase reporter gene (1153-2802 bp), a 32 bp sequence in sense orientation (2815-2846 bp), a spacer (2847-2852 bp), the 32 bp sequence in inverted orientation (2853-2884 bp), and an SV40 polyA sequence (2893-3131 bp), of SEQ ID NO: 812.

pITA-032, which contains, from 5' to 3': a CMV IE enhancer/promoter (1-832 bp), a Promega™ intron (833-1029 bp), the 32 bp sequence in sense orientation (1069-1100 bp), a Kozak sequence (1115-1120 bp), the coding sequence for a luciferase reporter gene (1121-2770 bp), and an SV40 polyA sequence (2791-3029 bp), of SEQ ID NO: 813.

pITA-033, which contains, from 5' to 3': a CMV IE enhancer/promoter (1-832 bp), a Promega™ intron (833-1029 bp), the 32 bp sequence in sense orientation (1069-1100 bp), a Kozak sequence (1115-1120 bp), the coding sequence for a luciferase reporter gene (1121-2770 bp), the 32 bp sequence in sense orientation (2783-2814 bp), and an SV40 polyA sequence (2829-3067 bp), of SEQ ID NO: 814.

pITA-034, which contains, from 5' to 3': a CMV IE enhancer/promoter (1-832 bp), a Promega™ intron (833-1029 bp), the 32 bp sequence in sense orientation (1069-1100 bp), a Kozak sequence (1115-1120 bp), the coding sequence for a luciferase reporter gene (1121-2770 bp), the 32 bp sequence in direct orientation (2789-2820 bp), and an SV40 polyA sequence (2829-3067 bp), of SEQ ID NO: 815.

pITA-005 (control) contains from 5' to 3': a CMV IE enhancer/promoter (1-832 bp), a Promega™ intron (833-1029 bp), a Kozak sequence (1077-1082 bp), the coding sequence for a luciferase reporter gene (1083-2732 bp), and an SV40 polyA sequence (2752-2991 bp).

These reporter plasmids were studied in dose-dependent studies, of SEQ ID NO: 810.

(A) Increasing concentrations of the expression plasmid encoding FokI tethered to DNA via 10×ZF fusion (1.56, 3.13, 6.25, 12.5, 25, 50 and 100 ng) were co-transfected into 293 cells with 50 ng pCMV.32 bp-Luciferase (pITA-032, single specific site for 10×ZF protein at 5' end of luciferase gene). The cells were assayed for reporter gene expression as described above 48 hours post-transfection.

(B) Increasing concentrations of the expression plasmid encoding FokI tethered to DNA via 10×ZF fusion (1.56, 3.13, 6.25, 12.5, 25, 50 and 100 ng) were co-transfected into 293 cells with 50 ng pCMV.32 bp-Luciferase-32 bp (pITA-033, single specific site for 10×ZF protein at 5' and at 3' end of luciferase gene in head-to-tail orientation). The cells were assayed for reporter gene expression as described above 48 hours post-transfection.

(C) Increasing concentrations of the expression plasmid encoding FokI tethered to DNA via 10×ZF fusion (1.56, 3.13, 6.25, 12.5, 25, 50 and 100 ng) were co-transfected into 293 cells with 50 ng pCMV.32 bp-Luciferase-32 bp (pITA-034, single specific site for 10×ZF protein at 5' end of luciferase and a single specific inverted site at the 3' end of luciferase gene). The cells were assayed for reporter gene expression as described above 48 hours post-transfection.

(D) Increasing concentrations of the expression plasmid encoding FokI tethered to DNA via 10×ZF fusion (1.56, 3.13, 6.25, 12.5, 25, 50 and 100 ng) were co-transfected with 50 ng pCMV.32 bpSpacer32 bp-Luciferase (pITA-030, single combined specific site for 10×ZF containing a 32 bp site with a spacer separating an identical but inverted 32 bp at the 5' end of the luciferase gene). The cells were assayed for reporter gene expression as described above 48 hours post-transfection.

(E) Increasing concentrations of the expression plasmid encoding FokI tethered to DNA via 10×ZF fusion (1.56, 3.13, 6.25, 12.5, 25, 50 and 100 ng) were co-transfected with 50 ng pCMV.32 bpSpacer32 bp-Luciferase-32 bpSpacer32 bp (pITA-031, single combined specific site for 10×ZF containing a 32 bp site with a spacer separating an identical but inverted 32 bp at both the 5' end and the 3' end of the luciferase gene). The cells were assayed for reporter gene expression as described above 48 hours post-transfection. (F) Increasing concentrations of the expression plasmid encoding FokI tethered to DNA via 10×ZF fusion (1.56, 3.13, 6.25, 12.5, 25, 50 and 100 ng) were co-transfected with 50 ng pCMV.Luciferase (pITA-005, luciferase expression plasmid containing no specific site for 10×ZF). The cells were assayed for reporter gene expression as described above 24 hours post-transfection.

(G) Increasing concentrations of the expression plasmid encoding FokI tethered to DNA via 10×ZF fusion (1.56, 3.13, 6.25, 12.5, 25, 50 and 100 ng) were co-transfected with 50 ng pCMV.Luciferase (pITA-005, luciferase expression plasmid containing no specific site for 10×ZF). The cells were assayed for reporter gene expression as described above 48 hours post-transfection.

In each of (A)-(E), dose-dependent ablation was observed for all five reporter plasmids, demonstrating that the 10×ZF design provided by this invention requires only one 32 bp sequence to be present within the reporter and, therefore, within the vector in the applications described herein.

Different orientations of the reporter plasmid were studied in dose-dependent studies.

(H) Increasing concentrations of the expression plasmid encoding FokI tethered to DNA via 10×ZF fusion with the 10×ZF domain at the N-terminus of the protein (1.56, 3.13, 6.25, 12.5, 25 and 50 ng) were co-transfected into 293 cells with 50 ng pCMV.32 bpSpacer32bpLuciferase (pITA-030, single combined specific site for 10×ZF containing a 32 bp site with a spacer separating an identical but inverted 32 bp at the 5' end of the luciferase gene). The cells were assayed for reporter gene expression as described above 48 hours post-transfection.

(I) Increasing concentrations of the expression plasmid encoding FokI tethered to DNA via 10×ZF fusion with the FokI catalytic domain at the N-terminus of the protein (1.56, 3.13, 6.25, 12.5, 25 and 50 ng) were co-transfected into 293 cells with 50 ng pCMV.32 bpSpacer32bpLuciferase (pITA-030, single combined specific site for 10×ZF containing a 32 bp site with a spacer separating an identical but inverted 32 bp at the 5' end of the luciferase gene). The cells were assayed for reporter gene expression as described above 48 hours post-transfection.

All publications, patents, and patent applications cited in this application, as well as priority applications PCT/US2011/030213, filed Mar. 28, 2011 and U.S. Patent Application No. 61/318,755 and the Sequence Listing, are hereby incorporated by reference in their entireties as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims.

What is claimed is:

1. A composition for AAV-mediated delivery of a therapeutic product, said composition comprising:
   (a) a first recombinant AAV vector containing a nucleic acid molecule comprising:
      (i) a nucleic acid sequence encoding a therapeutic product operably linked to a promoter that controls transcription of the therapeutic product; and
      (ii) at least one endonuclease ablation site which comprises a sequence of at least 30 nucleic acid base pairs which are specifically recognized by at least ten (10×) zinc fingers, said at least one endonuclease ablation site being located at least 5' to the sequence encoding the therapeutic product; and
   (b) a second recombinant AAV vector containing the coding sequence for at least one ablator which is a chimeric endonuclease comprising at least ten copies of a zinc finger domain linked to a functional endonuclease catalytic domain in operative association with a promoter, wherein transcription of the at least one ablator and/or ablation activity is induced in response to a pharmacological agent and said ablator recognizes at least one endonuclease ablation site in the first recombinant AAV vector;
   wherein the nucleic acid sequence in (a)(i) consists of at least one endonuclease ablation site on the first strand of the nucleic acid sequence and at least one second endonuclease ablation is located on the second strand of the nucleic acid sequence, wherein said second endonuclease ablation site is distinct from said endonuclease ablation site on the first strand and is specifically and selectively recognized by different zinc fingers.

2. The composition according to claim 1, wherein the endonuclease catalytic domain is a FokI catalytic domain.

3. The composition according to claim 1, wherein the at least 10 independently selected recognition helices are all different.

4. The composition according to claim 3, wherein the at least 10 independently selected recognition helices include different recognition helices to the same triplet of base pairs in the ablation site.

5. The composition according to claim 1, wherein the at least 10 independently selected recognition helices contain 1 to 3 helices which are the same.

6. The composition according to claim 1, wherein the base pair sequence in the endonuclease ablation site comprises at least 32 base pairs.

7. The composition according to claim 1, wherein the nucleic acid molecule comprises a first endonuclease ablation site and a second endonuclease ablation site, wherein said first and said second endonuclease ablation site may be the same or are different sequences.

8. The composition according to claim 7, wherein the first endonuclease ablation site and the second endonuclease ablation site are both located 5' to the sequence encoding the therapeutic product and said first ablation site and second ablation site are separated by a spacer sequence.

9. The composition according to claim 8, wherein the second endonuclease ablation site is a spacer sequence which is inverted.

10. The composition according to claim 8, wherein the spacer sequence is a non-coding sequence.

11. The composition according to claim 7, wherein said second endonuclease ablation site is located 3' to the coding sequence.

12. The composition according to claim 1, wherein the catalytic domain of the endonuclease is linked to the zinc finger domain sequence on the N or C terminus of the zinc finger domain sequence.

13. The composition according to claim 12, wherein the catalytic domain is linked to the zinc finger domain sequence via a linker sequence.

14. The composition according to claim 1, wherein the catalytic domain of the endonuclease is located within the zinc finger domain sequence.

15. The composition according to claim 1, wherein the at least 30base pair sequence is selected from the group consisting of:

```
(i) SEQ ID NO: 806: 5'-
GGTCGATGTTCGCAACGTCGATCGTACGTGCA-3';

(ii) SEQ ID NO: 801: 5'-
GGTCGGCGACGCGAATCGTCGATTGGCGTAC-3'
and (iii) SEQ ID NO: 803: 5'-
ACTATTCGCACGCCGTACGATAGTCGGCGCGA-3'.
```

16. The composition according to claim 1, wherein said zinc finger domain comprises a nucleic acid sequence encoding at least ten zinc fingers consisting of : (a) a first N-terminal zinc finger comprising a recognition helix which specifically binds to TGC; (b) second zinc finger comprising a recognition helix which specifically binds to ACG; (c) a third zinc finger comprising a recognition helix which specifically binds to CGT; (d) a fourth zinc finger comprising a recognition helix which specifically binds to GAT; (e) a fifth zinc finger comprising a recognition helix which specifically binds to GTC; (f) a sixth zinc finger comprising a recognition helix which specifically binds to AAC; (g) a seventh zinc finger comprising a recognition helix which binds to CGC; (h) an eighth zinc finger comprising a recognition helix that specifically binds to GTT; (i) an ninth zinc finger comprising a recognition helix that specifically binds to GAT; and (j) a tenth zinc finger comprising a recognition helix which specifically binds to GTC.

17. The composition according to claim 16, wherein:

the recognition helix of (a) which specifically binds to TGC is selected from the group consisting of: ARNTLVH, QRRSLGH, QARSLRA, QQRSLKN, and QNRSLAH, QGRSLRA, RARNLTL, RGRNLEM, RKRNLIM, RMRNLII, RNRNLVL, RRRNLHL, RRRNLTL, RSRNLDI, RSRNLLL, and RSRNLTL (SEQ ID NO: 658-673);

the recognition helix of (b) which specifically binds to ACG is selected form the group consisting of: KNNDLTR; KRIDLQR; RKHDLNM; RRQTLRQ; KGNDLTR; PSQTLAWQ; RNITLVR, RSHDLTV, ASADLTR, QNATRKR, QSGDLTR, RSQTLAQ; and RTDTLRD (SEQ ID NO: 104-119);

the recognition helix of (c) which specifically binds to CGT is selected from the group consisting of RSQTRKT (SEQ ID NO: 154) and SRRTCRA (SEQ ID NO: 155);

the recognition helix of (d) which specifically binds to GAT is selected from the group consisting of VRHNLTR, ISHNLAR,ISSNLQR, LGNNLKR, LNSNLAR, LSTNLTR, LTHNLRR, QSSNLAR, RSDALIQ, SKQALAV, TGQQLRV, TKQRLVV, TRQRLRI, TSANLSR, TSGNLVR, TSQMLVV, TSSNLSR, TTSNLRR, VGHNLSR, VGSNLTR (SEQ ID NO: 251-270);

the recognition helix of (e) which specifically binds to GTC is selected from the group consisting of DRTSLAR, DHSSLKR, APSSLRR, DATQLVR, DPGALVR, DPTSLNR, DRSALAR, DRSALSR, DRSSLRR, DRTPLNR, DRTPLQN, EGGALRR, ESGALRR, NTSLLRR, RSDVLSE, TGAVLRR, TGAVLTR, TKKILTV, TKSLLAR, TMAVLRR, TRAVLRR, TSTILAR, TSTLLKR, and TSTLLNR (SEQ ID NO: 530-553);

the recognition helix of (f) which specifically binds to AAC is selected from the group consisting of DRSNRKT , DSGNLRV , GASALRQ , GASALRS , GGTALRM , GGTALVM , GHTALAL , GHTALRH , GHTALRN , GPTALVN , and HRTNLIA (SEQ ID NO: 63-73);

the recognition helix of (g) which specifically binds to CGC is HTGHLLE (SEQ ID NO: 151);

the recognition helix of (h) which specifically binds to GTT is selected from the group consisting of HKSSLTR, TNQALGV, AATALRR, HHNSLTR, HSSSLVR, IKAILTR, INHSLRR , IRTSLKR, MNSVLKR, MTSSLRR, QATLLRR, QSSALTR, THTVLAR, TKPVLKI, TNSVLGR, TRHSLGR, TSGALTR, TSGSLTR, TSGSLVR, TSTLLKR, TSTRLDI, TTALLKR, TTSALTR, TTTVLAR, and VGGSLNR (SEQ ID NO: 583-607);

the recognition helix of (i) which specifically binds to GAT is selected from the group consisting of ISHNLAR, VRHNLTR, ISSNLQR, LGNNLKR, LNSNLAR, LSTNLTR, LTHNLRR, QSSNLAR, RSDALIQ, SKQALAV, TGQQLRV, TKQRLVV, TRQRLRI, TSANLSR, TSGNLVR, TSQMLVV, TSSNLSR, TTSNLRR, VGHNLSR, and VGSNLTR (SEQ ID NO: 251-270); and the recognition helix of (j) which specifically binds to GTC is selected from the group consisting of DRTSLAR, DHSSLRKR, APSSLRR, DATQLVR, DPGALVR, DPTSLNR, DRSALAR, DRSALSR, DRSSLRR, DRTPLNR, DRTPLQN, EGGALRR, ESGALRR, NTSLLRR, RSDVLSE, TGAVLRR, TGAVLTR, TKKILTV, TKSLLAR, TMAVLRR, TRAVLRR, TSTILAR, TSTLLKR, and TSTLLNR (SEQ ID NO: 530-553).

18. The composition according to claim 17, wherein each of the zinc fingers (a)-(j) has the selected recognition domain inserted in a zinc-finger construct selected from :
SEQ ID NO: 745: (N-terminus)-PGEK-PYKCPECGKSFS-XXXXXXX-HQRTH (carboxy terminus), COOH and
SEQ ID NO: 807: (N-terminus)-TGEKPFQCRICM-RNFS-XXXXXXXX-HLRTH (carboxy terminus), COOH,
wherein XXXXXXX is the zinc finger recognition domain.

19. The composition according to claim 17, wherein:
the recognition helix of (a) which specifically binds to TGC is QRRSLGH (SEQ ID NO: 663);
the recognition helix of (b) which specifically binds to ACG is KKNDLTR (aa 29-56 of SEQ ID NO: 60);
the recognition helix of (c) which specifically binds to CGT is SRRTCRA (SEQ ID NO: 155);
the recognition helix of (d) which specifically binds to GAT is VRHNLTR (SEQ ID NO: 270);
the recognition helix of (e) which specifically binds to GTC is DRTSLAR (SEQ ID NO: 64);
the recognition helix of (f) which specifically binds to AAC is DSGNLRV (SEQ ID NO: 540);
the recognition helix of (g) which specifically binds to CGC is HTGHLLE (SEQ ID NO: 151);
the recognition helix of (h) which specifically binds to GTT is TNQALGV (aa 197-224 of SEQ ID NO: 60);
the recognition helix of (j) which specifically binds to GAT is VRHNLTR (SEQ ID NO: 270); and
the recognition helix of (k) which specifically binds to GTC is DRTSLAR (SEQ ID NO: 540).

20. The composition according to claim 2, wherein the zinc finger domain is linked to the sequence encoding the FokI catalytic domain through a sequence encoding five amino acids GTSGK (SEQ ID NO: 805), whereby the resulting chimeric ablator cuts 6 bp directly following the zinc finger binding site.

21. The composition according to claim 1, wherein the promoter is controlled by a rapamycin-regulatable system.

22. The composition according to claim 18, wherein the pharmacological agent is rapamycin or a rapalog.

23. The composition according to claim 1, wherein the ablator defined in (b) is controlled by expression of a cassette that is activated by a transcription factor following being dimerized by a pharmacologic agent, said cassette comprising two transcription units, wherein:
(c) one of said two transcription units encoding the DNA binding domain of the transcription factor fused to a binding domain for the pharmacological agent in operative association with a first promoter; and
(d) a second of said two transcription units encoding the activation domain of the transcription factor fused to a binding domain for the pharmacological agent in operative association with a second promoter.

24. The composition of claim 23, wherein the first promoter of (c) and the second promoter of (d) are independently selected from a constitutive promoter and an inducible promoter.

25. The composition of claim 24, wherein the first and second promoters are both constitutive promoters and the pharmacological agent is a dimerizer that dimerizes the domains of the transcription factor.

26. The composition of claim 17, wherein one of the first promoter and the second promoters is an inducible promoter.

* * * * *

SEQUENCE LISTING

```
<160> NUMBER OF SEQ ID NOS: 817

<210> SEQ ID NO 1
<211> LENGTH: 579
<212> TYPE: DNA
<213> ORGANISM: Artificial Sequence
<220> FEATURE:
<223> OTHER INFORMATION: modified Gin enzyme
<220> FEATURE:
<221> NAME/KEY: CDS
<222> LOCATION: (1)..(579)

<400> SEQUENCE: 1 atg ctg atc ggc tac gtg cgg gtg tcc acc aac gac cag aac acc gac        48
Met Leu Ile Gly Tyr Val Arg Val Ser Thr Asn Asp Gln Asn Thr Asp
1               5                   10                  15 ctg cag cgg aac gcc ctg gtc tgc gcc ggc tgc gag cag atc ttc gag        96
Leu Gln Arg Asn Ala Leu Val Cys Ala Gly Cys Glu Gln Ile Phe Glu
            20                  25                  30 gac aag ctg agc ggc acc cgg acc gac aga ccc gga ctg aag cgg gcc       144
Asp Lys Leu Ser Gly Thr Arg Thr Asp Arg Pro Gly Leu Lys Arg Ala
        35                  40                  45 ctg aag cgg ctg cag aaa ggc gac acc ctg gtg gtc tgg aag ctg gac       192
Leu Lys Arg Leu Gln Lys Gly Asp Thr Leu Val Val Trp Lys Leu Asp
    50                  55                  60 cgg ctg ggc aga tcc atg aag cac ctg atc agc ctg gtc gga gag ctg       240
Arg Leu Gly Arg Ser Met Lys His Leu Ile Ser Leu Val Gly Glu Leu
65                  70                  75                  80 aga gag cgg ggc atc aac ttc aga agc ctg acc gac agc atc gac acc       288
Arg Glu Arg Gly Ile Asn Phe Arg Ser Leu Thr Asp Ser Ile Asp Thr
                85                  90                  95 agc agc cct atg ggc cgg ttc ttc ttc tac gtg atg ggc gcc ctg gcc       336
Ser Ser Pro Met Gly Arg Phe Phe Phe Tyr Val Met Gly Ala Leu Ala
            100                 105                 110 gag atg gaa aga gag ctg atc atc gag cgg aca atg gcc gga ctg gcc       384
Glu Met Glu Arg Glu Leu Ile Ile Glu Arg Thr Met Ala Gly Leu Ala
        115                 120                 125 gct gcc cgg aac aag ggc aga atc ggc ggc aga ccc cct agg ctg acc       432
Ala Ala Arg Asn Lys Gly Arg Ile Gly Gly Arg Pro Pro Arg Leu Thr
    130                 135                 140 aag gcc gag tgg gaa cag gct ggc aga ctg ctg gcc cag gga atc ccc       480
Lys Ala Glu Trp Glu Gln Ala Gly Arg Leu Leu Ala Gln Gly Ile Pro
145                 150                 155                 160
```

```
cgg aaa cag gtg gcc ctg atc tac gac gtg gcc ctg agc acc ctg tat    528
Arg Lys Gln Val Ala Leu Ile Tyr Asp Val Ala Leu Ser Thr Leu Tyr
            165                 170                 175 aag aag cac ccc gcc aag aga gcc cac atc gag aac gac gac cgg atc    576
Lys Lys His Pro Ala Lys Arg Ala His Ile Glu Asn Asp Asp Arg Ile
        180                 185                 190 aac                                                                579
Asn
```

<210> SEQ ID NO 2
<211> LENGTH: 193
<212> TYPE: PRT
<213> ORGANISM: Artificial Sequence
<220> FEATURE:
<223> OTHER INFORMATION: Synthetic Construct

<400> SEQUENCE: 2

Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
    50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Phe Tyr Val Met Gly Ala Leu Ala
            100                 105                 110

Glu Met Glu Arg Glu Leu Ile Ile Glu Arg Thr Met Ala Gly Leu Ala
        115                 120                 125

Ala Ala Arg Asn Lys Gly Arg Ile Gly Gly Arg Pro Pro Arg Leu Thr
    130                 135                 140

Lys Ala Glu Trp Glu Gln Ala Gly Arg Leu Leu Ala Gln Gly Ile Pro
145                 150                 155                 160

Arg Lys Gln Val Ala Leu Ile Tyr Asp Val Ala Leu Ser Thr Leu Tyr
                165                 170                 175

Lys Lys His Pro Ala Lys Arg Ala His Ile Glu Asn Asp Asp Arg Ile
            180                 185                 190

Asn

<210> SEQ ID NO 3
<211> LENGTH: 171
<212> TYPE: DNA
<213> ORGANISM: Artificial Sequence
<220> FEATURE:
<223> OTHER INFORMATION: modified Gin enzyme
<220> FEATURE:
<221> NAME/KEY: CDS
<222> LOCATION: (1)..(171)

<400> SEQUENCE: 3

```
atg ggc aga ccc cct agg ctg acc aag gcc gag tgg gaa cag gct ggc     48
Met Gly Arg Pro Pro Arg Leu Thr Lys Ala Glu Trp Glu Gln Ala Gly
1               5                   10                  15 aga ctg ctg gcc cag gga atc ccc cgg aaa cag gtg gcc ctg atc tac     96
Arg Leu Leu Ala Gln Gly Ile Pro Arg Lys Gln Val Ala Leu Ile Tyr
            20                  25                  30
```

```
gac gtg gcc ctg agc acc ctg tat aag aag cac ccc gcc aag aga gcc    144
Asp Val Ala Leu Ser Thr Leu Tyr Lys Lys His Pro Ala Lys Arg Ala
        35                  40                  45 cac atc gag aac gac gac cgg atc aac                                171
His Ile Glu Asn Asp Asp Arg Ile Asn
50                  55

<210> SEQ ID NO 4
<211> LENGTH: 57
<212> TYPE: PRT
<213> ORGANISM: Artificial Sequence
<220> FEATURE:
<223> OTHER INFORMATION: Synthetic Construct

<400> SEQUENCE: 4

Met Gly Arg Pro Pro Arg Leu Thr Lys Ala Glu Trp Glu Gln Ala Gly
1               5                   10                  15

Arg Leu Leu Ala Gln Gly Ile Pro Arg Lys Gln Val Ala Leu Ile Tyr
            20                  25                  30

Asp Val Ala Leu Ser Thr Leu Tyr Lys Lys His Pro Ala Lys Arg Ala
        35                  40                  45

His Ile Glu Asn Asp Asp Arg Ile Asn
50                  55

<210> SEQ ID NO 5
<211> LENGTH: 768
<212> TYPE: DNA
<213> ORGANISM: Artificial Sequence
<220> FEATURE:
<223> OTHER INFORMATION: modified enzyme from Gin and FokI
<220> FEATURE:
<221> NAME/KEY: CDS
<222> LOCATION: (1)..(768)

<400> SEQUENCE: 5 atg ggc aga ccc cct agg ctg acc aag gcc gag tgg gaa cag gct ggc     48
Met Gly Arg Pro Pro Arg Leu Thr Lys Ala Glu Trp Glu Gln Ala Gly
1               5                   10                  15 aga ctg ctg gcc cag gga atc ccc cgg aaa cag gtg gcc ctg atc tac     96
Arg Leu Leu Ala Gln Gly Ile Pro Arg Lys Gln Val Ala Leu Ile Tyr
            20                  25                  30 gac gtg gcc ctg agc acc ctg tat aag aag cac ccc gcc aag aga gcc    144
Asp Val Ala Leu Ser Thr Leu Tyr Lys Lys His Pro Ala Lys Arg Ala
        35                  40                  45 cac atc gag aac gac gac cgg atc aac ggt acc aag cag ctg gtg aaa    192
His Ile Glu Asn Asp Asp Arg Ile Asn Gly Thr Lys Gln Leu Val Lys
50                  55                  60 agc gag ctg gaa gag aag aag tcc gag ctg cgg cac aag ctg aaa tac    240
Ser Glu Leu Glu Glu Lys Lys Ser Glu Leu Arg His Lys Leu Lys Tyr
65                  70                  75                  80 gtg ccc cac gag tac atc gag ctg atc gag atc gcc cgg aac ccc acc    288
Val Pro His Glu Tyr Ile Glu Leu Ile Glu Ile Ala Arg Asn Pro Thr
                85                  90                  95 cag gac aga atc ctg gaa atg aag gtc atg gaa ttt ttc atg aag gtg    336
Gln Asp Arg Ile Leu Glu Met Lys Val Met Glu Phe Phe Met Lys Val
            100                 105                 110 tac ggc tac cgg ggc gag cac ctg ggc ggc agc aga aaa ccc gac ggc    384
Tyr Gly Tyr Arg Gly Glu His Leu Gly Gly Ser Arg Lys Pro Asp Gly
        115                 120                 125 gcc atc tac acc gtg ggc agc ccc atc gac tac ggc gtg atc gtg gac    432
Ala Ile Tyr Thr Val Gly Ser Pro Ile Asp Tyr Gly Val Ile Val Asp
130                 135                 140
```

```
acc aag gcc tac agc ggc ggc tac aac ctg ccc atc gga cag gcc gac       480
Thr Lys Ala Tyr Ser Gly Gly Tyr Asn Leu Pro Ile Gly Gln Ala Asp
145                 150                 155                 160 gag atg cag aga tac gtg gaa gag aac cag acc cgg aac aag cac atc       528
Glu Met Gln Arg Tyr Val Glu Glu Asn Gln Thr Arg Asn Lys His Ile
                165                 170                 175 aac ccc aac gag tgg tgg aag gtg tac ccc agc agc gtg acc gag ttc       576
Asn Pro Asn Glu Trp Trp Lys Val Tyr Pro Ser Ser Val Thr Glu Phe
            180                 185                 190 aag ttc ctg ttc gtg tcc ggc cac ttc aag ggc aac tac aag gcc cag       624
Lys Phe Leu Phe Val Ser Gly His Phe Lys Gly Asn Tyr Lys Ala Gln
        195                 200                 205 ctg acc cgg ctg aac cac atc acc aac tgc aac ggc gct gtg ctg agc       672
Leu Thr Arg Leu Asn His Ile Thr Asn Cys Asn Gly Ala Val Leu Ser
    210                 215                 220 gtg gaa gaa ctg ctg atc ggc ggc gag atg atc aag gcc ggc acc ctg       720
Val Glu Glu Leu Leu Ile Gly Gly Glu Met Ile Lys Ala Gly Thr Leu
225                 230                 235                 240 acc ctg gaa gaa gtg cgg cgg aag ttc aac aac ggc gag atc aac ttc       768
Thr Leu Glu Glu Val Arg Arg Lys Phe Asn Asn Gly Glu Ile Asn Phe
                245                 250                 255

<210> SEQ ID NO 6
<211> LENGTH: 256
<212> TYPE: PRT
<213> ORGANISM: Artificial Sequence
<220> FEATURE:
<223> OTHER INFORMATION: Synthetic Construct

<400> SEQUENCE: 6

Met Gly Arg Pro Pro Arg Leu Thr Lys Ala Glu Trp Glu Gln Ala Gly
1               5                   10                  15

Arg Leu Leu Ala Gln Gly Ile Pro Arg Lys Gln Val Ala Leu Ile Tyr
            20                  25                  30

Asp Val Ala Leu Ser Thr Leu Tyr Lys Lys His Pro Ala Lys Arg Ala
        35                  40                  45

His Ile Glu Asn Asp Asp Arg Ile Asn Gly Thr Lys Gln Leu Val Lys
    50                  55                  60

Ser Glu Leu Glu Glu Lys Lys Ser Glu Leu Arg His Lys Leu Lys Tyr
65                  70                  75                  80

Val Pro His Glu Tyr Ile Glu Leu Ile Glu Ile Ala Arg Asn Pro Thr
                85                  90                  95

Gln Asp Arg Ile Leu Glu Met Lys Val Met Glu Phe Phe Met Lys Val
            100                 105                 110

Tyr Gly Tyr Arg Gly Glu His Leu Gly Gly Ser Arg Lys Pro Asp Gly
        115                 120                 125

Ala Ile Tyr Thr Val Gly Ser Pro Ile Asp Tyr Gly Val Ile Val Asp
    130                 135                 140

Thr Lys Ala Tyr Ser Gly Gly Tyr Asn Leu Pro Ile Gly Gln Ala Asp
145                 150                 155                 160

Glu Met Gln Arg Tyr Val Glu Glu Asn Gln Thr Arg Asn Lys His Ile
                165                 170                 175

Asn Pro Asn Glu Trp Trp Lys Val Tyr Pro Ser Ser Val Thr Glu Phe
            180                 185                 190

Lys Phe Leu Phe Val Ser Gly His Phe Lys Gly Asn Tyr Lys Ala Gln
        195                 200                 205

Leu Thr Arg Leu Asn His Ile Thr Asn Cys Asn Gly Ala Val Leu Ser
```

Val Glu Glu Leu Leu Ile Gly Gly Glu Met Ile Lys Ala Gly Thr Leu
225                 230                 235                 240

Thr Leu Glu Glu Val Arg Arg Lys Phe Asn Asn Gly Glu Ile Asn Phe
            245                 250                 255

<210> SEQ ID NO 7
<211> LENGTH: 192
<212> TYPE: DNA
<213> ORGANISM: Artificial Sequence
<220> FEATURE:
<223> OTHER INFORMATION: modified enzyme from SV40 and Gin
<220> FEATURE:
<221> NAME/KEY: CDS
<222> LOCATION: (1)..(192)

<400> SEQUENCE: 7 atg ccc aag aag aag aga aag gtg ggc aga ccc cct agg ctg acc aag      48
Met Pro Lys Lys Lys Arg Lys Val Gly Arg Pro Pro Arg Leu Thr Lys
1               5                   10                  15 gcc gag tgg gaa cag gct ggc aga ctg ctg gcc cag gga atc ccc cgg      96
Ala Glu Trp Glu Gln Ala Gly Arg Leu Leu Ala Gln Gly Ile Pro Arg
            20                  25                  30 aaa cag gtg gcc ctg atc tac gac gtg gcc ctg agc acc ctg tat aag     144
Lys Gln Val Ala Leu Ile Tyr Asp Val Ala Leu Ser Thr Leu Tyr Lys
        35                  40                  45 aag cac ccc gcc aag aga gcc cac atc gag aac gac gac cgg atc aac     192
Lys His Pro Ala Lys Arg Ala His Ile Glu Asn Asp Asp Arg Ile Asn
    50                  55                  60

<210> SEQ ID NO 8
<211> LENGTH: 64
<212> TYPE: PRT
<213> ORGANISM: Artificial Sequence
<220> FEATURE:
<223> OTHER INFORMATION: Synthetic Construct

<400> SEQUENCE: 8

Met Pro Lys Lys Lys Arg Lys Val Gly Arg Pro Pro Arg Leu Thr Lys
1               5                   10                  15

Ala Glu Trp Glu Gln Ala Gly Arg Leu Leu Ala Gln Gly Ile Pro Arg
            20                  25                  30

Lys Gln Val Ala Leu Ile Tyr Asp Val Ala Leu Ser Thr Leu Tyr Lys
        35                  40                  45

Lys His Pro Ala Lys Arg Ala His Ile Glu Asn Asp Asp Arg Ile Asn
    50                  55                  60

<210> SEQ ID NO 9
<211> LENGTH: 789
<212> TYPE: DNA
<213> ORGANISM: Artificial Sequence
<220> FEATURE:
<223> OTHER INFORMATION: modified enzyme from SV40, Gin and FokI
<220> FEATURE:
<221> NAME/KEY: CDS
<222> LOCATION: (1)..(789)

<400> SEQUENCE: 9 atg ccc aag aag aag aga aag gtg ggc aga ccc cct agg ctg acc aag      48
Met Pro Lys Lys Lys Arg Lys Val Gly Arg Pro Pro Arg Leu Thr Lys
1               5                   10                  15 gcc gag tgg gaa cag gct ggc aga ctg ctg gcc cag gga atc ccc cgg      96
Ala Glu Trp Glu Gln Ala Gly Arg Leu Leu Ala Gln Gly Ile Pro Arg
            20                  25                  30

```
aaa cag gtg gcc ctg atc tac gac gtg gcc ctg agc acc ctg tat aag      144
Lys Gln Val Ala Leu Ile Tyr Asp Val Ala Leu Ser Thr Leu Tyr Lys
         35                  40                  45 aag cac ccc gcc aag aga gcc cac atc gag aac gac gac cgg atc aac      192
Lys His Pro Ala Lys Arg Ala His Ile Glu Asn Asp Asp Arg Ile Asn
 50                  55                  60 ggt acc aag cag ctg gtg aaa agc gag ctg gaa gag aag aag tcc gag      240
Gly Thr Lys Gln Leu Val Lys Ser Glu Leu Glu Glu Lys Lys Ser Glu
 65                  70                  75                  80 ctg cgg cac aag ctg aaa tac gtg ccc cac gag tac atc gag ctg atc      288
Leu Arg His Lys Leu Lys Tyr Val Pro His Glu Tyr Ile Glu Leu Ile
                 85                  90                  95 gag atc gcc cgg aac ccc acc cag gac aga atc ctg gaa atg aag gtc      336
Glu Ile Ala Arg Asn Pro Thr Gln Asp Arg Ile Leu Glu Met Lys Val
        100                 105                 110 atg gaa ttt ttc atg aag gtg tac ggc tac cgg ggc gag cac ctg ggc      384
Met Glu Phe Phe Met Lys Val Tyr Gly Tyr Arg Gly Glu His Leu Gly
            115                 120                 125 ggc agc aga aaa ccc gac ggc gcc atc tac acc gtg ggc agc ccc atc      432
Gly Ser Arg Lys Pro Asp Gly Ala Ile Tyr Thr Val Gly Ser Pro Ile
        130                 135                 140 gac tac ggc gtg atc gtg gac acc aag gcc tac agc ggc ggc tac aac      480
Asp Tyr Gly Val Ile Val Asp Thr Lys Ala Tyr Ser Gly Gly Tyr Asn
145                 150                 155                 160 ctg ccc atc gga cag gcc gac gag atg cag aga tac gtg gaa gag aac      528
Leu Pro Ile Gly Gln Ala Asp Glu Met Gln Arg Tyr Val Glu Glu Asn
                165                 170                 175 cag acc cgg aac aag cac atc aac ccc aac gag tgg tgg aag gtg tac      576
Gln Thr Arg Asn Lys His Ile Asn Pro Asn Glu Trp Trp Lys Val Tyr
            180                 185                 190 ccc agc agc gtg acc gag ttc aag ttc ctg ttc gtg tcc ggc cac ttc      624
Pro Ser Ser Val Thr Glu Phe Lys Phe Leu Phe Val Ser Gly His Phe
        195                 200                 205 aag ggc aac tac aag gcc cag ctg acc cgg ctg aac cac atc acc aac      672
Lys Gly Asn Tyr Lys Ala Gln Leu Thr Arg Leu Asn His Ile Thr Asn
    210                 215                 220 tgc aac ggc gct gtg ctg agc gtg gaa gaa ctg ctg atc ggc ggc gag      720
Cys Asn Gly Ala Val Leu Ser Val Glu Glu Leu Leu Ile Gly Gly Glu
225                 230                 235                 240 atg atc aag gcc ggc acc ctg acc ctg gaa gaa gtg cgg cgg aag ttc      768
Met Ile Lys Ala Gly Thr Leu Thr Leu Glu Glu Val Arg Arg Lys Phe
                245                 250                 255 aac aac ggc gag atc aac ttc                                          789
Asn Asn Gly Glu Ile Asn Phe
            260

<210> SEQ ID NO 10
<211> LENGTH: 263
<212> TYPE: PRT
<213> ORGANISM: Artificial Sequence
<220> FEATURE:
<223> OTHER INFORMATION: Synthetic Construct

<400> SEQUENCE: 10

Met Pro Lys Lys Arg Lys Val Gly Arg Pro Pro Arg Leu Thr Lys
1               5                   10                  15

Ala Glu Trp Glu Gln Ala Gly Arg Leu Leu Ala Gln Gly Ile Pro Arg
            20                  25                  30

Lys Gln Val Ala Leu Ile Tyr Asp Val Ala Leu Ser Thr Leu Tyr Lys
         35                  40                  45
```

```
Lys His Pro Ala Lys Arg Ala His Ile Glu Asn Asp Arg Ile Asn
 50                  55                  60

Gly Thr Lys Gln Leu Val Lys Ser Glu Leu Glu Glu Lys Ser Glu
 65                  70                  75                  80

Leu Arg His Lys Leu Lys Tyr Val Pro His Glu Tyr Ile Glu Leu Ile
                 85                  90                  95

Glu Ile Ala Arg Asn Pro Thr Gln Asp Arg Ile Leu Glu Met Lys Val
                100                 105                 110

Met Glu Phe Phe Met Lys Val Tyr Gly Tyr Arg Gly Glu His Leu Gly
                115                 120                 125

Gly Ser Arg Lys Pro Asp Gly Ala Ile Tyr Thr Val Gly Ser Pro Ile
    130                 135                 140

Asp Tyr Gly Val Ile Val Asp Thr Lys Ala Tyr Ser Gly Gly Tyr Asn
145                 150                 155                 160

Leu Pro Ile Gly Gln Ala Asp Glu Met Gln Arg Tyr Val Glu Glu Asn
                165                 170                 175

Gln Thr Arg Asn Lys His Ile Asn Pro Asn Glu Trp Trp Lys Val Tyr
                180                 185                 190

Pro Ser Ser Val Thr Glu Phe Lys Phe Leu Phe Val Ser Gly His Phe
                195                 200                 205

Lys Gly Asn Tyr Lys Ala Gln Leu Thr Arg Leu Asn His Ile Thr Asn
    210                 215                 220

Cys Asn Gly Ala Val Leu Ser Val Glu Glu Leu Leu Ile Gly Gly Glu
225                 230                 235                 240

Met Ile Lys Ala Gly Thr Leu Thr Leu Glu Glu Val Arg Arg Lys Phe
                245                 250                 255

Asn Asn Gly Glu Ile Asn Phe
                260

<210> SEQ ID NO 11
<211> LENGTH: 1752
<212> TYPE: DNA
<213> ORGANISM: Artificial Sequence
<220> FEATURE:
<223> OTHER INFORMATION: modified FokI enzyme
<220> FEATURE:
<221> NAME/KEY: CDS
<222> LOCATION: (1)..(1752)

<400> SEQUENCE: 11 atg ttt ctg agc atg gtg tcc aag atc cgg acc ttc ggc tgg gtg cag    48
Met Phe Leu Ser Met Val Ser Lys Ile Arg Thr Phe Gly Trp Val Gln
  1               5                  10                  15 aac ccc ggc aag ttc gag aac ctg aag cgg gtg gtg cag gtg ttc gac    96
Asn Pro Gly Lys Phe Glu Asn Leu Lys Arg Val Val Gln Val Phe Asp
             20                  25                  30 cgg aac agc aag gtg cac aac gaa gtg aag aac atc aag atc ccc aca   144
Arg Asn Ser Lys Val His Asn Glu Val Lys Asn Ile Lys Ile Pro Thr
         35                  40                  45 ctg gtg aaa gag agc aag atc cag aaa gaa ctc gtc gcc atc atg aac   192
Leu Val Lys Glu Ser Lys Ile Gln Lys Glu Leu Val Ala Ile Met Asn
     50                  55                  60 cag cac gac ctg atc tac acc tac aaa gaa ctg gtc gga acc ggc acc   240
Gln His Asp Leu Ile Tyr Thr Tyr Lys Glu Leu Val Gly Thr Gly Thr
 65                  70                  75                  80 agc atc aga agc gag gcc ccc tgc gac gcc atc att cag gcc aca atc   288
Ser Ile Arg Ser Glu Ala Pro Cys Asp Ala Ile Ile Gln Ala Thr Ile
                 85                  90                  95
```

| | | |
|---|---|---|
| gcc gac cag ggc aac aag aag ggc tac atc gac aac tgg tcc agc gac<br>Ala Asp Gln Gly Asn Lys Lys Gly Tyr Ile Asp Asn Trp Ser Ser Asp<br>100 105 110 | | 336 |
| ggc ttc ctg aga tgg gcc cac gcc ctg ggc ttc atc gag tac atc aac<br>Gly Phe Leu Arg Trp Ala His Ala Leu Gly Phe Ile Glu Tyr Ile Asn<br>115 120 125 | | 384 |
| aag agc gac agc ttc gtg atc acc gac gtg ggc ctg gcc tac agc aag<br>Lys Ser Asp Ser Phe Val Ile Thr Asp Val Gly Leu Ala Tyr Ser Lys<br>130 135 140 | | 432 |
| agc gcc gat ggc agc gcc att gag aaa gag atc ctg atc gag gcc atc<br>Ser Ala Asp Gly Ser Ala Ile Glu Lys Glu Ile Leu Ile Glu Ala Ile<br>145 150 155 160 | | 480 |
| agc agc tac ccc cct gcc atc aga atc ctg acc ctg ctg gaa gat ggc<br>Ser Ser Tyr Pro Pro Ala Ile Arg Ile Leu Thr Leu Leu Glu Asp Gly<br>165 170 175 | | 528 |
| cag cac ctg acc aag ttc gac ctg ggc aag aac ctg ggc ttc tcc ggc<br>Gln His Leu Thr Lys Phe Asp Leu Gly Lys Asn Leu Gly Phe Ser Gly<br>180 185 190 | | 576 |
| gag agc ggc ttc acc agc ctg ccc gag gga atc ctg ctg gac acc ctg<br>Glu Ser Gly Phe Thr Ser Leu Pro Glu Gly Ile Leu Leu Asp Thr Leu<br>195 200 205 | | 624 |
| gcc aac gcc atg ccc aag gac aag ggc gag atc cgg aac aac tgg gag<br>Ala Asn Ala Met Pro Lys Asp Lys Gly Glu Ile Arg Asn Asn Trp Glu<br>210 215 220 | | 672 |
| ggc agc agc gat aag tac gcc aga atg atc ggc ggc tgg ctg gac aag<br>Gly Ser Ser Asp Lys Tyr Ala Arg Met Ile Gly Gly Trp Leu Asp Lys<br>225 230 235 240 | | 720 |
| ctg ggc ctg gtc aaa cag ggg aag aaa gag ttc atc att ccc acc ctg<br>Leu Gly Leu Val Lys Gln Gly Lys Lys Glu Phe Ile Ile Pro Thr Leu<br>245 250 255 | | 768 |
| ggc aag ccc gac aac aaa gag ttt atc agc cac gcc ttc aag atc aca<br>Gly Lys Pro Asp Asn Lys Glu Phe Ile Ser His Ala Phe Lys Ile Thr<br>260 265 270 | | 816 |
| ggc gag ggc ctg aag gtg ctg cgg aga gcc aag ggc agc acc aag ttc<br>Gly Glu Gly Leu Lys Val Leu Arg Arg Ala Lys Gly Ser Thr Lys Phe<br>275 280 285 | | 864 |
| aca cgg gtg ccc aag cgg gtg tac tgg gag atg ctg gcc acc aac ctg<br>Thr Arg Val Pro Lys Arg Val Tyr Trp Glu Met Leu Ala Thr Asn Leu<br>290 295 300 | | 912 |
| acc gac aaa gaa tac gtg cgg acc aga cgg gcc ctg atc ctg gaa atc<br>Thr Asp Lys Glu Tyr Val Arg Thr Arg Arg Ala Leu Ile Leu Glu Ile<br>305 310 315 320 | | 960 |
| ctg att aag gcc ggc agc ctg aag atc gag cag atc cag gac aac ctg<br>Leu Ile Lys Ala Gly Ser Leu Lys Ile Glu Gln Ile Gln Asp Asn Leu<br>325 330 335 | | 1008 |
| aag aag ctg ggc ttt gac gaa gtg atc gag aca atc gag aac gac atc<br>Lys Lys Leu Gly Phe Asp Glu Val Ile Glu Thr Ile Glu Asn Asp Ile<br>340 345 350 | | 1056 |
| aag ggc ctg atc aac acc ggc atc ttc atc gag atc aag ggc cgg ttc<br>Lys Gly Leu Ile Asn Thr Gly Ile Phe Ile Glu Ile Lys Gly Arg Phe<br>355 360 365 | | 1104 |
| tac cag ctg aag gac cac att ctg cag ttc gtg atc ccc aac cgg gga<br>Tyr Gln Leu Lys Asp His Ile Leu Gln Phe Val Ile Pro Asn Arg Gly<br>370 375 380 | | 1152 |
| gtg ggt acc aag cag ctg gtg aaa agc gag ctg gaa gag aag aag tcc<br>Val Gly Thr Lys Gln Leu Val Lys Ser Glu Leu Glu Glu Lys Lys Ser<br>385 390 395 400 | | 1200 |
| gag ctg cgg cac aag ctg aaa tac gtg ccc cac gag tac atc gag ctg<br>Glu Leu Arg His Lys Leu Lys Tyr Val Pro His Glu Tyr Ile Glu Leu | | 1248 |

```
atc gag atc gcc cgg aac ccc acc cag gac aga atc ctg gaa atg aag      1296
Ile Glu Ile Ala Arg Asn Pro Thr Gln Asp Arg Ile Leu Glu Met Lys
            420                 425                 430 gtc atg gaa ttt ttc atg aag gtg tac ggc tac cgg ggc gag cac ctg      1344
Val Met Glu Phe Phe Met Lys Val Tyr Gly Tyr Arg Gly Glu His Leu
        435                 440                 445 ggc ggc agc aga aaa ccc gac ggc gcc atc tac acc gtg ggc agc ccc      1392
Gly Gly Ser Arg Lys Pro Asp Gly Ala Ile Tyr Thr Val Gly Ser Pro
450                 455                 460 atc gac tac ggc gtg atc gtg gac acc aag gcc tac agc ggc ggc tac      1440
Ile Asp Tyr Gly Val Ile Val Asp Thr Lys Ala Tyr Ser Gly Gly Tyr
465                 470                 475                 480 aac ctg ccc atc gga cag gcc gac gag atg cag aga tac gtg gaa gag      1488
Asn Leu Pro Ile Gly Gln Ala Asp Glu Met Gln Arg Tyr Val Glu Glu
                485                 490                 495 aac cag acc cgg aac aag cac atc aac ccc aac gag tgg tgg aag gtg      1536
Asn Gln Thr Arg Asn Lys His Ile Asn Pro Asn Glu Trp Trp Lys Val
            500                 505                 510 tac ccc agc agc gtg acc gag ttc aag ttc ctg ttc gtg tcc ggc cac      1584
Tyr Pro Ser Ser Val Thr Glu Phe Lys Phe Leu Phe Val Ser Gly His
        515                 520                 525 ttc aag ggc aac tac aag gcc cag ctg acc cgg ctg aac cac atc acc      1632
Phe Lys Gly Asn Tyr Lys Ala Gln Leu Thr Arg Leu Asn His Ile Thr
530                 535                 540 aac tgc aac ggc gct gtg ctg agc gtg gaa gaa ctg ctg atc ggc ggc      1680
Asn Cys Asn Gly Ala Val Leu Ser Val Glu Glu Leu Leu Ile Gly Gly
545                 550                 555                 560 gag atg atc aag gcc ggc acc ctg acc ctg gaa gaa gtg cgg cgg aag      1728
Glu Met Ile Lys Ala Gly Thr Leu Thr Leu Glu Glu Val Arg Arg Lys
                565                 570                 575 ttc aac aac ggc gag atc aac ttc                                      1752
Phe Asn Asn Gly Glu Ile Asn Phe
            580

<210> SEQ ID NO 12
<211> LENGTH: 584
<212> TYPE: PRT
<213> ORGANISM: Artificial Sequence
<220> FEATURE:
<223> OTHER INFORMATION: Synthetic Construct

<400> SEQUENCE: 12

Met Phe Leu Ser Met Val Ser Lys Ile Arg Thr Phe Gly Trp Val Gln
1               5                   10                  15

Asn Pro Gly Lys Phe Glu Asn Leu Lys Arg Val Val Gln Val Phe Asp
            20                  25                  30

Arg Asn Ser Lys Val His Asn Glu Val Lys Asn Ile Lys Ile Pro Thr
        35                  40                  45

Leu Val Lys Glu Ser Lys Ile Gln Lys Glu Leu Val Ala Ile Met Asn
    50                  55                  60

Gln His Asp Leu Ile Tyr Thr Tyr Lys Glu Leu Val Gly Thr Gly Thr
65                  70                  75                  80

Ser Ile Arg Ser Glu Ala Pro Cys Asp Ala Ile Ile Gln Ala Thr Ile
                85                  90                  95

Ala Asp Gln Gly Asn Lys Lys Gly Tyr Ile Asp Asn Trp Ser Ser Asp
            100                 105                 110

Gly Phe Leu Arg Trp Ala His Ala Leu Gly Phe Ile Glu Tyr Ile Asn
        115                 120                 125
```

-continued

```
Lys Ser Asp Ser Phe Val Ile Thr Asp Val Gly Leu Ala Tyr Ser Lys
    130                 135                 140

Ser Ala Asp Gly Ser Ala Ile Glu Lys Glu Ile Leu Ile Glu Ala Ile
145                 150                 155                 160

Ser Ser Tyr Pro Pro Ala Ile Arg Ile Leu Thr Leu Leu Glu Asp Gly
                165                 170                 175

Gln His Leu Thr Lys Phe Asp Leu Gly Lys Asn Leu Gly Phe Ser Gly
            180                 185                 190

Glu Ser Gly Phe Thr Ser Leu Pro Glu Gly Ile Leu Leu Asp Thr Leu
        195                 200                 205

Ala Asn Ala Met Pro Lys Asp Lys Gly Glu Ile Arg Asn Asn Trp Glu
    210                 215                 220

Gly Ser Ser Asp Lys Tyr Ala Arg Met Ile Gly Gly Trp Leu Asp Lys
225                 230                 235                 240

Leu Gly Leu Val Lys Gln Gly Lys Lys Glu Phe Ile Ile Pro Thr Leu
                245                 250                 255

Gly Lys Pro Asp Asn Lys Glu Phe Ile Ser His Ala Phe Lys Ile Thr
            260                 265                 270

Gly Glu Gly Leu Lys Val Leu Arg Arg Ala Lys Gly Ser Thr Lys Phe
        275                 280                 285

Thr Arg Val Pro Lys Arg Val Tyr Trp Glu Met Leu Ala Thr Asn Leu
    290                 295                 300

Thr Asp Lys Glu Tyr Val Arg Thr Arg Arg Ala Leu Ile Leu Glu Ile
305                 310                 315                 320

Leu Ile Lys Ala Gly Ser Leu Lys Ile Glu Gln Ile Gln Asp Asn Leu
                325                 330                 335

Lys Lys Leu Gly Phe Asp Glu Val Ile Glu Thr Ile Glu Asn Asp Ile
            340                 345                 350

Lys Gly Leu Ile Asn Thr Gly Ile Phe Ile Glu Ile Lys Gly Arg Phe
        355                 360                 365

Tyr Gln Leu Lys Asp His Ile Leu Gln Phe Val Ile Pro Asn Arg Gly
    370                 375                 380

Val Gly Thr Lys Gln Leu Val Lys Ser Glu Leu Glu Glu Lys Lys Ser
385                 390                 395                 400

Glu Leu Arg His Lys Leu Lys Tyr Val Pro His Glu Tyr Ile Glu Leu
                405                 410                 415

Ile Glu Ile Ala Arg Asn Pro Thr Gln Asp Arg Ile Leu Glu Met Lys
            420                 425                 430

Val Met Glu Phe Phe Met Lys Val Tyr Gly Tyr Arg Gly Glu His Leu
        435                 440                 445

Gly Gly Ser Arg Lys Pro Asp Gly Ala Ile Tyr Thr Val Gly Ser Pro
    450                 455                 460

Ile Asp Tyr Gly Val Ile Val Asp Thr Lys Ala Tyr Ser Gly Gly Tyr
465                 470                 475                 480

Asn Leu Pro Ile Gly Gln Ala Asp Glu Met Gln Arg Tyr Val Glu Glu
                485                 490                 495

Asn Gln Thr Arg Asn Lys His Ile Asn Pro Asn Glu Trp Trp Lys Val
            500                 505                 510

Tyr Pro Ser Ser Val Thr Glu Phe Lys Phe Leu Phe Val Ser Gly His
        515                 520                 525

Phe Lys Gly Asn Tyr Lys Ala Gln Leu Thr Arg Leu Asn His Ile Thr
    530                 535                 540
```

```
Asn Cys Asn Gly Ala Val Leu Ser Val Glu Glu Leu Leu Ile Gly Gly
545                 550                 555                 560

Glu Met Ile Lys Ala Gly Thr Leu Thr Leu Glu Glu Val Arg Arg Lys
                565                 570                 575

Phe Asn Asn Gly Glu Ile Asn Phe
            580

<210> SEQ ID NO 13
<211> LENGTH: 594
<212> TYPE: DNA
<213> ORGANISM: Artificial Sequence
<220> FEATURE:
<223> OTHER INFORMATION: modified FokI enzyme
<220> FEATURE:
<221> NAME/KEY: CDS
<222> LOCATION: (1)..(594)

<400> SEQUENCE: 13 atg aag cag ctg gtg aaa agc gag ctg gaa gag aag aag tcc gag ctg      48
Met Lys Gln Leu Val Lys Ser Glu Leu Glu Glu Lys Lys Ser Glu Leu
1               5                   10                  15 cgg cac aag ctg aaa tac gtg ccc cac gag tac atc gag ctg atc gag      96
Arg His Lys Leu Lys Tyr Val Pro His Glu Tyr Ile Glu Leu Ile Glu
                20                  25                  30 atc gcc cgg aac ccc acc cag gac aga atc ctg gaa atg aag gtc atg     144
Ile Ala Arg Asn Pro Thr Gln Asp Arg Ile Leu Glu Met Lys Val Met
            35                  40                  45 gaa ttt ttc atg aag gtg tac ggc tac cgg ggc gag cac ctg ggc ggc     192
Glu Phe Phe Met Lys Val Tyr Gly Tyr Arg Gly Glu His Leu Gly Gly
        50                  55                  60 agc aga aaa ccc gac ggc gcc atc tac acc gtg ggc agc ccc atc gac     240
Ser Arg Lys Pro Asp Gly Ala Ile Tyr Thr Val Gly Ser Pro Ile Asp
65                  70                  75                  80 tac ggc gtg atc gtg gac acc aag gcc tac agc ggc ggc tac aac ctg     288
Tyr Gly Val Ile Val Asp Thr Lys Ala Tyr Ser Gly Gly Tyr Asn Leu
                85                  90                  95 ccc atc gga cag gcc gac gag atg cag aga tac gtg gaa gag aac cag     336
Pro Ile Gly Gln Ala Asp Glu Met Gln Arg Tyr Val Glu Glu Asn Gln
                100                 105                 110 acc cgg aac aag cac atc aac ccc aac gag tgg tgg aag gtg tac ccc     384
Thr Arg Asn Lys His Ile Asn Pro Asn Glu Trp Trp Lys Val Tyr Pro
            115                 120                 125 agc agc gtg acc gag ttc aag ttc ctg ttc gtg tcc ggc cac ttc aag     432
Ser Ser Val Thr Glu Phe Lys Phe Leu Phe Val Ser Gly His Phe Lys
        130                 135                 140 ggc aac tac aag gcc cag ctg acc cgg ctg aac cac atc acc aac tgc     480
Gly Asn Tyr Lys Ala Gln Leu Thr Arg Leu Asn His Ile Thr Asn Cys
145                 150                 155                 160 aac ggc gct gtg ctg agc gtg gaa gaa ctg ctg atc ggc ggc gag atg     528
Asn Gly Ala Val Leu Ser Val Glu Glu Leu Leu Ile Gly Gly Glu Met
                165                 170                 175 atc aag gcc ggc acc ctg acc ctg gaa gaa gtg cgg cgg aag ttc aac     576
Ile Lys Ala Gly Thr Leu Thr Leu Glu Glu Val Arg Arg Lys Phe Asn
            180                 185                 190 aac ggc gag atc aac ttc                                              594
Asn Gly Glu Ile Asn Phe
        195

<210> SEQ ID NO 14
<211> LENGTH: 198
<212> TYPE: PRT
<213> ORGANISM: Artificial Sequence
```

```
<220> FEATURE:
<223> OTHER INFORMATION: Synthetic Construct

<400> SEQUENCE: 14

Met Lys Gln Leu Val Lys Ser Glu Leu Glu Glu Lys Lys Ser Glu Leu
1               5                   10                  15

Arg His Lys Leu Lys Tyr Val Pro His Glu Tyr Ile Glu Leu Ile Glu
            20                  25                  30

Ile Ala Arg Asn Pro Thr Gln Asp Arg Ile Leu Glu Met Lys Val Met
        35                  40                  45

Glu Phe Phe Met Lys Val Tyr Gly Tyr Arg Gly Glu His Leu Gly Gly
    50                  55                  60

Ser Arg Lys Pro Asp Gly Ala Ile Tyr Thr Val Gly Ser Pro Ile Asp
65                  70                  75                  80

Tyr Gly Val Ile Val Asp Thr Lys Ala Tyr Ser Gly Gly Tyr Asn Leu
                85                  90                  95

Pro Ile Gly Gln Ala Asp Glu Met Gln Arg Tyr Val Glu Glu Asn Gln
            100                 105                 110

Thr Arg Asn Lys His Ile Asn Pro Asn Glu Trp Trp Lys Val Tyr Pro
        115                 120                 125

Ser Ser Val Thr Glu Phe Lys Phe Leu Phe Val Ser Gly His Phe Lys
    130                 135                 140

Gly Asn Tyr Lys Ala Gln Leu Thr Arg Leu Asn His Ile Thr Asn Cys
145                 150                 155                 160

Asn Gly Ala Val Leu Ser Val Glu Glu Leu Leu Ile Gly Gly Glu Met
                165                 170                 175

Ile Lys Ala Gly Thr Leu Thr Leu Glu Glu Val Arg Arg Lys Phe Asn
            180                 185                 190

Asn Gly Glu Ile Asn Phe
            195

<210> SEQ ID NO 15
<211> LENGTH: 615
<212> TYPE: DNA
<213> ORGANISM: Artificial Sequence
<220> FEATURE:
<223> OTHER INFORMATION: modified enzyme from SV40 and FokI
<220> FEATURE:
<221> NAME/KEY: CDS
<222> LOCATION: (1)..(615)

<400> SEQUENCE: 15 atg ccc aag aag aag aga aag gtg aag cag ctg gtg aaa agc gag ctg      48
Met Pro Lys Lys Lys Arg Lys Val Lys Gln Leu Val Lys Ser Glu Leu
1               5                   10                  15 gaa gag aag aag tcc gag ctg cgg cac aag ctg aaa tac gtg ccc cac      96
Glu Glu Lys Lys Ser Glu Leu Arg His Lys Leu Lys Tyr Val Pro His
            20                  25                  30 gag tac atc gag ctg atc gag atc gcc cgg aac ccc acc cag gac aga     144
Glu Tyr Ile Glu Leu Ile Glu Ile Ala Arg Asn Pro Thr Gln Asp Arg
        35                  40                  45 atc ctg gaa atg aag gtc atg gaa ttt ttc atg aag gtg tac ggc tac     192
Ile Leu Glu Met Lys Val Met Glu Phe Phe Met Lys Val Tyr Gly Tyr
    50                  55                  60 cgg ggc gag cac ctg ggc ggc agc aga aaa ccc gac ggc gcc atc tac     240
Arg Gly Glu His Leu Gly Gly Ser Arg Lys Pro Asp Gly Ala Ile Tyr
65                  70                  75                  80 acc gtg ggc agc ccc atc gac tac ggc gtg atc gtg gac acc aag gcc     288
Thr Val Gly Ser Pro Ile Asp Tyr Gly Val Ile Val Asp Thr Lys Ala
```

```
                    85                      90                       95
tac agc ggc ggc tac aac ctg ccc atc gga cag gcc gac gag atg cag        336
Tyr Ser Gly Gly Tyr Asn Leu Pro Ile Gly Gln Ala Asp Glu Met Gln
            100                 105                 110 aga tac gtg gaa gag aac cag acc cgg aac aag cac atc aac ccc aac        384
Arg Tyr Val Glu Glu Asn Gln Thr Arg Asn Lys His Ile Asn Pro Asn
            115                 120                 125 gag tgg tgg aag gtg tac ccc agc agc gtg acc gag ttc aag ttc ctg        432
Glu Trp Trp Lys Val Tyr Pro Ser Ser Val Thr Glu Phe Lys Phe Leu
130                 135                 140 ttc gtg tcc ggc cac ttc aag ggc aac tac aag gcc cag ctg acc cgg        480
Phe Val Ser Gly His Phe Lys Gly Asn Tyr Lys Ala Gln Leu Thr Arg
145                 150                 155                 160 ctg aac cac atc acc aac tgc aac ggc gct gtg ctg agc gtg gaa gaa        528
Leu Asn His Ile Thr Asn Cys Asn Gly Ala Val Leu Ser Val Glu Glu
                165                 170                 175 ctg ctg atc ggc ggc gag atg atc aag gcc ggc acc ctg acc ctg gaa        576
Leu Leu Ile Gly Gly Glu Met Ile Lys Ala Gly Thr Leu Thr Leu Glu
            180                 185                 190 gaa gtg cgg cgg aag ttc aac aac ggc gag atc aac ttc                    615
Glu Val Arg Arg Lys Phe Asn Asn Gly Glu Ile Asn Phe
            195                 200                 205

<210> SEQ ID NO 16
<211> LENGTH: 205
<212> TYPE: PRT
<213> ORGANISM: Artificial Sequence
<220> FEATURE:
<223> OTHER INFORMATION: Synthetic Construct

<400> SEQUENCE: 16

Met Pro Lys Lys Arg Lys Val Lys Gln Leu Val Lys Ser Glu Leu
1               5                   10                  15

Glu Glu Lys Lys Ser Glu Leu Arg His Lys Leu Lys Tyr Val Pro His
                20                  25                  30

Glu Tyr Ile Glu Leu Ile Glu Ile Ala Arg Asn Pro Thr Gln Asp Arg
            35                  40                  45

Ile Leu Glu Met Lys Val Met Glu Phe Phe Met Lys Val Tyr Gly Tyr
        50                  55                  60

Arg Gly Glu His Leu Gly Gly Ser Arg Lys Pro Asp Gly Ala Ile Tyr
65                  70                  75                  80

Thr Val Gly Ser Pro Ile Asp Tyr Gly Val Ile Val Asp Thr Lys Ala
                85                  90                  95

Tyr Ser Gly Gly Tyr Asn Leu Pro Ile Gly Gln Ala Asp Glu Met Gln
            100                 105                 110

Arg Tyr Val Glu Glu Asn Gln Thr Arg Asn Lys His Ile Asn Pro Asn
        115                 120                 125

Glu Trp Trp Lys Val Tyr Pro Ser Ser Val Thr Glu Phe Lys Phe Leu
    130                 135                 140

Phe Val Ser Gly His Phe Lys Gly Asn Tyr Lys Ala Gln Leu Thr Arg
145                 150                 155                 160

Leu Asn His Ile Thr Asn Cys Asn Gly Ala Val Leu Ser Val Glu Glu
                165                 170                 175

Leu Leu Ile Gly Gly Glu Met Ile Lys Ala Gly Thr Leu Thr Leu Glu
            180                 185                 190

Glu Val Arg Arg Lys Phe Asn Asn Gly Glu Ile Asn Phe
        195                 200                 205
```

```
<210> SEQ ID NO 17
<211> LENGTH: 366
<212> TYPE: DNA
<213> ORGANISM: Artificial Sequence
<220> FEATURE:
<223> OTHER INFORMATION: modified ZFHD enzyme
<220> FEATURE:
<221> NAME/KEY: CDS
<222> LOCATION: (1)..(366)

<400> SEQUENCE: 17 atg gag aga ccc tac gcc tgc ccc gtg gag agc tgc gac aga aga ttc      48
Met Glu Arg Pro Tyr Ala Cys Pro Val Glu Ser Cys Asp Arg Arg Phe
1               5                   10                  15 agc aga agc gac gag ctg acc aga cac atc aga atc cac acc ggc cag      96
Ser Arg Ser Asp Glu Leu Thr Arg His Ile Arg Ile His Thr Gly Gln
            20                  25                  30 aag ccc ttc cag tgc aga atc tgc atg aga aac ttc agc aga agc gac     144
Lys Pro Phe Gln Cys Arg Ile Cys Met Arg Asn Phe Ser Arg Ser Asp
        35                  40                  45 cac ctg acc acc cac atc aga acc cac aca ggc ggc ggc aga aga aga     192
His Leu Thr Thr His Ile Arg Thr His Thr Gly Gly Gly Arg Arg Arg
    50                  55                  60 aag aag aga acc agc atc gag acc aac atc aga gtg gcc ctg gag aaa     240
Lys Lys Arg Thr Ser Ile Glu Thr Asn Ile Arg Val Ala Leu Glu Lys
65                  70                  75                  80 agc ttc ctg gag aac cag aag ccc acc agc gag gag atc acc atg atc     288
Ser Phe Leu Glu Asn Gln Lys Pro Thr Ser Glu Glu Ile Thr Met Ile
                85                  90                  95 gcc gac cag ctg aac atg gag aag gag gtg atc aga gtg tgg ttc tgc     336
Ala Asp Gln Leu Asn Met Glu Lys Glu Val Ile Arg Val Trp Phe Cys
            100                 105                 110 aac aga aga cag aag gag aag aga atc aac                             366
Asn Arg Arg Gln Lys Glu Lys Arg Ile Asn
        115                 120

<210> SEQ ID NO 18
<211> LENGTH: 122
<212> TYPE: PRT
<213> ORGANISM: Artificial Sequence
<220> FEATURE:
<223> OTHER INFORMATION: Synthetic Construct

<400> SEQUENCE: 18

Met Glu Arg Pro Tyr Ala Cys Pro Val Glu Ser Cys Asp Arg Arg Phe
1               5                   10                  15

Ser Arg Ser Asp Glu Leu Thr Arg His Ile Arg Ile His Thr Gly Gln
            20                  25                  30

Lys Pro Phe Gln Cys Arg Ile Cys Met Arg Asn Phe Ser Arg Ser Asp
        35                  40                  45

His Leu Thr Thr His Ile Arg Thr His Thr Gly Gly Gly Arg Arg Arg
    50                  55                  60

Lys Lys Arg Thr Ser Ile Glu Thr Asn Ile Arg Val Ala Leu Glu Lys
65                  70                  75                  80

Ser Phe Leu Glu Asn Gln Lys Pro Thr Ser Glu Glu Ile Thr Met Ile
                85                  90                  95

Ala Asp Gln Leu Asn Met Glu Lys Glu Val Ile Arg Val Trp Phe Cys
            100                 105                 110

Asn Arg Arg Gln Lys Glu Lys Arg Ile Asn
        115                 120
```

<210> SEQ ID NO 19
<211> LENGTH: 387
<212> TYPE: DNA
<213> ORGANISM: Artificial Sequence
<220> FEATURE:
<223> OTHER INFORMATION: modified enzyme from SV40 and ZFHD
<220> FEATURE:
<221> NAME/KEY: CDS
<222> LOCATION: (1)..(387)

<400> SEQUENCE: 19

```
atg ccc aag aag aag aga aag gtg gag aga ccc tac gcc tgc ccc gtg     48
Met Pro Lys Lys Lys Arg Lys Val Glu Arg Pro Tyr Ala Cys Pro Val
1               5                   10                  15 gag agc tgc gac aga aga ttc agc aga agc gac gag ctg acc aga cac     96
Glu Ser Cys Asp Arg Arg Phe Ser Arg Ser Asp Glu Leu Thr Arg His
            20                  25                  30 atc aga atc cac acc ggc cag aag ccc ttc cag tgc aga atc tgc atg    144
Ile Arg Ile His Thr Gly Gln Lys Pro Phe Gln Cys Arg Ile Cys Met
        35                  40                  45 aga aac ttc agc aga agc gac cac ctg acc acc cac atc aga acc cac    192
Arg Asn Phe Ser Arg Ser Asp His Leu Thr Thr His Ile Arg Thr His
    50                  55                  60 aca ggc ggc ggc aga aga aga aag aag aga acc agc atc gag acc aac    240
Thr Gly Gly Gly Arg Arg Arg Lys Lys Arg Thr Ser Ile Glu Thr Asn
65                  70                  75                  80 atc aga gtg gcc ctg gag aaa agc ttc ctg gag aac cag aag ccc acc    288
Ile Arg Val Ala Leu Glu Lys Ser Phe Leu Glu Asn Gln Lys Pro Thr
                85                  90                  95 agc gag gag atc acc atg atc gcc gac cag ctg aac atg gag aag gag    336
Ser Glu Glu Ile Thr Met Ile Ala Asp Gln Leu Asn Met Glu Lys Glu
            100                 105                 110 gtg atc aga gtg tgg ttc tgc aac aga aga cag aag gag aag aga atc    384
Val Ile Arg Val Trp Phe Cys Asn Arg Arg Gln Lys Glu Lys Arg Ile
        115                 120                 125 aac                                                                387
Asn
```

<210> SEQ ID NO 20
<211> LENGTH: 129
<212> TYPE: PRT
<213> ORGANISM: Artificial Sequence
<220> FEATURE:
<223> OTHER INFORMATION: Synthetic Construct

<400> SEQUENCE: 20

```
Met Pro Lys Lys Lys Arg Lys Val Glu Arg Pro Tyr Ala Cys Pro Val
1               5                   10                  15

Glu Ser Cys Asp Arg Arg Phe Ser Arg Ser Asp Glu Leu Thr Arg His
            20                  25                  30

Ile Arg Ile His Thr Gly Gln Lys Pro Phe Gln Cys Arg Ile Cys Met
        35                  40                  45

Arg Asn Phe Ser Arg Ser Asp His Leu Thr Thr His Ile Arg Thr His
    50                  55                  60

Thr Gly Gly Gly Arg Arg Arg Lys Lys Arg Thr Ser Ile Glu Thr Asn
65                  70                  75                  80

Ile Arg Val Ala Leu Glu Lys Ser Phe Leu Glu Asn Gln Lys Pro Thr
                85                  90                  95

Ser Glu Glu Ile Thr Met Ile Ala Asp Gln Leu Asn Met Glu Lys Glu
            100                 105                 110
```

```
Val Ile Arg Val Trp Phe Cys Asn Arg Arg Gln Lys Glu Lys Arg Ile
            115                 120                 125

Asn

<210> SEQ ID NO 21
<211> LENGTH: 963
<212> TYPE: DNA
<213> ORGANISM: Artificial Sequence
<220> FEATURE:
<223> OTHER INFORMATION: modified enzyme from ZFHD and FokI
<220> FEATURE:
<221> NAME/KEY: CDS
<222> LOCATION: (1)..(963)

<400> SEQUENCE: 21 atg gag aga ccc tac gcc tgc ccc gtg gag agc tgc gac aga aga ttc       48
Met Glu Arg Pro Tyr Ala Cys Pro Val Glu Ser Cys Asp Arg Arg Phe
 1               5                  10                  15 agc aga agc gac gag ctg acc aga cac atc aga atc cac acc ggc cag       96
Ser Arg Ser Asp Glu Leu Thr Arg His Ile Arg Ile His Thr Gly Gln
             20                  25                  30 aag ccc ttc cag tgc aga atc tgc atg aga aac ttc agc aga agc gac      144
Lys Pro Phe Gln Cys Arg Ile Cys Met Arg Asn Phe Ser Arg Ser Asp
         35                  40                  45 cac ctg acc acc cac atc aga acc cac aca ggc ggc ggc aga aga aga      192
His Leu Thr Thr His Ile Arg Thr His Thr Gly Gly Gly Arg Arg Arg
     50                  55                  60 aag aag aga acc agc atc gag acc aac atc aga gtg gcc ctg gag aaa      240
Lys Lys Arg Thr Ser Ile Glu Thr Asn Ile Arg Val Ala Leu Glu Lys
 65                  70                  75                  80 agc ttc ctg gag aac cag aag ccc acc agc gag gag atc acc atg atc      288
Ser Phe Leu Glu Asn Gln Lys Pro Thr Ser Glu Glu Ile Thr Met Ile
                 85                  90                  95 gcc gac cag ctg aac atg gag aag gag gtg atc aga gtg tgg ttc tgc      336
Ala Asp Gln Leu Asn Met Glu Lys Glu Val Ile Arg Val Trp Phe Cys
            100                 105                 110 aac aga aga cag aag gag aag aga atc aac ggt acc aag cag ctg gtg      384
Asn Arg Arg Gln Lys Glu Lys Arg Ile Asn Gly Thr Lys Gln Leu Val
        115                 120                 125 aaa agc gag ctg gaa gag aag aag tcc gag ctg cgg cac aag ctg aaa      432
Lys Ser Glu Leu Glu Glu Lys Lys Ser Glu Leu Arg His Lys Leu Lys
    130                 135                 140 tac gtg ccc cac gag tac atc gag ctg atc gag atc gcc cgg aac ccc      480
Tyr Val Pro His Glu Tyr Ile Glu Leu Ile Glu Ile Ala Arg Asn Pro
145                 150                 155                 160 acc cag gac aga atc ctg gaa atg aag gtc atg gaa ttt ttc atg aag      528
Thr Gln Asp Arg Ile Leu Glu Met Lys Val Met Glu Phe Phe Met Lys
                165                 170                 175 gtg tac ggc tac cgg ggc gag cac ctg ggc ggc agc aga aaa ccc gac      576
Val Tyr Gly Tyr Arg Gly Glu His Leu Gly Gly Ser Arg Lys Pro Asp
            180                 185                 190 ggc gcc atc tac acc gtg ggc agc ccc atc gac tac ggc gtg atc gtg      624
Gly Ala Ile Tyr Thr Val Gly Ser Pro Ile Asp Tyr Gly Val Ile Val
        195                 200                 205 gac acc aag gcc tac agc ggc ggc tac aac ctg ccc atc gga cag gcc      672
Asp Thr Lys Ala Tyr Ser Gly Gly Tyr Asn Leu Pro Ile Gly Gln Ala
    210                 215                 220 gac gag atg cag aga tac gtg gaa gag aac cag acc cgg aac aag cac      720
Asp Glu Met Gln Arg Tyr Val Glu Glu Asn Gln Thr Arg Asn Lys His
225                 230                 235                 240 atc aac ccc aac gag tgg tgg aag gtg tac ccc agc agc gtg acc gag      768
Ile Asn Pro Asn Glu Trp Trp Lys Val Tyr Pro Ser Ser Val Thr Glu
```

```
Ile Asn Pro Asn Glu Trp Trp Lys Val Tyr Pro Ser Ser Val Thr Glu
                245                 250                 255 ttc aag ttc ctg ttc gtg tcc ggc cac ttc aag ggc aac tac aag gcc      816
Phe Lys Phe Leu Phe Val Ser Gly His Phe Lys Gly Asn Tyr Lys Ala
        260                 265                 270 cag ctg acc cgg ctg aac cac atc acc aac tgc aac ggc gct gtg ctg      864
Gln Leu Thr Arg Leu Asn His Ile Thr Asn Cys Asn Gly Ala Val Leu
            275                 280                 285 agc gtg gaa gaa ctg ctg atc ggc ggc gag atg atc aag gcc ggc acc      912
Ser Val Glu Glu Leu Leu Ile Gly Gly Glu Met Ile Lys Ala Gly Thr
290                 295                 300 ctg acc ctg gaa gaa gtg cgg cgg aag ttc aac aac ggc gag atc aac      960
Leu Thr Leu Glu Glu Val Arg Arg Lys Phe Asn Asn Gly Glu Ile Asn
305                 310                 315                 320 ttc                                                                  963
Phe

<210> SEQ ID NO 22
<211> LENGTH: 321
<212> TYPE: PRT
<213> ORGANISM: Artificial Sequence
<220> FEATURE:
<223> OTHER INFORMATION: Synthetic Construct

<400> SEQUENCE: 22

Met Glu Arg Pro Tyr Ala Cys Pro Val Glu Ser Cys Asp Arg Arg Phe
1               5                   10                  15

Ser Arg Ser Asp Glu Leu Thr Arg His Ile Arg Ile His Thr Gly Gln
            20                  25                  30

Lys Pro Phe Gln Cys Arg Ile Cys Met Arg Asn Phe Ser Arg Ser Asp
        35                  40                  45

His Leu Thr Thr His Ile Arg Thr His Thr Gly Gly Gly Arg Arg Arg
    50                  55                  60

Lys Lys Arg Thr Ser Ile Glu Thr Asn Ile Arg Val Ala Leu Glu Lys
65                  70                  75                  80

Ser Phe Leu Glu Asn Gln Lys Pro Thr Ser Glu Glu Ile Thr Met Ile
                85                  90                  95

Ala Asp Gln Leu Asn Met Glu Lys Glu Val Ile Arg Val Trp Phe Cys
            100                 105                 110

Asn Arg Arg Gln Lys Glu Lys Arg Ile Asn Gly Thr Lys Gln Leu Val
        115                 120                 125

Lys Ser Glu Leu Glu Glu Lys Ser Glu Leu Arg His Lys Leu Lys
    130                 135                 140

Tyr Val Pro His Glu Tyr Ile Glu Leu Ile Glu Ile Ala Arg Asn Pro
145                 150                 155                 160

Thr Gln Asp Arg Ile Leu Glu Met Lys Val Met Glu Phe Phe Met Lys
                165                 170                 175

Val Tyr Gly Tyr Arg Gly Glu His Leu Gly Gly Ser Arg Lys Pro Asp
            180                 185                 190

Gly Ala Ile Tyr Thr Val Gly Ser Pro Ile Asp Tyr Gly Val Ile Val
        195                 200                 205

Asp Thr Lys Ala Tyr Ser Gly Gly Tyr Asn Leu Pro Ile Gly Gln Ala
    210                 215                 220

Asp Glu Met Gln Arg Tyr Val Glu Glu Asn Gln Thr Arg Asn Lys His
225                 230                 235                 240

Ile Asn Pro Asn Glu Trp Trp Lys Val Tyr Pro Ser Ser Val Thr Glu
                245                 250                 255
```

```
Phe Lys Phe Leu Phe Val Ser Gly His Phe Lys Gly Asn Tyr Lys Ala
            260                 265                 270

Gln Leu Thr Arg Leu Asn His Ile Thr Asn Cys Asn Gly Ala Val Leu
        275                 280                 285

Ser Val Glu Glu Leu Leu Ile Gly Gly Glu Met Ile Lys Ala Gly Thr
290                 295                 300

Leu Thr Leu Glu Glu Val Arg Arg Lys Phe Asn Asn Gly Glu Ile Asn
305                 310                 315                 320

Phe

<210> SEQ ID NO 23
<211> LENGTH: 984
<212> TYPE: DNA
<213> ORGANISM: Artificial Sequence
<220> FEATURE:
<223> OTHER INFORMATION: modified enzyme from SV40, ZFHD and FokI
<220> FEATURE:
<221> NAME/KEY: CDS
<222> LOCATION: (1)..(984)

<400> SEQUENCE: 23 atg ccc aag aag aag aga aag gtg gag aga ccc tac gcc tgc ccc gtg      48
Met Pro Lys Lys Lys Arg Lys Val Glu Arg Pro Tyr Ala Cys Pro Val
1               5                   10                  15 gag agc tgc gac aga aga ttc agc aga agc gac gag ctg acc aga cac      96
Glu Ser Cys Asp Arg Arg Phe Ser Arg Ser Asp Glu Leu Thr Arg His
            20                  25                  30 atc aga atc cac acc ggc cag aag ccc ttc cag tgc aga atc tgc atg     144
Ile Arg Ile His Thr Gly Gln Lys Pro Phe Gln Cys Arg Ile Cys Met
        35                  40                  45 aga aac ttc agc aga agc gac cac ctg acc acc cac atc aga acc cac     192
Arg Asn Phe Ser Arg Ser Asp His Leu Thr Thr His Ile Arg Thr His
    50                  55                  60 aca ggc ggc gga aga aga aga aag aag aga acc agc atc gag acc aac     240
Thr Gly Gly Gly Arg Arg Arg Lys Lys Arg Thr Ser Ile Glu Thr Asn
65                  70                  75                  80 atc aga gtg gcc ctg gag aaa agc ttc ctg gag aac cag aag ccc acc     288
Ile Arg Val Ala Leu Glu Lys Ser Phe Leu Glu Asn Gln Lys Pro Thr
                85                  90                  95 agc gag gag atc acc atg atc gcc gac cag ctg aac atg gag aag gag     336
Ser Glu Glu Ile Thr Met Ile Ala Asp Gln Leu Asn Met Glu Lys Glu
            100                 105                 110 gtg atc aga gtg tgg ttc tgc aac aga aga cag aag gag aag aga atc     384
Val Ile Arg Val Trp Phe Cys Asn Arg Arg Gln Lys Glu Lys Arg Ile
        115                 120                 125 aac ggt acc aag cag ctg gtg aaa agc gag ctg gaa gag aag aag tcc     432
Asn Gly Thr Lys Gln Leu Val Lys Ser Glu Leu Glu Glu Lys Lys Ser
    130                 135                 140 gag ctg cgg cac aag ctg aaa tac gtg ccc cac gag tac atc gag ctg     480
Glu Leu Arg His Lys Leu Lys Tyr Val Pro His Glu Tyr Ile Glu Leu
145                 150                 155                 160 atc gag atc gcc cgg aac ccc acc cag gac aga atc ctg gaa atg aag     528
Ile Glu Ile Ala Arg Asn Pro Thr Gln Asp Arg Ile Leu Glu Met Lys
                165                 170                 175 gtc atg gaa ttt ttc atg aag gtg tac ggc tac cgg ggc gag cac ctg     576
Val Met Glu Phe Phe Met Lys Val Tyr Gly Tyr Arg Gly Glu His Leu
            180                 185                 190 ggc ggc agc aga aaa ccc gac ggc gcc atc tac acc gtg ggc agc ccc     624
Gly Gly Ser Arg Lys Pro Asp Gly Ala Ile Tyr Thr Val Gly Ser Pro
        195                 200                 205
```

```
atc gac tac ggc gtg atc gtg gac acc aag gcc tac agc ggc ggc tac      672
Ile Asp Tyr Gly Val Ile Val Asp Thr Lys Ala Tyr Ser Gly Gly Tyr
    210                 215                 220 aac ctg ccc atc gga cag gcc gac gag atg cag aga tac gtg gaa gag      720
Asn Leu Pro Ile Gly Gln Ala Asp Glu Met Gln Arg Tyr Val Glu Glu
225                 230                 235                 240 aac cag acc cgg aac aag cac atc aac ccc aac gag tgg tgg aag gtg      768
Asn Gln Thr Arg Asn Lys His Ile Asn Pro Asn Glu Trp Trp Lys Val
                245                 250                 255 tac ccc agc agc gtg acc gag ttc aag ttc ctg ttc gtg tcc ggc cac      816
Tyr Pro Ser Ser Val Thr Glu Phe Lys Phe Leu Phe Val Ser Gly His
                260                 265                 270 ttc aag ggc aac tac aag gcc cag ctg acc cgg ctg aac cac atc acc      864
Phe Lys Gly Asn Tyr Lys Ala Gln Leu Thr Arg Leu Asn His Ile Thr
        275                 280                 285 aac tgc aac ggc gct gtg ctg agc gtg gaa gaa ctg ctg atc ggc ggc      912
Asn Cys Asn Gly Ala Val Leu Ser Val Glu Glu Leu Leu Ile Gly Gly
    290                 295                 300 gag atg atc aag gcc ggc acc ctg acc ctg gaa gaa gtg cgg cgg aag      960
Glu Met Ile Lys Ala Gly Thr Leu Thr Leu Glu Glu Val Arg Arg Lys
305                 310                 315                 320 ttc aac aac ggc gag atc aac ttc                                      984
Phe Asn Asn Gly Glu Ile Asn Phe
                325

<210> SEQ ID NO 24
<211> LENGTH: 328
<212> TYPE: PRT
<213> ORGANISM: Artificial Sequence
<220> FEATURE:
<223> OTHER INFORMATION: Synthetic Construct

<400> SEQUENCE: 24

Met Pro Lys Lys Arg Lys Val Glu Arg Pro Tyr Ala Cys Pro Val
1               5                   10                  15

Glu Ser Cys Asp Arg Arg Phe Ser Arg Ser Asp Glu Leu Thr Arg His
                20                  25                  30

Ile Arg Ile His Thr Gly Gln Lys Pro Phe Gln Cys Arg Ile Cys Met
            35                  40                  45

Arg Asn Phe Ser Arg Ser Asp His Leu Thr Thr His Ile Arg Thr His
    50                  55                  60

Thr Gly Gly Gly Arg Arg Arg Lys Lys Arg Thr Ser Ile Glu Thr Asn
65                  70                  75                  80

Ile Arg Val Ala Leu Glu Lys Ser Phe Leu Glu Asn Gln Lys Pro Thr
                85                  90                  95

Ser Glu Glu Ile Thr Met Ile Ala Asp Gln Leu Asn Met Glu Lys Glu
                100                 105                 110

Val Ile Arg Val Trp Phe Cys Asn Arg Arg Gln Lys Glu Lys Arg Ile
            115                 120                 125

Asn Gly Thr Lys Gln Leu Val Lys Ser Glu Leu Glu Glu Lys Lys Ser
    130                 135                 140

Glu Leu Arg His Lys Leu Lys Tyr Val Pro His Glu Tyr Ile Glu Leu
145                 150                 155                 160

Ile Glu Ile Ala Arg Asn Pro Thr Gln Asp Arg Ile Leu Glu Met Lys
                165                 170                 175

Val Met Glu Phe Phe Met Lys Val Tyr Gly Tyr Arg Gly Glu His Leu
            180                 185                 190
```

```
Gly Gly Ser Arg Lys Pro Asp Gly Ala Ile Tyr Thr Val Gly Ser Pro
            195                 200                 205

Ile Asp Tyr Gly Val Ile Val Asp Thr Lys Ala Tyr Ser Gly Gly Tyr
    210                 215                 220

Asn Leu Pro Ile Gly Gln Ala Asp Glu Met Gln Arg Tyr Val Glu Glu
225                 230                 235                 240

Asn Gln Thr Arg Asn Lys His Ile Asn Pro Asn Glu Trp Trp Lys Val
                245                 250                 255

Tyr Pro Ser Ser Val Thr Glu Phe Lys Phe Leu Phe Val Ser Gly His
            260                 265                 270

Phe Lys Gly Asn Tyr Lys Ala Gln Leu Thr Arg Leu Asn His Ile Thr
    275                 280                 285

Asn Cys Asn Gly Ala Val Leu Ser Val Glu Glu Leu Leu Ile Gly Gly
    290                 295                 300

Glu Met Ile Lys Ala Gly Thr Leu Thr Leu Glu Glu Val Arg Arg Lys
305                 310                 315                 320

Phe Asn Asn Gly Glu Ile Asn Phe
                325

<210> SEQ ID NO 25
<211> LENGTH: 18
<212> TYPE: DNA
<213> ORGANISM: Homo sapiens

<400> SEQUENCE: 25
tagggataac agggtaat                                                      18

<210> SEQ ID NO 26
<211> LENGTH: 168
<212> TYPE: DNA
<213> ORGANISM: adeno-associated virus 2

<400> SEQUENCE: 26
ctgcgcgctc gctcgctcac tgaggccgcc cgggcaaagc ccgggcgtcg ggcgaccttt         60
ggtcgcccgg cctcagtgag cgagcgagcg cgcagagagg gagtggccaa ctccatcact       120 agggggttcct tgtagttaat gattaacccg ccatgctact tatctacg                   168

<210> SEQ ID NO 27
<211> LENGTH: 832
<212> TYPE: DNA
<213> ORGANISM: Unknown
<220> FEATURE:
<223> OTHER INFORMATION: cytomegalovirus

<400> SEQUENCE: 27
taggaagatc ttcaatattg gccattagcc atattattca ttggttatat agcataaatc         60
aatattggct attggccatt gcatacgttg tatctatatc ataatatgta catttatatt       120
ggctcatgtc caatatgacc gccatgttgg cattgattat tgactagtta ttaatagtaa       180
tcaattacgg ggtcattagt tcatagccca tatatggagt tccgcgttac ataacttacg       240
gtaaatggcc cgcctggctg accgcccaac gacccccgcc cattgacgtc aataatgacg       300
tatgttccca tagtaacgcc aatagggact ttccattgac gtcaatgggt ggagtattta       360
cggtaaactg cccacttggc agtacatcaa gtgtatcata tgccaagtcc gccccctatt       420
gacgtcaatg acggtaaatg gcccgcctgg cattatgccc agtacatgac cttacgggac       480
tttcctactt ggcagtacat ctacgtatta gtcatcgcta ttaccatggt gatgcggttt       540
```

```
tggcagtaca ccaatgggcg tggatagcgg tttgactcac ggggatttcc aagtctccac    600
cccattgacg tcaatgggag tttgttttgg caccaaaatc aacgggactt tccaaaatgt    660
cgtaataacc ccgccccgtt gacgcaaatg ggcggtaggc gtgtacggtg ggaggtctat    720
ataagcagag ctcgtttagt gaaccgtcag atcactagaa gctttattgc ggtagtttat    780
cacagttaaa ttgctaacgc agtcagtgct tctgacacaa cagtctcgaa ct            832

<210> SEQ ID NO 28
<211> LENGTH: 173
<212> TYPE: DNA
<213> ORGANISM: Unknown
<220> FEATURE:
<223> OTHER INFORMATION: cytomegalovirus

<400> SEQUENCE: 28
actcacgggg atttccaagt ctccacccca ttgacgtcaa tgggagtttg ttttggcacc     60
aaaatcaacg ggactttcca aaatgtcgta ataaccccgc cccgttgacg caaatgggcg    120
gtaggcgtgt acggtgggag gtctatataa gcagagctcg tttagtgaac cgt           173

<210> SEQ ID NO 29
<211> LENGTH: 900
<212> TYPE: DNA
<213> ORGANISM: Artificial Sequence
<220> FEATURE:
<223> OTHER INFORMATION: modified construct from c-Myc NLS, FRAP and
      Homo sapiens
<220> FEATURE:
<221> NAME/KEY: CDS
<222> LOCATION: (1)..(900)

<400> SEQUENCE: 29 atg gac tat cct gct gcc aag agg gtc aag ttg gac tct aga atc ctc      48
Met Asp Tyr Pro Ala Ala Lys Arg Val Lys Leu Asp Ser Arg Ile Leu
1               5                   10                  15 tgg cat gag atg tgg cat gaa ggc ctg gaa gag gca tct cgt ttg tac      96
Trp His Glu Met Trp His Glu Gly Leu Glu Glu Ala Ser Arg Leu Tyr
            20                  25                  30 ttt ggg gaa agg aac gtg aaa ggc atg ttt gag gtg ctg gag ccc ttg     144
Phe Gly Glu Arg Asn Val Lys Gly Met Phe Glu Val Leu Glu Pro Leu
        35                  40                  45 cat gct atg atg gaa cgg ggc ccc cag act ctg aag gaa aca tcc ttt     192
His Ala Met Met Glu Arg Gly Pro Gln Thr Leu Lys Glu Thr Ser Phe
    50                  55                  60 aat cag gcc tat ggt cga gat tta atg gag gcc caa gag tgg tgc agg     240
Asn Gln Ala Tyr Gly Arg Asp Leu Met Glu Ala Gln Glu Trp Cys Arg
65                  70                  75                  80 aag tac atg aaa tca ggg aat gtc aag gac ctc ctc caa gcc tgg gac     288
Lys Tyr Met Lys Ser Gly Asn Val Lys Asp Leu Leu Gln Ala Trp Asp
                85                  90                  95 ctc tat tat cat gtg ttc cga cga atc tca aag act aga gat gag ttt     336
Leu Tyr Tyr His Val Phe Arg Arg Ile Ser Lys Thr Arg Asp Glu Phe
            100                 105                 110 ccc acc atg gtg ttt cct tct ggg cag atc agc cag gcc tcg gcc ttg     384
Pro Thr Met Val Phe Pro Ser Gly Gln Ile Ser Gln Ala Ser Ala Leu
        115                 120                 125 gcc ccg gcc cct ccc caa gtc ctg ccc cag gct cca gcc cct gcc cct     432
Ala Pro Ala Pro Pro Gln Val Leu Pro Gln Ala Pro Ala Pro Ala Pro
    130                 135                 140 gct cca gcc atg gta tca gct ctg gcc cag gcc cca gcc cct gtc cca     480
Ala Pro Ala Met Val Ser Ala Leu Ala Gln Ala Pro Ala Pro Val Pro
145                 150                 155                 160
```

```
gtc cta gcc cca ggc cct cct cag gct gtg gcc cca cct gcc ccc aag       528
Val Leu Ala Pro Gly Pro Pro Gln Ala Val Ala Pro Pro Ala Pro Lys
            165                 170                 175 ccc acc cag gct ggg gaa gga acg ctg tca gag gcc ctg ctg cag ctg       576
Pro Thr Gln Ala Gly Glu Gly Thr Leu Ser Glu Ala Leu Leu Gln Leu
        180                 185                 190 cag ttt gat gat gaa gac ctg ggg gcc ttg ctt ggc aac agc aca gac       624
Gln Phe Asp Asp Glu Asp Leu Gly Ala Leu Leu Gly Asn Ser Thr Asp
    195                 200                 205 cca gct gtg ttc aca gac ctg gca tcc gtc gac aac tcc gag ttt cag       672
Pro Ala Val Phe Thr Asp Leu Ala Ser Val Asp Asn Ser Glu Phe Gln
210                 215                 220 cag ctg ctg aac cag ggc ata cct gtg gcc ccc cac aca act gag ccc       720
Gln Leu Leu Asn Gln Gly Ile Pro Val Ala Pro His Thr Thr Glu Pro
225                 230                 235                 240 atg ctg atg gag tac cct gag gct ata act cgc cta gtg aca ggg gcc       768
Met Leu Met Glu Tyr Pro Glu Ala Ile Thr Arg Leu Val Thr Gly Ala
            245                 250                 255 cag agg ccc ccc gac cca gct cct gct cca ctg ggg gcc ccg ggc ctc       816
Gln Arg Pro Pro Asp Pro Ala Pro Ala Pro Leu Gly Ala Pro Gly Leu
        260                 265                 270 ccc aat ggc ctc ctt tca gga gat gaa gac ttc tcc tcc att gcg gac       864
Pro Asn Gly Leu Leu Ser Gly Asp Glu Asp Phe Ser Ser Ile Ala Asp
    275                 280                 285 atg gac ttc tca gcc ctg ctg agt cag atc agc tcc                       900
Met Asp Phe Ser Ala Leu Leu Ser Gln Ile Ser Ser
290                 295                 300

<210> SEQ ID NO 30
<211> LENGTH: 300
<212> TYPE: PRT
<213> ORGANISM: Artificial Sequence
<220> FEATURE:
<223> OTHER INFORMATION: Synthetic Construct

<400> SEQUENCE: 30

Met Asp Tyr Pro Ala Ala Lys Arg Val Lys Leu Asp Ser Arg Ile Leu
1               5                   10                  15

Trp His Glu Met Trp His Glu Gly Leu Glu Glu Ala Ser Arg Leu Tyr
                20                  25                  30

Phe Gly Glu Arg Asn Val Lys Gly Met Phe Glu Val Leu Glu Pro Leu
            35                  40                  45

His Ala Met Met Glu Arg Gly Pro Gln Thr Leu Lys Glu Thr Ser Phe
        50                  55                  60

Asn Gln Ala Tyr Gly Arg Asp Leu Met Glu Ala Gln Glu Trp Cys Arg
65                  70                  75                  80

Lys Tyr Met Lys Ser Gly Asn Val Lys Asp Leu Leu Gln Ala Trp Asp
                85                  90                  95

Leu Tyr Tyr His Val Phe Arg Arg Ile Ser Lys Thr Arg Asp Glu Phe
            100                 105                 110

Pro Thr Met Val Phe Pro Ser Gly Gln Ile Ser Gln Ala Ser Ala Leu
        115                 120                 125

Ala Pro Ala Pro Pro Gln Val Leu Pro Gln Ala Pro Ala Pro Ala Pro
    130                 135                 140

Ala Pro Ala Met Val Ser Ala Leu Ala Gln Ala Pro Ala Pro Val Pro
145                 150                 155                 160

Val Leu Ala Pro Gly Pro Pro Gln Ala Val Ala Pro Pro Ala Pro Lys
                165                 170                 175
```

```
Pro Thr Gln Ala Gly Glu Gly Thr Leu Ser Glu Ala Leu Leu Gln Leu
                175                 180                 185                 190

Gln Phe Asp Asp Glu Asp Leu Gly Ala Leu Leu Gly Asn Ser Thr Asp
        195                 200                 205

Pro Ala Val Phe Thr Asp Leu Ala Ser Val Asp Asn Ser Glu Phe Gln
    210                 215                 220

Gln Leu Leu Asn Gln Gly Ile Pro Val Ala Pro His Thr Thr Glu Pro
225                 230                 235                 240

Met Leu Met Glu Tyr Pro Glu Ala Ile Thr Arg Leu Val Thr Gly Ala
                245                 250                 255

Gln Arg Pro Pro Asp Pro Ala Pro Ala Pro Leu Gly Ala Pro Gly Leu
        260                 265                 270

Pro Asn Gly Leu Leu Ser Gly Asp Glu Asp Phe Ser Ser Ile Ala Asp
    275                 280                 285

Met Asp Phe Ser Ala Leu Leu Ser Gln Ile Ser Ser
290                 295                 300

<210> SEQ ID NO 31
<211> LENGTH: 54
<212> TYPE: DNA
<213> ORGANISM: Artificial Sequence
<220> FEATURE:
<223> OTHER INFORMATION: modified construct from insect virus

<400> SEQUENCE: 31
gagggccgcg gaagcttact aacatgcggt gacgtcgagg agaacccggg ccct           54

<210> SEQ ID NO 32
<211> LENGTH: 145
<212> TYPE: DNA
<213> ORGANISM: Artificial Sequence
<220> FEATURE:
<223> OTHER INFORMATION: modified construct from zinc finger
      homeodomain and human IL-2 minimal promoter

<400> SEQUENCE: 32
aatgatgggc gctcgagtaa tgatgggcgg tcgactaatg atgggcgctc gagtaatgat      60
gggcgtctag ctaatgatgg gcgctcgagt aatgatgggc ggtcgactaa tgatgggcgc     120
tcgagtaatg atgggcgtct agaac                                          145

<210> SEQ ID NO 33
<211> LENGTH: 1029
<212> TYPE: DNA
<213> ORGANISM: Bacteriophage P1
<220> FEATURE:
<221> NAME/KEY: CDS
<222> LOCATION: (1)..(1029)

<400> SEQUENCE: 33 atg tcc aat tta ctg acc gta cac caa aat ttg cct gca tta ccg gtc       48
Met Ser Asn Leu Leu Thr Val His Gln Asn Leu Pro Ala Leu Pro Val
1               5                   10                  15 gat gca acg agt gat gag gtt cgc aag aac ctg atg gac atg ttc agg       96
Asp Ala Thr Ser Asp Glu Val Arg Lys Asn Leu Met Asp Met Phe Arg
            20                  25                  30 gat cgc cag gcg ttt tct gag cat acc tgg aaa atg ctt ctg tcc gtt      144
Asp Arg Gln Ala Phe Ser Glu His Thr Trp Lys Met Leu Leu Ser Val
        35                  40                  45 tgc cgg tcg tgg gcg gca tgg tgc aag ttg aat aac cgg aaa tgg ttt      192
Cys Arg Ser Trp Ala Ala Trp Cys Lys Leu Asn Asn Arg Lys Trp Phe
```

```
            50                  55                  60
ccc gca gaa cct gaa gat gtt cgc gat tat ctt cta tat ctt cag gcg      240
Pro Ala Glu Pro Glu Asp Val Arg Asp Tyr Leu Leu Tyr Leu Gln Ala
65                  70                  75                  80 cgc ggt ctg gca gta aaa act atc cag caa cat ttg ggc cag cta aac      288
Arg Gly Leu Ala Val Lys Thr Ile Gln Gln His Leu Gly Gln Leu Asn
                85                  90                  95 atg ctt cat cgt cgg tcc ggg ctg cca cga cca agt gac agc aat gct      336
Met Leu His Arg Arg Ser Gly Leu Pro Arg Pro Ser Asp Ser Asn Ala
            100                 105                 110 gtt tca ctg gtt atg cgg cgg atc cga aaa gaa aac gtt gat gcc ggt      384
Val Ser Leu Val Met Arg Arg Ile Arg Lys Glu Asn Val Asp Ala Gly
        115                 120                 125 gaa cgt gca aaa cag gct cta gcg ttc gaa cgc act gat ttc gac cag      432
Glu Arg Ala Lys Gln Ala Leu Ala Phe Glu Arg Thr Asp Phe Asp Gln
    130                 135                 140 gtt cgt tca ctc atg gaa aat agc gat cgc tgc cag gat ata cgt aat      480
Val Arg Ser Leu Met Glu Asn Ser Asp Arg Cys Gln Asp Ile Arg Asn
145                 150                 155                 160 ctg gca ttt ctg ggg att gct tat aac acc ctg tta cgt ata gcc gaa      528
Leu Ala Phe Leu Gly Ile Ala Tyr Asn Thr Leu Leu Arg Ile Ala Glu
                165                 170                 175 att gcc agg atc agg gtt aaa gat atc tca cgt act gac ggt ggg aga      576
Ile Ala Arg Ile Arg Val Lys Asp Ile Ser Arg Thr Asp Gly Gly Arg
            180                 185                 190 atg tta atc cat att ggc aga acg aaa acg ctg gtt agc acc gca ggt      624
Met Leu Ile His Ile Gly Arg Thr Lys Thr Leu Val Ser Thr Ala Gly
        195                 200                 205 gta gag aag gca ctt agc ctg ggg gta act aaa ctg gtc gag cga tgg      672
Val Glu Lys Ala Leu Ser Leu Gly Val Thr Lys Leu Val Glu Arg Trp
    210                 215                 220 att tcc gtc tct ggt gta gct gat gat ccg aat aac tac ctg ttt tgc      720
Ile Ser Val Ser Gly Val Ala Asp Asp Pro Asn Asn Tyr Leu Phe Cys
225                 230                 235                 240 cgg gtc aga aaa aat ggt gtt gcc gcg cca tct gcc acc agc cag cta      768
Arg Val Arg Lys Asn Gly Val Ala Ala Pro Ser Ala Thr Ser Gln Leu
                245                 250                 255 tca act cgc gcc ctg gaa ggg att ttt gaa gca act cat cga ttg att      816
Ser Thr Arg Ala Leu Glu Gly Ile Phe Glu Ala Thr His Arg Leu Ile
            260                 265                 270 tac ggc gct aag gat gac tct ggt cag aga tac ctg gcc tgg tct gga      864
Tyr Gly Ala Lys Asp Asp Ser Gly Gln Arg Tyr Leu Ala Trp Ser Gly
        275                 280                 285 cac agt gcc cgt gtc gga gcc gcg cga gat atg gcc cgc gct gga gtt      912
His Ser Ala Arg Val Gly Ala Ala Arg Asp Met Ala Arg Ala Gly Val
    290                 295                 300 tca ata ccg gag atc atg caa gct ggt ggc tgg acc aat gta aat att      960
Ser Ile Pro Glu Ile Met Gln Ala Gly Gly Trp Thr Asn Val Asn Ile
305                 310                 315                 320 gtc atg aac tat atc cgt aac ctg gat agt gaa aca ggg gca atg gtg     1008
Val Met Asn Tyr Ile Arg Asn Leu Asp Ser Glu Thr Gly Ala Met Val
                325                 330                 335 cgc ctg ctg gaa gat ggc gat                                         1029
Arg Leu Leu Glu Asp Gly Asp
            340

<210> SEQ ID NO 34
<211> LENGTH: 343
<212> TYPE: PRT
<213> ORGANISM: Bacteriophage P1
```

<400> SEQUENCE: 34

| | | | | | | | | | | | | | | | |
|---|---|---|---|---|---|---|---|---|---|---|---|---|---|---|---|
| Met | Ser | Asn | Leu | Leu | Thr | Val | His | Gln | Asn | Leu | Pro | Ala | Leu | Pro | Val |
| 1 | | | | 5 | | | | | 10 | | | | | 15 | |
| Asp | Ala | Thr | Ser | Asp | Glu | Val | Arg | Lys | Asn | Leu | Met | Asp | Met | Phe | Arg |
| | | | 20 | | | | | 25 | | | | | 30 | | |
| Asp | Arg | Gln | Ala | Phe | Ser | Glu | His | Thr | Trp | Lys | Met | Leu | Leu | Ser | Val |
| | | | 35 | | | | | 40 | | | | | 45 | | |
| Cys | Arg | Ser | Trp | Ala | Ala | Trp | Cys | Lys | Leu | Asn | Asn | Arg | Lys | Trp | Phe |
| | 50 | | | | | 55 | | | | | 60 | | | | |
| Pro | Ala | Glu | Pro | Glu | Asp | Val | Arg | Asp | Tyr | Leu | Leu | Tyr | Leu | Gln | Ala |
| 65 | | | | | 70 | | | | | 75 | | | | | 80 |
| Arg | Gly | Leu | Ala | Val | Lys | Thr | Ile | Gln | Gln | His | Leu | Gly | Gln | Leu | Asn |
| | | | | 85 | | | | | 90 | | | | | 95 | |
| Met | Leu | His | Arg | Arg | Ser | Gly | Leu | Pro | Arg | Pro | Ser | Asp | Ser | Asn | Ala |
| | | | 100 | | | | | 105 | | | | | 110 | | |
| Val | Ser | Leu | Val | Met | Arg | Arg | Ile | Arg | Lys | Glu | Asn | Val | Asp | Ala | Gly |
| | | | 115 | | | | | 120 | | | | | 125 | | |
| Glu | Arg | Ala | Lys | Gln | Ala | Leu | Ala | Phe | Glu | Arg | Thr | Asp | Phe | Asp | Gln |
| | 130 | | | | | 135 | | | | | 140 | | | | |
| Val | Arg | Ser | Leu | Met | Glu | Asn | Ser | Asp | Arg | Cys | Gln | Asp | Ile | Arg | Asn |
| 145 | | | | | 150 | | | | | 155 | | | | | 160 |
| Leu | Ala | Phe | Leu | Gly | Ile | Ala | Tyr | Asn | Thr | Leu | Leu | Arg | Ile | Ala | Glu |
| | | | | 165 | | | | | 170 | | | | | 175 | |
| Ile | Ala | Arg | Ile | Arg | Val | Lys | Asp | Ile | Ser | Arg | Thr | Asp | Gly | Gly | Arg |
| | | | 180 | | | | | 185 | | | | | 190 | | |
| Met | Leu | Ile | His | Ile | Gly | Arg | Thr | Lys | Thr | Leu | Val | Ser | Thr | Ala | Gly |
| | | | 195 | | | | | 200 | | | | | 205 | | |
| Val | Glu | Lys | Ala | Leu | Ser | Leu | Gly | Val | Thr | Lys | Leu | Val | Glu | Arg | Trp |
| | 210 | | | | | 215 | | | | | 220 | | | | |
| Ile | Ser | Val | Ser | Gly | Val | Ala | Asp | Asp | Pro | Asn | Asn | Tyr | Leu | Phe | Cys |
| 225 | | | | | 230 | | | | | 235 | | | | | 240 |
| Arg | Val | Arg | Lys | Asn | Gly | Val | Ala | Ala | Pro | Ser | Ala | Thr | Ser | Gln | Leu |
| | | | | 245 | | | | | 250 | | | | | 255 | |
| Ser | Thr | Arg | Ala | Leu | Glu | Gly | Ile | Phe | Glu | Ala | Thr | His | Arg | Leu | Ile |
| | | | 260 | | | | | 265 | | | | | 270 | | |
| Tyr | Gly | Ala | Lys | Asp | Asp | Ser | Gly | Gln | Arg | Tyr | Leu | Ala | Trp | Ser | Gly |
| | | | 275 | | | | | 280 | | | | | 285 | | |
| His | Ser | Ala | Arg | Val | Gly | Ala | Ala | Arg | Asp | Met | Ala | Arg | Ala | Gly | Val |
| | 290 | | | | | 295 | | | | | 300 | | | | |
| Ser | Ile | Pro | Glu | Ile | Met | Gln | Ala | Gly | Gly | Trp | Thr | Asn | Val | Asn | Ile |
| 305 | | | | | 310 | | | | | 315 | | | | | 320 |
| Val | Met | Asn | Tyr | Ile | Arg | Asn | Leu | Asp | Ser | Glu | Thr | Gly | Ala | Met | Val |
| | | | | 325 | | | | | 330 | | | | | 335 | |
| Arg | Leu | Leu | Glu | Asp | Gly | Asp | | | | | | | | | |
| | | | | 340 | | | | | | | | | | | |

```
<210> SEQ ID NO 35
<211> LENGTH: 705
<212> TYPE: DNA
<213> ORGANISM: Unknown
<220> FEATURE:
<223> OTHER INFORMATION: yeast endonuclease
<220> FEATURE:
<221> NAME/KEY: CDS
<222> LOCATION: (1)..(705)
```

<400> SEQUENCE: 35

```
atg aag aac att aag aaa aat cag gtc atc aac ctg ggg ccc att tcc      48
Met Lys Asn Ile Lys Lys Asn Gln Val Ile Asn Leu Gly Pro Ile Ser
1               5                   10                  15 aag ctg ctg aaa gag tac aag tct cag ctg atc gaa ctg aat att gag      96
Lys Leu Leu Lys Glu Tyr Lys Ser Gln Leu Ile Glu Leu Asn Ile Glu
            20                  25                  30 cag ttt gaa gca ggg atc ggc ctg att ctg ggc gac gcc tac atc agg     144
Gln Phe Glu Ala Gly Ile Gly Leu Ile Leu Gly Asp Ala Tyr Ile Arg
        35                  40                  45 agc aga gat gag gga aag acc tat tgc atg cag ttc gaa tgg aag aac     192
Ser Arg Asp Glu Gly Lys Thr Tyr Cys Met Gln Phe Glu Trp Lys Asn
    50                  55                  60 aaa gct tac atg gac cac gtg tgc ctg ctg tat gat cag tgg gtc ctg     240
Lys Ala Tyr Met Asp His Val Cys Leu Leu Tyr Asp Gln Trp Val Leu
65                  70                  75                  80 tct ccc cct cac aag aaa gag cgg gtg aat cat ctg gga aac ctg gtc     288
Ser Pro Pro His Lys Lys Glu Arg Val Asn His Leu Gly Asn Leu Val
                85                  90                  95 att act tgg ggg gca cag acc ttc aag cat cag gcc ttc aac aag ctg     336
Ile Thr Trp Gly Ala Gln Thr Phe Lys His Gln Ala Phe Asn Lys Leu
            100                 105                 110 gct aac ctg ttt att gtg aac aat aag aag ctg atc cct aac aat ctg     384
Ala Asn Leu Phe Ile Val Asn Asn Lys Lys Leu Ile Pro Asn Asn Leu
        115                 120                 125 gtc gaa aac tac ctg aca cca atg agt ctg gcc tat tgg ttc atg gac     432
Val Glu Asn Tyr Leu Thr Pro Met Ser Leu Ala Tyr Trp Phe Met Asp
    130                 135                 140 gat ggc gga aaa tgg gac tac aac aag aac agc ctg aac aag agc atc     480
Asp Gly Gly Lys Trp Asp Tyr Asn Lys Asn Ser Leu Asn Lys Ser Ile
145                 150                 155                 160 gtg ctg aac acc cag tcc ttc aca ttt gag gaa gtc gag tat ctg ctg     528
Val Leu Asn Thr Gln Ser Phe Thr Phe Glu Glu Val Glu Tyr Leu Leu
                165                 170                 175 aag gga ctg agg aac aag ttc cag ctg aac tgc tac gtg aag att aac     576
Lys Gly Leu Arg Asn Lys Phe Gln Leu Asn Cys Tyr Val Lys Ile Asn
            180                 185                 190 aag aac aag ccc atc atc tac atc gat tct atg agt tac ctg atc ttt     624
Lys Asn Lys Pro Ile Ile Tyr Ile Asp Ser Met Ser Tyr Leu Ile Phe
        195                 200                 205 tat aat ctg att aag cca tac ctg atc ccc cag atg atg tat aaa ctg     672
Tyr Asn Leu Ile Lys Pro Tyr Leu Ile Pro Gln Met Met Tyr Lys Leu
    210                 215                 220 cct aac aca atc agc tcc gag act ttc ctg aag                         705
Pro Asn Thr Ile Ser Ser Glu Thr Phe Leu Lys
225                 230                 235
```

<210> SEQ ID NO 36
<211> LENGTH: 235
<212> TYPE: PRT
<213> ORGANISM: Unknown
<220> FEATURE:
<223> OTHER INFORMATION: Synthetic Construct

<400> SEQUENCE: 36

```
Met Lys Asn Ile Lys Lys Asn Gln Val Ile Asn Leu Gly Pro Ile Ser
1               5                   10                  15

Lys Leu Leu Lys Glu Tyr Lys Ser Gln Leu Ile Glu Leu Asn Ile Glu
            20                  25                  30
```

```
Gln Phe Glu Ala Gly Ile Gly Leu Ile Leu Gly Asp Ala Tyr Ile Arg
         35                  40                  45

Ser Arg Asp Glu Gly Lys Thr Tyr Cys Met Gln Phe Glu Trp Lys Asn
 50                  55                  60

Lys Ala Tyr Met Asp His Val Cys Leu Leu Tyr Asp Gln Trp Val Leu
 65                  70                  75                  80

Ser Pro Pro His Lys Lys Glu Arg Val Asn His Leu Gly Asn Leu Val
                 85                  90                  95

Ile Thr Trp Gly Ala Gln Thr Phe Lys His Gln Ala Phe Asn Lys Leu
                100                 105                 110

Ala Asn Leu Phe Ile Val Asn Asn Lys Lys Leu Ile Pro Asn Asn Leu
            115                 120                 125

Val Glu Asn Tyr Leu Thr Pro Met Ser Leu Ala Tyr Trp Phe Met Asp
        130                 135                 140

Asp Gly Gly Lys Trp Asp Tyr Asn Lys Asn Ser Leu Asn Lys Ser Ile
145                 150                 155                 160

Val Leu Asn Thr Gln Ser Phe Thr Phe Glu Val Glu Tyr Leu Leu
                165                 170                 175

Lys Gly Leu Arg Asn Lys Phe Gln Leu Asn Cys Tyr Val Lys Ile Asn
            180                 185                 190

Lys Asn Lys Pro Ile Ile Tyr Ile Asp Ser Met Ser Tyr Leu Ile Phe
        195                 200                 205

Tyr Asn Leu Ile Lys Pro Tyr Leu Ile Pro Gln Met Met Tyr Lys Leu
    210                 215                 220

Pro Asn Thr Ile Ser Ser Glu Thr Phe Leu Lys
225                 230                 235

<210> SEQ ID NO 37
<211> LENGTH: 221
<212> TYPE: DNA
<213> ORGANISM: Homo sapiens

<400> SEQUENCE: 37
cgggtggcat ccctgtgacc cctccccagt gcctctcctg gccctggaag ttgccactcc      60
agtgcccacc agccttgtcc taataaaatt aagttgcatc attttgtctg actaggtgtc     120
cttctataat attatggggt ggagggggggt ggtatggagc aaggggcaag ttgggaagac    180
aacctgtagg gcctgcgggg tctattcggg aaccaagctg g                         221

<210> SEQ ID NO 38
<211> LENGTH: 491
<212> TYPE: DNA
<213> ORGANISM: Unknown
<220> FEATURE:
<223> OTHER INFORMATION: encephalomyocarditis virus

<400> SEQUENCE: 38
attttccacc atattgccgt cttttggcaa tgtgagggcc cggaaacctg gccctgtctt      60
cttgacgagc attcctaggg gtctttcccc tctcgccaaa ggaatgcaag gtctgttgaa     120
tgtcgtgaag gaagcagttc ctctggaagc ttcttgaaga caaacaacgt ctgtagcgac     180
cctttgcagg cagcggaacc ccccacctgg cgacaggtgc ctctgcggcc aaaagccacg     240
tgtataagat acacctgcaa aggcggcaca accccagtgc cacgttgtga gttggatagt     300
tgtggaaaga gtcaaatggc tctcctcaag cgtattcaac aagggctga aggatgccca      360 gaaggtaccc cattgtatgg gatctgatct ggggcctcgg tgcacatgct ttacatgtgt     420
```

```
ttagtcgagg ttaaaaaacg tctaggcccc ccgaaccacg gggacgtggt tttcctttga      480
aaaacacgat c                                                          491
```

```
<210> SEQ ID NO 39
<211> LENGTH: 34
<212> TYPE: DNA
<213> ORGANISM: Bacteriophage P1

<400> SEQUENCE: 39
ataacttcgt atagcataca ttatacgaag ttat                                 34

<210> SEQ ID NO 40
<211> LENGTH: 1650
<212> TYPE: DNA
<213> ORGANISM: Unknown
<220> FEATURE:
<223> OTHER INFORMATION: wild-type native firefly luciferase
<220> FEATURE:
<221> NAME/KEY: CDS
<222> LOCATION: (1)..(1650)

<400> SEQUENCE: 40
```

```
atg gaa gat gcc aaa aac att aag aag ggc cca gcg cca ttc tac cca      48
Met Glu Asp Ala Lys Asn Ile Lys Lys Gly Pro Ala Pro Phe Tyr Pro
1               5                   10                  15 ctc gaa gac ggg acc gcc ggc gag cag ctg cac aaa gcc atg aag cgc      96
Leu Glu Asp Gly Thr Ala Gly Glu Gln Leu His Lys Ala Met Lys Arg
            20                  25                  30 tac gcc ctg gtg ccc ggc acc atc gcc ttt acc gac gca cat atc gag      144
Tyr Ala Leu Val Pro Gly Thr Ile Ala Phe Thr Asp Ala His Ile Glu
        35                  40                  45 gtg gac att acc tac gcc gag tac ttc gag atg agc gtt cgg ctg gca      192
Val Asp Ile Thr Tyr Ala Glu Tyr Phe Glu Met Ser Val Arg Leu Ala
    50                  55                  60 gaa gct atg aag cgc tat ggg ctg aat aca aac cat cgg atc gtg gtg      240
Glu Ala Met Lys Arg Tyr Gly Leu Asn Thr Asn His Arg Ile Val Val
65                  70                  75                  80 tgc agc gag aat agc ttg cag ttc ttc atg ccc gtg ttg ggt gcc ctg      288
Cys Ser Glu Asn Ser Leu Gln Phe Phe Met Pro Val Leu Gly Ala Leu
                85                  90                  95 ttc atc ggt gtg gct gtg gcc cca gct aac gac atc tac aac gag cgc      336
Phe Ile Gly Val Ala Val Ala Pro Ala Asn Asp Ile Tyr Asn Glu Arg
            100                 105                 110 gag ctg ctg aac agc atg ggc atc agc cag ccc acc gtc gta ttc gtg      384
Glu Leu Leu Asn Ser Met Gly Ile Ser Gln Pro Thr Val Val Phe Val
        115                 120                 125 agc aag aaa ggg ctg caa aag atc ctc aac gtg caa aag aag cta ccg      432
Ser Lys Lys Gly Leu Gln Lys Ile Leu Asn Val Gln Lys Lys Leu Pro
    130                 135                 140 atc ata caa aag atc atc atc atg gat agc aag acc gac tac cag ggc      480
Ile Ile Gln Lys Ile Ile Ile Met Asp Ser Lys Thr Asp Tyr Gln Gly
145                 150                 155                 160 ttc caa agc atg tac acc ttc gtg act tcc cat ttg cca ccc ggc ttc      528
Phe Gln Ser Met Tyr Thr Phe Val Thr Ser His Leu Pro Pro Gly Phe
                165                 170                 175 aac gag tac gac ttc gtg ccc gag agc ttc gac cgg gac aaa acc atc      576
Asn Glu Tyr Asp Phe Val Pro Glu Ser Phe Asp Arg Asp Lys Thr Ile
            180                 185                 190 gcc ctg atc atg aac agt agt ggc agt acc gga ttg ccc aag ggc gta      624
Ala Leu Ile Met Asn Ser Ser Gly Ser Thr Gly Leu Pro Lys Gly Val
        195                 200                 205
```

| | | |
|---|---|---|
| gcc cta ccg cac cgc acc gct tgt gtc cga ttc agt cat gcc cgc gac<br>Ala Leu Pro His Arg Thr Ala Cys Val Arg Phe Ser His Ala Arg Asp<br>210                             215                          220 | 672 |
| ccc atc ttc ggc aac cag atc atc ccc gac acc gct atc ctc agc gtg<br>Pro Ile Phe Gly Asn Gln Ile Ile Pro Asp Thr Ala Ile Leu Ser Val<br>225                             230                         235                240 | 720 |
| gtg cca ttt cac cac ggc ttc ggc atg ttc acc acg ctg ggc tac ttg<br>Val Pro Phe His His Gly Phe Gly Met Phe Thr Thr Leu Gly Tyr Leu<br>                       245                         250                        255 | 768 |
| atc tgc ggc ttt cgg gtc gtg ctc atg tac cgc ttc gag gag gag cta<br>Ile Cys Gly Phe Arg Val Val Leu Met Tyr Arg Phe Glu Glu Glu Leu<br>            260                         265                         270 | 816 |
| ttc ttg cgc agc ttg caa gac tat aag att caa tct gcc ctg ctg gtg<br>Phe Leu Arg Ser Leu Gln Asp Tyr Lys Ile Gln Ser Ala Leu Leu Val<br>         275                       280                        285 | 864 |
| ccc aca cta ttt agc ttc ttc gct aag agc act ctc atc gac aag tac<br>Pro Thr Leu Phe Ser Phe Phe Ala Lys Ser Thr Leu Ile Asp Lys Tyr<br>290                            295                         300 | 912 |
| gac cta agc aac ttg cac gag atc gcc agc ggc ggg gcg ccg ctc agc<br>Asp Leu Ser Asn Leu His Glu Ile Ala Ser Gly Gly Ala Pro Leu Ser<br>305                             310                         315                320 | 960 |
| aag gag gta ggt gag gcc gtg gcc aaa cgc ttc cac cta cca ggc atc<br>Lys Glu Val Gly Glu Ala Val Ala Lys Arg Phe His Leu Pro Gly Ile<br>                       325                         330                         335 | 1008 |
| cgc cag ggc tac ggc ctg aca gaa aca acc agc gcc att ctg atc acc<br>Arg Gln Gly Tyr Gly Leu Thr Glu Thr Thr Ser Ala Ile Leu Ile Thr<br>                   340                        345                         350 | 1056 |
| ccc gaa ggg gac gac aag cct ggc gca gta ggc aag gtg gtg ccc ttc<br>Pro Glu Gly Asp Asp Lys Pro Gly Ala Val Gly Lys Val Val Pro Phe<br>                 355                         360                         365 | 1104 |
| ttc gag gct aag gtg gtg gac ttg gac acc ggt aag aca ctg ggt gtg<br>Phe Glu Ala Lys Val Val Asp Leu Asp Thr Gly Lys Thr Leu Gly Val<br>370                             375                         380 | 1152 |
| aac cag cgc ggc gag ctg tgc gtc cgt ggc ccc atg atc atg agc ggc<br>Asn Gln Arg Gly Glu Leu Cys Val Arg Gly Pro Met Ile Met Ser Gly<br>385                             390                         395                400 | 1200 |
| tac gtt aac aac ccc gag gct aca aac gct ctc atc gac aag gac ggc<br>Tyr Val Asn Asn Pro Glu Ala Thr Asn Ala Leu Ile Asp Lys Asp Gly<br>                       405                         410                         415 | 1248 |
| tgg ctg cac agc ggc gac atc gcc tac tgg gac gag gac gag cac ttc<br>Trp Leu His Ser Gly Asp Ile Ala Tyr Trp Asp Glu Asp Glu His Phe<br>                 420                         425                         430 | 1296 |
| ttc atc gtg gac cgg ctg aag agc ctg atc aaa tac aag ggc tac cag<br>Phe Ile Val Asp Arg Leu Lys Ser Leu Ile Lys Tyr Lys Gly Tyr Gln<br>             435                         440                         445 | 1344 |
| gta gcc cca gcc gaa ctg gag agc atc ctg ctg caa cac ccc aac atc<br>Val Ala Pro Ala Glu Leu Glu Ser Ile Leu Leu Gln His Pro Asn Ile<br>450                             455                         460 | 1392 |
| ttc gac gcc ggg gtc gcc ggc ctg ccc gac gac gat gcc ggc gag ctg<br>Phe Asp Ala Gly Val Ala Gly Leu Pro Asp Asp Asp Ala Gly Glu Leu<br>465                             470                         475                480 | 1440 |
| tcc gcc gca gtc gtc gtg ctg gaa cac ggt aaa acc atg acc gag aag<br>Ser Ala Ala Val Val Val Leu Glu His Gly Lys Thr Met Thr Glu Lys<br>                       485                         490                         495 | 1488 |
| gag atc gtg gac tat gtg gcc agc cag gtt aca acc gcc aag aag ctg<br>Glu Ile Val Asp Tyr Val Ala Ser Gln Val Thr Thr Ala Lys Lys Leu<br>                          500                         505                         510 | 1536 |
| cgc ggt ggt gtt gtg ttc gtg gac gag gtg cct aaa gga ctg acc ggc<br>Arg Gly Gly Val Val Phe Val Asp Glu Val Pro Lys Gly Leu Thr Gly<br>             515                         520                         525 | 1584 |

```
aag ttg gac gcc cgc aag atc cgc gag att ctc att aag gcc aag aag    1632
Lys Leu Asp Ala Arg Lys Ile Arg Glu Ile Leu Ile Lys Ala Lys Lys
    530                 535                 540 ggc ggc aag atc gcc gtg                                            1650
Gly Gly Lys Ile Ala Val
545                 550

<210> SEQ ID NO 41
<211> LENGTH: 550
<212> TYPE: PRT
<213> ORGANISM: Unknown
<220> FEATURE:
<223> OTHER INFORMATION: Synthetic Construct

<400> SEQUENCE: 41

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320
```

-continued

```
Lys Glu Val Gly Glu Ala Val Ala Lys Arg Phe His Leu Pro Gly Ile
            325                 330                 335
Arg Gln Gly Tyr Gly Leu Thr Glu Thr Thr Ser Ala Ile Leu Ile Thr
        340                 345                 350
Pro Glu Gly Asp Asp Lys Pro Gly Ala Val Gly Lys Val Val Pro Phe
    355                 360                 365
Phe Glu Ala Lys Val Val Asp Leu Asp Thr Gly Lys Thr Leu Gly Val
370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
Trp Leu His Ser Gly Asp Ile Ala Tyr Trp Asp Glu Asp Glu His Phe
            420                 425                 430
Phe Ile Val Asp Arg Leu Lys Ser Leu Ile Lys Tyr Lys Gly Tyr Gln
        435                 440                 445
Val Ala Pro Ala Glu Leu Glu Ser Ile Leu Leu Gln His Pro Asn Ile
    450                 455                 460
Phe Asp Ala Gly Val Ala Gly Leu Pro Asp Asp Asp Ala Gly Glu Leu
465                 470                 475                 480
Ser Ala Ala Val Val Val Leu Glu His Gly Lys Thr Met Thr Glu Lys
                485                 490                 495
Glu Ile Val Asp Tyr Val Ala Ser Gln Val Thr Thr Ala Lys Lys Leu
            500                 505                 510
Arg Gly Gly Val Val Phe Val Asp Glu Val Pro Lys Gly Leu Thr Gly
        515                 520                 525
Lys Leu Asp Ala Arg Lys Ile Arg Glu Ile Leu Ile Lys Ala Lys Lys
    530                 535                 540
Gly Gly Lys Ile Ala Val
545                 550

<210> SEQ ID NO 42
<211> LENGTH: 239
<212> TYPE: DNA
<213> ORGANISM: Simian virus 40

<400> SEQUENCE: 42
ggccgcttcg agcagacatg ataagataca ttgatgagtt tggacaaacc acaactagaa    60
tgcagtgaaa aaaatgcttt atttgtgaaa tttgtgatgc tattgcttta tttgtaacca   120
ttataagctg caataaacaa gttaacaaca acaattgcat tcattttatg tttcaggttc   180
agggggagat gtgggaggtt ttttaaagca agtaaaacct ctacaaatgt ggtaaaatc    239

<210> SEQ ID NO 43
<211> LENGTH: 1650
<212> TYPE: DNA
<213> ORGANISM: Artificial Sequence
<220> FEATURE:
<223> OTHER INFORMATION: firefly luciferase
<220> FEATURE:
<221> NAME/KEY: CDS
<222> LOCATION: (1)..(1650)

<400> SEQUENCE: 43 atg gag gac gcc aag aac atc aag aag ggc ccc gcc ccc ttc tac ccc     48
Met Glu Asp Ala Lys Asn Ile Lys Lys Gly Pro Ala Pro Phe Tyr Pro
1               5                   10                  15 ctg gag gac ggc acc gcc gga gag cag ctg cac aag gcc atg aag aga    96
```

```
Leu Glu Asp Gly Thr Ala Gly Glu Gln Leu His Lys Ala Met Lys Arg
            20                  25                  30 tac gcc ctg gtg ccc ggc acc atc gcc ttc acc gac gcc cac atc gag      144
Tyr Ala Leu Val Pro Gly Thr Ile Ala Phe Thr Asp Ala His Ile Glu
        35                  40                  45 gtg gac atc acc tac gcc gag tac ttc gag atg agc gtg aga ctg gcc      192
Val Asp Ile Thr Tyr Ala Glu Tyr Phe Glu Met Ser Val Arg Leu Ala
50                  55                  60 gag gcc atg aag aga tac ggc ctg aac acc aac cac aga atc gtg gtg      240
Glu Ala Met Lys Arg Tyr Gly Leu Asn Thr Asn His Arg Ile Val Val
65                  70                  75                  80 tgc agc gag aac agc ctg cag ttc ttc atg ccc gtg ctg gga gcc ctg      288
Cys Ser Glu Asn Ser Leu Gln Phe Phe Met Pro Val Leu Gly Ala Leu
                85                  90                  95 ttc atc ggc gtg gcc gtg gcc ccc gcc aac gac atc tac aac gag aga      336
Phe Ile Gly Val Ala Val Ala Pro Ala Asn Asp Ile Tyr Asn Glu Arg
            100                 105                 110 gag ctg ctg aac agc atg ggc atc agc cag ccc acc gtg gtg ttc gtg      384
Glu Leu Leu Asn Ser Met Gly Ile Ser Gln Pro Thr Val Val Phe Val
        115                 120                 125 agc aag aag ggc ctg cag aag atc ctg aac gtg cag aag aag ctg ccc      432
Ser Lys Lys Gly Leu Gln Lys Ile Leu Asn Val Gln Lys Lys Leu Pro
130                 135                 140 atc atc cag aag atc atc atc atg gac agc aag acc gac tac cag ggc      480
Ile Ile Gln Lys Ile Ile Ile Met Asp Ser Lys Thr Asp Tyr Gln Gly
145                 150                 155                 160 ttc cag agc atg tat acc ttc gtg acc agc cac ctg ccc ccc ggc ttc      528
Phe Gln Ser Met Tyr Thr Phe Val Thr Ser His Leu Pro Pro Gly Phe
                165                 170                 175 aac gag tac gac ttc gtg ccc gag agc ttc gac aga gac aag acc atc      576
Asn Glu Tyr Asp Phe Val Pro Glu Ser Phe Asp Arg Asp Lys Thr Ile
            180                 185                 190 gcc ctg atc atg aac agc agc ggc agc acc ggc ctg ccc aag ggc gtg      624
Ala Leu Ile Met Asn Ser Ser Gly Ser Thr Gly Leu Pro Lys Gly Val
        195                 200                 205 gcc ctg ccc cac aga acc gcc tgc gtg aga ttc agc cac gcc aga gac      672
Ala Leu Pro His Arg Thr Ala Cys Val Arg Phe Ser His Ala Arg Asp
210                 215                 220 ccc atc ttc ggc aac cag atc atc ccc gac acc gcc atc ctg agc gtg      720
Pro Ile Phe Gly Asn Gln Ile Ile Pro Asp Thr Ala Ile Leu Ser Val
225                 230                 235                 240 gtg ccc ttc cac cac ggc ttc ggc atg ttc acc acc ctg ggc tac ctg      768
Val Pro Phe His His Gly Phe Gly Met Phe Thr Thr Leu Gly Tyr Leu
                245                 250                 255 atc tgc ggc ttc aga gtg gtg ctg atg tat aga ttc gag gag gag ctg      816
Ile Cys Gly Phe Arg Val Val Leu Met Tyr Arg Phe Glu Glu Glu Leu
            260                 265                 270 ttc ctg aga agc ctg cag gac tac aag atc cag agc gcc ctg ctg gtg      864
Phe Leu Arg Ser Leu Gln Asp Tyr Lys Ile Gln Ser Ala Leu Leu Val
        275                 280                 285 ccc acc ctg ttc agc ttc ttc gcc aag agc acc ctg atc gac aag tac      912
Pro Thr Leu Phe Ser Phe Phe Ala Lys Ser Thr Leu Ile Asp Lys Tyr
290                 295                 300 gac ctg agc aac ctg cac gag atc gcc agc ggc gga gcc ccc ctg agc      960
Asp Leu Ser Asn Leu His Glu Ile Ala Ser Gly Gly Ala Pro Leu Ser
305                 310                 315                 320 aag gag gtg ggc gag gcc gtg gcc aag aga ttc cac ctg ccc ggc atc     1008
Lys Glu Val Gly Glu Ala Val Ala Lys Arg Phe His Leu Pro Gly Ile
                325                 330                 335
```

| | | |
|---|---|---|
| aga cag ggc tac ggc ctg acc gag acc acc agc gcc atc ctg atc acc<br>Arg Gln Gly Tyr Gly Leu Thr Glu Thr Thr Ser Ala Ile Leu Ile Thr<br>340 345 350 | | 1056 |
| ccc gag ggc gac gac aag ccc gga gcc gtg ggc aag gtg gtg ccc ttc<br>Pro Glu Gly Asp Asp Lys Pro Gly Ala Val Gly Lys Val Val Pro Phe<br>355 360 365 | | 1104 |
| ttc gag gcc aag gtg gtg gac ctg gac acc ggc aag acc ctg ggc gtg<br>Phe Glu Ala Lys Val Val Asp Leu Asp Thr Gly Lys Thr Leu Gly Val<br>370 375 380 | | 1152 |
| aac cag aga ggc gag ctg tgc gtg aga ggc ccc atg att atg tcc ggc<br>Asn Gln Arg Gly Glu Leu Cys Val Arg Gly Pro Met Ile Met Ser Gly<br>385 390 395 400 | | 1200 |
| tac gtg aac aac ccc gag gcc acc aac gcc ctg atc gac aag gac ggc<br>Tyr Val Asn Asn Pro Glu Ala Thr Asn Ala Leu Ile Asp Lys Asp Gly<br>405 410 415 | | 1248 |
| tgg ctg cac agc ggc gac atc gcc tac tgg gac gag gac gag cac ttc<br>Trp Leu His Ser Gly Asp Ile Ala Tyr Trp Asp Glu Asp Glu His Phe<br>420 425 430 | | 1296 |
| ttc atc gtg gac aga ctg aag agc ctg atc aag tac aag ggc tac cag<br>Phe Ile Val Asp Arg Leu Lys Ser Leu Ile Lys Tyr Lys Gly Tyr Gln<br>435 440 445 | | 1344 |
| gtg gcc ccc gcc gag ctg gag agc atc ctg ctg cag cac ccc aac atc<br>Val Ala Pro Ala Glu Leu Glu Ser Ile Leu Leu Gln His Pro Asn Ile<br>450 455 460 | | 1392 |
| ttc gac gcc gga gtg gcc gga ctg ccc gac gac gac gcc gga gag ctg<br>Phe Asp Ala Gly Val Ala Gly Leu Pro Asp Asp Asp Ala Gly Glu Leu<br>465 470 475 480 | | 1440 |
| ccc gcc gcc gtg gtg gtg ctg gag cac ggc aag acc atg acc gag aag<br>Pro Ala Ala Val Val Val Leu Glu His Gly Lys Thr Met Thr Glu Lys<br>485 490 495 | | 1488 |
| gag atc gtg gac tac gtg gcc agc cag gtg aca acc gcc aag aag ctg<br>Glu Ile Val Asp Tyr Val Ala Ser Gln Val Thr Thr Ala Lys Lys Leu<br>500 505 510 | | 1536 |
| aga ggc ggc gtg gtg ttc gtg gac gag gtg ccc aag ggc ctg acc ggc<br>Arg Gly Gly Val Val Phe Val Asp Glu Val Pro Lys Gly Leu Thr Gly<br>515 520 525 | | 1584 |
| aag ctg gac gcc aga aag atc aga gag atc ctg atc aag gcc aag aag<br>Lys Leu Asp Ala Arg Lys Ile Arg Glu Ile Leu Ile Lys Ala Lys Lys<br>530 535 540 | | 1632 |
| ggc ggc aag atc gcc gtg<br>Gly Gly Lys Ile Ala Val<br>545 550 | | 1650 |

<210> SEQ ID NO 44
<211> LENGTH: 550
<212> TYPE: PRT
<213> ORGANISM: Artificial Sequence
<220> FEATURE:
<223> OTHER INFORMATION: Synthetic Construct

<400> SEQUENCE: 44

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val

```
                65                  70                  75                  80
Cys Ser Glu Asn Ser Leu Gln Phe Phe Met Pro Val Leu Gly Ala Leu
                    85                  90                  95
Phe Ile Gly Val Ala Val Ala Pro Ala Asn Asp Ile Tyr Asn Glu Arg
                100                 105                 110
Glu Leu Leu Asn Ser Met Gly Ile Ser Gln Pro Thr Val Val Phe Val
                115                 120                 125
Ser Lys Lys Gly Leu Gln Lys Ile Leu Asn Val Gln Lys Lys Leu Pro
            130                 135                 140
Ile Ile Gln Lys Ile Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                    165                 170                 175
Asn Glu Tyr Asp Phe Val Pro Glu Ser Phe Asp Arg Asp Lys Thr Ile
                180                 185                 190
Ala Leu Ile Met Asn Ser Ser Gly Ser Thr Gly Leu Pro Lys Gly Val
                195                 200                 205
Ala Leu Pro His Arg Thr Ala Cys Val Arg Phe Ser His Ala Arg Asp
                210                 215                 220
Pro Ile Phe Gly Asn Gln Ile Ile Pro Asp Thr Ala Ile Leu Ser Val
225                 230                 235                 240
Val Pro Phe His His Gly Phe Gly Met Phe Thr Thr Leu Gly Tyr Leu
                    245                 250                 255
Ile Cys Gly Phe Arg Val Val Leu Met Tyr Arg Phe Glu Glu Glu Leu
                260                 265                 270
Phe Leu Arg Ser Leu Gln Asp Tyr Lys Ile Gln Ser Ala Leu Leu Val
                275                 280                 285
Pro Thr Leu Phe Ser Phe Phe Ala Lys Ser Thr Leu Ile Asp Lys Tyr
            290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                    325                 330                 335
Arg Gln Gly Tyr Gly Leu Thr Glu Thr Thr Ser Ala Ile Leu Ile Thr
                340                 345                 350
Pro Glu Gly Asp Asp Lys Pro Gly Ala Val Gly Lys Val Val Pro Phe
                355                 360                 365
Phe Glu Ala Lys Val Val Asp Leu Asp Thr Gly Lys Thr Leu Gly Val
            370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                    405                 410                 415
Trp Leu His Ser Gly Asp Ile Ala Tyr Trp Asp Glu Asp Glu His Phe
                420                 425                 430
Phe Ile Val Asp Arg Leu Lys Ser Leu Ile Lys Tyr Lys Gly Tyr Gln
                435                 440                 445
Val Ala Pro Ala Glu Leu Glu Ser Ile Leu Leu Gln His Pro Asn Ile
            450                 455                 460
Phe Asp Ala Gly Val Ala Gly Leu Pro Asp Asp Asp Ala Gly Glu Leu
465                 470                 475                 480
Pro Ala Ala Val Val Val Leu Glu His Gly Lys Thr Met Thr Glu Lys
                    485                 490                 495
```

```
Glu Ile Val Asp Tyr Val Ala Ser Gln Val Thr Thr Ala Lys Lys Leu
            500                 505                 510
Arg Gly Gly Val Val Phe Val Asp Glu Val Pro Lys Gly Leu Thr Gly
        515                 520                 525
Lys Leu Asp Ala Arg Lys Ile Arg Glu Ile Leu Ile Lys Ala Lys Lys
    530                 535                 540
Gly Gly Lys Ile Ala Val
545             550

<210> SEQ ID NO 45
<211> LENGTH: 411
<212> TYPE: DNA
<213> ORGANISM: Artificial Sequence
<220> FEATURE:
<223> OTHER INFORMATION: modified construct from c-Myc NLS, zinc finger
      homeodomain and FKBP
<220> FEATURE:
<221> NAME/KEY: CDS
<222> LOCATION: (1)..(411)

<400> SEQUENCE: 45 atg gac tat cct gct gcc aag agg gtc aag ttg gac tct aga gaa cgc    48
Met Asp Tyr Pro Ala Ala Lys Arg Val Lys Leu Asp Ser Arg Glu Arg
1               5                   10                  15 cca tat gct tgc cct gtc gag tcc tgc gat cgc cgc ttt tct cgc tcg    96
Pro Tyr Ala Cys Pro Val Glu Ser Cys Asp Arg Arg Phe Ser Arg Ser
                20                  25                  30 gat gag ctt acc cgc cat atc cgc atc cac aca ggc cag aag ccc ttc   144
Asp Glu Leu Thr Arg His Ile Arg Ile His Thr Gly Gln Lys Pro Phe
            35                  40                  45 cag tgt cga atc tgc atg cgt aac ttc agt cgt agt gac cac ctt acc   192
Gln Cys Arg Ile Cys Met Arg Asn Phe Ser Arg Ser Asp His Leu Thr
        50                  55                  60 acc cac atc cgc acc cac aca ggc ggc ggc cgc agg agg aag aaa cgc   240
Thr His Ile Arg Thr His Thr Gly Gly Gly Arg Arg Arg Lys Lys Arg
65                  70                  75                  80 acc agc ata gag acc aac atc cgt gtg gcc tta gag aag agt ttc ttg   288
Thr Ser Ile Glu Thr Asn Ile Arg Val Ala Leu Glu Lys Ser Phe Leu
                85                  90                  95 gag aat caa aag cct acc tcg gaa gag atc act atg att gct gat cag   336
Glu Asn Gln Lys Pro Thr Ser Glu Glu Ile Thr Met Ile Ala Asp Gln
                100                 105                 110 ctc aat atg gaa aaa gag gtg att cgt gtt tgg ttc tgt aac cgc cgc   384
Leu Asn Met Glu Lys Glu Val Ile Arg Val Trp Phe Cys Asn Arg Arg
            115                 120                 125 cag aaa gaa aaa aga atc aac act aga                               411
Gln Lys Glu Lys Arg Ile Asn Thr Arg
        130                 135

<210> SEQ ID NO 46
<211> LENGTH: 137
<212> TYPE: PRT
<213> ORGANISM: Artificial Sequence
<220> FEATURE:
<223> OTHER INFORMATION: Synthetic Construct

<400> SEQUENCE: 46

Met Asp Tyr Pro Ala Ala Lys Arg Val Lys Leu Asp Ser Arg Glu Arg
1               5                   10                  15

Pro Tyr Ala Cys Pro Val Glu Ser Cys Asp Arg Arg Phe Ser Arg Ser
                20                  25                  30
```

```
Asp Glu Leu Thr Arg His Ile Arg Ile His Thr Gly Gln Lys Pro Phe
         35                  40                  45

Gln Cys Arg Ile Cys Met Arg Asn Phe Ser Arg Ser Asp His Leu Thr
     50                  55                  60

Thr His Ile Arg Thr His Thr Gly Gly Gly Arg Arg Arg Lys Lys Arg
 65                  70                  75                  80

Thr Ser Ile Glu Thr Asn Ile Arg Val Ala Leu Glu Lys Ser Phe Leu
                 85                  90                  95

Glu Asn Gln Lys Pro Thr Ser Glu Glu Ile Thr Met Ile Ala Asp Gln
             100                 105                 110

Leu Asn Met Glu Lys Glu Val Ile Arg Val Trp Phe Cys Asn Arg Arg
         115                 120                 125

Gln Lys Glu Lys Arg Ile Asn Thr Arg
     130                 135

<210> SEQ ID NO 47
<211> LENGTH: 897
<212> TYPE: DNA
<213> ORGANISM: Artificial Sequence
<220> FEATURE:
<223> OTHER INFORMATION: modified construct from SV40 and FRAP
<220> FEATURE:
<221> NAME/KEY: CDS
<222> LOCATION: (1)..(897)

<400> SEQUENCE: 47 atg ccc aag aag aag aga aag gtg atc ctg tgg cac gag atg tgg cac      48
Met Pro Lys Lys Lys Arg Lys Val Ile Leu Trp His Glu Met Trp His
 1               5                  10                  15 gag ggc ctg gag gag gcc agc aga ctg tac ttc ggc gag aga aac gtg      96
Glu Gly Leu Glu Glu Ala Ser Arg Leu Tyr Phe Gly Glu Arg Asn Val
             20                  25                  30 aag ggc atg ttc gag gtg ctg gag ccc ctg cac gcc atg atg gag aga     144
Lys Gly Met Phe Glu Val Leu Glu Pro Leu His Ala Met Met Glu Arg
         35                  40                  45 ggc ccc cag acc ctg aag gag acc agc ttc aac cag gct tac ggc aga     192
Gly Pro Gln Thr Leu Lys Glu Thr Ser Phe Asn Gln Ala Tyr Gly Arg
     50                  55                  60 gac ctg atg gag gcc cag gag tgg tgc aga aag tac atg aag tcc ggc     240
Asp Leu Met Glu Ala Gln Glu Trp Cys Arg Lys Tyr Met Lys Ser Gly
 65                  70                  75                  80 aac gtg aag gac ctg ctg cag gct tgg gac ctg tac tac cac gtg ttc     288
Asn Val Lys Asp Leu Leu Gln Ala Trp Asp Leu Tyr Tyr His Val Phe
                 85                  90                  95 aga aga atc agc aag cag ctg ccc cag ctg act agt gac gag ttc ccc     336
Arg Arg Ile Ser Lys Gln Leu Pro Gln Leu Thr Ser Asp Glu Phe Pro
            100                 105                 110 acc atg gtg ttc ccc agc ggc cag atc agc cag gcc agc gcc ctg gcc     384
Thr Met Val Phe Pro Ser Gly Gln Ile Ser Gln Ala Ser Ala Leu Ala
        115                 120                 125 ccc gcc ccc ccc cag gtg ctg ccc cag gcc ccc gcc ccc gcc ccc gcc     432
Pro Ala Pro Pro Gln Val Leu Pro Gln Ala Pro Ala Pro Ala Pro Ala
    130                 135                 140 ccc gcc atg gtg agc gcc ctg gcc cag gcc ccc gcc ccc gtg ccc gtg     480
Pro Ala Met Val Ser Ala Leu Ala Gln Ala Pro Ala Pro Val Pro Val
145                 150                 155                 160 ctg gcc ccc ggc ccc ccc cag gcc gtg gcc ccc ccc gcc ccc aag ccc     528
Leu Ala Pro Gly Pro Pro Gln Ala Val Ala Pro Pro Ala Pro Lys Pro
                165                 170                 175 acc cag gcc gga gag ggc acc ctg agc gag gcc ctg ctg cag ctg cag     576
Thr Gln Ala Gly Glu Gly Thr Leu Ser Glu Ala Leu Leu Gln Leu Gln
```

```
Thr Gln Ala Gly Glu Gly Thr Leu Ser Glu Ala Leu Leu Gln Leu Gln
                180                 185                 190 ttc gac gac gag gac ctg gga gcc ctg ctg ggc aac agc acc gac ccc      624
Phe Asp Asp Glu Asp Leu Gly Ala Leu Leu Gly Asn Ser Thr Asp Pro
            195                 200                 205 gcc gtg ttc acc gac ctg gcc agc gtg gac aac agc gag ttc cag cag      672
Ala Val Phe Thr Asp Leu Ala Ser Val Asp Asn Ser Glu Phe Gln Gln
210                 215                 220 ctg ctg aac cag ggc atc ccc gtg gcc ccc cac acc acc gag ccc atg      720
Leu Leu Asn Gln Gly Ile Pro Val Ala Pro His Thr Thr Glu Pro Met
225                 230                 235                 240 ctg atg gag tac ccc gag gcc atc acc aga ctg gtc aca gga gcc cag      768
Leu Met Glu Tyr Pro Glu Ala Ile Thr Arg Leu Val Thr Gly Ala Gln
                245                 250                 255 aga ccc ccc gac ccc gcc ccc gcc ccc ctg gga gcc ccc ggc ctg ccc      816
Arg Pro Pro Asp Pro Ala Pro Ala Pro Leu Gly Ala Pro Gly Leu Pro
            260                 265                 270 aac ggc ctg ctc agc ggc gac gag gac ttc agc agc atc gcc gac atg      864
Asn Gly Leu Leu Ser Gly Asp Glu Asp Phe Ser Ser Ile Ala Asp Met
        275                 280                 285 gac ttc agc gcc ctg ctg agc cag atc agc agc                          897
Asp Phe Ser Ala Leu Leu Ser Gln Ile Ser Ser
290                 295

<210> SEQ ID NO 48
<211> LENGTH: 299
<212> TYPE: PRT
<213> ORGANISM: Artificial Sequence
<220> FEATURE:
<223> OTHER INFORMATION: Synthetic Construct

<400> SEQUENCE: 48

Met Pro Lys Lys Lys Arg Lys Val Ile Leu Trp His Glu Met Trp His
1               5                   10                  15

Glu Gly Leu Glu Glu Ala Ser Arg Leu Tyr Phe Gly Glu Arg Asn Val
            20                  25                  30

Lys Gly Met Phe Glu Val Leu Glu Pro Leu His Ala Met Met Glu Arg
        35                  40                  45

Gly Pro Gln Thr Leu Lys Glu Thr Ser Phe Asn Gln Ala Tyr Gly Arg
    50                  55                  60

Asp Leu Met Glu Ala Gln Glu Trp Cys Arg Lys Tyr Met Lys Ser Gly
65                  70                  75                  80

Asn Val Lys Asp Leu Leu Gln Ala Trp Asp Leu Tyr Tyr His Val Phe
                85                  90                  95

Arg Arg Ile Ser Lys Gln Leu Pro Gln Leu Thr Ser Asp Glu Phe Pro
            100                 105                 110

Thr Met Val Phe Pro Ser Gly Gln Ile Ser Gln Ala Ser Ala Leu Ala
        115                 120                 125

Pro Ala Pro Pro Gln Val Leu Pro Gln Ala Pro Ala Pro Ala Pro Ala
    130                 135                 140

Pro Ala Met Val Ser Ala Leu Ala Gln Ala Pro Ala Pro Val Pro Val
145                 150                 155                 160

Leu Ala Pro Gly Pro Pro Gln Ala Val Ala Pro Pro Ala Pro Lys Pro
                165                 170                 175

Thr Gln Ala Gly Glu Gly Thr Leu Ser Glu Ala Leu Leu Gln Leu Gln
            180                 185                 190

Phe Asp Asp Glu Asp Leu Gly Ala Leu Leu Gly Asn Ser Thr Asp Pro
        195                 200                 205
```

```
Ala Val Phe Thr Asp Leu Ala Ser Val Asp Asn Ser Glu Phe Gln Gln
    210                 215                 220

Leu Leu Asn Gln Gly Ile Pro Val Ala Pro His Thr Thr Glu Pro Met
225                 230                 235                 240

Leu Met Glu Tyr Pro Glu Ala Ile Thr Arg Leu Val Thr Gly Ala Gln
                245                 250                 255

Arg Pro Asp Pro Ala Pro Ala Pro Leu Gly Ala Pro Gly Leu Pro
            260                 265                 270

Asn Gly Leu Leu Ser Gly Asp Glu Asp Phe Ser Ser Ile Ala Asp Met
        275                 280                 285

Asp Phe Ser Ala Leu Leu Ser Gln Ile Ser Ser
        290                 295

<210> SEQ ID NO 49
<211> LENGTH: 366
<212> TYPE: DNA
<213> ORGANISM: Artificial Sequence
<220> FEATURE:
<223> OTHER INFORMATION: modified construct from ZFHD
<220> FEATURE:
<221> NAME/KEY: CDS
<222> LOCATION: (1)..(366)

<400> SEQUENCE: 49 atg gag aga ccc tac gcc tgc ccc gtg gag agc tgc gac aga aga ttc    48
Met Glu Arg Pro Tyr Ala Cys Pro Val Glu Ser Cys Asp Arg Arg Phe
1               5                   10                  15 agc aga agc gac gag ctg acc aga cac atc aga atc cac acc ggc cag    96
Ser Arg Ser Asp Glu Leu Thr Arg His Ile Arg Ile His Thr Gly Gln
            20                  25                  30 aag ccc ttc cag tgc aga atc tgc atg aga aac ttc agc aga agc gac   144
Lys Pro Phe Gln Cys Arg Ile Cys Met Arg Asn Phe Ser Arg Ser Asp
        35                  40                  45 cac ctg acc acc cac atc aga acc cac aca ggc ggc ggc aga aga aga   192
His Leu Thr Thr His Ile Arg Thr His Thr Gly Gly Gly Arg Arg Arg
    50                  55                  60 aag aag aga acc agc atc gag acc aac atc aga gtg gcc ctg gag aaa   240
Lys Lys Arg Thr Ser Ile Glu Thr Asn Ile Arg Val Ala Leu Glu Lys
65                  70                  75                  80 agc ttc ctg gag aac cag aag ccc acc agc gag gag atc acc atg atc   288
Ser Phe Leu Glu Asn Gln Lys Pro Thr Ser Glu Glu Ile Thr Met Ile
                85                  90                  95 gcc gac cag ctg aac atg gag aag gag gtg atc aga gtg tgg ttc tgc   336
Ala Asp Gln Leu Asn Met Glu Lys Glu Val Ile Arg Val Trp Phe Cys
            100                 105                 110 aac aga aga cag aag gag aag aga atc aac                           366
Asn Arg Arg Gln Lys Glu Lys Arg Ile Asn
        115                 120

<210> SEQ ID NO 50
<211> LENGTH: 122
<212> TYPE: PRT
<213> ORGANISM: Artificial Sequence
<220> FEATURE:
<223> OTHER INFORMATION: Synthetic Construct

<400> SEQUENCE: 50

Met Glu Arg Pro Tyr Ala Cys Pro Val Glu Ser Cys Asp Arg Arg Phe
1               5                   10                  15

Ser Arg Ser Asp Glu Leu Thr Arg His Ile Arg Ile His Thr Gly Gln
            20                  25                  30
```

```
Lys Pro Phe Gln Cys Arg Ile Cys Met Arg Asn Phe Ser Arg Ser Asp
            35                  40                  45

His Leu Thr Thr His Ile Arg Thr His Thr Gly Gly Gly Arg Arg Arg
     50                  55                  60

Lys Lys Arg Thr Ser Ile Glu Thr Asn Ile Arg Val Ala Leu Glu Lys
 65                  70                  75                  80

Ser Phe Leu Glu Asn Gln Lys Pro Thr Ser Glu Glu Ile Thr Met Ile
                 85                  90                  95

Ala Asp Gln Leu Asn Met Glu Lys Glu Val Ile Arg Val Trp Phe Cys
            100                 105                 110

Asn Arg Arg Gln Lys Glu Lys Arg Ile Asn
            115                 120
```

<210> SEQ ID NO 51
<211> LENGTH: 387
<212> TYPE: DNA
<213> ORGANISM: Artificial Sequence
<220> FEATURE:
<223> OTHER INFORMATION: modified construct from SV40 and ZFHD
<220> FEATURE:
<221> NAME/KEY: CDS
<222> LOCATION: (1)..(387)

<400> SEQUENCE: 51

```
atg ccc aag aag aag aga aag gtg gag aga ccc tac gcc tgc ccc gtg      48
Met Pro Lys Lys Lys Arg Lys Val Glu Arg Pro Tyr Ala Cys Pro Val
 1               5                  10                  15 gag agc tgc gac aga aga ttc agc aga agc gac gag ctg acc aga cac      96
Glu Ser Cys Asp Arg Arg Phe Ser Arg Ser Asp Glu Leu Thr Arg His
                20                  25                  30 atc aga atc cac acc ggc cag aag ccc ttc cag tgc aga atc tgc atg     144
Ile Arg Ile His Thr Gly Gln Lys Pro Phe Gln Cys Arg Ile Cys Met
            35                  40                  45 aga aac ttc agc aga agc gac cac ctg acc acc cac atc aga acc cac     192
Arg Asn Phe Ser Arg Ser Asp His Leu Thr Thr His Ile Arg Thr His
         50                  55                  60 aca ggc ggc aga aga aga aag aag aga acc agc atc gag acc aac         240
Thr Gly Gly Arg Arg Arg Lys Lys Arg Thr Ser Ile Glu Thr Asn
 65                  70                  75                  80 atc aga gtg gcc ctg gag aaa agc ttc ctg gag aac cag aag ccc acc     288
Ile Arg Val Ala Leu Glu Lys Ser Phe Leu Glu Asn Gln Lys Pro Thr
                85                  90                  95 agc gag gag atc acc atg atc gcc gac cag ctg aac atg gag aag gag     336
Ser Glu Glu Ile Thr Met Ile Ala Asp Gln Leu Asn Met Glu Lys Glu
            100                 105                 110 gtg atc aga gtg tgg ttc tgc aac aga aga cag aag gag aag aga atc     384
Val Ile Arg Val Trp Phe Cys Asn Arg Arg Gln Lys Glu Lys Arg Ile
        115                 120                 125 aac                                                                 387
Asn
```

<210> SEQ ID NO 52
<211> LENGTH: 129
<212> TYPE: PRT
<213> ORGANISM: Artificial Sequence
<220> FEATURE:
<223> OTHER INFORMATION: Synthetic Construct

<400> SEQUENCE: 52

```
Met Pro Lys Lys Lys Arg Lys Val Glu Arg Pro Tyr Ala Cys Pro Val
 1               5                  10                  15
```

```
Glu Ser Cys Asp Arg Arg Phe Ser Arg Ser Asp Glu Leu Thr Arg His
            20                  25                  30

Ile Arg Ile His Thr Gly Gln Lys Pro Phe Gln Cys Arg Ile Cys Met
        35                  40                  45

Arg Asn Phe Ser Arg Ser Asp His Leu Thr Thr His Ile Arg Thr His
    50                  55                  60

Thr Gly Gly Gly Arg Arg Lys Lys Arg Thr Ser Ile Glu Thr Asn
65                  70                  75                  80

Ile Arg Val Ala Leu Glu Lys Ser Phe Leu Glu Asn Gln Lys Pro Thr
                85                  90                  95

Ser Glu Glu Ile Thr Met Ile Ala Asp Gln Leu Asn Met Glu Lys Glu
            100                 105                 110

Val Ile Arg Val Trp Phe Cys Asn Arg Arg Gln Lys Glu Lys Arg Ile
        115                 120                 125

Asn

<210> SEQ ID NO 53
<211> LENGTH: 324
<212> TYPE: DNA
<213> ORGANISM: Unknown
<220> FEATURE:
<223> OTHER INFORMATION: wild type FKBP
<220> FEATURE:
<221> NAME/KEY: CDS
<222> LOCATION: (1)..(324)

<400> SEQUENCE: 53 atg gga gtg cag gtg gaa acc atc tcc cca gga gac ggg cgc acc ttc      48
Met Gly Val Gln Val Glu Thr Ile Ser Pro Gly Asp Gly Arg Thr Phe
1               5                   10                  15 ccc aag cgc ggc cag acc tgc gtg gtg cac tac acc ggg atg ctt gaa      96
Pro Lys Arg Gly Gln Thr Cys Val Val His Tyr Thr Gly Met Leu Glu
            20                  25                  30 gat gga aag aaa ttt gat tcc tcc cgg gac aga aac aag ccc ttt aag     144
Asp Gly Lys Lys Phe Asp Ser Ser Arg Asp Arg Asn Lys Pro Phe Lys
        35                  40                  45 ttt atg cta ggc aag cag gag gtg atc cga ggc tgg gaa gaa ggg gtt     192
Phe Met Leu Gly Lys Gln Glu Val Ile Arg Gly Trp Glu Glu Gly Val
    50                  55                  60 gcc cag atg agt gtg ggt cag aga gcc aaa ctg act ata tct cca gat     240
Ala Gln Met Ser Val Gly Gln Arg Ala Lys Leu Thr Ile Ser Pro Asp
65                  70                  75                  80 tat gcc tat ggt gcc act ggg cac cca ggc atc atc cca cca cat gcc     288
Tyr Ala Tyr Gly Ala Thr Gly His Pro Gly Ile Ile Pro Pro His Ala
                85                  90                  95 act ctc gtc ttc gat gtg gag ctt cta aaa ctg gaa                     324
Thr Leu Val Phe Asp Val Glu Leu Leu Lys Leu Glu
            100                 105

<210> SEQ ID NO 54
<211> LENGTH: 108
<212> TYPE: PRT
<213> ORGANISM: Unknown
<220> FEATURE:
<223> OTHER INFORMATION: Synthetic Construct

<400> SEQUENCE: 54

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
```

```
                    20                  25                  30
Asp Gly Lys Lys Phe Asp Ser Ser Arg Asp Arg Asn Lys Pro Phe Lys
                35                  40                  45

Phe Met Leu Gly Lys Gln Glu Val Ile Arg Gly Trp Glu Glu Gly Val
            50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu
                100                 105

<210> SEQ ID NO 55
<211> LENGTH: 321
<212> TYPE: DNA
<213> ORGANISM: Artificial Sequence
<220> FEATURE:
<223> OTHER INFORMATION: modified construct from FKBP

<400> SEQUENCE: 55
ggcgtgcagg tggagaccat cagccccggc gacggcagaa ccttccccaa gagaggccag      60
acctgcgtgt gcactacac  cggaatgctg gaggacggca agaagttcga cagcagcaga     120
gacagaaaca agcccttcaa gttcatgctg ggcaagcagg aggtgatcag aggctgggag     180
gagggcgtgg cccagatgag cgtgggccag agagccaagc tgaccatcag ccccgactac     240
gcctacggag ccaccggcca ccccggcatc atccccccc  acgccaccct ggtgttcgac     300
gtggagctgc tgaagctgga g                                                321

<210> SEQ ID NO 56
<211> LENGTH: 324
<212> TYPE: DNA
<213> ORGANISM: Artificial Sequence
<220> FEATURE:
<223> OTHER INFORMATION: modified construct from FKBP

<400> SEQUENCE: 56
ggcgtgcagg tcgagaccat cagccccggc gacggccgca cctttcccaa gagaggccag      60
acttgcgtgg tccactacac cggcatgctg gaggacggca agaagttcga cagcagccgc     120
gaccgcaaca agcccttcaa gttcatgctg ggcaaacagg aagtgatccg cggctgggag     180
gaaggcgtgg ctcagatgag cgtggggcag cgggccaagc tgaccatcag ccccgactat     240
gcctacggcg ccaccggcca ccccggcatc atccccccc  acgccaccct ggtgttcgac     300
gtggagctgc tgaagctgga gtga                                             324

<210> SEQ ID NO 57
<211> LENGTH: 321
<212> TYPE: DNA
<213> ORGANISM: Artificial Sequence
<220> FEATURE:
<223> OTHER INFORMATION: modified construct from FKBP

<400> SEQUENCE: 57
ggcgttcagg tggaaaccat cagtccaggg gatggccgaa cttttccaaa gagagggcag      60
acttgcgtcg tgcattatac tggtatgctg gaggatggga aaaagttcga ctcttccaga     120
gatcggaaca aaccattcaa attcatgctc gggaaacagg aagttatccg ggatgggag      180 gagggcgtgg cccagatgtc cgtgggccag cgcgccaagc taaccatctc cccagactac     240
```

```
gcctacggag ccaccggaca ccccggtatc ataccccac acgccaccct tgtgtttgac        300
gtggaactgc ttaagctaga g                                                 321
```

<210> SEQ ID NO 58
<211> LENGTH: 321
<212> TYPE: DNA
<213> ORGANISM: Artificial Sequence
<220> FEATURE:
<223> OTHER INFORMATION: modified construct from FKBP

<400> SEQUENCE: 58

```
ggcgtacaag tagagactat aagtcctggt gatggaagga cttttccaaa aagaggacaa        60
acatgtgtag ttcattatac gggtatgttg gaggacggca aaagttcga cagtagtaga       120 gatcgtaata aaccattcaa attcatgttg ggtaaacaag aagtcattag gggatgggag       180
gagggagtcg ctcaaatgtc ggttggacaa cgtgctaagt taacaatcag ccctgactac       240
gcatacggag ctacaggaca tcctggtatt atacctcccc acgctacctt ggtgtttgac       300
gtcgaactgc tgaagttaga g                                                 321
```

<210> SEQ ID NO 59
<211> LENGTH: 1449
<212> TYPE: DNA
<213> ORGANISM: Artificial Sequence
<220> FEATURE:
<223> OTHER INFORMATION: modified FokI enzyme
<220> FEATURE:
<221> NAME/KEY: CDS
<222> LOCATION: (1)..(1449)
<220> FEATURE:
<221> NAME/KEY: misc_feature
<222> LOCATION: (1)..(84)
<223> OTHER INFORMATION: zinc finger N1
<220> FEATURE:
<221> NAME/KEY: misc_feature
<222> LOCATION: (85)..(168)
<223> OTHER INFORMATION: zinc finger N2
<220> FEATURE:
<221> NAME/KEY: misc_feature
<222> LOCATION: (169)..(252)
<223> OTHER INFORMATION: zinc finger N3
<220> FEATURE:
<221> NAME/KEY: misc_feature
<222> LOCATION: (253)..(336)
<223> OTHER INFORMATION: zinc finger N4
<220> FEATURE:
<221> NAME/KEY: misc_feature
<222> LOCATION: (337)..(420)
<223> OTHER INFORMATION: zinc finger N5
<220> FEATURE:
<221> NAME/KEY: misc_feature
<222> LOCATION: (421)..(504)
<223> OTHER INFORMATION: zinc finger N6
<220> FEATURE:
<221> NAME/KEY: misc_feature
<222> LOCATION: (505)..(588)
<223> OTHER INFORMATION: zinc finger N7
<220> FEATURE:
<221> NAME/KEY: misc_feature
<222> LOCATION: (589)..(672)
<223> OTHER INFORMATION: zinc finger N8
<220> FEATURE:
<221> NAME/KEY: misc_feature
<222> LOCATION: (673)..(756)
<223> OTHER INFORMATION: zinc finger N9
<220> FEATURE:
<221> NAME/KEY: misc_feature
<222> LOCATION: (757)..(840)
<223> OTHER INFORMATION: zinc finger N10
<220> FEATURE:
<221> NAME/KEY: misc_feature
<222> LOCATION: (841)..(855)

```
<223> OTHER INFORMATION: 5 amino acid linker
<220> FEATURE:
<221> NAME/KEY: misc_feature
<222> LOCATION: (856)..(1443)
<223> OTHER INFORMATION: FokI catalytic domain

<400> SEQUENCE: 59 atg ggc gag aag ccc tac aag tgc cct gag tgc ggc aag agc ttc agc        48
Met Gly Glu Lys Pro Tyr Lys Cys Pro Glu Cys Gly Lys Ser Phe Ser
1               5                   10                  15 cag aga aga agc ctg ggc cac cac cag cgt acg cac ccc ggc gag aaa        96
Gln Arg Arg Ser Leu Gly His His Gln Arg Thr His Pro Gly Glu Lys
                20                  25                  30 cct tat aag tgt ccc gaa tgt ggc aag tcc ttc agc aag aag aac gac        144
Pro Tyr Lys Cys Pro Glu Cys Gly Lys Ser Phe Ser Lys Lys Asn Asp
            35                  40                  45 ctg acc cgg cac cag cgg aca cac ccc ggg gaa aag cca tac aaa tgt        192
Leu Thr Arg His Gln Arg Thr His Pro Gly Glu Lys Pro Tyr Lys Cys
        50                  55                  60 cca gag tgt ggg aag tct ttc tcc agc cgg cgg acc tgc aga gcc cat        240
Pro Glu Cys Gly Lys Ser Phe Ser Ser Arg Arg Thr Cys Arg Ala His
65                  70                  75                  80 cag aga aca cat acc ggg gag aag cct ttc cag tgc cgg atc tgc atg        288
Gln Arg Thr His Thr Gly Glu Lys Pro Phe Gln Cys Arg Ile Cys Met
                85                  90                  95 aga aac ttc agc gtg cgg cac aac ctg acc aga cac ctg agg acc cat        336
Arg Asn Phe Ser Val Arg His Asn Leu Thr Arg His Leu Arg Thr His
                100                 105                 110 acc ggc gaa aaa ccc ttt cag tgc aga atc tgt atg cgg aac ttc tcc        384
Thr Gly Glu Lys Pro Phe Gln Cys Arg Ile Cys Met Arg Asn Phe Ser
            115                 120                 125 gac cgg acc agc ctg gcc cgg cat ctg aga act cat cct ggg gaa aag        432
Asp Arg Thr Ser Leu Ala Arg His Leu Arg Thr His Pro Gly Glu Lys
        130                 135                 140 ccc tat aag tgt cca gaa tgc ggg aaa tcc ttt agc gac agc ggc aac        480
Pro Tyr Lys Cys Pro Glu Cys Gly Lys Ser Phe Ser Asp Ser Gly Asn
145                 150                 155                 160 ctg cgg gtg cac cag agg act cat cca ggc gag aaa ccc tac aaa tgc        528
Leu Arg Val His Gln Arg Thr His Pro Gly Glu Lys Pro Tyr Lys Cys
                165                 170                 175 ccc gaa tgc gga aag tca ttc tcc cac acc ggc cat ctg ctc gag cat        576
Pro Glu Cys Gly Lys Ser Phe Ser His Thr Gly His Leu Leu Glu His
                180                 185                 190 cag cgg acc cac act ggg gag aaa cca ttt cag tgt cgc atc tgt atg        624
Gln Arg Thr His Thr Gly Glu Lys Pro Phe Gln Cys Arg Ile Cys Met
            195                 200                 205 agg aat ttc agc acc aac cag gcc ctg ggc gtg cac ctg aga aca cac        672
Arg Asn Phe Ser Thr Asn Gln Ala Leu Gly Val His Leu Arg Thr His
        210                 215                 220 cca ggc gag aag cct tac aag tgt cca gag tgc gga aag tca ttt tcc        720
Pro Gly Glu Lys Pro Tyr Lys Cys Pro Glu Cys Gly Lys Ser Phe Ser
225                 230                 235                 240 gtg cgc cac aat ctg aca cgg cat cag cgc acc cat ccc ggc gag aag        768
Val Arg His Asn Leu Thr Arg His Gln Arg Thr His Pro Gly Glu Lys
                245                 250                 255 cct tac aaa tgc ccc gag tgt ggc aaa tct ttc agt gac cgg acc tct        816
Pro Tyr Lys Cys Pro Glu Cys Gly Lys Ser Phe Ser Asp Arg Thr Ser
            260                 265                 270 ctg gcc aga cat cag agg aca cac ggc act agt ggc aag cag ctg gtg        864
Leu Ala Arg His Gln Arg Thr His Gly Thr Ser Gly Lys Gln Leu Val
        275                 280                 285
```

```
aaa agc gag ctg gaa gag aag aag tcc gag ctg cgg cac aag ctg aaa        912
Lys Ser Glu Leu Glu Glu Lys Lys Ser Glu Leu Arg His Lys Leu Lys
    290                 295                 300 tac gtg ccc cac gag tac atc gag ctg atc gag atc gcc cgg aac ccc        960
Tyr Val Pro His Glu Tyr Ile Glu Leu Ile Glu Ile Ala Arg Asn Pro
305                 310                 315                 320 acc cag gac aga atc ctg gaa atg aag gtc atg gaa ttt ttc atg aag       1008
Thr Gln Asp Arg Ile Leu Glu Met Lys Val Met Glu Phe Phe Met Lys
                325                 330                 335 gtg tac ggc tac cgg ggc gag cac ctg ggc ggc agc aga aaa ccc gac       1056
Val Tyr Gly Tyr Arg Gly Glu His Leu Gly Gly Ser Arg Lys Pro Asp
        340                 345                 350 ggc gcc atc tac acc gtg ggc agc ccc atc gac tac ggc gtg atc gtg       1104
Gly Ala Ile Tyr Thr Val Gly Ser Pro Ile Asp Tyr Gly Val Ile Val
            355                 360                 365 gac acc aag gcc tac agc ggc ggc tac aac ctg ccc atc gga cag gcc       1152
Asp Thr Lys Ala Tyr Ser Gly Gly Tyr Asn Leu Pro Ile Gly Gln Ala
370                 375                 380 gac gag atg cag aga tac gtg gaa gag aac cag acc cgg aac aag cac       1200
Asp Glu Met Gln Arg Tyr Val Glu Glu Asn Gln Thr Arg Asn Lys His
385                 390                 395                 400 atc aac ccc aac gag tgg tgg aag gtg tac ccc agc agc gtg acc gag       1248
Ile Asn Pro Asn Glu Trp Trp Lys Val Tyr Pro Ser Ser Val Thr Glu
                405                 410                 415 ttc aag ttc ctg ttc gtg tcc ggc cac ttc aag ggc aac tac aag gcc       1296
Phe Lys Phe Leu Phe Val Ser Gly His Phe Lys Gly Asn Tyr Lys Ala
        420                 425                 430 cag ctg acc cgg ctg aac cac atc acc aac tgc aac ggc gct gtg ctg       1344
Gln Leu Thr Arg Leu Asn His Ile Thr Asn Cys Asn Gly Ala Val Leu
            435                 440                 445 agc gtg gaa gaa ctg ctg atc ggc ggc gag atg atc aag gcc ggc acc       1392
Ser Val Glu Glu Leu Leu Ile Gly Gly Glu Met Ile Lys Ala Gly Thr
450                 455                 460 ctg acc ctg gaa gaa gtg cgg cgg aag ttc aac aac ggc gag atc aac       1440
Leu Thr Leu Glu Glu Val Arg Arg Lys Phe Asn Asn Gly Glu Ile Asn
465                 470                 475                 480 ttc tga tag                                                            1449
Phe

<210> SEQ ID NO 60
<211> LENGTH: 481
<212> TYPE: PRT
<213> ORGANISM: Artificial Sequence
<220> FEATURE:
<223> OTHER INFORMATION: Synthetic Construct

<400> SEQUENCE: 60

Met Gly Glu Lys Pro Tyr Lys Cys Pro Glu Cys Gly Lys Ser Phe Ser
1               5                   10                  15

Gln Arg Arg Ser Leu Gly His His Gln Arg Thr His Pro Gly Glu Lys
            20                  25                  30

Pro Tyr Lys Cys Pro Glu Cys Gly Lys Ser Phe Ser Lys Lys Asn Asp
        35                  40                  45

Leu Thr Arg His Gln Arg Thr His Pro Gly Glu Lys Pro Tyr Lys Cys
    50                  55                  60

Pro Glu Cys Gly Lys Ser Phe Ser Ser Arg Arg Thr Cys Arg Ala His
65                  70                  75                  80

Gln Arg Thr His Thr Gly Glu Lys Pro Phe Gln Cys Arg Ile Cys Met
                85                  90                  95
```

Arg Asn Phe Ser Val Arg His Asn Leu Thr Arg His Leu Arg Thr His
            100                 105                 110
Thr Gly Glu Lys Pro Phe Gln Cys Arg Ile Cys Met Arg Asn Phe Ser
            115                 120                 125
Asp Arg Thr Ser Leu Ala Arg His Leu Arg Thr His Pro Gly Glu Lys
130                 135                 140
Pro Tyr Lys Cys Pro Glu Cys Gly Lys Ser Phe Ser Asp Ser Gly Asn
145                 150                 155                 160
Leu Arg Val His Gln Arg Thr His Pro Gly Glu Lys Pro Tyr Lys Cys
            165                 170                 175
Pro Glu Cys Gly Lys Ser Phe Ser His Thr Gly His Leu Leu Glu His
            180                 185                 190
Gln Arg Thr His Thr Gly Glu Lys Pro Phe Gln Cys Arg Ile Cys Met
            195                 200                 205
Arg Asn Phe Ser Thr Asn Gln Ala Leu Gly Val His Leu Arg Thr His
            210                 215                 220
Pro Gly Glu Lys Pro Tyr Lys Cys Pro Glu Cys Gly Lys Ser Phe Ser
225                 230                 235                 240
Val Arg His Asn Leu Thr Arg His Gln Arg Thr His Pro Gly Glu Lys
            245                 250                 255
Pro Tyr Lys Cys Pro Glu Cys Gly Lys Ser Phe Ser Asp Arg Thr Ser
            260                 265                 270
Leu Ala Arg His Gln Arg Thr His Gly Thr Ser Gly Lys Gln Leu Val
            275                 280                 285
Lys Ser Glu Leu Glu Glu Lys Ser Glu Leu Arg His Lys Leu Lys
            290                 295                 300
Tyr Val Pro His Glu Tyr Ile Glu Leu Ile Glu Ile Ala Arg Asn Pro
305                 310                 315                 320
Thr Gln Asp Arg Ile Leu Glu Met Lys Val Met Glu Phe Phe Met Lys
            325                 330                 335
Val Tyr Gly Tyr Arg Gly Glu His Leu Gly Gly Ser Arg Lys Pro Asp
            340                 345                 350
Gly Ala Ile Tyr Thr Val Gly Ser Pro Ile Asp Tyr Gly Val Ile Val
            355                 360                 365
Asp Thr Lys Ala Tyr Ser Gly Gly Tyr Asn Leu Pro Ile Gly Gln Ala
            370                 375                 380
Asp Glu Met Gln Arg Tyr Val Glu Glu Asn Gln Thr Arg Asn Lys His
385                 390                 395                 400
Ile Asn Pro Asn Glu Trp Trp Lys Val Tyr Pro Ser Ser Val Thr Glu
            405                 410                 415
Phe Lys Phe Leu Phe Val Ser Gly His Phe Lys Gly Asn Tyr Lys Ala
            420                 425                 430
Gln Leu Thr Arg Leu Asn His Ile Thr Asn Cys Asn Gly Ala Val Leu
            435                 440                 445
Ser Val Glu Glu Leu Leu Ile Gly Gly Glu Met Ile Lys Ala Gly Thr
            450                 455                 460
Leu Thr Leu Glu Glu Val Arg Arg Lys Phe Asn Asn Gly Glu Ile Asn
465                 470                 475                 480
Phe

<210> SEQ ID NO 61
<211> LENGTH: 7
<212> TYPE: PRT

```
<213> ORGANISM: Artificial Sequence
<220> FEATURE:
<223> OTHER INFORMATION: recognition helices for each of the zinc finger
      triplet binding sites

<400> SEQUENCE: 61

Gln Arg Ala Asn Leu Arg Ala
1               5

<210> SEQ ID NO 62
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 62

Gln Arg Ser Asn Leu Lys Val
1               5

<210> SEQ ID NO 63
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 63

Asp Arg Ser Asn Arg Lys Thr
1               5

<210> SEQ ID NO 64
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 64

Asp Ser Gly Asn Leu Arg Val
1               5

<210> SEQ ID NO 65
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 65

Gly Ala Ser Ala Leu Arg Gln
1               5

<210> SEQ ID NO 66
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 66

Gly Ala Ser Ala Leu Arg Ser
1               5
```

<210> SEQ ID NO 67
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 67

Gly Gly Thr Ala Leu Arg Met
1               5

<210> SEQ ID NO 68
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 68

Gly Gly Thr Ala Leu Val Met
1               5

<210> SEQ ID NO 69
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 69

Gly His Thr Ala Leu Ala Leu
1               5

<210> SEQ ID NO 70
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 70

Gly His Thr Ala Leu Arg His
1               5

<210> SEQ ID NO 71
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 71

Gly His Thr Ala Leu Arg Asn
1               5

<210> SEQ ID NO 72
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

```
<400> SEQUENCE: 72

Gly Pro Thr Ala Leu Val Asn
1               5

<210> SEQ ID NO 73
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 73

His Arg Thr Asn Leu Ile Ala
1               5

<210> SEQ ID NO 74
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 74

Arg Lys Asp Asn Leu Lys Asn
1               5

<210> SEQ ID NO 75
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 75

Arg Ser Ala Asn Leu Ser Val
1               5

<210> SEQ ID NO 76
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 76

Arg Ser Asp Asn Leu Ser Val
1               5

<210> SEQ ID NO 77
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 77

Arg Ser Asp Asn Leu Thr Gln
1               5

<210> SEQ ID NO 78
<211> LENGTH: 7
```

-continued

```
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 78

Thr Ser Ser Asn Arg Lys Thr
1               5

<210> SEQ ID NO 79
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 79

Thr Thr Gly Asn Leu Thr Val
1               5

<210> SEQ ID NO 80
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 80

Val Ser Ser Asn Leu Asn Val
1               5

<210> SEQ ID NO 81
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 81

Gln Asn Ala Thr Arg Ile Asn
1               5

<210> SEQ ID NO 82
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 82

Ser Pro Ala Asp Leu Thr Arg
1               5

<210> SEQ ID NO 83
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 83

Asp Lys Lys Asp Leu Thr Arg
```

```
1               5

<210> SEQ ID NO 84
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 84

Ala Ser Ala Asp Leu Thr Arg
1               5

<210> SEQ ID NO 85
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 85

Lys Gly Asn Asp Leu Thr Arg
1               5

<210> SEQ ID NO 86
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 86

Lys Asn Asn Asp Leu Thr Arg
1               5

<210> SEQ ID NO 87
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 87

Lys Arg Ile Asp Leu Gln Arg
1               5

<210> SEQ ID NO 88
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 88

Gln Asn Ala Thr Arg Lys Arg
1               5

<210> SEQ ID NO 89
<211> LENGTH: 7
<212> TYPE: PRT
<213> ORGANISM: Artificial Sequence
<220> FEATURE:
<223> OTHER INFORMATION: recognition helices for each of the zinc finger
``` triplet binding sites

<400> SEQUENCE: 89

Gln Ser Gly Asp Leu Thr Arg
1               5

<210> SEQ ID NO 90
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 90

Arg Lys His Asp Leu Asn Met
1               5

<210> SEQ ID NO 91
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 91

Arg Asn Ile Thr Leu Val Arg
1               5

<210> SEQ ID NO 92
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 92

Arg Arg Gln Thr Leu Arg Gln
1               5

<210> SEQ ID NO 93
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 93

Arg Ser His Asp Leu Thr Val
1               5

<210> SEQ ID NO 94
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 94

Arg Ser Gln Thr Leu Ala Gln
1               5

<210> SEQ ID NO 95

```
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 95

Arg Thr Asp Thr Leu Arg Asp
1               5

<210> SEQ ID NO 96
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 96

Ala Arg Ser Thr Arg Thr Asn
1               5

<210> SEQ ID NO 97
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 97

His Ala Ser Thr Arg His Cys
1               5

<210> SEQ ID NO 98
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 98

Thr His Leu Asp Leu Ile Arg
1               5

<210> SEQ ID NO 99
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 99

Lys Asn Trp Lys Leu Gln Ala
1               5

<210> SEQ ID NO 100
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 100
```

Gln Leu Ala His Leu Arg Ala
1               5

<210> SEQ ID NO 101
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 101

Gln Ser Ser His Leu Thr Thr
1               5

<210> SEQ ID NO 102
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 102

Arg Ser Ala Asn Leu Ala Arg
1               5

<210> SEQ ID NO 103
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 103

Glu Arg Ser His Leu Arg Glu
1               5

<210> SEQ ID NO 104
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 104

Asp Ser Ala His Leu Thr Arg
1               5

<210> SEQ ID NO 105
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 105

Gln Ser Ala His Arg Thr Lys
1               5

<210> SEQ ID NO 106
<211> LENGTH: 7
<212> TYPE: PRT
<213> ORGANISM: Artificial Sequence
<220> FEATURE:

```
<223> OTHER INFORMATION: recognition helices for each of the zinc finger
      triplet binding sites

<400> SEQUENCE: 106

Arg Gly Asn His Leu Val Val
1               5

<210> SEQ ID NO 107
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 107

Arg Met Ala His Leu His Ala
1               5

<210> SEQ ID NO 108
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 108

Arg Asn Glu His Leu Lys Val
1               5

<210> SEQ ID NO 109
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 109

Arg Pro His His Leu Asp Ala
1               5

<210> SEQ ID NO 110
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 110

Arg Arg Ala His Leu Leu Asn
1               5

<210> SEQ ID NO 111
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 111

Arg Arg Ala His Leu Leu Ser
1               5
```

-continued

```
<210> SEQ ID NO 112
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 112

Arg Arg Ala His Leu Arg Gln
1               5

<210> SEQ ID NO 113
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 113

Arg Arg Thr His Leu Arg Val
1               5

<210> SEQ ID NO 114
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 114

Arg Ser Asp His Leu Lys Thr
1               5

<210> SEQ ID NO 115
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 115

Arg Ser Asp His Leu Ser Ala
1               5

<210> SEQ ID NO 116
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 116

Arg Ser Asp His Leu Ser Gln
1               5

<210> SEQ ID NO 117
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 117
```

Arg Ser Asp His Leu Thr Asn
1               5

<210> SEQ ID NO 118
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 118

Arg Ser Asp His Leu Thr Gln
1               5

<210> SEQ ID NO 119
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 119

Arg Ser Ser His Leu Lys Met
1               5

<210> SEQ ID NO 120
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 120

His Arg Thr Thr Leu Thr Asn
1               5

<210> SEQ ID NO 121
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 121

Gln Ser Ala His Leu Ser Thr
1               5

<210> SEQ ID NO 122
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 122

Gln Lys Ser Ser Leu Ile Ala
1               5

<210> SEQ ID NO 123
<211> LENGTH: 7
<212> TYPE: PRT
<213> ORGANISM: Artificial Sequence

```
<220> FEATURE:
<223> OTHER INFORMATION: recognition helices for each of the zinc finger
      triplet binding sites

<400> SEQUENCE: 123

Arg Arg Asp Glu Leu Asn Val
1               5

<210> SEQ ID NO 124
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 124

Arg Ser Asp Ser Leu Ser Val
1               5

<210> SEQ ID NO 125
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 125

His Lys Asn Ala Leu Gln Asn
1               5

<210> SEQ ID NO 126
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 126

Asp Arg Ala Asn Leu Ser Thr
1               5

<210> SEQ ID NO 127
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 127

Gln Lys Ser Asn Leu Ile Ile
1               5

<210> SEQ ID NO 128
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 128

Gln Ser Gly Asn Leu Thr Glu
1               5
```

<210> SEQ ID NO 129
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 129

Gln Ser Ser Asn Leu Thr Val
1               5

<210> SEQ ID NO 130
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 130

Ser Lys Lys Ala Leu Thr Glu
1               5

<210> SEQ ID NO 131
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 131

Asp Ser Ala Asn Arg Thr Lys
1               5

<210> SEQ ID NO 132
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 132

Arg Ala Asp Asn Leu Thr Glu
1               5

<210> SEQ ID NO 133
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 133

Arg Ser Asp Asn Leu Arg Glu
1               5

<210> SEQ ID NO 134
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites -continued

<400> SEQUENCE: 134

Arg Ser Asp Asn Leu Ser Glu
1               5

<210> SEQ ID NO 135
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 135

Arg Thr Asp Tyr Leu Val Asp
1               5

<210> SEQ ID NO 136
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 136

Asp Arg Ser Asn Arg Ile Lys
1               5

<210> SEQ ID NO 137
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 137

Thr Ser Gly Asn Leu Thr Glu
1               5

<210> SEQ ID NO 138
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 138

Asp Arg Ser Asp Leu Ser Arg
1               5

<210> SEQ ID NO 139
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 139

Asn Arg Thr Asp Leu Ile Arg
1               5

<210> SEQ ID NO 140
<211> LENGTH: 7
<212> TYPE: PRT

```
<213> ORGANISM: Artificial Sequence
<220> FEATURE:
<223> OTHER INFORMATION: recognition helices for each of the zinc finger
      triplet binding sites

<400> SEQUENCE: 140

Gln Asn Ser Thr Arg Ile Gly
1               5

<210> SEQ ID NO 141
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 141

Thr Ser His Ser Leu Thr Glu
1               5

<210> SEQ ID NO 142
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 142

Ser Lys Lys His Leu Ala Glu
1               5

<210> SEQ ID NO 143
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 143

Asp Ser Ser Ser Leu Thr Arg
1               5

<210> SEQ ID NO 144
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 144

Asp Tyr Asp Val Arg Lys Arg
1               5

<210> SEQ ID NO 145
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 145

Arg Asn Asp Thr Leu Thr Glu
1               5
```

<210> SEQ ID NO 146
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 146

Arg Ser Asp Thr Leu Ser Glu
1               5

<210> SEQ ID NO 147
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 147

Thr Lys Asn Ser Leu Thr Glu
1               5

<210> SEQ ID NO 148
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 148

Gln Ser Gly His Leu Thr Glu
1               5

<210> SEQ ID NO 149
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 149

Gln Ser Ser His Leu Asn Val
1               5

<210> SEQ ID NO 150
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 150

Gln Ser Thr His Leu Thr Gln
1               5

<210> SEQ ID NO 151
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 151

His Thr Gly His Leu Leu Glu
1               5

<210> SEQ ID NO 152
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 152

Arg Ser Asp Asn Leu Thr Glu
1               5

<210> SEQ ID NO 153
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 153

Arg Ser Asp Lys Leu Thr Glu
1               5

<210> SEQ ID NO 154
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 154

Arg Ser Gln Thr Arg Lys Thr
1               5

<210> SEQ ID NO 155
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 155

Ser Arg Arg Thr Cys Arg Ala
1               5

<210> SEQ ID NO 156
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 156

Asp Ser Ser Ser Arg Thr Lys
1               5

<210> SEQ ID NO 157
<211> LENGTH: 7

```
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 157

Gln Asn Ser Thr Leu Thr Glu
1               5

<210> SEQ ID NO 158
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 158

Ala Ser Asp Asp Leu Thr Gln
1               5

<210> SEQ ID NO 159
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 159

His Asn Tyr Ala Arg Asp Cys
1               5

<210> SEQ ID NO 160
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 160

Arg Asn Asp Ala Leu Thr Glu
1               5

<210> SEQ ID NO 161
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 161

Arg Ser Asp Ala Leu Arg Glu
1               5

<210> SEQ ID NO 162
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 162

Arg Ser Asp Ala Leu Ser Ala
```

```
1               5
```

<210> SEQ ID NO 163
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 163

```
Arg Ser Asp Ala Leu Ser Asn
1               5
```

<210> SEQ ID NO 164
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 164

```
Arg Ser Asp Thr Leu Ser Glu
1               5
```

<210> SEQ ID NO 165
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 165

```
Thr Thr Gly Ala Leu Thr Glu
1               5
```

<210> SEQ ID NO 166
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 166

```
His Lys Pro Asn Leu His Arg
1               5
```

<210> SEQ ID NO 167
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 167

```
His Arg Pro Asn Leu Thr Arg
1               5
```

<210> SEQ ID NO 168
<211> LENGTH: 7
<212> TYPE: PRT
<213> ORGANISM: Artificial Sequence
<220> FEATURE:
<223> OTHER INFORMATION: recognition helices for each of the zinc finger

```
                        triplet binding sites

<400> SEQUENCE: 168

Leu Gly Glu Asn Leu Arg Arg
1               5

<210> SEQ ID NO 169
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 169

Gln Ala Ser Asn Leu Ala Arg
1               5

<210> SEQ ID NO 170
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 170

Gln Ala Ser Asn Leu Leu Arg
1               5

<210> SEQ ID NO 171
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 171

Gln Ala Ser Asn Leu Thr Arg
1               5

<210> SEQ ID NO 172
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 172

Gln Asp Gly Asn Leu Gly Arg
1               5

<210> SEQ ID NO 173
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 173

Gln Asp Gly Asn Leu Thr Arg
1               5

<210> SEQ ID NO 174
```

```
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 174

Gln Gly Ser Asn Leu Ala Arg
1               5

<210> SEQ ID NO 175
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 175

Gln His Pro Asn Leu Thr Arg
1               5

<210> SEQ ID NO 176
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 176

Gln Lys Gly Asn Leu Leu Arg
1               5

<210> SEQ ID NO 177
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 177

Gln Lys Ser Asn Leu Ile Arg
1               5

<210> SEQ ID NO 178
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 178

Gln Leu Ser Asn Leu Thr Arg
1               5

<210> SEQ ID NO 179
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 179
```

Gln Gln Ser Asn Leu Ser Arg
1               5

<210> SEQ ID NO 180
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 180

Gln Gln Thr Asn Leu Thr Arg
1               5

<210> SEQ ID NO 181
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 181

Gln Arg Asn Asn Leu Gly Arg
1               5

<210> SEQ ID NO 182
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 182

Gln Arg Ser Asn Leu Ala Arg
1               5

<210> SEQ ID NO 183
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 183

Gln Arg Ser Asn Leu Val Arg
1               5

<210> SEQ ID NO 184
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 184

Gln Arg Thr Asn Leu Gln Arg
1               5

<210> SEQ ID NO 185
<211> LENGTH: 7
<212> TYPE: PRT
<213> ORGANISM: Artificial Sequence
<220> FEATURE:

```
<223> OTHER INFORMATION: recognition helices for each of the zinc finger
      triplet binding sites

<400> SEQUENCE: 185

Gln Ser Gly Asn Leu Ala Arg
1               5

<210> SEQ ID NO 186
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 186

Gln Ser Asn Asn Leu Asn Arg
1               5

<210> SEQ ID NO 187
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 187

Gln Ser Ser Asn Leu Thr Lys
1               5

<210> SEQ ID NO 188
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 188

Gln Ser Ser Asn Leu Thr Arg
1               5

<210> SEQ ID NO 189
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 189

Gln Ser Ser Asn Leu Val Arg
1               5

<210> SEQ ID NO 190
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 190

Gln Thr Asn Asn Leu Gly Arg
1               5
```

```
<210> SEQ ID NO 191
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 191

Gln Thr Asn Asn Leu Asn Arg
1               5

<210> SEQ ID NO 192
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 192

Gln Thr Asn Asn Leu Thr Arg
1               5

<210> SEQ ID NO 193
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 193

Gln Thr Val Asn Leu Asp Arg
1               5

<210> SEQ ID NO 194
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 194

Arg Lys Pro Asn Leu Leu Arg
1               5

<210> SEQ ID NO 195
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 195

Thr Thr Thr Asn Leu Arg Arg
1               5

<210> SEQ ID NO 196
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 196
```

Cys Pro Ser Asn Leu Arg Arg
1               5

<210> SEQ ID NO 197
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 197

Asp Asp Ala Asn Leu Arg Arg
1               5

<210> SEQ ID NO 198
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 198

Asp Glu Ala Asn Leu Arg Arg
1               5

<210> SEQ ID NO 199
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 199

Asp Leu Ser Asn Leu Lys Arg
1               5

<210> SEQ ID NO 200
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 200

Asp Met Gly Asn Leu Gly Arg
1               5

<210> SEQ ID NO 201
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 201

Asp Pro Ala Asn Leu Arg Arg
1               5

<210> SEQ ID NO 202
<211> LENGTH: 7
<212> TYPE: PRT
<213> ORGANISM: Artificial Sequence

```
<220> FEATURE:
<223> OTHER INFORMATION: recognition helices for each of the zinc finger
      triplet binding sites

<400> SEQUENCE: 202

Asp Pro Gly Asn Leu Val Arg
1               5

<210> SEQ ID NO 203
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 203

Asp Pro Ser Asn Leu Ile Arg
1               5

<210> SEQ ID NO 204
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 204

Asp Pro Ser Asn Leu Gln Arg
1               5

<210> SEQ ID NO 205
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 205

Asp Pro Ser Asn Leu Arg Arg
1               5

<210> SEQ ID NO 206
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 206

Asp Gln Gly Asn Leu Ile Arg
1               5

<210> SEQ ID NO 207
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 207

Asp Arg Ala Asn Leu Ser Arg
1               5
```

<210> SEQ ID NO 208
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 208

Asp Arg Gly Asn Leu Thr Arg
1               5

<210> SEQ ID NO 209
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 209

Asp Arg Ser Asn Leu Thr Arg
1               5

<210> SEQ ID NO 210
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 210

Glu Glu Ala Asn Leu Arg Arg
1               5

<210> SEQ ID NO 211
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 211

Glu Glu Ser Asn Leu Arg Arg
1               5

<210> SEQ ID NO 212
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 212

Glu Glu Val Asn Leu Arg Arg
1               5

<210> SEQ ID NO 213
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

```
<400> SEQUENCE: 213

Glu Gly Gly Asn Leu Met Arg
1               5

<210> SEQ ID NO 214
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 214

Glu Lys Ala Asn Leu Thr Arg
1               5

<210> SEQ ID NO 215
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 215

Glu Gln Ala Asn Leu Arg Arg
1               5

<210> SEQ ID NO 216
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 216

His Ser Ser Asn Phe Asn Lys
1               5

<210> SEQ ID NO 217
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 217

Arg Ser Asp Asn Leu Ser Glu
1               5

<210> SEQ ID NO 218
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 218

Lys His Ser Asn Leu Ala Arg
1               5

<210> SEQ ID NO 219
<211> LENGTH: 7
<212> TYPE: PRT
```

```
<213> ORGANISM: Artificial Sequence
<220> FEATURE:
<223> OTHER INFORMATION: recognition helices for each of the zinc finger
      triplet binding sites

<400> SEQUENCE: 219

Lys His Ser Asn Leu Thr Arg
1               5

<210> SEQ ID NO 220
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 220

Lys Lys Thr Asn Leu Thr Arg
1               5

<210> SEQ ID NO 221
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 221

Lys Ser Ser Asn Leu Arg Arg
1               5

<210> SEQ ID NO 222
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 222

Gln Ser Phe Asn Leu Arg Arg
1               5

<210> SEQ ID NO 223
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 223

Arg Glu Asp Asn Leu Gly Arg
1               5

<210> SEQ ID NO 224
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 224

Arg Gly Asp Asn Leu Lys Arg
1               5
```

```
<210> SEQ ID NO 225
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 225

Arg Gly Asp Asn Leu Asn Arg
1               5

<210> SEQ ID NO 226
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 226

Arg His Asp Gln Leu Thr Arg
1               5

<210> SEQ ID NO 227
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 227

Arg Ile Asp Asn Leu Gly Arg
1               5

<210> SEQ ID NO 228
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 228

Arg Lys Ser Asn Leu Ile Arg
1               5

<210> SEQ ID NO 229
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 229

Arg Met Ser Asn Leu Asp Arg
1               5

<210> SEQ ID NO 230
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites
```

```
<400> SEQUENCE: 230

Arg Asn Thr Asn Leu Thr Arg
1               5

<210> SEQ ID NO 231
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 231

Arg Pro His Asn Leu Leu Arg
1               5

<210> SEQ ID NO 232
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 232

Arg Gln Asp Asn Leu Gly Arg
1               5

<210> SEQ ID NO 233
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 233

Arg Gln Asp Asn Leu Gln Arg
1               5

<210> SEQ ID NO 234
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 234

Arg Gln Met Asn Leu Asp Arg
1               5

<210> SEQ ID NO 235
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 235

Arg Arg Asp Asn Leu Leu Arg
1               5

<210> SEQ ID NO 236
<211> LENGTH: 7
```

```
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 236

Arg Arg Asp Asn Leu Asn Arg
1               5

<210> SEQ ID NO 237
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 237

Arg Ser Ala Asn Leu Thr Arg
1               5

<210> SEQ ID NO 238
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 238

Arg Ser Asp His Leu Ser Arg
1               5

<210> SEQ ID NO 239
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 239

Arg Ser Asp Asn Leu Ala Arg
1               5

<210> SEQ ID NO 240
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 240

Arg Ser Asp Asn Leu Ser Arg
1               5

<210> SEQ ID NO 241
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 241

Arg Ser Asp Asn Leu Ser Thr
```

<210> SEQ ID NO 242
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 242

Arg Ser Asp Asn Leu Thr Arg
1               5

<210> SEQ ID NO 243
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 243

Arg Ser Asp Asn Leu Val Arg
1               5

<210> SEQ ID NO 244
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 244

Arg Ser Ser Asn Leu Gln Arg
1               5

<210> SEQ ID NO 245
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 245

Arg Thr His Asn Leu Lys Arg
1               5

<210> SEQ ID NO 246
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 246

Arg Thr His Asn Leu Thr Arg
1               5

<210> SEQ ID NO 247
<211> LENGTH: 7
<212> TYPE: PRT
<213> ORGANISM: Artificial Sequence
<220> FEATURE:
<223> OTHER INFORMATION: recognition helices for each of the zinc finger -continued triplet binding sites

<400> SEQUENCE: 247

Arg Val Asp Asn Leu Pro Arg
1               5

<210> SEQ ID NO 248
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 248

Ser Gly Ser Asn Phe Thr Arg
1               5

<210> SEQ ID NO 249
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 249

Thr Asn Asn Asn Leu Ala Arg
1               5

<210> SEQ ID NO 250
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 250

Val His Trp Asn Leu Met Arg
1               5

<210> SEQ ID NO 251
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 251

Ile Ser His Asn Leu Ala Arg
1               5

<210> SEQ ID NO 252
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 252

Ile Ser Ser Asn Leu Gln Arg
1               5

<210> SEQ ID NO 253

```
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 253

Leu Gly Asn Asn Leu Lys Arg
1               5

<210> SEQ ID NO 254
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 254

Leu Asn Ser Asn Leu Ala Arg
1               5

<210> SEQ ID NO 255
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 255

Leu Ser Thr Asn Leu Thr Arg
1               5

<210> SEQ ID NO 256
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 256

Leu Thr His Asn Leu Arg Arg
1               5

<210> SEQ ID NO 257
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 257

Gln Ser Ser Asn Leu Ala Arg
1               5

<210> SEQ ID NO 258
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 258
```

```
Arg Ser Asp Ala Leu Ile Gln
1               5

<210> SEQ ID NO 259
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 259

Ser Lys Gln Ala Leu Ala Val
1               5

<210> SEQ ID NO 260
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 260

Thr Gly Gln Gln Leu Arg Val
1               5

<210> SEQ ID NO 261
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 261

Thr Lys Gln Arg Leu Val Val
1               5

<210> SEQ ID NO 262
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 262

Thr Arg Gln Arg Leu Arg Ile
1               5

<210> SEQ ID NO 263
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 263

Thr Ser Ala Asn Leu Ser Arg
1               5

<210> SEQ ID NO 264
<211> LENGTH: 7
<212> TYPE: PRT
<213> ORGANISM: Artificial Sequence
<220> FEATURE:
```

```
<223> OTHER INFORMATION: recognition helices for each of the zinc finger
      triplet binding sites

<400> SEQUENCE: 264

Thr Ser Gly Asn Leu Val Arg
1               5

<210> SEQ ID NO 265
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 265

Thr Ser Gln Met Leu Val Val
1               5

<210> SEQ ID NO 266
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 266

Thr Ser Ser Asn Leu Ser Arg
1               5

<210> SEQ ID NO 267
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 267

Thr Thr Ser Asn Leu Arg Arg
1               5

<210> SEQ ID NO 268
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 268

Val Gly His Asn Leu Ser Arg
1               5

<210> SEQ ID NO 269
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 269

Val Gly Ser Asn Leu Thr Arg
1               5
```

```
<210> SEQ ID NO 270
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 270

Val Arg His Asn Leu Thr Arg
1               5

<210> SEQ ID NO 271
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 271

Asp Lys Ala Gln Leu Gly Arg
1               5

<210> SEQ ID NO 272
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 272

Asp Arg Ser Ala Leu Ser Arg
1               5

<210> SEQ ID NO 273
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 273

Asp Arg Ser Gln Leu Ala Arg
1               5

<210> SEQ ID NO 274
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 274

Glu Arg Gly Thr Leu Ala Arg
1               5

<210> SEQ ID NO 275
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 275
```

```
His Asn Gly Thr Leu Lys Arg
1               5

<210> SEQ ID NO 276
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 276

Lys Asn Thr Arg Leu Ser Val
1               5

<210> SEQ ID NO 277
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 277

Leu Lys His Ser Leu Leu Arg
1               5

<210> SEQ ID NO 278
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 278

Leu Asn His Thr Leu Lys Arg
1               5

<210> SEQ ID NO 279
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 279

Leu Arg His Ser Leu Ser Arg
1               5

<210> SEQ ID NO 280
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 280

Gln Asp Asn Thr Leu Arg Arg
1               5

<210> SEQ ID NO 281
<211> LENGTH: 7
<212> TYPE: PRT
<213> ORGANISM: Artificial Sequence
```

```
<220> FEATURE:
<223> OTHER INFORMATION: recognition helices for each of the zinc finger
      triplet binding sites

<400> SEQUENCE: 281

Gln Asp Val Ser Leu Val Arg
1               5

<210> SEQ ID NO 282
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 282

Gln Gly Gly Thr Leu Arg Arg
1               5

<210> SEQ ID NO 283
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 283

Gln Gly Asn Thr Leu Thr Arg
1               5

<210> SEQ ID NO 284
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 284

Gln Lys Gly Thr Leu Gly Arg
1               5

<210> SEQ ID NO 285
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 285

Gln Asn Gly Thr Leu Thr Arg
1               5

<210> SEQ ID NO 286
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 286

Gln Pro Asn Thr Leu Thr Arg
1               5
```

```
<210> SEQ ID NO 287
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 287

Gln Arg Gly Thr Leu Asn Arg
1               5

<210> SEQ ID NO 288
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 288

Gln Ser Gly Asp Leu Arg Arg
1               5

<210> SEQ ID NO 289
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 289

Gln Ser Gly Asp Leu Thr Arg
1               5

<210> SEQ ID NO 290
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 290

Gln Ser Gly Ser Leu Thr Arg
1               5

<210> SEQ ID NO 291
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 291

Gln Ser Asn Val Leu Ser Arg
1               5

<210> SEQ ID NO 292
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites
```

```
<400> SEQUENCE: 292

Gln Ser Thr Thr Leu Lys Arg
1               5

<210> SEQ ID NO 293
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 293

Gln Thr Ala Thr Leu Lys Arg
1               5

<210> SEQ ID NO 294
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 294

Gln Thr Asn Thr Leu Lys Arg
1               5

<210> SEQ ID NO 295
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 295

Arg Gly Gln Glu Leu Arg Arg
1               5

<210> SEQ ID NO 296
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 296

Arg Arg Gln Glu Leu His Arg
1               5

<210> SEQ ID NO 297
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 297

Arg Arg Gln Glu Leu Lys Arg
1               5

<210> SEQ ID NO 298
<211> LENGTH: 7
<212> TYPE: PRT
```

```
<213> ORGANISM: Artificial Sequence
<220> FEATURE:
<223> OTHER INFORMATION: recognition helices for each of the zinc finger
      triplet binding sites

<400> SEQUENCE: 298

Arg Arg Gln Glu Leu Thr Arg
1               5

<210> SEQ ID NO 299
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 299

Arg Arg Val Asp Leu Leu Arg
1               5

<210> SEQ ID NO 300
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 300

Ser Pro Glu Gln Leu Ala Arg
1               5

<210> SEQ ID NO 301
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 301

Asp Cys Arg Asp Leu Ala Arg
1               5

<210> SEQ ID NO 302
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 302

Asp Gly Ser Thr Leu Asn Arg
1               5

<210> SEQ ID NO 303
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 303

Asp Gly Ser Thr Leu Arg Arg
1               5
```

```
<210> SEQ ID NO 304
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 304

Asp His Ser Asn Leu Ser Arg
1               5

<210> SEQ ID NO 305
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 305

Asp Lys Ser Cys Leu Asn Arg
1               5

<210> SEQ ID NO 306
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 306

Asp Lys Ser Val Leu Ala Arg
1               5

<210> SEQ ID NO 307
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 307

Asp Pro Ser Asn Leu Arg Arg
1               5

<210> SEQ ID NO 308
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 308

Asp Pro Ser Thr Leu Arg Arg
1               5

<210> SEQ ID NO 309
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites
```

-continued

<400> SEQUENCE: 309

Asp Arg Arg Thr Leu Asp Arg
1               5

<210> SEQ ID NO 310
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 310

Asp Arg Ser Asp Leu Thr Arg
1               5

<210> SEQ ID NO 311
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 311

Asp Arg Ser Ser Leu Thr Arg
1               5

<210> SEQ ID NO 312
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 312

Asp Arg Ser Ser Arg Thr Lys
1               5

<210> SEQ ID NO 313
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 313

Asp Ser Pro Thr Leu Arg Arg
1               5

<210> SEQ ID NO 314
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 314

Asp Ser Ser Val Leu Arg Arg
1               5

<210> SEQ ID NO 315
<211> LENGTH: 7

```
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 315

Glu His Arg Gly Leu Lys Arg
1               5

<210> SEQ ID NO 316
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 316

Glu Arg Gly Thr Leu Ala Arg
1               5

<210> SEQ ID NO 317
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 317

Glu Arg Arg Gly Leu Ala Arg
1               5

<210> SEQ ID NO 318
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 318

Glu Arg Arg Gly Leu Asp Arg
1               5

<210> SEQ ID NO 319
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 319

Lys Arg Arg Asp Leu Asp Arg
1               5

<210> SEQ ID NO 320
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 320

Leu Lys Lys Asp Leu Leu Arg
```

<210> SEQ ID NO 321
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 321

Ser His Thr Val Leu Thr Arg
1               5

<210> SEQ ID NO 322
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 322

Ser Lys Lys Ser Leu Thr Arg
1               5

<210> SEQ ID NO 323
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 323

Ser Asn Lys Asp Leu Thr Arg
1               5

<210> SEQ ID NO 324
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 324

Val Arg Lys Asp Leu Thr Arg
1               5

<210> SEQ ID NO 325
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 325

Lys Ala Asp Thr Leu Val Arg
1               5

<210> SEQ ID NO 326
<211> LENGTH: 7
<212> TYPE: PRT
<213> ORGANISM: Artificial Sequence
<220> FEATURE:
<223> OTHER INFORMATION: recognition helices for each of the zinc finger

```
                         triplet binding sites

<400> SEQUENCE: 326

Lys His Asp Thr Leu His Arg
1               5

<210> SEQ ID NO 327
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 327

Lys Asn Asn Asp Leu Thr Arg
1               5

<210> SEQ ID NO 328
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 328

Arg Ala Asp Thr Leu Arg Arg
1               5

<210> SEQ ID NO 329
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 329

Arg Ala His Thr Leu Arg Arg
1               5

<210> SEQ ID NO 330
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 330

Arg Glu Asp Ser Leu Pro Arg
1               5

<210> SEQ ID NO 331
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 331

Arg His Ala Ala Leu Leu Ser
1               5

<210> SEQ ID NO 332
```

```
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 332

Arg Lys Asp Gly Leu Thr Arg
1               5

<210> SEQ ID NO 333
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 333

Arg Lys Gly Thr Leu Asp Arg
1               5

<210> SEQ ID NO 334
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 334

Arg Lys Leu Gly Leu Leu Arg
1               5

<210> SEQ ID NO 335
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 335

Arg Leu Asp Met Leu Ala Arg
1               5

<210> SEQ ID NO 336
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 336

Arg Leu Arg Asp Leu Pro Arg
1               5

<210> SEQ ID NO 337
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 337
```

Arg Asn Leu Thr Leu Ala Arg
1               5

<210> SEQ ID NO 338
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 338

Arg Asn Leu Thr Leu Val Arg
1               5

<210> SEQ ID NO 339
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 339

Arg Pro Asp Gly Leu Ala Arg
1               5

<210> SEQ ID NO 340
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 340

Arg Arg Asp Asp Leu Thr Arg
1               5

<210> SEQ ID NO 341
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 341

Arg Arg Asp Gly Leu Thr Arg
1               5

<210> SEQ ID NO 342
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 342

Arg Arg His Gly Leu Asp Arg
1               5

<210> SEQ ID NO 343
<211> LENGTH: 7
<212> TYPE: PRT
<213> ORGANISM: Artificial Sequence
<220> FEATURE:

```
<223> OTHER INFORMATION: recognition helices for each of the zinc finger
      triplet binding sites

<400> SEQUENCE: 343

Arg Arg His Thr Leu Thr Arg
1               5

<210> SEQ ID NO 344
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 344

Arg Arg Leu Thr Leu Leu Arg
1               5

<210> SEQ ID NO 345
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 345

Arg Ser Asp Asp Leu Gln Arg
1               5

<210> SEQ ID NO 346
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 346

Arg Ser Asp Asp Leu Thr Arg
1               5

<210> SEQ ID NO 347
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 347

Arg Ser Asp Asp Leu Val Arg
1               5

<210> SEQ ID NO 348
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 348

Arg Ser Asp Glu Leu Asn Arg
1               5
```

<210> SEQ ID NO 349
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 349

Arg Ser Asp Glu Leu Gln Arg
1               5

<210> SEQ ID NO 350
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 350

Arg Ser Asp Glu Leu Ser Arg
1               5

<210> SEQ ID NO 351
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 351

Arg Ser Asp Glu Leu Thr Arg
1               5

<210> SEQ ID NO 352
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 352

Arg Ser Asp Glu Arg Lys Arg
1               5

<210> SEQ ID NO 353
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 353

Arg Ser Asp Ser Leu Ser Lys
1               5

<210> SEQ ID NO 354
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 354

```
Arg Ser Asp Thr Leu Lys Lys
1               5

<210> SEQ ID NO 355
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 355

Arg Ser Asp Val Leu Thr Arg
1               5

<210> SEQ ID NO 356
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 356

Arg Ser Asn Thr Leu Leu Arg
1               5

<210> SEQ ID NO 357
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 357

Arg Thr Asp Leu Leu Arg Arg
1               5

<210> SEQ ID NO 358
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 358

Arg Thr Asp Ser Leu Pro Arg
1               5

<210> SEQ ID NO 359
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 359

Arg Thr Asp Thr Leu Ala Arg
1               5

<210> SEQ ID NO 360
<211> LENGTH: 7
<212> TYPE: PRT
<213> ORGANISM: Artificial Sequence
```

```
<220> FEATURE:
<223> OTHER INFORMATION: recognition helices for each of the zinc finger
      triplet binding sites

<400> SEQUENCE: 360

Arg Val Asp Asp Leu Gly Arg
1               5

<210> SEQ ID NO 361
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 361

Ala Arg Ser Thr Arg Thr Thr
1               5

<210> SEQ ID NO 362
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 362

Glu Gly Ser Gly Leu Lys Arg
1               5

<210> SEQ ID NO 363
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 363

Gly Ala Thr Ala Leu Lys Arg
1               5

<210> SEQ ID NO 364
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 364

Lys His Gln Thr Leu Gln Arg
1               5

<210> SEQ ID NO 365
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 365

Leu Lys His Asp Leu Arg Arg
1               5
```

```
<210> SEQ ID NO 366
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 366

Leu Arg Ala Ser Leu Arg Arg
1               5

<210> SEQ ID NO 367
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 367

Leu Arg Gln Thr Leu Ala Arg
1               5

<210> SEQ ID NO 368
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 368

Leu Arg Thr Ser Leu Val Arg
1               5

<210> SEQ ID NO 369
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 369

Met Lys Asn Thr Leu Thr Arg
1               5

<210> SEQ ID NO 370
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 370

Asn Gly Gln Gly Leu Arg Arg
1               5

<210> SEQ ID NO 371
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites
```

```
<400> SEQUENCE: 371

Asn Lys Gln Ala Leu Asp Arg
1               5

<210> SEQ ID NO 372
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 372

Asn Arg Ser Asp Arg Thr Arg
1               5

<210> SEQ ID NO 373
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 373

Gln Arg Gln Ala Leu Asp Arg
1               5

<210> SEQ ID NO 374
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 374

Gln Arg Ser Asp Leu His Arg
1               5

<210> SEQ ID NO 375
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 375

Gln Arg Ser Asp Leu Thr Arg
1               5

<210> SEQ ID NO 376
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 376

Gln Ser Ser Asp Leu Gln Arg
1               5

<210> SEQ ID NO 377
<211> LENGTH: 7
<212> TYPE: PRT
```

```
<213> ORGANISM: Artificial Sequence
<220> FEATURE:
<223> OTHER INFORMATION: recognition helices for each of the zinc finger
      triplet binding sites

<400> SEQUENCE: 377

Gln Ser Ser Asp Leu Arg Arg
1               5

<210> SEQ ID NO 378
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 378

Gln Ser Ser Asp Leu Ser Arg
1               5

<210> SEQ ID NO 379
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 379

Gln Ser Ser Asp Leu Thr Arg
1               5

<210> SEQ ID NO 380
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 380

Thr His Ser Met Leu Ala Arg
1               5

<210> SEQ ID NO 381
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 381

Thr Lys Pro Ile Leu Val Arg
1               5

<210> SEQ ID NO 382
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 382

Thr Lys Gln Ile Leu Gly Arg
1               5
```

<210> SEQ ID NO 383
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 383

Thr Lys Gln Val Leu Asp Arg
1               5

<210> SEQ ID NO 384
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 384

Thr Ser Gly Glu Leu Val Arg
1               5

<210> SEQ ID NO 385
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 385

Thr Ser Ser Gly Leu Thr Arg
1               5

<210> SEQ ID NO 386
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 386

Thr Thr Gln Ala Leu Arg Arg
1               5

<210> SEQ ID NO 387
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 387

Val Gly Ala Ser Leu Lys Arg
1               5

<210> SEQ ID NO 388
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

```
<400> SEQUENCE: 388

Val Gly Asn Ser Leu Thr Arg
1               5

<210> SEQ ID NO 389
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 389

Val Lys Asn Thr Leu Thr Arg
1               5

<210> SEQ ID NO 390
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 390

Val Arg Gln Gly Leu Thr Arg
1               5

<210> SEQ ID NO 391
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 391

Val Ser Asn Ser Leu Ala Arg
1               5

<210> SEQ ID NO 392
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 392

Val Ser Asn Thr Leu Thr Arg
1               5

<210> SEQ ID NO 393
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 393

Asp Lys Thr Lys Leu Asn Val
1               5

<210> SEQ ID NO 394
<211> LENGTH: 7
```

```
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 394

Asp Lys Thr Lys Leu Arg Val
1               5

<210> SEQ ID NO 395
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 395

Asp Asn Ala His Leu Ala Arg
1               5

<210> SEQ ID NO 396
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 396

Gln Ala Asn His Leu Ser Arg
1               5

<210> SEQ ID NO 397
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 397

Gln Gly Gly His Leu Lys Arg
1               5

<210> SEQ ID NO 398
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 398

Gln His Ser His Leu Val Arg
1               5

<210> SEQ ID NO 399
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 399

Gln Lys Pro His Leu Ser Arg
```

```
<210> SEQ ID NO 400
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 400

Gln Met Ser His Leu Lys Arg
1               5

<210> SEQ ID NO 401
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 401

Gln Asn Ser His Leu Arg Arg
1               5

<210> SEQ ID NO 402
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 402

Gln Asn Ser His Leu Arg Arg
1               5

<210> SEQ ID NO 403
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 403

Gln Arg Ala His Leu Glu Arg
1               5

<210> SEQ ID NO 404
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 404

Gln Arg Ala His Leu Ile Arg
1               5

<210> SEQ ID NO 405
<211> LENGTH: 7
<212> TYPE: PRT
<213> ORGANISM: Artificial Sequence
<220> FEATURE:
<223> OTHER INFORMATION: recognition helices for each of the zinc finger
```

```
                         triplet binding sites

<400> SEQUENCE: 405

Gln Ser Ala His Leu Lys Arg
1               5

<210> SEQ ID NO 406
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 406

Gln Ser Gly His Leu Ala Arg
1               5

<210> SEQ ID NO 407
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 407

Gln Ser Gly His Leu Gln Arg
1               5

<210> SEQ ID NO 408
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 408

Gln Ser Gly His Leu Ser Arg
1               5

<210> SEQ ID NO 409
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 409

Gln Ser Gln His Leu Val Arg
1               5

<210> SEQ ID NO 410
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 410

Gln Ser Thr His Leu Thr Arg
1               5

<210> SEQ ID NO 411
```

```
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 411

Gln Thr Thr His Leu Arg Arg
1               5

<210> SEQ ID NO 412
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 412

Gln Thr Thr His Leu Ser Arg
1               5

<210> SEQ ID NO 413
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 413

Gln Thr Thr His Leu Ser Arg
1               5

<210> SEQ ID NO 414
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 414

Gln Val Ser His Leu Thr Arg
1               5

<210> SEQ ID NO 415
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 415

Arg Met Glu Arg Leu Asp Arg
1               5

<210> SEQ ID NO 416
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 416
```

Arg Pro Ala Lys Leu Val Leu
1               5

<210> SEQ ID NO 417
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 417

Arg Pro Ser Lys Leu Val Leu
1               5

<210> SEQ ID NO 418
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 418

Arg Arg Asp His Arg Thr Thr
1               5

<210> SEQ ID NO 419
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 419

Arg Ser Thr His Leu Arg Val
1               5

<210> SEQ ID NO 420
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 420

Arg Thr Asp Arg Leu Ile Arg
1               5

<210> SEQ ID NO 421
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 421

Thr His Ala His Leu Thr Arg
1               5

<210> SEQ ID NO 422
<211> LENGTH: 7
<212> TYPE: PRT
<213> ORGANISM: Artificial Sequence
<220> FEATURE:

```
<223> OTHER INFORMATION: recognition helices for each of the zinc finger
      triplet binding sites

<400> SEQUENCE: 422

Thr Ser Ala His Leu Ala Arg
1               5

<210> SEQ ID NO 423
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 423

Tyr Asn Thr His Leu Thr Arg
1               5

<210> SEQ ID NO 424
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 424

Ala Lys Ser Lys Leu Asp Arg
1               5

<210> SEQ ID NO 425
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 425

Ala Pro Ser Lys Leu Asp Arg
1               5

<210> SEQ ID NO 426
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 426

Asp Gly Gly His Leu Thr Arg
1               5

<210> SEQ ID NO 427
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 427

Asp Lys Ser His Leu Pro Arg
1               5
```

-continued

```
<210> SEQ ID NO 428
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 428

Asp Pro Gly His Leu Val Arg
1               5

<210> SEQ ID NO 429
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 429

Asp Arg Ser His Leu Ala Arg
1               5

<210> SEQ ID NO 430
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 430

Asp Arg Ser His Leu Ser Arg
1               5

<210> SEQ ID NO 431
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 431

Asp Arg Ser His Leu Thr Arg
1               5

<210> SEQ ID NO 432
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 432

Glu Lys Ser His Leu Lys Arg
1               5

<210> SEQ ID NO 433
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 433
```

```
Glu Lys Ser His Leu Thr Arg
1               5

<210> SEQ ID NO 434
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 434

Glu Asn Ser Lys Leu Asn Arg
1               5

<210> SEQ ID NO 435
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 435

Glu Ser Gly His Leu Lys Arg
1               5

<210> SEQ ID NO 436
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 436

Glu Ser Gly His Leu Arg Arg
1               5

<210> SEQ ID NO 437
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 437

Lys Asn His Ser Leu Asn Asn
1               5

<210> SEQ ID NO 438
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 438

Lys Asn Val Ser Leu Thr His
1               5

<210> SEQ ID NO 439
<211> LENGTH: 7
<212> TYPE: PRT
<213> ORGANISM: Artificial Sequence
```

```
<220> FEATURE:
<223> OTHER INFORMATION: recognition helices for each of the zinc finger
      triplet binding sites

<400> SEQUENCE: 439

Leu Lys Glu His Leu Thr Arg
1               5

<210> SEQ ID NO 440
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 440

Gln Ser Ser His Leu Ala Arg
1               5

<210> SEQ ID NO 441
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 441

Ser Lys His Lys Leu Glu Arg
1               5

<210> SEQ ID NO 442
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 442

Ser Pro Ser Lys Leu Ala Arg
1               5

<210> SEQ ID NO 443
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 443

Ser Pro Ser Lys Leu Val Arg
1               5

<210> SEQ ID NO 444
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 444

Thr Asn Ser Lys Leu Thr Arg
1               5
```

```
<210> SEQ ID NO 445
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 445

Thr Pro Ser Lys Leu Asp Arg
1               5

<210> SEQ ID NO 446
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 446

Thr Arg Ala Lys Leu His Ile
1               5

<210> SEQ ID NO 447
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 447

Val Pro Ser Lys Leu Ala Arg
1               5

<210> SEQ ID NO 448
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 448

Val Pro Ser Lys Leu Lys Arg
1               5

<210> SEQ ID NO 449
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 449

Val Pro Ser Lys Leu Leu Arg
1               5

<210> SEQ ID NO 450
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites
```

```
<400> SEQUENCE: 450

Lys Gly Asp His Leu Arg Arg
1               5

<210> SEQ ID NO 451
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 451

Lys Lys Asp His Leu His Arg
1               5

<210> SEQ ID NO 452
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 452

Lys Arg Glu Arg Leu Asp Arg
1               5

<210> SEQ ID NO 453
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 453

Lys Arg Glu Arg Leu Glu Arg
1               5

<210> SEQ ID NO 454
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 454

Lys Ser Asn His Leu His Val
1               5

<210> SEQ ID NO 455
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 455

Lys Thr Ser His Leu Arg Ala
1               5

<210> SEQ ID NO 456
<211> LENGTH: 7
<212> TYPE: PRT
```

```
<213> ORGANISM: Artificial Sequence
<220> FEATURE:
<223> OTHER INFORMATION: recognition helices for each of the zinc finger
      triplet binding sites

<400> SEQUENCE: 456

Arg Gly Asp Lys Leu Ala Leu
1               5

<210> SEQ ID NO 457
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 457

Arg Gly Asp Lys Leu Gly Pro
1               5

<210> SEQ ID NO 458
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 458

Arg Gly Asn His Leu Arg Arg
1               5

<210> SEQ ID NO 459
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 459

Arg Ile Asp Lys Leu Gly Gly
1               5

<210> SEQ ID NO 460
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 460

Arg Lys His His Leu Gly Arg
1               5

<210> SEQ ID NO 461
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 461

Arg Lys His Arg Leu Asp Gly
1               5
```

<210> SEQ ID NO 462
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 462

Arg Asn Asp Lys Leu Val Pro
1               5

<210> SEQ ID NO 463
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 463

Arg Asn His Gly Leu Val Arg
1               5

<210> SEQ ID NO 464
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 464

Arg Asn Thr His Leu Ala Arg
1               5

<210> SEQ ID NO 465
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 465

Arg Gln Gly His Leu Lys Arg
1               5

<210> SEQ ID NO 466
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 466

Arg Arg Ala His Leu Gln Asn
1               5

<210> SEQ ID NO 467
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

```
<400> SEQUENCE: 467

Arg Arg Glu His Leu Val Arg
1               5

<210> SEQ ID NO 468
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 468

Arg Arg Ser His Leu Thr Arg
1               5

<210> SEQ ID NO 469
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 469

Arg Ser Ala His Leu Ala Arg
1               5

<210> SEQ ID NO 470
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 470

Arg Ser Ala His Leu Ser Arg
1               5

<210> SEQ ID NO 471
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 471

Arg Ser Asp His Leu Ala Arg
1               5

<210> SEQ ID NO 472
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 472

Arg Ser Asp His Leu Ser Lys
1               5

<210> SEQ ID NO 473
<211> LENGTH: 7
```

```
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 473

Arg Ser Asp His Leu Ser Arg
1               5

<210> SEQ ID NO 474
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 474

Arg Ser Asp His Leu Thr Arg
1               5

<210> SEQ ID NO 475
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 475

Arg Ser Asp Lys Leu Asn Arg
1               5

<210> SEQ ID NO 476
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 476

Arg Ser Asp Lys Leu Val Arg
1               5

<210> SEQ ID NO 477
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 477

Arg Thr Glu His Leu Ala Arg
1               5

<210> SEQ ID NO 478
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 478

Asp Ser Ser Lys Leu Ser Arg
```

<210> SEQ ID NO 479
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 479

Glu Ala His His Leu Ser Arg
1               5

<210> SEQ ID NO 480
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 480

His Gly His Arg Leu Lys Thr
1               5

<210> SEQ ID NO 481
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 481

Ile Pro Asn His Leu Ala Arg
1               5

<210> SEQ ID NO 482
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 482

Ile Arg His His Leu Lys Arg
1               5

<210> SEQ ID NO 483
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 483

Leu Thr Gln Gly Leu Arg Arg
1               5

<210> SEQ ID NO 484
<211> LENGTH: 7
<212> TYPE: PRT
<213> ORGANISM: Artificial Sequence
<220> FEATURE:
<223> OTHER INFORMATION: recognition helices for each of the zinc finger -continued triplet binding sites

<400> SEQUENCE: 484

Met Gly His His Leu Lys Arg
1               5

<210> SEQ ID NO 485
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 485

Met Lys His His Leu Ala Arg
1               5

<210> SEQ ID NO 486
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 486

Met Lys His His Leu Asp Ala
1               5

<210> SEQ ID NO 487
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 487

Met Ser Asp His Leu Ser Arg
1               5

<210> SEQ ID NO 488
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 488

Met Ser His His Leu Ser Arg
1               5

<210> SEQ ID NO 489
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 489

Gln Pro His His Leu Pro Arg
1               5

<210> SEQ ID NO 490

-continued

```
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 490

Gln Ser Ser His Leu Ala Arg
1               5

<210> SEQ ID NO 491
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 491

Gln Ser Ser His Leu Thr Arg
1               5

<210> SEQ ID NO 492
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 492

Arg Gln Ser Arg Leu Gln Arg
1               5

<210> SEQ ID NO 493
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 493

Arg Arg Gln Lys Leu Thr Ile
1               5

<210> SEQ ID NO 494
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 494

Arg Arg Ser Arg Leu Val Arg
1               5

<210> SEQ ID NO 495
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 495
```

Arg Ser Asp His Leu Ser Thr
1               5

<210> SEQ ID NO 496
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 496

Arg Ser Asp His Leu Thr Thr
1               5

<210> SEQ ID NO 497
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 497

Thr Lys Gln Lys Leu Gln Thr
1               5

<210> SEQ ID NO 498
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 498

Thr Lys Gln Arg Leu Glu Val
1               5

<210> SEQ ID NO 499
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 499

Thr Arg Gln Lys Leu Glu Thr
1               5

<210> SEQ ID NO 500
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 500

Thr Arg Thr Arg Leu Val Ile
1               5

<210> SEQ ID NO 501
<211> LENGTH: 7
<212> TYPE: PRT
<213> ORGANISM: Artificial Sequence
<220> FEATURE:

<223> OTHER INFORMATION: recognition helices for each of the zinc finger
      triplet binding sites

<400> SEQUENCE: 501

Thr Ser Gly His Leu Ser Arg
1               5

<210> SEQ ID NO 502
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 502

Thr Ser Gly His Leu Val Arg
1               5

<210> SEQ ID NO 503
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 503

Thr Thr Thr Lys Leu Ala Ile
1               5

<210> SEQ ID NO 504
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 504

Val Asp His His Leu Arg Arg
1               5

<210> SEQ ID NO 505
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 505

Val Lys His Gly Leu Gly Arg
1               5

<210> SEQ ID NO 506
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 506

Val Lys His Gly Leu Thr Arg
1               5

-continued

```
<210> SEQ ID NO 507
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 507

Trp Pro Ser Asn Leu Thr Arg
1               5

<210> SEQ ID NO 508
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 508

Tyr Asn Trp His Leu Gln Arg
1               5

<210> SEQ ID NO 509
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 509

Gln Gly Gly Ala Leu Gln Arg
1               5

<210> SEQ ID NO 510
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 510

Gln Gly Thr Ser Leu Ala Arg
1               5

<210> SEQ ID NO 511
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 511

Gln Lys Gln Ala Leu Asp Arg
1               5

<210> SEQ ID NO 512
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 512
```

Gln Lys Gln Ala Leu Thr Arg
1               5

<210> SEQ ID NO 513
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 513

Gln Lys Val Ser Leu Lys Arg
1               5

<210> SEQ ID NO 514
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 514

Gln Met Asn Ala Leu Gln Arg
1               5

<210> SEQ ID NO 515
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 515

Gln Gln Gln Ala Leu Lys Arg
1               5

<210> SEQ ID NO 516
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 516

Gln Gln Gln Ala Leu Thr Arg
1               5

<210> SEQ ID NO 517
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 517

Gln Gln Gln Ala Leu Val Arg
1               5

<210> SEQ ID NO 518
<211> LENGTH: 7
<212> TYPE: PRT
<213> ORGANISM: Artificial Sequence

```
<220> FEATURE:
<223> OTHER INFORMATION: recognition helices for each of the zinc finger
      triplet binding sites

<400> SEQUENCE: 518

Gln Gln Ser Ser Leu Leu Arg
1               5

<210> SEQ ID NO 519
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 519

Gln Arg Ala Ser Leu Thr Arg
1               5

<210> SEQ ID NO 520
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 520

Gln Arg Ser Ser Leu Val Arg
1               5

<210> SEQ ID NO 521
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 521

Gln Ser Gly Ala Leu Ala Arg
1               5

<210> SEQ ID NO 522
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 522

Gln Ser Gly Ala Leu Thr Arg
1               5

<210> SEQ ID NO 523
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 523

Gln Ser Gly Ser Leu Thr Arg
1               5
```

<210> SEQ ID NO 524
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 524

Gln Ser Gly Thr Leu Thr Arg
1               5

<210> SEQ ID NO 525
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 525

Gln Ser Ser Ser Leu Ile Arg
1               5

<210> SEQ ID NO 526
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 526

Gln Ser Ser Ser Leu Val Arg
1               5

<210> SEQ ID NO 527
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 527

Gln Ser Ser Thr Leu Thr Arg
1               5

<210> SEQ ID NO 528
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 528

Gln Ser Thr Ser Leu Gln Arg
1               5

<210> SEQ ID NO 529
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

```
<400> SEQUENCE: 529

Thr Ser Ser Ala Arg Thr Thr
1               5

<210> SEQ ID NO 530
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 530

Ala Pro Ser Ser Leu Arg Arg
1               5

<210> SEQ ID NO 531
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 531

Asp Ala Thr Gln Leu Val Arg
1               5

<210> SEQ ID NO 532
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 532

Asp His Ser Ser Leu Lys Arg
1               5

<210> SEQ ID NO 533
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 533

Asp Pro Gly Ala Leu Val Arg
1               5

<210> SEQ ID NO 534
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 534

Asp Pro Thr Ser Leu Asn Arg
1               5

<210> SEQ ID NO 535
<211> LENGTH: 7
<212> TYPE: PRT
```

```
<213> ORGANISM: Artificial Sequence
<220> FEATURE:
<223> OTHER INFORMATION: recognition helices for each of the zinc finger
      triplet binding sites

<400> SEQUENCE: 535

Asp Arg Ser Ala Leu Ala Arg
1               5

<210> SEQ ID NO 536
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 536

Asp Arg Ser Ala Leu Ser Arg
1               5

<210> SEQ ID NO 537
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 537

Asp Arg Ser Ser Leu Arg Arg
1               5

<210> SEQ ID NO 538
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 538

Asp Arg Thr Pro Leu Asn Arg
1               5

<210> SEQ ID NO 539
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 539

Asp Arg Thr Pro Leu Gln Asn
1               5

<210> SEQ ID NO 540
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 540

Asp Arg Thr Ser Leu Ala Arg
1               5
```

<210> SEQ ID NO 541
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 541

Glu Gly Gly Ala Leu Arg Arg
1               5

<210> SEQ ID NO 542
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 542

Glu Ser Gly Ala Leu Arg Arg
1               5

<210> SEQ ID NO 543
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 543

Asn Thr Ser Leu Leu Arg Arg
1               5

<210> SEQ ID NO 544
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 544

Arg Ser Asp Val Leu Ser Glu
1               5

<210> SEQ ID NO 545
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 545

Thr Gly Ala Val Leu Arg Arg
1               5

<210> SEQ ID NO 546
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites -continued

<400> SEQUENCE: 546

Thr Gly Ala Val Leu Thr Arg
1               5

<210> SEQ ID NO 547
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 547

Thr Lys Lys Ile Leu Thr Val
1               5

<210> SEQ ID NO 548
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 548

Thr Lys Ser Leu Leu Ala Arg
1               5

<210> SEQ ID NO 549
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 549

Thr Met Ala Val Leu Arg Arg
1               5

<210> SEQ ID NO 550
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 550

Thr Arg Ala Val Leu Arg Arg
1               5

<210> SEQ ID NO 551
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 551

Thr Ser Thr Ile Leu Ala Arg
1               5

<210> SEQ ID NO 552
<211> LENGTH: 7

```
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 552

Thr Ser Thr Leu Leu Lys Arg
1               5

<210> SEQ ID NO 553
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 553

Thr Ser Thr Leu Leu Asn Arg
1               5

<210> SEQ ID NO 554
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 554

Arg Ala Ser Val Leu Asp Ile
1               5

<210> SEQ ID NO 555
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 555

Arg Gly Asp Ala Leu Ala Arg
1               5

<210> SEQ ID NO 556
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 556

Arg His Thr Ser Leu Thr Arg
1               5

<210> SEQ ID NO 557
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 557

Arg Lys Asp Ala Leu His Val
```

```
<210> SEQ ID NO 558
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 558

Arg Lys His Ile Leu Ile His
1               5

<210> SEQ ID NO 559
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 559

Arg Lys Thr Ala Leu Asn Arg
1               5

<210> SEQ ID NO 560
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 560

Arg Asn Phe Ile Leu Ala Arg
1               5

<210> SEQ ID NO 561
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 561

Arg Asn Phe Ile Leu Gln Arg
1               5

<210> SEQ ID NO 562
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 562

Arg Asn Phe Val Leu Ala Arg
1               5

<210> SEQ ID NO 563
<211> LENGTH: 7
<212> TYPE: PRT
<213> ORGANISM: Artificial Sequence
<220> FEATURE:
<223> OTHER INFORMATION: recognition helices for each of the zinc finger
```

```
      triplet binding sites

<400> SEQUENCE: 563

Arg Asn Thr Ala Leu Gln His
1               5

<210> SEQ ID NO 564
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 564

Arg Asn Val Ala Leu Gly Asn
1               5

<210> SEQ ID NO 565
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 565

Arg Asn Val Asn Leu Val Thr
1               5

<210> SEQ ID NO 566
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 566

Arg Pro Asp Ala Leu Pro Arg
1               5

<210> SEQ ID NO 567
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 567

Arg Arg Ala Ala Leu Gly Pro
1               5

<210> SEQ ID NO 568
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 568

Arg Arg Glu Val Leu Glu Asn
1               5

<210> SEQ ID NO 569
```

```
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 569

Arg Arg Phe Ile Leu Ser Arg
1               5

<210> SEQ ID NO 570
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 570

Arg Arg His Ile Leu Asp Arg
1               5

<210> SEQ ID NO 571
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 571

Arg Ser Ala Ala Leu Ser Arg
1               5

<210> SEQ ID NO 572
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 572

Arg Ser Asp Ala Leu Ala Arg
1               5

<210> SEQ ID NO 573
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 573

Arg Ser Asp Ala Leu Arg Thr
1               5

<210> SEQ ID NO 574
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 574
```

Arg Ser Asp Ala Leu Ser Arg
1               5

<210> SEQ ID NO 575
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 575

Arg Ser Asp Ala Leu Thr Arg
1               5

<210> SEQ ID NO 576
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 576

Arg Ser Asp Glu Leu Val Arg
1               5

<210> SEQ ID NO 577
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 577

Arg Ser His Ile Leu Thr Asn
1               5

<210> SEQ ID NO 578
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 578

Arg Thr Ser Ser Leu Lys Arg
1               5

<210> SEQ ID NO 579
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 579

Arg Thr Val Ala Leu Asn Arg
1               5

<210> SEQ ID NO 580
<211> LENGTH: 7
<212> TYPE: PRT
<213> ORGANISM: Artificial Sequence
<220> FEATURE:

```
<223> OTHER INFORMATION: recognition helices for each of the zinc finger
      triplet binding sites

<400> SEQUENCE: 580

Ser Arg Phe Thr Leu Gly Arg
1               5

<210> SEQ ID NO 581
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 581

Ser Arg Phe Thr Leu Gly Arg
1               5

<210> SEQ ID NO 582
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 582

Val Ser Ser Ser Leu Arg Arg
1               5

<210> SEQ ID NO 583
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 583

Ala Ala Thr Ala Leu Arg Arg
1               5

<210> SEQ ID NO 584
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 584

His His Asn Ser Leu Thr Arg
1               5

<210> SEQ ID NO 585
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 585

His Lys Ser Ser Leu Thr Arg
1               5
```

```
<210> SEQ ID NO 586
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 586

His Ser Ser Ser Leu Val Arg
1               5

<210> SEQ ID NO 587
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 587

Ile Lys Ala Ile Leu Thr Arg
1               5

<210> SEQ ID NO 588
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 588

Ile Asn His Ser Leu Arg Arg
1               5

<210> SEQ ID NO 589
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 589

Ile Arg Thr Ser Leu Lys Arg
1               5

<210> SEQ ID NO 590
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 590

Met Asn Ser Val Leu Lys Arg
1               5

<210> SEQ ID NO 591
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 591
```

```
Met Thr Ser Ser Leu Arg Arg
1               5

<210> SEQ ID NO 592
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 592

Gln Ala Thr Leu Leu Arg Arg
1               5

<210> SEQ ID NO 593
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 593

Gln Ser Ser Ala Leu Thr Arg
1               5

<210> SEQ ID NO 594
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 594

Thr His Thr Val Leu Ala Arg
1               5

<210> SEQ ID NO 595
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 595

Thr Lys Pro Val Leu Lys Ile
1               5

<210> SEQ ID NO 596
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 596

Thr Asn Gln Ala Leu Gly Val
1               5

<210> SEQ ID NO 597
<211> LENGTH: 7
<212> TYPE: PRT
<213> ORGANISM: Artificial Sequence
```

<220> FEATURE:
<223> OTHER INFORMATION: recognition helices for each of the zinc finger
      triplet binding sites

<400> SEQUENCE: 597

Thr Asn Ser Val Leu Gly Arg
1               5

<210> SEQ ID NO 598
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 598

Thr Arg His Ser Leu Gly Arg
1               5

<210> SEQ ID NO 599
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 599

Thr Ser Gly Ala Leu Thr Arg
1               5

<210> SEQ ID NO 600
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 600

Thr Ser Gly Ser Leu Thr Arg
1               5

<210> SEQ ID NO 601
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 601

Thr Ser Gly Ser Leu Val Arg
1               5

<210> SEQ ID NO 602
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 602

Thr Ser Thr Leu Leu Lys Arg
1               5

```
<210> SEQ ID NO 603
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 603

Thr Ser Thr Arg Leu Asp Ile
1               5

<210> SEQ ID NO 604
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 604

Thr Thr Ala Leu Leu Lys Arg
1               5

<210> SEQ ID NO 605
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 605

Thr Thr Ser Ala Leu Thr Arg
1               5

<210> SEQ ID NO 606
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 606

Thr Thr Thr Val Leu Ala Arg
1               5

<210> SEQ ID NO 607
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 607

Val Gly Gly Ser Leu Asn Arg
1               5

<210> SEQ ID NO 608
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites
```

```
<400> SEQUENCE: 608

Gln Gly Gly Asn Leu Ala Leu
1               5

<210> SEQ ID NO 609
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 609

Gln Gly Gly Asn Leu Thr Leu
1               5

<210> SEQ ID NO 610
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 610

Gln Gln Gly Asn Leu Gln Leu
1               5

<210> SEQ ID NO 611
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 611

Gln Gln Gly Asn Leu Arg Asn
1               5

<210> SEQ ID NO 612
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 612

Gln Arg Gly Asn Leu Asn Met
1               5

<210> SEQ ID NO 613
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 613

Gln Ser Gly Asn Leu His Thr
1               5

<210> SEQ ID NO 614
<211> LENGTH: 7
<212> TYPE: PRT
```

```
<213> ORGANISM: Artificial Sequence
<220> FEATURE:
<223> OTHER INFORMATION: recognition helices for each of the zinc finger
      triplet binding sites

<400> SEQUENCE: 614

Asn Ser Asp His Leu Thr Asn
1               5

<210> SEQ ID NO 615
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 615

Gln Gly Tyr Asn Leu Ala Gly
1               5

<210> SEQ ID NO 616
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 616

Arg Ala His Asn Leu Leu Leu
1               5

<210> SEQ ID NO 617
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 617

Arg Glu Asp Asn Leu His Thr
1               5

<210> SEQ ID NO 618
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 618

Arg Gly His Asn Leu Leu Val
1               5

<210> SEQ ID NO 619
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 619

Arg Gly Thr Asn Leu Arg Thr
1               5
```

```
<210> SEQ ID NO 620
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 620

Arg His Asp Gly Leu Ala Gly
1               5

<210> SEQ ID NO 621
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 621

Arg Ile Asp His Leu Val Pro
1               5

<210> SEQ ID NO 622
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 622

Arg Lys Thr Gly Leu Leu Ile
1               5

<210> SEQ ID NO 623
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 623

Arg Leu Asp Gly Leu Ala Gly
1               5

<210> SEQ ID NO 624
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 624

Arg Pro Glu Gly Leu Ser Thr
1               5

<210> SEQ ID NO 625
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites
```

<400> SEQUENCE: 625

Arg Pro Glu Ser Leu Ala Pro
1               5

<210> SEQ ID NO 626
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 626

Arg Pro Glu Ser Leu Arg Pro
1               5

<210> SEQ ID NO 627
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 627

Arg Arg Asp Gly Leu Ala Gly
1               5

<210> SEQ ID NO 628
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 628

Arg Arg Asp His Leu Ser Leu
1               5

<210> SEQ ID NO 629
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 629

Arg Arg Asp His Leu Ser Pro
1               5

<210> SEQ ID NO 630
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 630

Arg Arg Asp Asn Leu Pro Lys
1               5

<210> SEQ ID NO 631
<211> LENGTH: 7

```
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 631

Arg Arg Arg Asn Leu Gln Ile
1               5

<210> SEQ ID NO 632
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 632

Arg Ser His Asn Leu Lys Leu
1               5

<210> SEQ ID NO 633
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 633

Arg Ser His Asn Leu Arg Leu
1               5

<210> SEQ ID NO 634
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 634

Thr Ser Ser Asn Arg Lys Lys
1               5

<210> SEQ ID NO 635
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 635

Gln Ser Ala Asp Arg Thr Lys
1               5

<210> SEQ ID NO 636
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 636

Asp Lys Arg Ser Leu Pro His
```

```
1               5

<210> SEQ ID NO 637
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 637

Ala Ser Ser Thr Arg Thr Lys
1               5

<210> SEQ ID NO 638
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 638

His Ser Ser Asp Leu Thr Arg
1               5

<210> SEQ ID NO 639
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 639

Lys Asn Asn Asp Leu Leu Lys
1               5

<210> SEQ ID NO 640
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 640

Asn Arg Ser Asp Leu Ser Arg
1               5

<210> SEQ ID NO 641
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 641

Gln Ser Ser Asp Leu Ser Lys
1               5

<210> SEQ ID NO 642
<211> LENGTH: 7
<212> TYPE: PRT
<213> ORGANISM: Artificial Sequence
<220> FEATURE:
<223> OTHER INFORMATION: recognition helices for each of the zinc finger
```

```
            triplet binding sites

<400> SEQUENCE: 642

Arg Ala Asp Gly Leu Gln Leu
1               5

<210> SEQ ID NO 643
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 643

Arg Gly Asp Ser Leu Lys Lys
1               5

<210> SEQ ID NO 644
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 644

Arg Met Asp Ser Leu Gly Gly
1               5

<210> SEQ ID NO 645
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 645

Arg Arg Asp Gly Leu Ser Gly
1               5

<210> SEQ ID NO 646
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 646

Arg Ser Asp Glu Leu Arg Thr
1               5

<210> SEQ ID NO 647
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 647

Arg Ser Asp Gly Leu Arg Gly
1               5

<210> SEQ ID NO 648
```

```
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 648

Arg Ser Asp Thr Leu Pro Ala
1               5

<210> SEQ ID NO 649
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 649

Arg Ser Asp Thr Leu Pro Leu
1               5

<210> SEQ ID NO 650
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 650

Arg Ser Ser Asp Leu Ser Arg
1               5

<210> SEQ ID NO 651
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 651

Arg Thr Asp Ser Leu Gln Pro
1               5

<210> SEQ ID NO 652
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 652

Asn Asn Arg Asp Arg Thr Lys
1               5

<210> SEQ ID NO 653
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 653
```

```
Gln Arg Asn Thr Leu Lys Gly
1               5

<210> SEQ ID NO 654
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 654

Ser Lys Pro Asn Leu Lys Met
1               5

<210> SEQ ID NO 655
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 655

Gln Ala Gly His Leu Ala Ser
1               5

<210> SEQ ID NO 656
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 656

Gln Arg Glu His Leu Thr Thr
1               5

<210> SEQ ID NO 657
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 657

Gln Ser Gly His Leu Thr Lys
1               5

<210> SEQ ID NO 658
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 658

Ala Asn Arg Thr Leu Val His
1               5

<210> SEQ ID NO 659
<211> LENGTH: 7
<212> TYPE: PRT
<213> ORGANISM: Artificial Sequence
<220> FEATURE:
```

```
<223> OTHER INFORMATION: recognition helices for each of the zinc finger
      triplet binding sites

<400> SEQUENCE: 659

Gln Ala Arg Ser Leu Arg Ala
1               5

<210> SEQ ID NO 660
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 660

Gln Gly Arg Ser Leu Arg Ala
1               5

<210> SEQ ID NO 661
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 661

Gln Asn Arg Ser Leu Ala His
1               5

<210> SEQ ID NO 662
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 662

Gln Gln Arg Ser Leu Lys Asn
1               5

<210> SEQ ID NO 663
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 663

Gln Arg Arg Ser Leu Gly His
1               5

<210> SEQ ID NO 664
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 664

Arg Ala Arg Asn Leu Thr Leu
1               5
```

-continued

<210> SEQ ID NO 665
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 665

Arg Gly Arg Asn Leu Glu Met
1               5

<210> SEQ ID NO 666
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 666

Arg Lys Arg Asn Leu Ile Met
1               5

<210> SEQ ID NO 667
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 667

Arg Met Arg Asn Leu Ile Ile
1               5

<210> SEQ ID NO 668
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 668

Arg Asn Arg Asn Leu Val Leu
1               5

<210> SEQ ID NO 669
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 669

Arg Arg Arg Asn Leu His Leu
1               5

<210> SEQ ID NO 670
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 670

Arg Arg Arg Asn Leu Thr Leu
1               5

<210> SEQ ID NO 671
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 671

Arg Ser Arg Asn Leu Asp Ile
1               5

<210> SEQ ID NO 672
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 672

Arg Ser Arg Asn Leu Leu Leu
1               5

<210> SEQ ID NO 673
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 673

Arg Ser Arg Asn Leu Thr Leu
1               5

<210> SEQ ID NO 674
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 674

Arg Met Asp His Leu Ala Gly
1               5

<210> SEQ ID NO 675
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 675

Arg Asn Ala His Arg Ile Asn
1               5

<210> SEQ ID NO 676
<211> LENGTH: 7
<212> TYPE: PRT
<213> ORGANISM: Artificial Sequence

```
<220> FEATURE:
<223> OTHER INFORMATION: recognition helices for each of the zinc finger
      triplet binding sites

<400> SEQUENCE: 676

Arg Arg Asp His Leu Ser Leu
1               5

<210> SEQ ID NO 677
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 677

Arg Arg Glu His Leu Thr Ile
1               5

<210> SEQ ID NO 678
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 678

Arg Ser Asp His Leu Arg Glu
1               5

<210> SEQ ID NO 679
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 679

Arg Ser Asp His Leu Ser Leu
1               5

<210> SEQ ID NO 680
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 680

Arg Ser Asp His Leu Ser Thr
1               5

<210> SEQ ID NO 681
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 681

Arg Ser Asp His Leu Thr Thr
1               5
```

<210> SEQ ID NO 682
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 682

Arg Thr Glu Ser Leu His Ile
1               5

<210> SEQ ID NO 683
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 683

Lys Arg Gln His Leu Glu Tyr
1               5

<210> SEQ ID NO 684
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 684

Gln Ala His Gly Leu Thr Ala
1               5

<210> SEQ ID NO 685
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 685

Gln Ala His Gly Leu Thr Gly
1               5

<210> SEQ ID NO 686
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 686

Gln Pro Gly His Leu Thr Ala
1               5

<210> SEQ ID NO 687
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

```
<400> SEQUENCE: 687

Gln Pro His Gly Leu Ala His
1               5

<210> SEQ ID NO 688
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 688

Gln Pro His Gly Leu Gly Ala
1               5

<210> SEQ ID NO 689
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 689

Gln Pro His Gly Leu Arg Ala
1               5

<210> SEQ ID NO 690
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 690

Gln Pro His Gly Leu Arg His
1               5

<210> SEQ ID NO 691
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 691

Gln Gln His Gly Leu Arg His
1               5

<210> SEQ ID NO 692
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 692

Gln Arg His Gly Leu Ser Ser
1               5

<210> SEQ ID NO 693
<211> LENGTH: 7
<212> TYPE: PRT
```

```
<213> ORGANISM: Artificial Sequence
<220> FEATURE:
<223> OTHER INFORMATION: recognition helices for each of the zinc finger
      triplet binding sites

<400> SEQUENCE: 693

Arg His Gln His Leu Lys Leu
1               5

<210> SEQ ID NO 694
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 694

Arg Lys Gln His Leu Gln Leu
1               5

<210> SEQ ID NO 695
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 695

Arg Lys Gln His Leu Thr Leu
1               5

<210> SEQ ID NO 696
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 696

Arg Lys Gln His Leu Val Leu
1               5

<210> SEQ ID NO 697
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 697

Arg Arg Gln Ala Leu Glu Tyr
1               5

<210> SEQ ID NO 698
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 698

Arg Arg Gln His Leu Gln Tyr
1               5
```

<210> SEQ ID NO 699
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 699

Gln Gln Thr Gly Leu Asn Val
1               5

<210> SEQ ID NO 700
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 700

Gln Arg Asn Ala Leu Arg Gly
1               5

<210> SEQ ID NO 701
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 701

Arg Ala Asn His Leu Thr Ile
1               5

<210> SEQ ID NO 702
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 702

Arg Ala Asp Ala Leu Met Val
1               5

<210> SEQ ID NO 703
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 703

Arg Ser Asp Ser Leu Ser Ala
1               5

<210> SEQ ID NO 704
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 704

His Ser Asn Ala Arg Lys Thr
1               5

<210> SEQ ID NO 705
<211> LENGTH: 7
<212> TYPE: PRT
<213> ORGANISM: Artificial Sequence
<220> FEATURE:
<223> OTHER INFORMATION: recognition helices for each of the zinc finger
      triplet binding sites

<400> SEQUENCE: 705

Gln Arg Asn Ala Leu Ser Gly
1               5

<210> SEQ ID NO 706
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 706

Cys Arg Cys Asn Glu Cys Gly Lys Ser Phe Ser Xaa Xaa Xaa Xaa Xaa
1               5                   10                  15

Xaa Xaa His Gln Arg Thr His
            20

<210> SEQ ID NO 707
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 707

Phe Ala Cys Asp Ile Cys Gly Arg Lys Phe Ala Xaa Xaa Xaa Xaa Xaa
1               5                   10                  15

Xaa Xaa His Thr Lys Ile His
            20

<210> SEQ ID NO 708
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 708

Phe Ala Cys Glu Val Cys Gly Val Arg Phe Thr Xaa Xaa Xaa Xaa Xaa
1               5                   10                  15

```
Xaa Xaa His Met Arg Lys His
            20
```

<210> SEQ ID NO 709
<211> LENGTH: 25
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (14)..(20)
<223> OTHER INFORMATION: Xaa can be any naturally occurring amino acid

<400> SEQUENCE: 709

```
Phe Ala Cys Ser Trp Gln Asp Cys Asn Lys Lys Phe Ala Xaa Xaa Xaa
1               5                   10                  15

Xaa Xaa Xaa Xaa His Tyr Arg Thr His
            20                  25
```

<210> SEQ ID NO 710
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 710

```
Phe Glu Cys Lys Asp Cys Gly Lys Ala Phe Ile Xaa Xaa Xaa Xaa Xaa
1               5                   10                  15

Xaa Xaa His Gln Arg Thr His
            20
```

<210> SEQ ID NO 711
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 711

```
Phe His Cys Gly Tyr Cys Glu Lys Ser Phe Ser Xaa Xaa Xaa Xaa Xaa
1               5                   10                  15

Xaa Xaa His Ile Arg Thr His
            20
```

<210> SEQ ID NO 712
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 712

Phe Lys Cys Pro Val Cys Gly Lys Ala Phe Arg Xaa Xaa Xaa Xaa Xaa
1               5                   10                  15

Xaa Xaa His Gln Arg Thr His
            20

<210> SEQ ID NO 713
<211> LENGTH: 24
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 713

Phe Leu Cys Gln Tyr Cys Ala Gln Arg Phe Gly Xaa Xaa Xaa Xaa Xaa
1               5                   10                  15

Xaa Xaa His Met Lys Lys Ser His
            20

<210> SEQ ID NO 714
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 714

Phe Gln Cys Lys Thr Cys Gln Arg Lys Phe Ser Xaa Xaa Xaa Xaa Xaa
1               5                   10                  15

Xaa Xaa His Thr Arg Thr His
            20

<210> SEQ ID NO 715
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 715

Phe Gln Cys Asn Gln Cys Gly Ala Ser Phe Thr Xaa Xaa Xaa Xaa Xaa
1               5                   10                  15

Xaa Xaa His Ile Lys Leu His
            20

<210> SEQ ID NO 716
<211> LENGTH: 25
<212> TYPE: PRT
<213> ORGANISM: Artificial Sequence
<220> FEATURE:
<223> OTHER INFORMATION: the conserved regions of the zinc finger

```
        protein with insert for recognition helix
<220> FEATURE:
<221> NAME/KEY: misc_feature
<222> LOCATION: (14)..(20)
<223> OTHER INFORMATION: Xaa can be any naturally occurring amino acid

<400> SEQUENCE: 716

Phe Ser Cys Ser Trp Lys Gly Cys Glu Arg Arg Phe Ala Xaa Xaa Xaa
1               5                   10                  15

Xaa Xaa Xaa Xaa His Arg Arg Thr His
            20                  25

<210> SEQ ID NO 717
<211> LENGTH: 28
<212> TYPE: PRT
<213> ORGANISM: Artificial Sequence
<220> FEATURE:
<223> OTHER INFORMATION: the conserved regions of the zinc finger
        protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 717

Gly Ser Gln Lys Pro Phe Gln Cys Arg Ile Cys Met Arg Asn Phe Ser
1               5                   10                  15

Xaa Xaa Xaa Xaa Xaa Xaa Xaa His Ile Arg Thr His
            20                  25

<210> SEQ ID NO 718
<211> LENGTH: 23
<212> TYPE: PRT
<213> ORGANISM: Artificial Sequence
<220> FEATURE:
<223> OTHER INFORMATION: the conserved regions of the zinc finger
        protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 718

His Lys Cys Leu Glu Cys Gly Lys Cys Phe Ser Xaa Xaa Xaa Xaa Xaa
1               5                   10                  15

Xaa Xaa His Gln Arg Thr His
            20

<210> SEQ ID NO 719
<211> LENGTH: 28
<212> TYPE: PRT
<213> ORGANISM: Artificial Sequence
<220> FEATURE:
<223> OTHER INFORMATION: the conserved regions of the zinc finger
        protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 719

Met Ala Glu Arg Pro Phe Gln Cys Arg Ile Cys Met Arg Lys Phe Ala
1               5                   10                  15

Xaa Xaa Xaa Xaa Xaa Xaa Xaa His Thr Lys Ile His
            20                  25

<210> SEQ ID NO 720
```

```
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 720

Pro Gly Glu Lys Lys Phe Ala Cys Pro Glu Cys Pro Lys Arg Phe Met
1               5                   10                  15

Xaa Xaa Xaa Xaa Xaa Xaa Xaa His Ile Lys Thr His
            20                  25

<210> SEQ ID NO 721
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 721

Pro Gly Glu Lys Pro Phe Glu Cys Lys Asp Cys Gly Lys Ala Phe Ile
1               5                   10                  15

Xaa Xaa Xaa Xaa Xaa Xaa Xaa His Gln Arg Thr His
            20                  25

<210> SEQ ID NO 722
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 722

Pro Gly Glu Lys Pro Phe Lys Cys Pro Val Cys Gly Lys Ala Phe Arg
1               5                   10                  15

Xaa Xaa Xaa Xaa Xaa Xaa Xaa His Gln Arg Thr His
            20                  25

<210> SEQ ID NO 723
<211> LENGTH: 30
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (19)..(25)
<223> OTHER INFORMATION: Xaa can be any naturally occurring amino acid

<400> SEQUENCE: 723

Pro Gly Glu Lys Pro Phe Met Cys Thr Trp Ser Tyr Cys Gly Lys Arg
1               5                   10                  15
```

Phe Thr Xaa Xaa Xaa Xaa Xaa Xaa His Lys Arg Thr His
            20                  25                  30

<210> SEQ ID NO 724
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 724

Pro Gly Glu Lys Pro Phe Gln Cys Lys Thr Cys Gln Arg Lys Phe Ser
1               5                   10                  15

Xaa Xaa Xaa Xaa Xaa Xaa Xaa His Thr Arg Thr His
            20                  25

<210> SEQ ID NO 725
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 725

Pro Gly Glu Lys Pro Phe Gln Cys Asn Gln Cys Gly Ala Ser Phe Thr
1               5                   10                  15

Xaa Xaa Xaa Xaa Xaa Xaa Xaa His Ile Lys Leu His
            20                  25

<210> SEQ ID NO 726
<211> LENGTH: 30
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (19)..(25)
<223> OTHER INFORMATION: Xaa can be any naturally occurring amino acid

<400> SEQUENCE: 726

Pro Gly Glu Lys Pro His Ile Cys His Ile Gln Gly Cys Gly Lys Val
1               5                   10                  15

Tyr Gly Xaa Xaa Xaa Xaa Xaa Xaa Xaa His Leu Arg Trp His
            20                  25                  30

<210> SEQ ID NO 727
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid -continued

```
<400> SEQUENCE: 727

Pro Gly Glu Lys Pro Tyr Glu Cys Asp His Cys Gly Lys Ala Phe Ser
1               5                   10                  15

Xaa Xaa Xaa Xaa Xaa Xaa Xaa His Arg Arg Ile His
            20                  25

<210> SEQ ID NO 728
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 728

Pro Gly Glu Lys Pro Tyr Glu Cys Asp His Cys Gly Lys Ser Phe Ser
1               5                   10                  15

Xaa Xaa Xaa Xaa Xaa Xaa Xaa His Lys Arg Thr His
            20                  25

<210> SEQ ID NO 729
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 729

Pro Gly Glu Lys Pro Tyr Glu Cys Glu Lys Cys Gly Lys Ala Phe Asn
1               5                   10                  15

Xaa Xaa Xaa Xaa Xaa Xaa Xaa His Lys Lys Ser His
            20                  25

<210> SEQ ID NO 730
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 730

Pro Gly Glu Lys Pro Tyr Glu Cys His Asp Cys Gly Lys Ser Phe Arg
1               5                   10                  15

Xaa Xaa Xaa Xaa Xaa Xaa Xaa His Arg Arg Ile His
            20                  25

<210> SEQ ID NO 731
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
```

```
<220> FEATURE:
<221> NAME/KEY: misc_feature
<222> LOCATION: (17)..(23)
<223> OTHER INFORMATION: Xaa can be any naturally occurring amino acid

<400> SEQUENCE: 731

Pro Gly Glu Lys Pro Tyr Glu Cys Lys Glu Cys Gly Lys Ala Phe Ser
1               5                   10                  15

Xaa Xaa Xaa Xaa Xaa Xaa Xaa His Gln Arg Ile His
            20                  25

<210> SEQ ID NO 732
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 732

Pro Gly Glu Lys Pro Tyr Glu Cys Asn Tyr Cys Gly Lys Thr Phe Ser
1               5                   10                  15

Xaa Xaa Xaa Xaa Xaa Xaa Xaa His Gln Arg Ile His
            20                  25

<210> SEQ ID NO 733
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 733

Pro Gly Glu Lys Pro Tyr Gly Cys His Leu Cys Gly Lys Ala Phe Ser
1               5                   10                  15

Xaa Xaa Xaa Xaa Xaa Xaa Xaa His Glu Met Ile His
            20                  25

<210> SEQ ID NO 734
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 734

Pro Gly Glu Lys Pro Tyr Ile Cys Arg Lys Cys Gly Arg Gly Phe Ser
1               5                   10                  15

Xaa Xaa Xaa Xaa Xaa Xaa Xaa His Gln Arg Thr His
            20                  25

<210> SEQ ID NO 735
<211> LENGTH: 28
```

```
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 735

Pro Gly Glu Lys Pro Tyr Lys Cys Glu Glu Cys Gly Lys Ala Phe Asn
1               5                   10                  15

Xaa Xaa Xaa Xaa Xaa Xaa Xaa His Lys Ile Val His
            20                  25

<210> SEQ ID NO 736
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 736

Pro Gly Glu Lys Pro Tyr Lys Cys Glu Glu Cys Gly Lys Ala Phe Arg
1               5                   10                  15

Xaa Xaa Xaa Xaa Xaa Xaa Xaa His Lys Ile Ile His
            20                  25

<210> SEQ ID NO 737
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 737

Pro Gly Glu Lys Pro Tyr Lys Cys Glu Glu Cys Gly Lys Ala Phe Thr
1               5                   10                  15

Xaa Xaa Xaa Xaa Xaa Xaa Xaa His Lys Lys Ile His
            20                  25

<210> SEQ ID NO 738
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 738

Pro Gly Glu Lys Pro Tyr Lys Cys Gly Gln Cys Gly Lys Phe Tyr Ser
1               5                   10                  15

Xaa Xaa Xaa Xaa Xaa Xaa Xaa His Gln Lys Ile His
```

<210> SEQ ID NO 739
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 739

Pro Gly Glu Lys Pro Tyr Lys Cys His Gln Cys Gly Lys Ala Phe Ile
1               5                   10                  15

Xaa Xaa Xaa Xaa Xaa Xaa Xaa His Glu Arg Thr His
            20                  25

<210> SEQ ID NO 740
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 740

Pro Gly Glu Lys Pro Tyr Lys Cys Lys Glu Cys Gly Lys Ala Phe Asn
1               5                   10                  15

Xaa Xaa Xaa Xaa Xaa Xaa Xaa His His Arg Ile His
            20                  25

<210> SEQ ID NO 741
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 741

Pro Gly Glu Lys Pro Tyr Lys Cys Lys Glu Cys Gly Gln Ala Phe Arg
1               5                   10                  15

Xaa Xaa Xaa Xaa Xaa Xaa Xaa His His Lys Leu His
            20                  25

<210> SEQ ID NO 742
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 742

```
Pro Gly Glu Lys Pro Tyr Lys Cys Lys Gln Cys Gly Lys Ala Phe Gly
1               5                   10                  15

Xaa Xaa Xaa Xaa Xaa Xaa Xaa His Gly Arg Thr His
            20                  25

<210> SEQ ID NO 743
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 743

Pro Gly Glu Lys Pro Tyr Lys Cys Met Glu Cys Gly Lys Ala Phe Asn
1               5                   10                  15

Xaa Xaa Xaa Xaa Xaa Xaa Xaa His Gln Arg Ile His
            20                  25

<210> SEQ ID NO 744
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 744

Pro Gly Glu Lys Pro Tyr Lys Cys Pro Asp Cys Gly Lys Ser Phe Ser
1               5                   10                  15

Xaa Xaa Xaa Xaa Xaa Xaa Xaa His Gln Arg Thr His
            20                  25

<210> SEQ ID NO 745
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 745

Pro Gly Glu Lys Pro Tyr Lys Cys Pro Glu Cys Gly Lys Ser Phe Ser
1               5                   10                  15

Xaa Xaa Xaa Xaa Xaa Xaa Xaa His Gln Arg Thr His
            20                  25

<210> SEQ ID NO 746
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
```

```
<221> NAME/KEY: misc_feature
<222> LOCATION: (17)..(23)
<223> OTHER INFORMATION: Xaa can be any naturally occurring amino acid

<400> SEQUENCE: 746

Pro Gly Glu Lys Pro Tyr Met Cys Ser Glu Cys Gly Arg Gly Phe Ser
1               5                  10                  15

Xaa Xaa Xaa Xaa Xaa Xaa Xaa His Gln Arg Thr His
            20                  25

<210> SEQ ID NO 747
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 747

Pro Gly Glu Lys Pro Tyr Arg Cys Glu Glu Cys Gly Lys Ala Phe Arg
1               5                  10                  15

Xaa Xaa Xaa Xaa Xaa Xaa Xaa His Lys Arg Ile His
            20                  25

<210> SEQ ID NO 748
<211> LENGTH: 29
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 748

Pro Gly Glu Lys Pro Tyr Arg Cys Lys Tyr Cys Asp Arg Ser Phe Ser
1               5                  10                  15

Xaa Xaa Xaa Xaa Xaa Xaa Xaa His Val Arg Asn Ile His
            20                  25

<210> SEQ ID NO 749
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 749

Pro Gly Glu Lys Pro Tyr Thr Cys Lys Gln Cys Gly Lys Ala Phe Ser
1               5                  10                  15

Xaa Xaa Xaa Xaa Xaa Xaa Xaa His Glu Thr Thr His
            20                  25

<210> SEQ ID NO 750
<211> LENGTH: 28
<212> TYPE: PRT
```

<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 750

Pro Gly Glu Lys Pro Tyr Thr Cys Ser Asp Cys Gly Lys Ala Phe Arg
1               5                   10                  15

Xaa Xaa Xaa Xaa Xaa Xaa Xaa His Arg Arg Thr His
            20                  25

<210> SEQ ID NO 751
<211> LENGTH: 30
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (19)..(25)
<223> OTHER INFORMATION: Xaa can be any naturally occurring amino acid

<400> SEQUENCE: 751

Pro Gly Glu Lys Pro Tyr Val Cys Asp Val Glu Gly Cys Thr Trp Lys
1               5                   10                  15

Phe Ala Xaa Xaa Xaa Xaa Xaa Xaa Xaa His Lys Lys Arg His
            20                  25                  30

<210> SEQ ID NO 752
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 752

Pro Gly Glu Lys Pro Tyr Val Cys Arg Glu Cys Gly Arg Gly Phe Arg
1               5                   10                  15

Xaa Xaa Xaa Xaa Xaa Xaa Xaa His Lys Arg Thr His
            20                  25

<210> SEQ ID NO 753
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 753

Pro Gly Glu Lys Pro Tyr Val Cys Ser Lys Cys Gly Lys Ala Phe Thr
1               5                   10                  15

Xaa Xaa Xaa Xaa Xaa Xaa Xaa His Gln Lys Ile His
            20                  25

<210> SEQ ID NO 754
<211> LENGTH: 30
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (19)..(25)
<223> OTHER INFORMATION: Xaa can be any naturally occurring amino acid

<400> SEQUENCE: 754

Pro Gly Glu Arg Pro Phe Met Cys Thr Trp Ser Tyr Cys Gly Lys Arg
1               5                   10                  15

Phe Thr Xaa Xaa Xaa Xaa Xaa Xaa Xaa His Lys Arg Thr His
            20                  25                  30

<210> SEQ ID NO 755
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 755

Thr Gly Glu Lys Pro Phe Ala Cys Asp Ile Cys Gly Lys Lys Phe Ala
1               5                   10                  15

Xaa Xaa Xaa Xaa Xaa Xaa Xaa His Thr Lys Ile His
            20                  25

<210> SEQ ID NO 756
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 756

Thr Gly Glu Lys Pro Phe Ala Cys Asp Ile Cys Gly Lys Lys Phe Ala
1               5                   10                  15

Xaa Xaa Xaa Xaa Xaa Xaa Xaa His Thr Lys Ile His
            20                  25

<210> SEQ ID NO 757
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 757

```
Thr Gly Glu Lys Pro Phe Gln Cys Arg Ile Cys Met Arg Asn Phe Ser
1               5                   10                  15

Xaa Xaa Xaa Xaa Xaa Xaa Xaa His Ile Arg Thr His
            20                  25
```

<210> SEQ ID NO 758
<211> LENGTH: 29
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (18)..(24)
<223> OTHER INFORMATION: Xaa can be any naturally occurring amino acid

<400> SEQUENCE: 758

```
Thr Gly Ser Gln Lys Pro Phe Gln Cys Arg Ile Cys Met Arg Asn Phe
1               5                   10                  15

Ser Xaa Xaa Xaa Xaa Xaa Xaa Xaa His Ile Arg Thr His
            20                  25
```

<210> SEQ ID NO 759
<211> LENGTH: 28
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (17)..(23)
<223> OTHER INFORMATION: Xaa can be any naturally occurring amino acid

<400> SEQUENCE: 759

```
Val Pro Glu Arg Pro Phe Gln Cys Gln Ile Cys Met Arg Asn Phe Ser
1               5                   10                  15

Xaa Xaa Xaa Xaa Xaa Xaa Xaa His Ile Arg Thr His
            20                  25
```

<210> SEQ ID NO 760
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 760

```
Tyr Ala Cys His Leu Cys Ala Lys Ala Phe Ile Xaa Xaa Xaa Xaa Xaa
1               5                   10                  15

Xaa Xaa His Glu Lys Thr His
            20
```

<210> SEQ ID NO 761
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature

```
<222> LOCATION: (12)..(18)
<223> OTHER INFORMATION: Xaa can be any naturally occurring amino acid

<400> SEQUENCE: 761

Tyr Ala Cys His Leu Cys Gly Lys Ala Phe Thr Xaa Xaa Xaa Xaa Xaa
1               5                   10                  15

Xaa Xaa His Glu Lys Thr His
            20

<210> SEQ ID NO 762
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 762

Tyr Glu Cys Asp His Cys Gly Lys Ala Phe Ser Xaa Xaa Xaa Xaa Xaa
1               5                   10                  15

Xaa Xaa His Arg Arg Ile His
            20

<210> SEQ ID NO 763
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 763

Tyr Glu Cys Asp His Cys Gly Lys Ser Phe Ser Xaa Xaa Xaa Xaa Xaa
1               5                   10                  15

Xaa Xaa His Lys Arg Thr His
            20

<210> SEQ ID NO 764
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 764

Tyr Glu Cys Asp Val Cys Gly Lys Thr Phe Thr Xaa Xaa Xaa Xaa Xaa
1               5                   10                  15

Xaa Xaa His Gln Arg Thr His
            20

<210> SEQ ID NO 765
<211> LENGTH: 23
<212> TYPE: PRT
<213> ORGANISM: Artificial Sequence
```

```
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 765

Tyr Glu Cys Glu Lys Cys Gly Lys Ala Phe Asn Xaa Xaa Xaa Xaa Xaa
1               5                   10                  15

Xaa Xaa His Lys Lys Ser His
            20

<210> SEQ ID NO 766
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 766

Tyr Glu Cys His Asp Cys Gly Lys Ser Phe Arg Xaa Xaa Xaa Xaa Xaa
1               5                   10                  15

Xaa Xaa His Arg Arg Ile His
            20

<210> SEQ ID NO 767
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 767

Tyr Glu Cys Lys Glu Cys Gly Lys Ala Phe Ser Xaa Xaa Xaa Xaa Xaa
1               5                   10                  15

Xaa Xaa His Gln Arg Ile His
            20

<210> SEQ ID NO 768
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 768

Tyr Glu Cys Asn Glu Cys Gly Lys Ala Phe Ala Xaa Xaa Xaa Xaa Xaa
1               5                   10                  15

Xaa Xaa His Gln Arg Ile His
            20
```

```
<210> SEQ ID NO 769
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 769

Tyr Glu Cys Asn Glu Cys Gly Lys Phe Phe Ser Xaa Xaa Xaa Xaa Xaa
1               5                   10                  15

Xaa Xaa His Arg Arg Ser His
            20

<210> SEQ ID NO 770
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 770

Tyr Glu Cys Asn Thr Cys Arg Lys Thr Phe Ser Xaa Xaa Xaa Xaa Xaa
1               5                   10                  15

Xaa Xaa His Gln Arg Thr His
            20

<210> SEQ ID NO 771
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 771

Tyr Glu Cys Gln Asp Cys Gly Arg Ala Phe Asn Xaa Xaa Xaa Xaa Xaa
1               5                   10                  15

Xaa Xaa His Lys Arg Thr His
            20

<210> SEQ ID NO 772
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 772

Tyr Glu Cys Val Gln Cys Gly Lys Gly Phe Thr Xaa Xaa Xaa Xaa Xaa
```

```
                1               5                  10                 15

Xaa Xaa His Gln Arg Val His
            20

<210> SEQ ID NO 773
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 773

Tyr Glu Cys Val Gln Cys Gly Lys Ser Tyr Ser Xaa Xaa Xaa Xaa Xaa
1               5                  10                 15

Xaa Xaa His Gln Arg Arg His
            20

<210> SEQ ID NO 774
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 774

Tyr Gly Cys His Leu Cys Gly Lys Ala Phe Ser Xaa Xaa Xaa Xaa Xaa
1               5                  10                 15

Xaa Xaa His Glu Met Ile His
            20

<210> SEQ ID NO 775
<211> LENGTH: 25
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (14)..(20)
<223> OTHER INFORMATION: Xaa can be any naturally occurring amino acid

<400> SEQUENCE: 775

Tyr His Cys Asp Trp Asp Gly Cys Gly Trp Lys Phe Ala Xaa Xaa Xaa
1               5                  10                 15

Xaa Xaa Xaa Xaa His Tyr Arg Lys His
            20                  25

<210> SEQ ID NO 776
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
```

<223> OTHER INFORMATION: Xaa can be any naturally occurring amino acid

<400> SEQUENCE: 776

Tyr Ile Cys Arg Lys Cys Gly Arg Gly Phe Ser Xaa Xaa Xaa Xaa Xaa
1               5                   10                  15

Xaa Xaa His Gln Arg Thr His
            20

<210> SEQ ID NO 777
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 777

Tyr Lys Cys Asp Glu Cys Gly Lys Asn Phe Thr Xaa Xaa Xaa Xaa Xaa
1               5                   10                  15

Xaa Xaa His Lys Arg Ile His
            20

<210> SEQ ID NO 778
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 778

Tyr Lys Cys Glu Glu Cys Gly Lys Ala Phe Asn Xaa Xaa Xaa Xaa Xaa
1               5                   10                  15

Xaa Xaa His Lys Ile Val His
            20

<210> SEQ ID NO 779
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 779

Tyr Lys Cys Glu Glu Cys Gly Lys Ala Phe Arg Xaa Xaa Xaa Xaa Xaa
1               5                   10                  15

Xaa Xaa His Lys Ile Ile His
            20

<210> SEQ ID NO 780
<211> LENGTH: 23
<212> TYPE: PRT
<213> ORGANISM: Artificial Sequence
<220> FEATURE:

<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 780

Tyr Lys Cys Glu Glu Cys Gly Lys Ala Phe Thr Xaa Xaa Xaa Xaa Xaa
1               5                   10                  15

Xaa Xaa His Lys Lys Ile His
            20

<210> SEQ ID NO 781
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 781

Tyr Lys Cys Gly Gln Cys Gly Lys Phe Tyr Ser Xaa Xaa Xaa Xaa Xaa
1               5                   10                  15

Xaa Xaa His Gln Lys Ile His
            20

<210> SEQ ID NO 782
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 782

Tyr Lys Cys His Gln Cys Gly Lys Ala Phe Ile Xaa Xaa Xaa Xaa Xaa
1               5                   10                  15

Xaa Xaa His Glu Arg Thr His
            20

<210> SEQ ID NO 783
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 783

Tyr Lys Cys Lys Glu Cys Gly Lys Ala Phe Asn Xaa Xaa Xaa Xaa Xaa
1               5                   10                  15

Xaa Xaa His His Arg Ile His
            20

```
<210> SEQ ID NO 784
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 784

Tyr Lys Cys Lys Glu Cys Gly Gln Ala Phe Arg Xaa Xaa Xaa Xaa Xaa
1               5                   10                  15

Xaa Xaa His His Lys Leu His
            20

<210> SEQ ID NO 785
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 785

Tyr Lys Cys Lys Gln Cys Gly Lys Ala Phe Gly Xaa Xaa Xaa Xaa Xaa
1               5                   10                  15

Xaa Xaa His Gly Arg Thr His
            20

<210> SEQ ID NO 786
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 786

Tyr Lys Cys Met Glu Cys Gly Lys Ala Phe Asn Xaa Xaa Xaa Xaa Xaa
1               5                   10                  15

Xaa Xaa His Gln Arg Ile His
            20

<210> SEQ ID NO 787
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 787

Tyr Lys Cys Pro Asp Cys Gly Lys Ser Phe Ser Xaa Xaa Xaa Xaa Xaa
1               5                   10                  15
```

```
Xaa Xaa His Gln Arg Thr His
            20

<210> SEQ ID NO 788
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 788

Tyr Met Cys Ser Glu Cys Gly Arg Gly Phe Ser Xaa Xaa Xaa Xaa Xaa
1               5                   10                  15

Xaa Xaa His Gln Arg Thr His
            20

<210> SEQ ID NO 789
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 789

Tyr Gln Cys Asn Ile Cys Gly Lys Cys Phe Ser Xaa Xaa Xaa Xaa Xaa
1               5                   10                  15

Xaa Xaa His Gln Arg Thr His
            20

<210> SEQ ID NO 790
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 790

Tyr Arg Cys Glu Glu Cys Gly Lys Ala Phe Arg Xaa Xaa Xaa Xaa Xaa
1               5                   10                  15

Xaa Xaa His Lys Arg Ile His
            20

<210> SEQ ID NO 791
<211> LENGTH: 24
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid
```

```
<400> SEQUENCE: 791

Tyr Arg Cys Lys Tyr Cys Asp Arg Ser Phe Ser Xaa Xaa Xaa Xaa Xaa
1               5                   10                  15

Xaa Xaa His Val Arg Asn Ile His
            20

<210> SEQ ID NO 792
<211> LENGTH: 25
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (14)..(20)
<223> OTHER INFORMATION: Xaa can be any naturally occurring amino acid

<400> SEQUENCE: 792

Tyr Arg Cys Ser Trp Glu Gly Cys Glu Trp Arg Phe Ala Xaa Xaa Xaa
1               5                   10                  15

Xaa Xaa Xaa Xaa His Phe Arg Lys His
            20                  25

<210> SEQ ID NO 793
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 793

Tyr Ser Cys Gly Ile Cys Gly Lys Ser Phe Ser Xaa Xaa Xaa Xaa Xaa
1               5                   10                  15

Xaa Xaa His Cys Ile Leu His
            20

<210> SEQ ID NO 794
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 794

Tyr Thr Cys Lys Gln Cys Gly Lys Ala Phe Ser Xaa Xaa Xaa Xaa Xaa
1               5                   10                  15

Xaa Xaa His Glu Thr Thr His
            20

<210> SEQ ID NO 795
<211> LENGTH: 23
<212> TYPE: PRT
<213> ORGANISM: Artificial Sequence
<220> FEATURE:
<223> OTHER INFORMATION: the conserved regions of the zinc finger
```

```
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 795

Tyr Thr Cys Ser Asp Cys Gly Lys Ala Phe Arg Xaa Xaa Xaa Xaa Xaa
1               5                   10                  15

Xaa Xaa His Arg Arg Thr His
            20

<210> SEQ ID NO 796
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 796

Tyr Thr Cys Ser Tyr Cys Gly Lys Ser Phe Thr Xaa Xaa Xaa Xaa Xaa
1               5                   10                  15

Xaa Xaa His Thr Arg Ile His
            20

<210> SEQ ID NO 797
<211> LENGTH: 25
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (14)..(20)
<223> OTHER INFORMATION: Xaa can be any naturally occurring amino acid

<400> SEQUENCE: 797

Tyr Val Cys Asp Val Glu Gly Cys Thr Trp Lys Phe Ala Xaa Xaa Xaa
1               5                   10                  15

Xaa Xaa Xaa Xaa His Lys Lys Arg His
            20                  25

<210> SEQ ID NO 798
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 798

Tyr Val Cys Arg Glu Cys Gly Arg Gly Phe Arg Xaa Xaa Xaa Xaa Xaa
1               5                   10                  15

Xaa Xaa His Lys Arg Thr His
            20

<210> SEQ ID NO 799
```

```
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 799

Tyr Val Cys Arg Glu Cys Arg Arg Gly Phe Ser Xaa Xaa Xaa Xaa Xaa
1               5                   10                  15

Xaa Xaa His Gln Arg Thr His
            20

<210> SEQ ID NO 800
<211> LENGTH: 23
<212> TYPE: PRT
<213> ORGANISM: Artificial Sequence
<220> FEATURE:
<223> OTHER INFORMATION: the conserved regions of the zinc finger
      protein with insert for recognition helix
<220> FEATURE:
<221> NAME/KEY: misc_feature
<222> LOCATION: (12)..(18)
<223> OTHER INFORMATION: Xaa can be any naturally occurring amino acid

<400> SEQUENCE: 800

Tyr Val Cys Ser Lys Cys Gly Lys Ala Phe Thr Xaa Xaa Xaa Xaa Xaa
1               5                   10                  15

Xaa Xaa His Gln Lys Ile His
            20

<210> SEQ ID NO 801
<211> LENGTH: 32
<212> TYPE: DNA
<213> ORGANISM: Artificial Sequence
<220> FEATURE:
<223> OTHER INFORMATION: ablation recognition site

<400> SEQUENCE: 801
ggtcgatgtt cgcaacgtcg atcgtacgtg ca                                32

<210> SEQ ID NO 802
<211> LENGTH: 31
<212> TYPE: DNA
<213> ORGANISM: Artificial Sequence
<220> FEATURE:
<223> OTHER INFORMATION: ablation recognition site

<400> SEQUENCE: 802
ggtcggcgac gcgaatcgtc gattggcgta c                                 31

<210> SEQ ID NO 803
<211> LENGTH: 32
<212> TYPE: DNA
<213> ORGANISM: Artificial Sequence
<220> FEATURE:
<223> OTHER INFORMATION: ablation recognition site

<400> SEQUENCE: 803
actattcgca cgccgtacga tagtcggcgc ga                                32

<210> SEQ ID NO 804
<211> LENGTH: 28
```

```
<212> TYPE: DNA
<213> ORGANISM: Artificial Sequence
<220> FEATURE:
<223> OTHER INFORMATION: ablation recognition site

<400> SEQUENCE: 804
ggtcggcgac gcgtatcgat tggcgtac                                              28

<210> SEQ ID NO 805
<211> LENGTH: 5
<212> TYPE: PRT
<213> ORGANISM: Artificial Sequence
<220> FEATURE:
<223> OTHER INFORMATION: linker spacer

<400> SEQUENCE: 805

Gly Thr Ser Gly Lys
1               5

<210> SEQ ID NO 806
<211> LENGTH: 32
<212> TYPE: DNA
<213> ORGANISM: Artificial Sequence
<220> FEATURE:
<223> OTHER INFORMATION: a 32 bp sequence for ablation recognition site

<400> SEQUENCE: 806
ggtcgatgtt cgcaacgtcg atcgtacgtg ca                                         32

<210> SEQ ID NO 807
<211> LENGTH: 28
<212> TYPE: PRT
<213> ORGANISM: Artificial Sequence
<220> FEATURE:
<223> OTHER INFORMATION: a conserved sequence for zinc finger module
<220> FEATURE:
<221> NAME/KEY: misc_feature
<222> LOCATION: (17)..(23)
<223> OTHER INFORMATION: Xaa can be any naturally occurring amino acid

<400> SEQUENCE: 807

Thr Gly Glu Lys Pro Phe Gln Cys Arg Ile Cys Met Arg Asn Phe Ser
1               5                   10                  15

Xaa Xaa Xaa Xaa Xaa Xaa Xaa His Leu Arg Thr His
            20                  25

<210> SEQ ID NO 808
<211> LENGTH: 1443
<212> TYPE: DNA
<213> ORGANISM: Artificial Sequence
<220> FEATURE:
<223> OTHER INFORMATION: modified FokI_Cat enzyme
<220> FEATURE:
<221> NAME/KEY: CDS
<222> LOCATION: (1)..(1443)
<220> FEATURE:
<221> NAME/KEY: misc_feature
<222> LOCATION: (1)..(594)
<223> OTHER INFORMATION: FokI catalytic domain
<220> FEATURE:
<221> NAME/KEY: misc_feature
<222> LOCATION: (595)..(606)
<223> OTHER INFORMATION: 4 amino acid linker
<220> FEATURE:
<221> NAME/KEY: misc_feature
<222> LOCATION: (607)..(687)
<223> OTHER INFORMATION: zinc finger N1
<220> FEATURE:
<221> NAME/KEY: misc_feature
<222> LOCATION: (688)..(771)
```

```
<223> OTHER INFORMATION: zinc finger N2
<220> FEATURE:
<221> NAME/KEY: misc_feature
<222> LOCATION: (772)..(855)
<223> OTHER INFORMATION: zinc finger N3
<220> FEATURE:
<221> NAME/KEY: misc_feature
<222> LOCATION: (856)..(939)
<223> OTHER INFORMATION: zinc finger N4
<220> FEATURE:
<221> NAME/KEY: misc_feature
<222> LOCATION: (940)..(1023)
<223> OTHER INFORMATION: zinc finger N5
<220> FEATURE:
<221> NAME/KEY: misc_feature
<222> LOCATION: (1024)..(1107)
<223> OTHER INFORMATION: zinc finger N6
<220> FEATURE:
<221> NAME/KEY: misc_feature
<222> LOCATION: (1108)..(1191)
<223> OTHER INFORMATION: zinc finger N7
<220> FEATURE:
<221> NAME/KEY: misc_feature
<222> LOCATION: (1192)..(1275)
<223> OTHER INFORMATION: zinc finger N8
<220> FEATURE:
<221> NAME/KEY: misc_feature
<222> LOCATION: (1276)..(1359)
<223> OTHER INFORMATION: zinc finger N9
<220> FEATURE:
<221> NAME/KEY: misc_feature
<222> LOCATION: (1360)..(1443)
<223> OTHER INFORMATION: zinc finger N10

<400> SEQUENCE: 808 atg aag cag ctg gtg aaa agc gag ctg gaa gag aag aag tcc gag ctg      48
Met Lys Gln Leu Val Lys Ser Glu Leu Glu Glu Lys Lys Ser Glu Leu
1               5                   10                  15 cgg cac aag ctg aaa tac gtg ccc cac gag tac atc gag ctg atc gag      96
Arg His Lys Leu Lys Tyr Val Pro His Glu Tyr Ile Glu Leu Ile Glu
            20                  25                  30 atc gcc cgg aac ccc acc cag gac aga atc ctg gaa atg aag gtc atg     144
Ile Ala Arg Asn Pro Thr Gln Asp Arg Ile Leu Glu Met Lys Val Met
        35                  40                  45 gaa ttt ttc atg aag gtg tac ggc tac cgg ggc gag cac ctg ggc ggc     192
Glu Phe Phe Met Lys Val Tyr Gly Tyr Arg Gly Glu His Leu Gly Gly
    50                  55                  60 agc aga aaa ccc gac ggc gcc atc tac acc gtg ggc agc ccc atc gac     240
Ser Arg Lys Pro Asp Gly Ala Ile Tyr Thr Val Gly Ser Pro Ile Asp
65                  70                  75                  80 tac ggc gtg atc gtg gac acc aag gcc tac agc ggc ggc tac aac ctg     288
Tyr Gly Val Ile Val Asp Thr Lys Ala Tyr Ser Gly Gly Tyr Asn Leu
                85                  90                  95 ccc atc gga cag gcc gac gag atg cag aga tac gtg gaa gag aac cag     336
Pro Ile Gly Gln Ala Asp Glu Met Gln Arg Tyr Val Glu Glu Asn Gln
            100                 105                 110 acc cgg aac aag cac atc aac ccc aac gag tgg tgg aag gtg tac ccc     384
Thr Arg Asn Lys His Ile Asn Pro Asn Glu Trp Trp Lys Val Tyr Pro
        115                 120                 125 agc agc gtg acc gag ttc aag ttc ctg ttc gtg tcc ggc cac ttc aag     432
Ser Ser Val Thr Glu Phe Lys Phe Leu Phe Val Ser Gly His Phe Lys
    130                 135                 140 ggc aac tac aag gcc cag ctg acc cgg ctg aac cac atc acc aac tgc     480
Gly Asn Tyr Lys Ala Gln Leu Thr Arg Leu Asn His Ile Thr Asn Cys
145                 150                 155                 160 aac ggc gct gtg ctg agc gtg gaa gaa ctg ctg atc ggc ggc gag atg     528
Asn Gly Ala Val Leu Ser Val Glu Glu Leu Leu Ile Gly Gly Glu Met
                165                 170                 175
```

```
atc aag gcc ggc acc ctg acc ctg gaa gaa gtg cgg cgg aag ttc aac    576
Ile Lys Ala Gly Thr Leu Thr Leu Glu Glu Val Arg Arg Lys Phe Asn
            180                 185                 190 aac ggc gag atc aac ttc ggc act agt ggc ggc gag aag ccc tac aag    624
Asn Gly Glu Ile Asn Phe Gly Thr Ser Gly Gly Glu Lys Pro Tyr Lys
        195                 200                 205 tgc cct gag tgc ggc aag agc ttc agc cag aga aga agc ctg ggc cac    672
Cys Pro Glu Cys Gly Lys Ser Phe Ser Gln Arg Arg Ser Leu Gly His
    210                 215                 220 cac cag cgt acg cac ccc ggc gag aaa cct tat aag tgt ccc gaa tgt    720
His Gln Arg Thr His Pro Gly Glu Lys Pro Tyr Lys Cys Pro Glu Cys
225                 230                 235                 240 ggc aag tcc ttc agc aag aag aac gac ctg acc cgg cac cag cgg aca    768
Gly Lys Ser Phe Ser Lys Lys Asn Asp Leu Thr Arg His Gln Arg Thr
                245                 250                 255 cac ccc ggg gaa aag cca tac aaa tgt cca gag tgt ggg aag tct ttc    816
His Pro Gly Glu Lys Pro Tyr Lys Cys Pro Glu Cys Gly Lys Ser Phe
            260                 265                 270 tcc agc cgg cgg acc tgc aga gcc cat cag aga aca cat acc ggg gag    864
Ser Ser Arg Arg Thr Cys Arg Ala His Gln Arg Thr His Thr Gly Glu
        275                 280                 285 aag cct ttc cag tgc cgg atc tgc atg aga aac ttc agc gtg cgg cac    912
Lys Pro Phe Gln Cys Arg Ile Cys Met Arg Asn Phe Ser Val Arg His
    290                 295                 300 aac ctg acc aga cac ctg agg acc cat acc ggc gaa aaa ccc ttt cag    960
Asn Leu Thr Arg His Leu Arg Thr His Thr Gly Glu Lys Pro Phe Gln
305                 310                 315                 320 tgc aga atc tgt atg cgg aac ttc tcc gac cgg acc agc ctg gcc cgg   1008
Cys Arg Ile Cys Met Arg Asn Phe Ser Asp Arg Thr Ser Leu Ala Arg
                325                 330                 335 cat ctg aga act cat cct ggg gaa aag ccc tat aag tgt cca gaa tgc   1056
His Leu Arg Thr His Pro Gly Glu Lys Pro Tyr Lys Cys Pro Glu Cys
            340                 345                 350 ggg aaa tcc ttt agc gac agc ggc aac ctg cgg gtg cac cag agg act   1104
Gly Lys Ser Phe Ser Asp Ser Gly Asn Leu Arg Val His Gln Arg Thr
        355                 360                 365 cat cca ggc gag aaa ccc tac aaa tgc ccc gaa tgc gga aag tca ttc   1152
His Pro Gly Glu Lys Pro Tyr Lys Cys Pro Glu Cys Gly Lys Ser Phe
    370                 375                 380 tcc cac acc ggc cat ctg ctc gag cat cag cgg acc cac act ggg gag   1200
Ser His Thr Gly His Leu Leu Glu His Gln Arg Thr His Thr Gly Glu
385                 390                 395                 400 aaa cca ttt cag tgt cgc atc tgt atg agg aat ttc agc acc aac cag   1248
Lys Pro Phe Gln Cys Arg Ile Cys Met Arg Asn Phe Ser Thr Asn Gln
                405                 410                 415 gcc ctg ggc gtg cac ctg aga aca cac cca ggc gag aag cct tac aag   1296
Ala Leu Gly Val His Leu Arg Thr His Pro Gly Glu Lys Pro Tyr Lys
            420                 425                 430 tgt cca gag tgc gga aag tca ttt tcc gtg cgc cac aat ctg aca cgg   1344
Cys Pro Glu Cys Gly Lys Ser Phe Ser Val Arg His Asn Leu Thr Arg
        435                 440                 445 cat cag cgc acc cat ccc ggc gag aag cct tac aaa tgc ccc gag tgt   1392
His Gln Arg Thr His Pro Gly Glu Lys Pro Tyr Lys Cys Pro Glu Cys
    450                 455                 460 ggc aaa tct ttc agt gac cgg acc tct ctg gcc aga cat cag agg aca   1440
Gly Lys Ser Phe Ser Asp Arg Thr Ser Leu Ala Arg His Gln Arg Thr
465                 470                 475                 480 cac                                                               1443
His
```

<210> SEQ ID NO 809
<211> LENGTH: 481
<212> TYPE: PRT
<213> ORGANISM: Artificial Sequence
<220> FEATURE:
<223> OTHER INFORMATION: Synthetic Construct

<400> SEQUENCE: 809

```
Met Lys Gln Leu Val Lys Ser Glu Leu Glu Glu Lys Ser Glu Leu
1               5                   10                  15

Arg His Lys Leu Lys Tyr Val Pro His Glu Tyr Ile Glu Leu Ile Glu
                20                  25                  30

Ile Ala Arg Asn Pro Thr Gln Asp Arg Ile Leu Glu Met Lys Val Met
            35                  40                  45

Glu Phe Phe Met Lys Val Tyr Gly Tyr Arg Gly Glu His Leu Gly Gly
50                  55                  60

Ser Arg Lys Pro Asp Gly Ala Ile Tyr Thr Val Gly Ser Pro Ile Asp
65                  70                  75                  80

Tyr Gly Val Ile Val Asp Thr Lys Ala Tyr Ser Gly Gly Tyr Asn Leu
                85                  90                  95

Pro Ile Gly Gln Ala Asp Glu Met Gln Arg Tyr Val Glu Glu Asn Gln
            100                 105                 110

Thr Arg Asn Lys His Ile Asn Pro Asn Glu Trp Trp Lys Val Tyr Pro
        115                 120                 125

Ser Ser Val Thr Glu Phe Lys Phe Leu Phe Val Ser Gly His Phe Lys
130                 135                 140

Gly Asn Tyr Lys Ala Gln Leu Thr Arg Leu Asn His Ile Thr Asn Cys
145                 150                 155                 160

Asn Gly Ala Val Leu Ser Val Glu Glu Leu Leu Ile Gly Gly Glu Met
                165                 170                 175

Ile Lys Ala Gly Thr Leu Thr Leu Glu Glu Val Arg Arg Lys Phe Asn
            180                 185                 190

Asn Gly Glu Ile Asn Phe Gly Thr Ser Gly Gly Glu Lys Pro Tyr Lys
        195                 200                 205

Cys Pro Glu Cys Gly Lys Ser Phe Ser Gln Arg Arg Ser Leu Gly His
210                 215                 220

His Gln Arg Thr His Pro Gly Glu Lys Pro Tyr Lys Cys Pro Glu Cys
225                 230                 235                 240

Gly Lys Ser Phe Ser Lys Lys Asn Asp Leu Thr Arg His Gln Arg Thr
                245                 250                 255

His Pro Gly Glu Lys Pro Tyr Lys Cys Pro Glu Cys Gly Lys Ser Phe
            260                 265                 270

Ser Ser Arg Arg Thr Cys Arg Ala His Gln Arg Thr His Thr Gly Glu
        275                 280                 285

Lys Pro Phe Gln Cys Arg Ile Cys Met Arg Asn Phe Ser Val Arg His
290                 295                 300

Asn Leu Thr Arg His Leu Arg Thr His Thr Gly Glu Lys Pro Phe Gln
305                 310                 315                 320

Cys Arg Ile Cys Met Arg Asn Phe Ser Asp Arg Thr Ser Leu Ala Arg
                325                 330                 335

His Leu Arg Thr His Pro Gly Glu Lys Pro Tyr Lys Cys Pro Glu Cys
            340                 345                 350

Gly Lys Ser Phe Ser Asp Ser Gly Asn Leu Arg Val His Gln Arg Thr
        355                 360                 365
```

His Pro Gly Glu Lys Pro Tyr Lys Cys Pro Glu Cys Gly Lys Ser Phe
        370                 375                 380

Ser His Thr Gly His Leu Leu Glu His Gln Arg Thr His Thr Gly Glu
385                 390                 395                 400

Lys Pro Phe Gln Cys Arg Ile Cys Met Arg Asn Phe Ser Thr Asn Gln
            405                 410                 415

Ala Leu Gly Val His Leu Arg Thr His Pro Gly Glu Lys Pro Tyr Lys
            420                 425                 430

Cys Pro Glu Cys Gly Lys Ser Phe Ser Val Arg His Asn Leu Thr Arg
        435                 440                 445

His Gln Arg Thr His Pro Gly Glu Lys Pro Tyr Lys Cys Pro Glu Cys
    450                 455                 460

Gly Lys Ser Phe Ser Asp Arg Thr Ser Leu Ala Arg His Gln Arg Thr
465                 470                 475                 480

His

<210> SEQ ID NO 810
<211> LENGTH: 2991
<212> TYPE: DNA
<213> ORGANISM: Artificial Sequence
<220> FEATURE:
<223> OTHER INFORMATION: plasmid reporter gene expression
<220> FEATURE:
<221> NAME/KEY: misc_feature
<222> LOCATION: (1)..(832)
<223> OTHER INFORMATION: CMV I.E. enhancer and promoter
<220> FEATURE:
<221> NAME/KEY: misc_feature
<222> LOCATION: (833)..(1029)
<223> OTHER INFORMATION: Promega intron
<220> FEATURE:
<221> NAME/KEY: misc_feature
<222> LOCATION: (1077)..(1082)
<223> OTHER INFORMATION: Kozak sequence
<220> FEATURE:
<221> NAME/KEY: misc_feature
<222> LOCATION: (1083)..(2732)
<223> OTHER INFORMATION: Luciferase
<220> FEATURE:
<221> NAME/KEY: misc_feature
<222> LOCATION: (2752)..(2991)
<223> OTHER INFORMATION: SV40 polyA

<400> SEQUENCE: 810
taggaagatc ttcaatattg gccattagcc atattattca ttggttatat agcataaatc    60
aatattggct attggccatt gcatacgttg tatctatatc ataatatgta catttatatt   120
ggctcatgtc caatatgacc gccatgttgg cattgattat tgactagtta ttaatagtaa   180
tcaattacgg ggtcattagt tcatagccca tatatggagt tccgcgttac ataacttacg   240
gtaaatggcc cgcctggctg accgcccaac gacccccgcc cattgacgtc aataatgacg   300
tatgttccca tagtaacgcc aatagggact ttccattgac gtcaatgggt ggagtattta   360
cggtaaactg cccacttggc agtacatcaa gtgtatcata tgccaagtcc gccccctatt   420
gacgtcaatg acggtaaatg gcccgcctgg cattatgccc agtacatgac cttacgggac   480
tttcctactt ggcagtacat ctacgtatta gtcatcgcta ttaccatggt gatgcggttt   540
tggcagtaca ccaatgggcg tggatagcgg tttgactcac ggggatttcc aagtctccac   600
cccattgacg tcaatgggag tttgttttgg caccaaaatc aacgggactt tccaaaatgt   660
cgtaataacc ccgccccgtt gacgcaaatg ggcggtaggc gtgtacgtg ggaggtctat   720 ataagcagag ctcgtttagt gaaccgtcag atcactagaa gctttattgc ggtagtttat   780

```
cacagttaaa ttgctaacgc agtcagtgct tctgacacaa cagtctcgaa cttaagctgc      840
agaagttggt cgtgaggcac tgggcaggta agtatcaagg ttacaagaca ggtttaagga      900
gaccaataga aactgggctt gtcgagacag agaagactct tgcgtttctg ataggcacct      960
attggtctta ctgacatcca ctttgccttt ctctccacag gtgtccactc ccagttcaat     1020
tacagctctt aaggctagag tacttaatac gactcactat aggctagcgc gatcgcgcca     1080
ccatggaaga tgccaaaaac attaagaagg gcccagcgcc attctaccca ctcgaagacg     1140
ggaccgccgg cgagcagctg cacaaagcca tgaagcgcta cgccctggtg cccggcacca     1200
tcgcctttac cgacgcacat atcgaggtgg acattaccta cgccgagtac ttcgagatga     1260
gcgttcggct ggcagaagct atgaagcgct atgggctgaa tacaaaccat cggatcgtgg     1320
tgtgcagcga aatagcttg cagttcttca tgcccgtgtt gggtgccctg ttcatcggtg     1380
tggctgtggc cccagctaac gacatctaca acgagcgcga gctgctgaac agcatgggca     1440
tcagccagcc caccgtcgta ttcgtgagca agaaagggct gcaaaagatc ctcaacgtgc     1500
aaaagaagct accgatcata caaaagatca tcatcatgga tagcaagacc gactaccagg     1560
gcttccaaag catgtacacc ttcgtgactt cccatttgcc acccggcttc aacgagtacg     1620
acttcgtgcc cgagagcttc gaccgggaca aaaccatcgc cctgatcatg aacagtagtg     1680
gcagtaccgg attgcccaag ggcgtagccc taccgcaccg caccgcttgt gtccgattca     1740
gtcatgcccg cgacccatc ttcggcaacc agatcatccc cgacaccgct atcctcagcg     1800
tggtgccatt tcaccacggc ttcggcatgt tcaccacgct gggctacttg atctgcggct     1860
ttcgggtcgt gctcatgtac cgcttcgagg aggagctatt cttgcgcagc ttgcaagact     1920
ataagattca atctgccctg ctggtgccca cactatttag cttcttcgct aagagcactc     1980
tcatcgacaa gtacgaccta agcaacttgc acgagatcgc cagcggcggg gcgccgctca     2040
gcaaggaggt aggtgaggcc gtggccaaac gcttccacct accaggcatc cgccagggct     2100
acggcctgac agaaacaacc agcgccattc tgatcacccc cgaagggac gacaagcctg     2160 gcgcagtagg caaggtggtg cccttcttcg aggctaaggt ggtggacttg gacaccggta     2220
agacactggg tgtgaaccag cgcggcgagc tgtgcgtccg tggccccatg atcatgagcg     2280
gctacgttaa caacccccgag gctacaaacg ctctcatcga caaggacggc tggctgcaca     2340
gcggcgacat cgcctactgg gacgaggacg agcacttctt catcgtggac cggctgaaga     2400
gcctgatcaa atacaagggc taccaggtag ccccagccga actggagagc atcctgctgc     2460
aacaccccaa catcttcgac gccggggtcg ccggcctgcc cgacgacgat gccggcgagc     2520
tgcccgccgc agtcgtcgtg ctggaacacg gtaaaaccat gaccgagaag gagatcgtgg     2580
actatgtggc cagccaggtt acaaccgcca agaagctgcg cggtggtgtt gtgttcgtgg     2640
acgaggtgcc taaaggactg accggcaagt tggacgcccg caagatccgc gagattctca     2700
ttaaggccaa gaagggcggc aagatcgccg tgtaataagc atgcaagctt gcggccgctt     2760
cgagcagaca tgataagata cattgatgag tttggacaaa ccacaactag aatgcagtga     2820
aaaaaatgct ttatttgtga aatttgtgat gctattgctt tatttgtaac cattataagc     2880
tgcaataaac aagttaacaa caacaattgc attcatttta tgtttcaggt tcaggggag     2940 atgtgggagg ttttttaaag caagtaaaac ctctacaaat gtggtaaaat c              2991
```

<210> SEQ ID NO 811
<211> LENGTH: 3061
<212> TYPE: DNA

```
<213> ORGANISM: Artificial Sequence
<220> FEATURE:
<223> OTHER INFORMATION: plasmid reporter gene expression
<220> FEATURE:
<221> NAME/KEY: misc_feature
<222> LOCATION: (1)..(832)
<223> OTHER INFORMATION: CMV I.E. enhancer and promoter
<220> FEATURE:
<221> NAME/KEY: misc_feature
<222> LOCATION: (833)..(1029)
<223> OTHER INFORMATION: Promega intron
<220> FEATURE:
<221> NAME/KEY: misc_feature
<222> LOCATION: (1069)..(1100)
<223> OTHER INFORMATION: 32 bp sequence in direct orientation
<220> FEATURE:
<221> NAME/KEY: misc_feature
<222> LOCATION: (1101)..(1106)
<223> OTHER INFORMATION: spacer
<220> FEATURE:
<221> NAME/KEY: misc_feature
<222> LOCATION: (1107)..(1138)
<223> OTHER INFORMATION: 32 pb sequence in inverted orientation
<220> FEATURE:
<221> NAME/KEY: misc_feature
<222> LOCATION: (1147)..(1152)
<223> OTHER INFORMATION: Kozak sequence
<220> FEATURE:
<221> NAME/KEY: misc_feature
<222> LOCATION: (1153)..(2802)
<223> OTHER INFORMATION: Luciferase
<220> FEATURE:
<221> NAME/KEY: misc_feature
<222> LOCATION: (2822)..(3061)
<223> OTHER INFORMATION: SV40 polyA

<400> SEQUENCE: 811
taggaagatc ttcaatattg gccattagcc atattattca ttggttatat agcataaatc    60
aatattggct attggccatt gcatacgttg tatctatatc ataatatgta catttatatt   120
ggctcatgtc caatatgacc gccatgttgg cattgattat tgactagtta ttaatagtaa   180
tcaattacgg ggtcattagt tcatagccca tatatggagt tccgcgttac ataacttacg   240
gtaaatggcc cgcctggctg accgcccaac gacccccgcc cattgacgtc aataatgacg   300
tatgttccca tagtaacgcc aatagggact ttccattgac gtcaatgggt ggagtattta   360
cggtaaactg cccacttggc agtacatcaa gtgtatcata tgccaagtcc gccccctatt   420
gacgtcaatg acggtaaatg gcccgcctgg cattatgccc agtacatgac cttacgggac   480
tttcctactt ggcagtacat ctacgtatta gtcatcgcta ttaccatggt gatgcggttt   540
tggcagtaca ccaatgggcg tggatagcgg tttgactcac ggggatttcc aagtctccac   600
cccattgacg tcaatgggag tttgttttgg caccaaaatc aacgggactt tccaaaatgt   660
cgtaataacc ccgccccgtt gacgcaaatg ggcggtaggc gtgtacggtg ggaggtctat   720
ataagcagag ctcgtttagt gaaccgtcag atcactagaa gctttattgc ggtagtttat   780
cacagttaaa ttgctaacgc agtcagtgct tctgacacaa cagtctcgaa cttaagctgc   840
agaagttggt cgtgaggcac tgggcaggta agtatcaagg ttacaagaca ggtttaagga   900
gaccaataga aactgggctt gtcgagacag agaagactct tgcgtttctg ataggcacct   960
attggtctta ctgacatcca ctttgccttt ctctccacag gtgtccactc ccagttcaat  1020
tacagctctt aaggctagag tacttaatac gactcactat aggctagcgg tcgatgttcg  1080
caacgtcgat cgtacgtgca acgcgttgca cgtacgatcg acgttgcgaa catcgaccgc  1140
gatcgcgcca ccatggaaga tgccaaaaac attaagaagg gcccagcgcc attctaccca  1200
ctcgaagacg ggaccgccgg cgagcagctg cacaaagcca tgaagcgcta cgccctggtg  1260
```

```
cccggcacca tcgcctttac cgacgcacat atcgaggtgg acattaccta cgccgagtac   1320
ttcgagatga gcgttcggct ggcagaagct atgaagcgct atgggctgaa tacaaaccat   1380
cggatcgtgg tgtgcagcga gaatagcttg cagttcttca tgcccgtgtt gggtgccctg   1440
ttcatcggtg tggctgtggc cccagctaac gacatctaca cgagcgcga gctgctgaac   1500 agcatgggca tcagccagcc caccgtcgta ttcgtgagca agaaagggct gcaaaagatc   1560
ctcaacgtgc aaaagaagct accgatcata caaaagatca tcatcatgga tagcaagacc   1620
gactaccagg gcttccaaag catgtacacc ttcgtgactt cccatttgcc acccggcttc   1680
aacgagtacg acttcgtgcc cgagagcttc gaccgggaca aaaccatcgc cctgatcatg   1740
aacagtagtg gcagtaccgg attgcccaag ggcgtagccc taccgcaccg caccgcttgt   1800
gtccgattca gtcatgcccg cgaccccatc ttcggcaacc agatcatccc cgacaccgct   1860
atcctcagcg tggtgccatt tcaccacggc ttcggcatgt tcaccacgct gggctacttg   1920
atctgcggct ttcgggtcgt gctcatgtac cgcttcgagg aggagctatt cttgcgcagc   1980
ttgcaagact ataagattca atctgccctg ctggtgccca cactatttag cttcttcgct   2040
aagagcactc tcatcgacaa gtacgaccta agcaacttgc acgagatcgc cagcggcggg   2100
gcgccgctca gcaaggaggt aggtgaggcc gtggccaaac gcttccacct accaggcatc   2160
cgccagggct acggcctgac agaaacaacc agcgccattc tgatcacccc cgaaggggac   2220
gacaagcctg gcgcagtagg caaggtggtg cccttcttcg aggctaaggt ggtggacttg   2280
gacaccggta agacactggg tgtgaaccag cgcggcgagc tgtgcgtccg tggccccatg   2340
atcatgagcg gctacgttaa caaccccgag gctacaaacg ctctcatcga caaggacggc   2400
tggctgcaca gcggcgacat cgcctactgg gacgaggacg agcacttctt catcgtggac   2460
cggctgaaga gcctgatcaa atacaagggc taccaggtag ccccagccga actggagagc   2520
atcctgctgc aacaccccaa catcttcgac gccggggtcg ccggcctgcc cgacgacgat   2580
gccggcgagc tgcccgccgc agtcgtcgtg ctggaacacg gtaaaaccat gaccgagaag   2640
gagatcgtgg actatgtggc cagccaggtt acaaccgcca agaagctgcg cggtggtgtt   2700
gtgttcgtgg acgaggtgcc taaaggactg accggcaagt tggacgcccg caagatccgc   2760
gagattctca ttaaggccaa gaagggcggc aagatcgccg tgtaataagc atgcaagctt   2820
gcggccgctt cgagcagaca tgataagata cattgatgag tttggacaaa ccacaactag   2880
aatgcagtga aaaaaatgct ttatttgtga aatttgtgat gctattgctt tatttgtaac   2940
cattataagc tgcaataaac aagttaacaa caacaattgc attcatttta tgtttcaggt   3000
tcagggggag atgtgggagg ttttttaaag caagtaaaac ctctacaaat gtggtaaaat   3060
c                                                                   3061
```

<210> SEQ ID NO 812
<211> LENGTH: 3131
<212> TYPE: DNA
<213> ORGANISM: Artificial Sequence
<220> FEATURE:
<223> OTHER INFORMATION: plasmid reporter gene expression
<220> FEATURE:
<221> NAME/KEY: misc_feature
<222> LOCATION: (1)..(832)
<223> OTHER INFORMATION: CMV I.E. enhancer and promoter
<220> FEATURE:
<221> NAME/KEY: misc_feature
<222> LOCATION: (833)..(1029)
<223> OTHER INFORMATION: Promega intron
<220> FEATURE:

```
<221> NAME/KEY: misc_feature
<222> LOCATION: (1069)..(1100)
<223> OTHER INFORMATION: 32 bp sequence in direct orientation
<220> FEATURE:
<221> NAME/KEY: misc_feature
<222> LOCATION: (1101)..(1106)
<223> OTHER INFORMATION: spacer
<220> FEATURE:
<221> NAME/KEY: misc_feature
<222> LOCATION: (1107)..(1138)
<223> OTHER INFORMATION: 32 bp sequence in inverted orientation
<220> FEATURE:
<221> NAME/KEY: misc_feature
<222> LOCATION: (1147)..(1152)
<223> OTHER INFORMATION: Kozak sequence
<220> FEATURE:
<221> NAME/KEY: misc_feature
<222> LOCATION: (1153)..(2802)
<223> OTHER INFORMATION: Luciferase
<220> FEATURE:
<221> NAME/KEY: misc_feature
<222> LOCATION: (2815)..(2846)
<223> OTHER INFORMATION: 32 bp sequence in direct orientation
<220> FEATURE:
<221> NAME/KEY: misc_feature
<222> LOCATION: (2847)..(2852)
<223> OTHER INFORMATION: spacer
<220> FEATURE:
<221> NAME/KEY: misc_feature
<222> LOCATION: (2853)..(2884)
<223> OTHER INFORMATION: 32 bp sequence in inverted orientation
<220> FEATURE:
<221> NAME/KEY: misc_feature
<222> LOCATION: (2893)..(3131)
<223> OTHER INFORMATION: SV40 polyA

<400> SEQUENCE: 812
taggaagatc ttcaatattg gccattagcc atattattca ttggttatat agcataaatc      60
aatattggct attggccatt gcatacgttg tatctatatc ataatatgta catttatatt     120
ggctcatgtc caatatgacc gccatgttgg cattgattat tgactagtta ttaatagtaa     180
tcaattacgg ggtcattagt tcatagccca tatatggagt tccgcgttac ataacttacg     240
gtaaatggcc cgcctggctg accgcccaac gacccccgcc cattgacgtc aataatgacg     300
tatgttccca tagtaacgcc aatagggact ttccattgac gtcaatgggt ggagtattta     360
cggtaaactg cccacttggc agtacatcaa gtgtatcata tgccaagtcc gcccctatt      420 gacgtcaatg acggtaaatg gcccgcctgg cattatgccc agtacatgac cttacgggac     480
tttcctactt ggcagtacat ctacgtatta gtcatcgcta ttaccatggt gatgcggttt     540
tggcagtaca ccaatgggcg tggatagcgg tttgactcac ggggatttcc aagtctccac     600
cccattgacg tcaatgggag tttgttttgg caccaaaatc aacgggactt tccaaaatgt     660
cgtaataacc ccgccccgtt gacgcaaatg ggcggtaggc gtgtacggtg ggaggtctat     720
ataagcagag ctcgtttagt gaaccgtcag atcactagaa gctttattgc ggtagtttat     780
cacagttaaa ttgctaacgc agtcagtgct tctgacacaa cagtctcgaa cttaagctgc     840
agaagttggt cgtgaggcac tgggcaggta agtatcaagg ttacaagaca ggtttaagga     900
gaccaataga aactgggctt gtcgagacag agaagactct tgcgtttctg ataggcacct     960
attggtctta ctgacatcca ctttgccttt ctctccacag gtgtccactc ccagttcaat    1020
tacagctctt aaggctagag tacttaatac gactcactat aggctagcgg tcgatgttcg    1080
caacgtcgat cgtacgtgca acgcgttgca cgtacgatcg acgttgcgaa catcgaccgc    1140
gatcgcgcca ccatggaaga tgccaaaaac attaagaagg gcccagcgcc attctaccca    1200
ctcgaagacg ggaccgccgg cgagcagctg cacaaagcca tgaagcgcta cgccctggtg    1260
```

```
cccggcacca tcgcctttac cgacgcacat atcgaggtgg acattaccta cgccgagtac   1320
ttcgagatga gcgttcggct ggcagaagct atgaagcgct atgggctgaa tacaaaccat   1380
cggatcgtgg tgtgcagcga gaatagcttg cagttcttca tgcccgtgtt gggtgccctg   1440
ttcatcggtg tggctgtggc cccagctaac gacatctaca cgagcgcga gctgctgaac    1500 agcatgggca tcagccagcc caccgtcgta ttcgtgagca agaaagggct gcaaaagatc   1560
ctcaacgtgc aaaagaagct accgatcata caaaagatca tcatcatgga tagcaagacc   1620
gactaccagg gcttccaaag catgtacacc ttcgtgactt cccatttgcc acccggcttc   1680
aacgagtacg acttcgtgcc cgagagcttc gaccgggaca aaaccatcgc cctgatcatg   1740
aacagtagtg gcagtaccgg attgcccaag ggcgtagccc taccgcaccg caccgcttgt   1800
gtccgattca gtcatgcccg cgaccccatc ttcggcaacc agatcatccc cgacaccgct   1860
atcctcagcg tggtgccatt tcaccacggc ttcggcatgt tcaccacgct gggctacttg   1920
atctgcggct ttcgggtcgt gctcatgtac cgcttcgagg aggagctatt cttgcgcagc   1980
ttgcaagact ataagattca atctgccctg ctggtgccca cactatttag cttcttcgct   2040
aagagcactc tcatcgacaa gtacgaccta agcaacttgc acgagatcgc cagcggcggg   2100
gcgccgctca gcaaggaggt aggtgaggcc gtggccaaac gcttccacct accaggcatc   2160
cgccagggct acggcctgac agaaacaacc agcgccattc tgatcacccc cgaaggggac   2220
gacaagcctg gcgcagtagg caaggtggtg cccttcttcg aggctaaggt ggtggacttg   2280
gacaccggta agacactggg tgtgaaccag cgcggcgagc tgtgcgtccg tggccccatg   2340
atcatgagcg gctacgttaa caaccccgag gctacaaacg ctctcatcga caaggacggc   2400
tggctgcaca gcggcgacat cgcctactgg gacgaggacg agcacttctt catcgtggac   2460
cggctgaaga gcctgatcaa atacaagggc taccaggtag ccccagccga actggagagc   2520
atcctgctgc aacaccccaa catcttcgac gccggggtcg ccggcctgcc cgacgacgat   2580
gccggcgagc tgcccgccgc agtcgtcgtg ctggaacacg gtaaaaccat gaccgagaag   2640
gagatcgtgg actatgtggc cagccaggtt acaaccgcca agaagctgcg cggtggtgtt   2700
gtgttcgtgg acgaggtgcc taaaggactg accggcaagt tggacgcccg caagatccgc   2760
gagattctca ttaaggccaa gaagggcggc aagatcgccg tgtaataagc atgcggtcga   2820
tgttcgcaac gtcgatcgta cgtgcaacgc gttcacgta cgatcgacgt tgcgaacatc     2880
gaccaagctt gcggccgctt cgagcagaca tgataagata cattgatgag tttggacaaa   2940
ccacaactag aatgcagtga aaaaaatgct ttatttgtga aatttgtgat gctattgctt   3000
tatttgtaac cattataagc tgcaataaac aagttaacaa caacaattgc attcatttta   3060
tgtttcaggt tcaggggag atgtgggagg ttttttaaag caagtaaaac ctctacaaat   3120
gtggtaaaat c                                                        3131
```

<210> SEQ ID NO 813
<211> LENGTH: 3029
<212> TYPE: DNA
<213> ORGANISM: Artificial Sequence
<220> FEATURE:
<223> OTHER INFORMATION: plasmid reporter gene expression
<220> FEATURE:
<221> NAME/KEY: misc_feature
<222> LOCATION: (1)..(832)
<223> OTHER INFORMATION: CMV I.E. enhancer and promoter
<220> FEATURE:
<221> NAME/KEY: misc_feature
<222> LOCATION: (833)..(1029)

<223> OTHER INFORMATION: Promega intron
<220> FEATURE:
<221> NAME/KEY: misc_feature
<222> LOCATION: (1069)..(1100)
<223> OTHER INFORMATION: 32 bp sequence in direct orientation
<220> FEATURE:
<221> NAME/KEY: misc_feature
<222> LOCATION: (1115)..(1120)
<223> OTHER INFORMATION: Kozak sequence
<220> FEATURE:
<221> NAME/KEY: misc_feature
<222> LOCATION: (1121)..(2770)
<223> OTHER INFORMATION: Luciferase
<220> FEATURE:
<221> NAME/KEY: misc_feature
<222> LOCATION: (2791)..(3029)
<223> OTHER INFORMATION: SV40 polyA

<400> SEQUENCE: 813

| | | | | | |
|---|---|---|---|---|---|
| taggaagatc | ttcaatattg | gccattagcc | atattattca | ttggttatat | agcataaatc | 60 |
| aatattggct | attggccatt | gcatacgttg | tatctatatc | ataatatgta | catttatatt | 120 |
| ggctcatgtc | caatatgacc | gccatgttgg | cattgattat | tgactagtta | ttaatagtaa | 180 |
| tcaattacgg | ggtcattagt | tcatagccca | tatatggagt | tccgcgttac | ataacttacg | 240 |
| gtaaatggcc | cgcctggctg | accgcccaac | gacccccgcc | cattgacgtc | aataatgacg | 300 |
| tatgttccca | tagtaacgcc | aatagggact | ttccattgac | gtcaatgggt | ggagtattta | 360 |
| cggtaaactg | cccacttggc | agtacatcaa | gtgtatcata | tgccaagtcc | gccccctatt | 420 |
| gacgtcaatg | acggtaaatg | gcccgcctgg | cattatgccc | agtacatgac | cttacgggac | 480 |
| tttcctactt | ggcagtacat | ctacgtatta | gtcatcgcta | ttaccatggt | gatgcggttt | 540 |
| tggcagtaca | ccaatgggcg | tggatagcgg | tttgactcac | ggggatttcc | aagtctccac | 600 |
| cccattgacg | tcaatgggag | tttgttttgg | caccaaaatc | aacgggactt | tccaaaatgt | 660 |
| cgtaataacc | ccgccccgtt | gacgcaaatg | ggcggtaggc | gtgtacggtg | ggaggtctat | 720 |
| ataagcagag | ctcgtttagt | gaaccgtcag | atcactagaa | gctttattgc | ggtagtttat | 780 |
| cacagttaaa | ttgctaacgc | agtcagtgct | tctgacacaa | cagtctcgaa | cttaagctgc | 840 |
| agaagttggt | cgtgaggcac | tgggcaggta | agtatcaagg | ttacaagaca | ggtttaagga | 900 |
| gaccaataga | aactgggctt | gtcgagacag | agaagactct | tgcgtttctg | ataggcacct | 960 |
| attggtctta | ctgacatcca | ctttgccttt | ctctccacag | tgtccactc | ccagttcaat | 1020 |
| tacagctctt | aaggctagag | tacttaatac | gactcactat | aggctagcgg | tcgatgttcg | 1080 |
| caacgtcgat | cgtacgtgca | acgcgtgcga | tcgcgccacc | atggaagatg | ccaaaaacat | 1140 |
| taagaagggc | ccagcgccat | tctacccact | cgaagacggg | accgccggcg | agcagctgca | 1200 |
| caaagccatg | aagcgctacg | ccctggtgcc | cggcaccatc | gcctttaccg | acgcacatat | 1260 |
| cgaggtggac | attacctacg | ccgagtactt | cgagatgagc | gttcggctgg | cagaagctat | 1320 |
| gaagcgctat | gggctgaata | caaaccatcg | gatcgtggtg | tgcagcgaga | atagcttgca | 1380 |
| gttcttcatg | cccgtgttgg | gtgccctgtt | catcggtgtg | gctgtggccc | cagctaacga | 1440 |
| catctacaac | gagcgcgagc | tgctgaacag | catgggcatc | agccagccca | ccgtcgtatt | 1500 |
| cgtgagcaag | aaagggctgc | aaaagatcct | caacgtgcaa | aagaagctac | cgatcataca | 1560 |
| aaagatcatc | atcatggata | gcaagaccga | ctaccagggc | ttccaaagca | tgtacacctt | 1620 |
| cgtgacttcc | catttgccac | ccggcttcaa | cgagtacgac | ttcgtgcccg | agagcttcga | 1680 |
| ccgggacaaa | accatcgccc | tgatcatgaa | cagtagtggc | agtaccggat | tgcccaaggg | 1740 |
| cgtagcccta | ccgcaccgca | ccgcttgtgt | ccgattcagt | catgcccgcg | acccccatctt | 1800 |

```
cggcaaccag atcatccccg acaccgctat cctcagcgtg gtgccatttc accacggctt    1860
cggcatgttc accacgctgg gctacttgat ctgcggcttt cgggtcgtgc tcatgtaccg    1920
cttcgaggag gagctattct tgcgcagctt gcaagactat aagattcaat ctgccctgct    1980
ggtgcccaca ctatttagct tcttcgctaa gagcactctc atcgacaagt acgacctaag    2040
caacttgcac gagatcgcca gcggcggggc gccgctcagc aaggaggtag gtgaggccgt    2100
ggccaaacgc ttccacctac caggcatccg ccagggctac ggcctgacag aaacaaccag    2160
cgccattctg atcacccccg aaggggacga caagcctggc gcagtaggca aggtggtgcc    2220
cttcttcgag gctaaggtgg tggacttgga caccggtaag acactgggtg tgaaccagcg    2280
cggcgagctg tgcgtccgtg gccccatgat catgagcggc tacgttaaca accccgaggc    2340
tacaaacgct ctcatcgaca aggacggctg gctgcacagc ggcgacatcg cctactggga    2400
cgaggacgag cacttcttca tcgtggaccg gctgaagagc ctgatcaaat acaagggcta    2460
ccaggtagcc ccagccgaac tggagagcat cctgctgcaa cacccaaaca tcttcgacgc    2520
cggggtcgcc ggcctgcccg acgacgatgc cggcgagctg cccgccgcag tcgtcgtgct    2580
ggaacacggt aaaaccatga ccgagaagga gatcgtggac tatgtggcca gccaggttac    2640
aaccgccaag aagctgcgcg gtggtgttgt gttcgtggac gaggtgccta aaggactgac    2700
cggcaagttg gacgcccgca agatccgcga gattctcatt aaggcaagaa agggcggcaa    2760
gatcgccgtg taataagcat gcaagcttgc ggccgcttcg agcagacatg ataagataca    2820
ttgatgagtt tggacaaacc acaactagaa tgcagtgaaa aaaatgcttt atttgtgaaa    2880
tttgtgatgc tattgcttta tttgtaacca ttataagctg caataaacaa gttaacaaca    2940
acaattgcat tcattttatg tttcaggttc agggggagat gtgggaggtt ttttaaagca    3000
agtaaaacct ctacaaatgt ggtaaaatc                                     3029

<210> SEQ ID NO 814
<211> LENGTH: 3067
<212> TYPE: DNA
<213> ORGANISM: Artificial Sequence
<220> FEATURE:
<223> OTHER INFORMATION: plasmid reporter gene expression
<220> FEATURE:
<221> NAME/KEY: misc_feature
<222> LOCATION: (1)..(832)
<223> OTHER INFORMATION: CMV I.E. enhancer and promoter
<220> FEATURE:
<221> NAME/KEY: misc_feature
<222> LOCATION: (833)..(1029)
<223> OTHER INFORMATION: Promega intron
<220> FEATURE:
<221> NAME/KEY: misc_feature
<222> LOCATION: (1069)..(1100)
<223> OTHER INFORMATION: 32 bp sequence in direct orientation
<220> FEATURE:
<221> NAME/KEY: misc_feature
<222> LOCATION: (1115)..(1120)
<223> OTHER INFORMATION: Kozak sequence
<220> FEATURE:
<221> NAME/KEY: misc_feature
<222> LOCATION: (1121)..(2770)
<223> OTHER INFORMATION: Luciferase
<220> FEATURE:
<221> NAME/KEY: misc_feature
<222> LOCATION: (2783)..(2814)
<223> OTHER INFORMATION: 32 bp sequence in direct orientation
<220> FEATURE:
<221> NAME/KEY: misc_feature
<222> LOCATION: (2829)..(3067)
<223> OTHER INFORMATION: SV40 polyA
```

```
<400> SEQUENCE: 814
taggaagatc ttcaatattg gccattagcc atattattca ttggttatat agcataaatc    60
aatattggct attggccatt gcatacgttg tatctatatc ataatatgta catttatatt   120
ggctcatgtc caatatgacc gccatgttgg cattgattat tgactagtta ttaatagtaa   180
tcaattacgg ggtcattagt tcatagccca tatatggagt tccgcgttac ataacttacg   240
gtaaatggcc cgcctggctg accgcccaac gaccccgcc cattgacgtc aataatgacg   300
tatgttccca tagtaacgcc aatagggact ttccattgac gtcaatgggt ggagtattta   360
cggtaaactg cccacttggc agtacatcaa gtgtatcata tgccaagtcc gccccctatt   420
gacgtcaatg acggtaaatg gcccgcctgg cattatgccc agtacatgac cttacgggac   480
tttcctactt ggcagtacat ctacgtatta gtcatcgcta ttaccatggt gatgcggttt   540
tggcagtaca ccaatgggcg tggatagcgg tttgactcac ggggatttcc aagtctccac   600
cccattgacg tcaatgggag tttgttttgg caccaaaatc aacgggactt tccaaaatgt   660
cgtaataacc ccgccccgtt gacgcaaatg ggcggtaggc gtgtacggtg ggaggtctat   720
ataagcagag ctcgtttagt gaaccgtcag atcactagaa gctttattgc ggtagtttat   780
cacagttaaa ttgctaacgc agtcagtgct tctgacacaa cagtctcgaa cttaagctgc   840
agaagttggt cgtgaggcac tgggcaggta agtatcaagg ttacaagaca ggtttaagga   900
gaccaataga aactgggctt gtcgagacag agaagactct tgcgtttctg ataggcacct   960
attggtctta ctgacatcca ctttgccttt ctctccacag gtgtccactc ccagttcaat  1020
tacagctctt aaggctagag tacttaatac gactcactat aggctagcgg tcgatgttcg  1080
caacgtcgat cgtacgtgca acgcgtgcga tcgcgccacc atggaagatg ccaaaaacat  1140
taagaagggc ccagcgccat tctacccact cgaagacggg accgccggcg agcagctgca  1200
caaagccatg aagcgctacg ccctggtgcc cggcaccatc gcctttaccg acgcacatat  1260
cgaggtggac attacctacg ccgagtactt cgagatgagc gttcggctgg cagaagctat  1320
gaagcgctat gggctgaata caaaccatcg gatcgtggtg tgcagcgaga atagcttgca  1380
gttcttcatg cccgtgttgg gtgccctgtt catcggtgtg gctgtggccc cagctaacga  1440
catctacaac gagcgcgagc tgctgaacag catgggcatc agccagccca ccgtcgtatt  1500
cgtgagcaag aaagggctgc aaaagatcct caacgtgcaa agaagctac cgatcataca  1560
aaagatcatc atcatggata gcaagaccga ctaccagggc ttccaaagca tgtacacctt  1620
cgtgacttcc catttgccac ccggcttcaa cgagtacgac ttcgtgcccg agagcttcga  1680
ccgggacaaa accatcgccc tgatcatgaa cagtagtggc agtaccggat tgcccaaggg  1740
cgtagccta ccgcaccgca ccgcttgtgt ccgattcagt catgcccgcg accccatctt  1800
cggcaaccag atcatccccg acaccgctat cctcagcgtg gtgccatttc accacggctt  1860
cggcatgttc accacgctgg gctacttgat ctgcggcttt cgggtcgtgc tcatgtaccg  1920
cttcgaggag gagctattct tgcgcagctt gcaagactat aagattcaat ctgccctgct  1980
ggtgcccaca ctatttagct tcttcgctaa gagcactctc atcgacaagt acgacctaag  2040
caacttgcac gagatcgcca gcggcggggc cgcctcagc aaggaggtag gtgaggccgt  2100
ggccaaacgc ttccacctac caggcatccg ccagggctac ggcctgacag aaacaaccag  2160
cgccattctg atcaccccg aaggggacga caagcctggc gcagtaggca aggtggtgcc  2220
cttcttcgag gctaaggtgg tggacttgga caccggtaag acactgggtg tgaaccagcg  2280
cggcgagctg tgcgtccgtg gccccatgat catgagcggc tacgttaaca accccgaggc  2340
```

```
tacaaacgct ctcatcgaca aggacggctg gctgcacagc ggcgacatcg cctactggga    2400
cgaggacgag cacttcttca tcgtggaccg gctgaagagc ctgatcaaat acaagggcta    2460
ccaggtagcc ccagccgaac tggagagcat cctgctgcaa caccccaaca tcttcgacgc    2520
cggggtcgcc ggcctgcccg acgacgatgc cggcgagctg cccgccgcag tcgtcgtgct    2580
ggaacacggt aaaaccatga ccgagaagga gatcgtggac tatgtggcca gccaggttac    2640
aaccgccaag aagctgcgcg gtggtgttgt gttcgtggac gaggtgccta aaggactgac    2700
cggcaagttg gacgcccgca agatccgcga gattctcatt aaggccaaga agggcggcaa    2760
gatcgccgtg taataagcat gcggtcgatg ttcgcaacgt cgatcgtacg tgcaacgcgt    2820
aagcttgcgg ccgcttcgag cagacatgat aagatacatt gatgagtttg gacaaaccac    2880
aactagaatg cagtgaaaaa aatgctttat ttgtgaaatt tgtgatgcta ttgctttatt    2940
tgtaaccatt ataagctgca ataaacaagt taacaacaac aattgcattc attttatgtt    3000
tcaggttcag ggggagatgt gggaggtttt ttaaagcaag taaaacctct acaaatgtgg    3060
taaaatc                                                              3067
```

<210> SEQ ID NO 815
<211> LENGTH: 3067
<212> TYPE: DNA
<213> ORGANISM: Artificial Sequence
<220> FEATURE:
<223> OTHER INFORMATION: plasmid reporter gene expression
<220> FEATURE:
<221> NAME/KEY: misc_feature
<222> LOCATION: (1)..(832)
<223> OTHER INFORMATION: CMV I.E. enhancer and promoter
<220> FEATURE:
<221> NAME/KEY: misc_feature
<222> LOCATION: (833)..(1029)
<223> OTHER INFORMATION: Promega intron
<220> FEATURE:
<221> NAME/KEY: misc_feature
<222> LOCATION: (1069)..(1100)
<223> OTHER INFORMATION: 32 bp sequence in direct orientation
<220> FEATURE:
<221> NAME/KEY: misc_feature
<222> LOCATION: (1115)..(1120)
<223> OTHER INFORMATION: Kozak sequence
<220> FEATURE:
<221> NAME/KEY: misc_feature
<222> LOCATION: (1121)..(2770)
<223> OTHER INFORMATION: Luciferase
<220> FEATURE:
<221> NAME/KEY: misc_feature
<222> LOCATION: (2789)..(2820)
<223> OTHER INFORMATION: 32 bp sequence in direct orientation
<220> FEATURE:
<221> NAME/KEY: misc_feature
<222> LOCATION: (2829)..(3067)
<223> OTHER INFORMATION: SV40 polyA

<400> SEQUENCE: 815

```
taggaagatc ttcaatattg gccattagcc atattattca ttggttatat agcataaatc      60
aatattggct attggccatt gcatacgttg tatctatatc ataatatgta catttatatt     120
ggctcatgtc caatatgacc gccatgttgg cattgattat tgactagtta ttaatagtaa     180
tcaattacgg ggtcattagt tcatagccca tatatggagt tccgcgttac ataacttacg     240
gtaaatggcc cgcctggctg accgcccaac gacccccgcc cattgacgtc aataatgacg     300
tatgttccca tagtaacgcc aatagggact ttccattgac gtcaatgggt ggagtattta     360
cggtaaactg cccacttggc agtacatcaa gtgtatcata tgccaagtcc gccccctatt     420
```

-continued

```
gacgtcaatg acggtaaatg ccccgcctgg cattatgccc agtacatgac cttacgggac    480
tttcctactt ggcagtacat ctacgtatta gtcatcgcta ttaccatggt gatgcggttt    540
tggcagtaca ccaatgggcg tggatagcgg tttgactcac ggggatttcc aagtctccac    600
cccattgacg tcaatgggag tttgttttgg caccaaaatc aacgggactt tccaaaatgt    660
cgtaataacc ccgccccgtt gacgcaaatg ggcggtaggc gtgtacggtg ggaggtctat    720
ataagcagag ctcgtttagt gaaccgtcag atcactagaa gctttattgc ggtagtttat    780
cacagttaaa ttgctaacgc agtcagtgct tctgacacaa cagtctcgaa cttaagctgc    840
agaagttggt cgtgaggcac tgggcaggta agtatcaagg ttacaagaca ggtttaagga    900
gaccaataga aactgggctt gtcgagacag agaagactct tgcgtttctg ataggcacct    960
attggtctta ctgacatcca ctttgccttt ctctccacag gtgtccactc ccagttcaat   1020
tacagctctt aaggctagag tacttaatac gactcactat aggctagcgg tcgatgttcg   1080
caacgtcgat cgtacgtgca acgcgtgcga tcgcgccacc atggaagatg ccaaaaacat   1140
taagaagggc ccagcgccat tctacccact cgaagacggg accgccggcg agcagctgca   1200
caaagccatg aagcgctacg ccctggtgcc cggcaccatc gcctttaccg acgcacatat   1260
cgaggtggac attacctacg ccgagtactt cgagatgagc gttcggctgg cagaagctat   1320
gaagcgctat gggctgaata caaaccatcg gatcgtggtg tgcagcgaga atagcttgca   1380
gttcttcatg cccgtgttgg gtgccctgtt catcggtgtg ctgtgggccc agctaacga   1440
catctacaac gagcgcgagc tgctgaacag catgggcatc agccagccca ccgtcgtatt   1500
cgtgagcaag aaagggctgc aaaagatcct caacgtgcaa aagaagctac cgatcataca   1560
aaagatcatc atcatggata gcaagaccga ctaccagggc ttccaaagca tgtacacctt   1620
cgtgacttcc catttgccac ccggcttcaa cgagtacgac ttcgtgcccg agagcttcga   1680
ccgggacaaa accatcgccc tgatcatgaa cagtagtggc agtaccggat tgcccaaggg   1740
cgtagcccta ccgcaccgca ccgcttgtgt ccgattcagt catgcccgcg accccatctt   1800
cggcaaccag atcatccccg acaccgctat cctcagcgtg gtgccatttc accacggctt   1860
cggcatgttc accacgctgg gctacttgat ctgcggcttt cgggtcgtgc tcatgtaccg   1920
cttcgaggag gagctattct tgcgcagctt gcaagactat aagattcaat ctgccctgct   1980
ggtgcccaca ctatttagct tcttcgctaa gagcactctc atcgacaagt acgacctaag   2040
caacttgcac gagatcgcca gcggcggggc gccgctcagc aaggaggtag gtgaggccgt   2100
ggccaaacgc ttccacctac caggcatccg ccagggctac ggcctgacag aaacaaccag   2160
cgccattctg atcaccccg aaggggacga caagcctggc gcagtaggca aggtggtgcc   2220
cttcttcgag gctaaggtgg tggacttgga caccggtaag acactgggtg tgaaccagcg   2280
cggcgagctg tgcgtccgtg gccccatgat catgagcggc tacgttaaca ccccgaggc   2340
tacaaacgct ctcatcgaca aggacggctg gctgcacagc ggcgacatcg cctactggga   2400
cgaggacgag cacttcttca tcgtggaccg gctgaagagc ctgatcaaat acaagggcta   2460
ccaggtagcc ccagccgaac tggagagcat cctgctgcaa caccccaaca tcttcgacgc   2520
cggggtcgcc ggcctgcccg acgacgatgc cggcgagctg cccgccgcag tcgtcgtgct   2580
ggaacacggt aaaaccatga ccgagaagga tcgtgtggac tatgtggcca gccaggttac   2640
aaccgccaag aagctgcgcg tggtgtttgt gttcgtggac gaggtgccta aaggactgac   2700
cggcaagttg gacgcccgca agatccgcga gattctcatt aaggccaaga agggcggcaa   2760
gatcgccgtg taataagcat gcacgcgttg cacgtacgat cgacgttgcg aacatcgacc   2820
```

```
aagcttgcgg ccgcttcgag cagacatgat aagatacatt gatgagtttg dacaaaccac   2880
aactagaatg cagtgaaaaa aatgctttat ttgtgaaatt tgtgatgcta ttgctttatt   2940
tgtaaccatt ataagctgca ataaacaagt taacaacaac aattgcattc attttatgtt   3000
tcaggttcag ggggagatgt gggaggtttt ttaaagcaag taaaacctct acaaatgtgg   3060
taaaatc                                                              3067
```

<210> SEQ ID NO 816
<211> LENGTH: 550
<212> TYPE: PRT
<213> ORGANISM: Renilla reniformis

<400> SEQUENCE: 816

```
Met Glu Asp Ala Lys Asn Ile Lys Lys Gly Pro Ala Pro Phe Tyr Pro
  1               5                  10                  15

Leu Glu Asp Gly Thr Ala Gly Glu Gln Leu His Lys Ala Met Lys Arg
             20                  25                  30

Tyr Ala Leu Val Pro Gly Thr Ile Ala Phe Thr Asp Ala His Ile Glu
         35                  40                  45

Val Asp Ile Thr Tyr Ala Glu Tyr Phe Glu Met Ser Val Arg Leu Ala
     50                  55                  60

Glu Ala Met Lys Arg Tyr Gly Leu Asn Thr Asn His Arg Ile Val Val
 65                  70                  75                  80

Cys Ser Glu Asn Ser Leu Gln Phe Phe Met Pro Val Leu Gly Ala Leu
                 85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320
```

-continued

```
Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
            355                 360                 365

Phe Glu Ala Lys Val Val Asp Leu Asp Thr Gly Lys Thr Leu Gly Val
        370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
            435                 440                 445

Val Ala Pro Ala Glu Leu Glu Ser Ile Leu Leu Gln His Pro Asn Ile
        450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
            515                 520                 525

Lys Leu Asp Ala Arg Lys Ile Arg Glu Ile Leu Ile Lys Ala Lys Lys
        530                 535                 540

Gly Gly Lys Ile Ala Val
545                 550

<210> SEQ ID NO 817
<211> LENGTH: 32
<212> TYPE: DNA
<213> ORGANISM: Artificial Sequence
<220> FEATURE:
<223> OTHER INFORMATION: ablation recognition site

<400> SEQUENCE: 817
ggtcggcgac gcgtaatcgt cgattggcgt ac                                     32
```